United States Patent
Holladay et al.

(10) Patent No.: US 6,403,575 B1
(45) Date of Patent: *Jun. 11, 2002

(54) 3-PYRIDYL ENANTIOMERS AND THEIR USE AS ANALGESICS

(75) Inventors: Mark W. Holladay, Tucson, AZ (US); Stephen P. Arneric, Landenberg, PA (US); Hao Bai, Libertyville, IL (US); Michael J. Dart, Highland Park, IL (US); Nan-Horng Lin, Vernon Hills, IL (US); John K. Lynch, Kenosha, WI (US); Yat Sun Or, Cambridge, MA (US); Keith B. Ryther, Round Lake Park; James P. Sullivan, Deerfield, both of IL (US); James T. Wasicak, Waterford, WI (US); Paul P. Ehrlich, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/619,229

(22) Filed: Jul. 19, 2000

Related U.S. Application Data

(60) Division of application No. 08/987,581, filed on Dec. 9, 1997, now Pat. No. 6,133,253, which is a continuation-in-part of application No. 08/763,278, filed on Dec. 10, 1996.
(60) Provisional application No. 60/032,321, filed on Dec. 10, 1996.

(51) Int. Cl.[7] ............... A61K 31/44; C07D 401/00; C07D 421/00

(52) U.S. Cl. .................. 514/210.2; 546/268.1
(58) Field of Search ............... 514/210.2; 546/268.1

(56) References Cited

U.S. PATENT DOCUMENTS 5,948,793 A * 9/1999 Abreo et al. .......... 514/318
6,054,451 A * 4/2000 Caruso ................. 514/210

* cited by examiner

*Primary Examiner*—Bruck Kifle
(74) *Attorney, Agent, or Firm*—Daniel W. Collins; Lawrence S. Pope

(57) ABSTRACT

The present invention relates to a method of controlling pain in mammals, including humans, comprising administering to a mammal or patient in need of treatment thereof selected compounds of formula I:

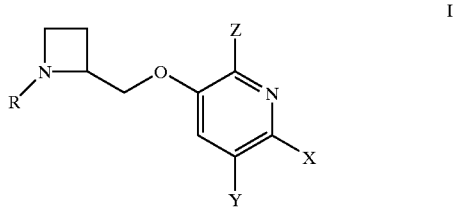

or a pharmaceutically acceptable salt thereof. The invention further relates to selected (R) and (S) compounds of formula I above which are useful as analgesics as well as neuronal cell death preventors and anti-inflammatories.

4 Claims, 6 Drawing Sheets

FIGURE 1

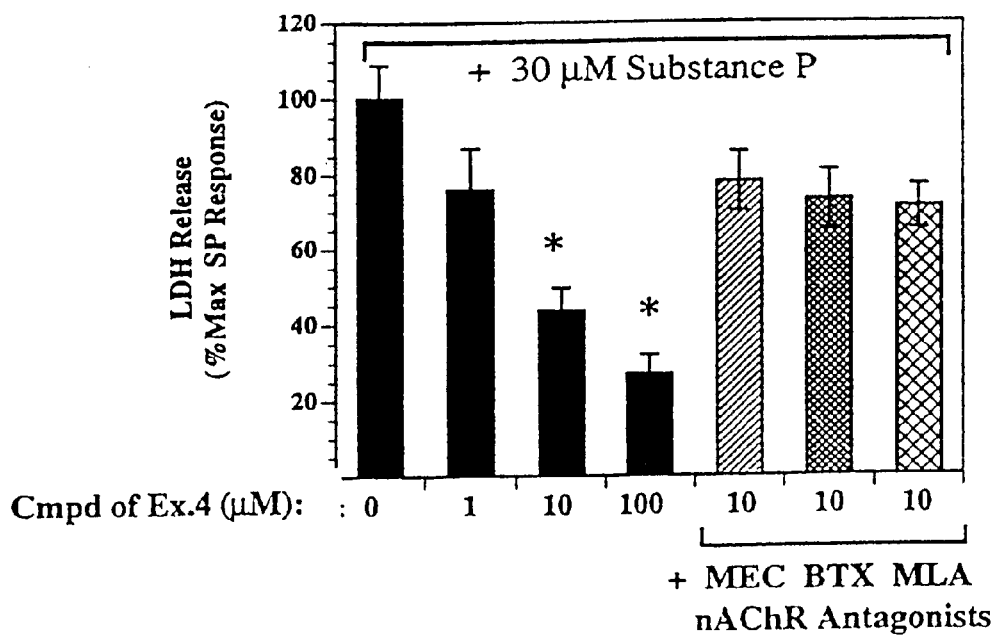

Fig. 1. Compound of Example 4 protects against SP-induced neurotoxicity in rat spinal cord cultures in a concentration-dependent manner. Similar effects are seen for glutamate-induced toxicity (data not shown). These effects are blocked by the nAChR antagonists mecamylamine (MEC; 10 μM), α-bungarotoxin (BTX; 1 nM) and methyllycaconitine, (MLA, 10 nM). Values are the means ± S.E.M.; N=4, * $p < 0.05$.

FIGURE 2

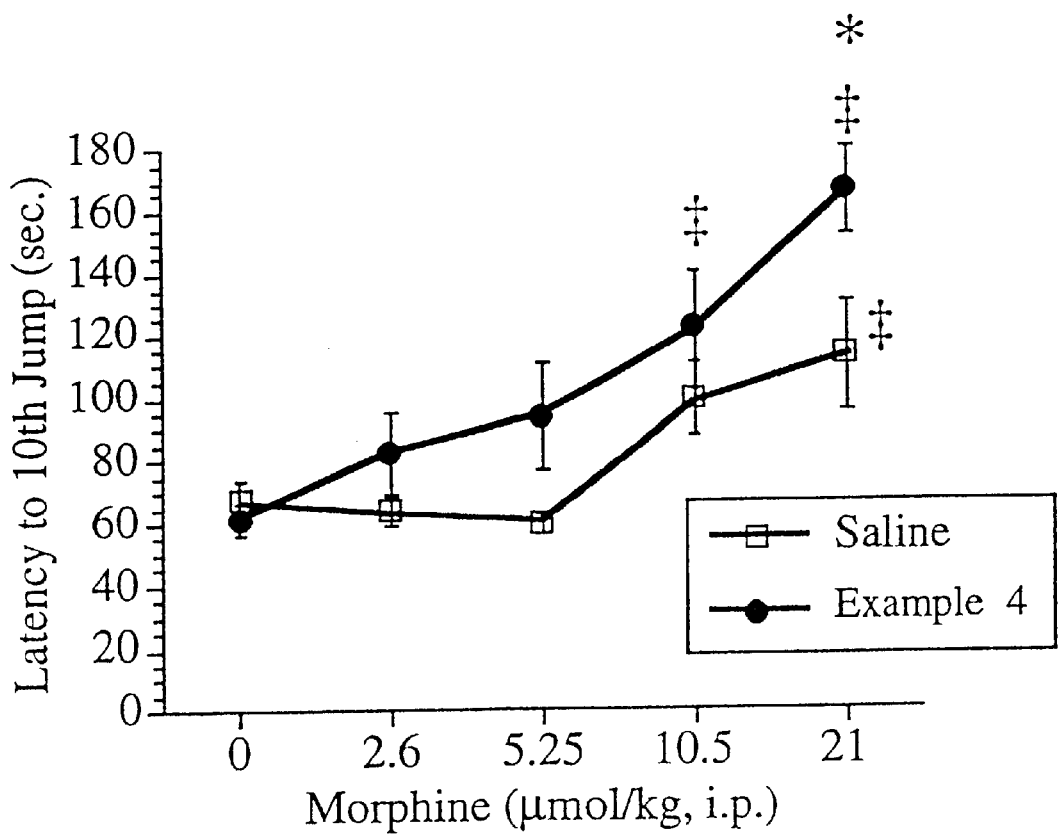

*different from morphine alone, $p < 0.05$

‡different from saline alone, $p < 0.05$

Fig. 2. Effect of co-administration of saline or compound of Example 4 (0.2 μmol/kg, i.p., a dose that does not have antinociceptive effects by itself) with various doses of morphine on latencies to jump from a hot plate maintained at 55°C. Compounds were administered 30 min. prior to testing. Represented are the means (± s.e.m) for groups of male, CD-1 mice (n = 7-8 per group).

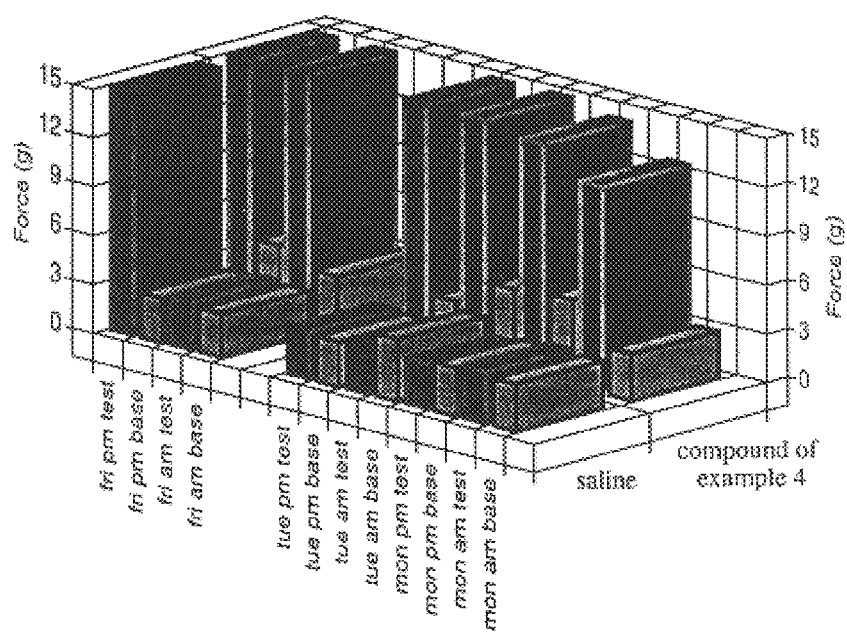
Fig. 3. Antiallodynic effect of compound of Example 4 during and following repeated administration of 0.3 μmol/kg, i.p., compared with response following repeated administration of saline.

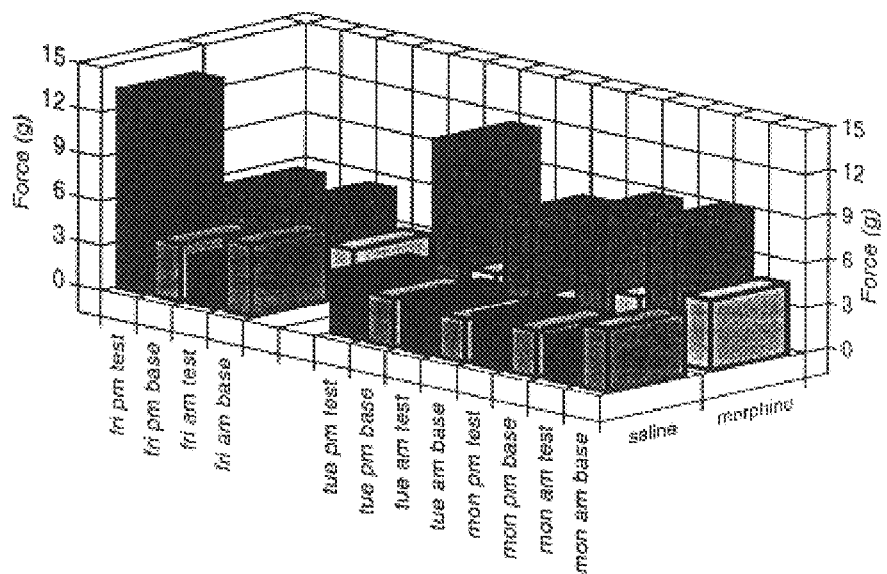
Fig. 4. Antiallodynic effect of morphine during and following repeated administration of 21 μmol/kg, i.p., compared with response following repeated administration of saline.

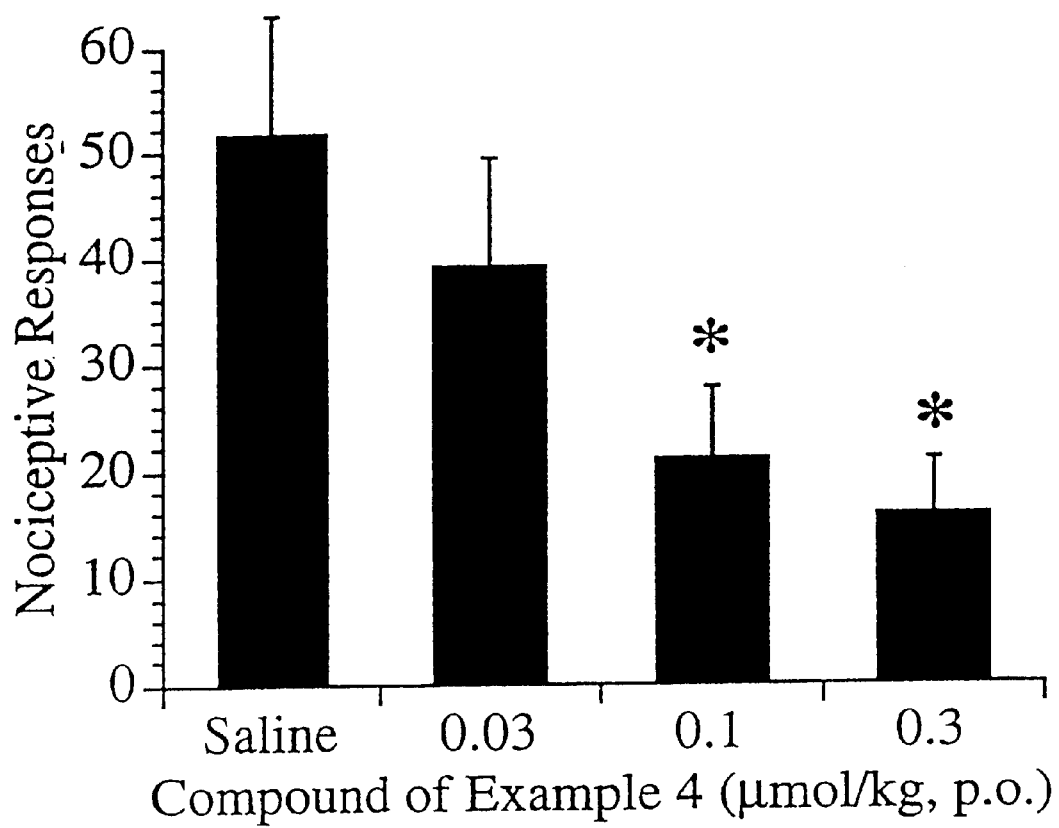
Figure 5. Each bar represents the mean (+s.e.m.) for 7 rats. *different from saline, p < 0.05.

Fig. 6. The anti-inflammatory effects of compound of Example 4. In the carrageenan paw edema model compound of Example 4 is as efficacious as dexamethasone (panel A). The effects of compound of Example 4 on carrageenan-induced paw edema can be prevented by a 5 μmol/kg injection of the nicotinic antagonist, mecamylamine (panel B). Values are the means ± S.E.M., N= 8.

3-PYRIDYL ENANTIOMERS AND THEIR USE AS ANALGESICS

This is a divisional of U.S. patent application Ser. No. 08/987,581, filed Dec. 9, 1997 now U.S. Pat. No. 6,133,253 which is a provisional of No. 60/032,321 filed Dec. 10, 1996.

This application is a continuation-in-part of copending U.S. patent application Ser. No. 08/763,278, filed Dec. 10, 1996.

FIELD OF THE INVENTION

The present invention relates to certain (R) and (S)-enantiomers of a class of substituted 3-pyridyloxy alkylene azetidin-2-yl compounds having significant activity as analgesics. In addition, some (R)-enantiomers have a surprisingly improved toxicity profile over the corresponding (S)-enantiomer of the same species. In addition to having activity as analgesics, the compounds are also effective in preventing neuronal cell death and are effective in treating or preventing inflammation.

BACKGROUND OF THE INVENTION

The search for more potent and more effective pain controllers or analgesics continues to be a significant research goal in the medical community. A substantial number of medical disorders and conditions produce pain as part of the disorder or condition. Relief of this pain is a major aspect of ameliorating or treating the overall disease or condition. Pain and the possible allievation thereof is also attributable to the individual patient's mental condition and physical condition. One pain reliever, or a class, may not be effective for a particular patient, or group of patients, which leads to a need for finding additional compounds or pharmaceuticals which are effective analgesics. Opioid and non-opioid drugs are the two major classes of analgesics (Dray, A. and Urban, L., Ann. Rev. Pharmacol. Toxicol., 36: 253–280, 1996). Opioids, such as morphine, act at opioid receptors in the brain to block transmission of the pain signals in the brain and spinal cord (Cherney, N. I., Drug, 51:713–737, 1996). Opioids such as morphine have abuse and addiction liability. Non-opioids such as non-steroid anti-inflammatory agents (NSAIDs) typically, but not exclusively, block the production of prostaglandins to prevent sensitization of nerve endings that facilitate the pain signal to the brain (Dray, et al, Trends in Pharmacol. Sci., 15: 190–197, 1994.; Carty, T. J. and Marfat, A., "COX-2 Inhibitors. Potential for reducing NSAID side-effects in treating inflammatory diseases", In: Emerging Drugs: Prospect for Improved Medicines. (W. C. Bowman, J. D. Fitzgerald, and J. B. Taylor, eds.), Ashley Publications Ltd., London, Chap. 19., pp. 391411). Most of the commonly prescribed or over-the-counter (OTC) NSAIDs are also commonly associated with at one side effect or another, such as stomach ulceration or pain. For example, NSAIDs such as aspirin are also known to cause irritation and ulceration of the stomach and duodenum.

WO 94/08922 describes pyridyl ether compounds which enhance cognitive function. U.S. patent applications Ser. Nos. 08/474,873 and 08/485,537 describe certain substituted pyridyl ether compounds as well as other compounds which also act at the nicotinic acetylcholine receptor to stimulate or inhibit neurotransmitter release. WO 96/31475 describes certain 3-substituted pyridine derivatives which are described as being useful for a variety of disorders as modulators of acetylcholine receptors. While some of these references have alluded to pain control as a potential use of the compounds or analogs recited therein, the Applicants have discovered that a certain narrow class of compounds of formula I shown below have a surprising and unexpected very effective analgesic effect. The Applicants have also found that activity at the nicotinic acetylcholine receptor site (e.g., binding thereto) is not necessarily correlated with a compound's effectiveness as an analgesic, since some of the compounds having very high binding affinity are ineffective as analgesics. The applicants have further found that some (R)-enantiomer in this series are particularly attractive because of an enhanced safety profile relative to the (S)-enantiomer. The Applicants have also found that the claimed azetidinyl substituted 3-pyridyl methylene ether compounds have enhanced activity over the non-azetidinyl class of known compounds in the treatment of pain as well as the prevention of neuronal cell death and inflammation.

BRIEF DESCRIPTION OF THE DRAWINGS

FIG. 1 shows that the compound of Example 4 as the (R)-enantiomer protects against SP-induced neurotoxicity in rat spinal cord cultures in a concentration dependent manner.

FIG. 2 shows that the compound of Example 4 when coadministered at a small dose (0.2 umol/kg,i.p.) with varying doses of morphine (0–21 umol/kg,i.p.) produced effective antinociceptive effects in the Mouse Hot Plate Paradigm.

FIG. 3 shows the antiallodynic effect of the compound of Example 4 in the Chung Model of Neuropathic Pain. Light Bars reflect responses before administration of the test compound (Ex. 4). Dark Bars represent responses 15 minutes following administration of the test compound. The compound of Ex. 4 is compared to saline.

FIG. 4 shows the antiallodynic effect of morphine during and following repeated administration of 21 umol/kg,i.p., compared with the response following repeated administration of saline.

FIG. 5 shows that the compound of Ex. 4 produced significant antinociceptive effects in the Formalin Model of Persistent Pain relative to saline (control) and that an increase in dosage diminished the nociceptive responses. The range of administration in this test was 0.1–0.3 umol/kg,p.o. (oral administration).

FIG. 6 also shows that the nicotinic antagonist, mecaamylamine, prevents this effect shown by the compound of Ex. 4 in this model.

SUMMARY OF THE INVENTION

Figure 6:
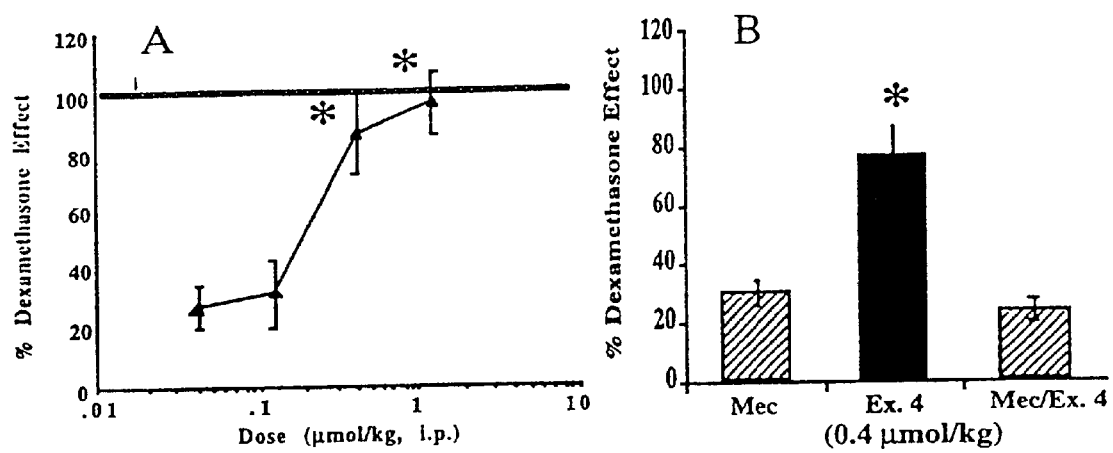
FIG. 6 shows the antiinflammatory effects of the compound of Example 4 in the carrageenan paw edema model wherein the compound is shown as effective as dexamethansone at the dosage shown (panel A).

The present invention relates to a method of controlling pain in mammals, including humans, comprising administering to a mammal or patient in need of treatment thereof a compound of formula I:

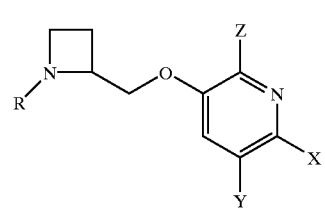

or a pharmaceutically acceptable salt thereof, wherein

R is selected from H, or a prodrug derivative;
Z is selected from H, F or Cl;
X is selected from H, F, Br, Cl, CN, CHF$_2$, OMe, CH$_2$F, or C$_{1-2}$ alkyl; and
Y is selected from H, F, Cl, Br, C$_{1-6}$ alkyl, vinyl, ethynyl, 3-propenyl, NO$_2$ or OC$_{1-2}$ alkyl.

In a preferred embodiment, the compound administered has formula IA:

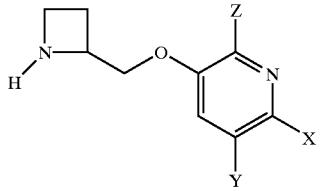

IA or a pharmaceutically acceptable salt thereof, wherein
R is selected from H, or a prodrug derivative;
Z is selected from H, F or Cl;
X is selected from H, F, Br, Cl, CN, CHF$_2$, OMe, CH$_2$F, or C$_{1-2}$ alkyl; and
Y is selected from H, F, Cl, Br, C$_{1-6}$ alkyl, vinyl, ethynyl, 3-propenyl, NO$_2$ or OC$_{1-2}$ alkyl.

The present invention also relates to a method of treating or controlling pain in a patient in need of treatment thereof, comprising administering a compound or pharmaceutically acceptable salt of formula I with the variables as recited above wherein the compound is the (S)-enantiomer at the chiral center at position 2 of the azetidine ring. Conversely, the invention also relates to a method of treating or controlling pain in a patient in need of treatment thereof, comprising administering the corresponding (R)-enantiomer, wherein X is selected from the group consisting of F and Cl; and Y is H, wherein the (R)-enantiomeric compound of formula II has an improved safety profile over the (S)-enantiomer of the same species.

The present invention also relates to a method of treating pain comprising coadministering a compound of Formula I with an opiate narcotic such as morphine wherein the combined regime more effectively treats pain and has a significant antinociceptive effect. The present invention relates to a method of treating or preventing pain in humans or animals comprising administering a dosage of about 0.2 umol/kg,i.p. of a compound of formula I with a dosage of morphine of about 2.6 to 21 umol/kg,i.p. to a patient in need of treatment thereof. The compounds of the invention may be coadministered with other known safe and effective narcotic pain relievers which are well known to those of skill in the pain relieving arts and such coadministration is included within the scope of the methods herein.

The present invention also relates to novel compounds which are effective nicotinic acetylcholine receptor modulators and effective pain controllers wherein said compounds are chosen from a compound of formula IA or a pharmaceutically acceptable salt thereof, wherein Z, Y, X and the 2-azetidine stereochemistry are, respectively, selected from the group consisting of:

H, H, Me (S);
H, H, Me (R);
H, H, CN (S);
H, H, Cl (S);
H, H, Cl (R);
H, H, Br (R);
H, H, F (S);
H, H, F (R);
H, H, CHF$_2$ (S);
H, H, OMe (R);
H, Me, Cl (S);
H, Me, Cl (R);
H, Et, F (S);
H, ethenyl, Cl (S);
H, ethenyl, Cl (R);
H, ethenyl, F (S);
H, ethenyl, F (R);
H, ethynyl, Cl (S);
H, ethynyl, Cl (R);
H, Cl, Cl (S);
H, Cl, Cl (R);
H, Cl, F (S);
H, Br, Me (S);
H, Br, Me (R);
H, Br, Cl (S);
H, Br, Cl (R);
H, Br, F (S);
H, Br, F (R);
H, Me, H (R);
H, n-Pr, H (S);
H, ethenyl, H (S);
H, ethenyl, H (R);
H, 3-propenyl, H (S);
H, Cl, H (R);
H, F, H (S);
H, NO$_2$, H (S);
H, OEt, H (S);
Cl, H, H (S);
Cl, H, H (R);
F, H, H (S);
F, H, F (S);
F, H, Me (S); and
F, H, Me (R).

The preferred compounds are those that are effective as analgesics, neuronal cell death modifiers, or anti-inflammatories.

The present invention also relates to pharmaceutical compositions comprising a compound of formula I with the variables R, X, Y, Z and the stereochemistry as described above and a pharmaceutically acceptable excipient or diluent and to dosage forms containing such a composition. The invention further relates to a process for producing compounds of formula I which is further described below and to key intermediates utilized in such process.

The present invention also relates to prodrug derivatives having formula I wherein R is selected from the group consisting of alkyl, acyl, alkoxycarbonyl, aryloxycarbonyl, amidomethyl, optionally substituted vinyl and carbamyl. Acyl can encompass a variety of substituents including an optionally derivatized amino acid attached to the nitrogen through an amide linkage.

DETAILED DESCRIPTION OF THE INVENTION

The present invention relates to a method of treating or controlling pain comprising administering a pharmaceutically effective amount of a compound of formula I with the variables Z, X and Y as defined above to a patient in need of treatment thereof. The invention also relates to certain compounds and pharmaceutical compositions. For purposes of this invention, the terms recited in the claims are defined below:

A "patient in need of treatment thereof" is broadly defined to mean a human or veterinary animal patient in need of a pain reliever or analgesic to diminish or control the feelings of pain associated with a temporary(acute) or chronic medical condition or disorder.

A "pharmaceutically acceptable salt" is defined to mean those salts, which are, with the scope of sound medical judgement, suitable for use in contact with tissues of humans and animals without undue toxicity, irration, allergic response and the like, and are effective for their intended use as pain modulators, neuronal cell death modulators or anti-inflammatories. Pharmaceutically acceptable salts are well known in the art. See, for example, S. M. Berge, et al., in *J. Pharm. Sci.*, 66:1–19 (1977). The salts may be prepared in situ during the final isolation and purification of the compounds of formula I-III or separately by reacting the free base function with a suitable organic acid. Representative acid addition salts include tosylate, benzoate, naphthalenesulfonate, hydrochloride, hydrobromide, sulfate, bisulfate, acetate, oxalate, valerate, oleate, palmitate, stearate, laurate, borate, benzoate, lactate, phosphate, toluenesulfonate, methanesulfonate, naphthalenesulfonate, citrate, malate, fumarate, succinate, tartrate, ascorbate, glucoheptonate, lactobionate, lauryl sulfate salts and the like. The preferred salt is the tosylate salt. The inventors have found that the tosylate salt is less hygroscopic, more crystalline, more stable, has a higher melting point, and is more readily purified than the other salts. In addition, the tosylate salt is better suited for pharmaceutical formulation.

A "prodrug" or "pharmaceutically acceptable prodrug" is defined to mean a compound that is rapidly transformed in vivo to yield a parent compound, as for example, by hydrolysis in blood and during delivery of the compound per se to the pharmacological site of action. T. Higuchi and V. Stella provide a thorough discussion of the prodrug concept in *Prodrugs as Novel Delivery Systems,* vol. 14 of the A.C.S. Symposium Series, A.C.S. (1975). Such prodrugs are included within the scope of the method of use herein. Examples of pro-drugs include pharmaceutically acceptable nontoxic derivatives of the azetidine nitrogen, including amides derived from $C_1$–$C_6$-alkyl carboxylic acids wherein the alkyl chain is straight or branched or from aromatic acids such as derivatives of benzoic acid. These may be prepared by conventional methods. The amides can also be derived from amino acids. Other prodrugs include alkyl derivatives and carbamate derivatives of the azetidine nitrogen. Specific examples of prodrug moieties are exemplified below.

The inventors have discovered that prodrugs of formula I, wherein R is not H, will cleave in vivo to the compound of formula I, wherein R is H. As an example, it has been demonstrated that metabolic dealkylation of N-alkyl azetidines occurs in vivo. Thus, analysis of samples of animal blood obtained over an eight hour period following IP injection of 1.9 $\mu$mol/kg of the N-methyl compound of example 98 indicated that substantial dealkylation to the N—H analog, example 8, occurs within 15 minutes. The resulting plasma levels of the compound of example 8 are in the range afforded by an effective IP dose of the compound, suggesting that the analgesic effect of the its N-methyl prodrug is due to its conversion in vivo to the active N—H form. Based on area under the curve measurements, a conversion efficiency of 16% is estimated for the N-methyl compound. Similarly, IP administration of the N-ethyl (example 99) or N-propyl (example 100) analogs to rat leads to in vivo conversion to the compound of example 8, with improved efficiencies (54% for N-ethyl, 30% for N-propyl) compared to the N-methyl analog.

Additional prodrugs that show analgesic effect are compounds of formula I, wherein R, Z, Y, X and the 2-azetidine stereochemistry are, respectively, as follows:

methyl, H, Cl, H, (S),
methyl, H, H, F, (S),
methyl, H, Br, Cl, (S),
methyl, H, H, Cl, (R),
methyl, H, Br, Cl, (R),
methyl, H, 3-propenyl, Cl, (S),
methyl, H, methyl, Cl, (S),
methyl, H, F, H, (R),
Boc, H, H, Cl, (R),
methyl, H, ethyl, F, (R),
ethyl, H, H, Cl, (R),
methyl, H, H, $CH_2F$, (S),
methyl, H, methyl, Cl, (R),
ethyl, H, H, methyl, (S),
methyl, H, methyl, ethyl, (S),
methyl, H, Cl, F, (S),
cyclohexylmethyl, H, H, F, (R),
t-pentyl, H, H, Cl, (R),
3-methylbutyn-3-yl, H, H, Cl, (R),
ethyl, H, H, methyl, (R),
methyl, H, methoxy, H, (S),
t-butyl, H, H, methyl, (S), A "pharmaceutically acceptable carrier or diluent" means a non-toxic, inert solid, semi-solid or liquid filler, diluent, encapsulating material or formulation auxiliarly of any type. Some of the examples include sugars, such as lactose, glucose and sucrose; starches such as corn starch and potato starch; celulose and its derivatives such as sodium carboxymethyl cellulose, ethyl cellulose and cellulose acetate; powdered tragacanth; malt; gelatin, talc; alginate gums; excipients such as cocoa butter and suppository waxes or other waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants may also be present in the composition, according to the judgement of the formulator. Examples of pharmaceutically acceptable antioxidants include water soluble antioxidants such as ascorbic acid, cysteine hydrochloride, sodium bisulfite, sodium metabisulfite, sodium sulfite, and the like. Oil soluble antioxidants and metal chelators may also be used.

A "therapeutically effective amount" of the analgesic agent is meant a sufficient amount of the compound to treat pain to obtain the desired therapeutic response. It also means the amount necessary to inhibit neuronal cell death in the conditions associated with central and peripheral neuropathic pain which may include but are not limited to AIDS, cancer, stroke, Parkinson's disease, diabetes, osteoarthritis, tissue trauma, surgical intervention, and postherpetic neuralgia or to alleviate, reduce or prevent inflammation at the targeted site. It is understood that the total daily dosage or usage of the compounds and compositions of the present invention will be decided by the attending physician within the scope of sound medical judgement. The specific therapeutically effective dose level for any particular patient will depend upon a variety of factors including the disorder being treated and the severity of the symptoms of pain or discomfort; the activity of the specific compound employed and the specific composition as well as the age, body weight, general health, sex and diet of the patient in need of treatment thereof. Other factors include the time of administration, route of administration, and rate of excretion of the specific compound employed; the duration of treatment; drugs used in combination or coincidentally with the specific compound employed and the like. Total daily dose of the compounds of the invention administered to a patient or animal in single or divided doses in various forms or routes of administration may range from amounts of about 0.001 to 100 mg/kg body weight daily and preferrably 0.01 to 10 mg/kg/day. Of course, this amount may vary depending upon the potency of the specific compound or drug wherein such ranges may vary accordingly to fall below the 0.001 mg/kg/body weight daily. Dosage unit compositions may contain such amounts or submultiples thereof to make up the total daily dose.

The term "$C_1$–$C_6$-alkyl" means straight or branched chain versions of methyl, ethyl, propyl, butyl, pentyl or hexyl.

The markush structures or other variables as described above or in the claims are self-explanatory and are standard chemical nomenclature or symbology. The 2-position of the azetidine ring is a chiral center.

The term "improved safety profile" means that an enantiomes of the invention typically elicited a lower response in the activation of peripheral ganglionic nicotinic acetylcholine receptors which, if occurring in vivo, could be associated with undesired side effects on the autonomic nervous (e.g. cardiovascular and gastrointestinal) systems. The safety profile is further supported by tabular data in the specification. Moreover, one (R)-enantiomer can be shown to have 12.8-fold less affinity at the skeletal muscle subtype of nicotinic acetylcholine receptor which, if occurring in vivo, could be associated with undesirable side effects with respect to muscle coordination and tone.

The term "effective nicotinic acetylcholine receptor binder" means that the compound has a binding affinity (Ki) in in vitro screens in at least micromolar ($\mu$M) range. The preferred binding affinity is in the nanomolar or picomolar range.

"Nitrogen protecting groups 'P'" are chosen from those protecting groups commonly known to protect nitrogen to enable chemical modification or manipulation at another molecular site on the molecule. Such groups are defined, for example, in the textbook by Stuart Warren *Organic Synthesis, The Disconnection Approach*, pp 68–69,(1982) and in a multitude of standard well known organic chemistry texts.

"Leaving groups 'L'" are chosen from those leaving groups well known in the art which are readily displaced by the desired nucleophile to form compounds of the invention. Tosylate is specifically utilized herein but any anionic leaving group commonly utilized for this purpose may also be utilized. Such groups are defined in Stuart Warren's reference above as well as standard organic treatises.

As indicated above, the present invention includes compounds of the invention and pharmaceutically acceptable excipients or diluents to form pharmaceutical compositions. Compositions suitable for parenteral injection may comprise pharmaceutically acceptable sterile aqueous or non-aqueous solutions, dispersions, suspensions or emulstions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, gylcerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by varous antibacterial and antifungal agents, for example, parabens, chlorobutanol, phenol, sorbic acid and the like. It may also be desirable to include isotonic agents, for example, sugars, sodium chloride and other salts and the like. Prolonged absorption of the injectable pharmaceutical form may be brought about by the use of agents delaying absorption, for example, aluminum monostearate and gelatin. If necessary, the agents for the treatment of pain or other conditions or indications described herein may be administered intraveneously (IV) over the duration necessary to alleviate the discomfort of the patient and in the dosage that is determined to be best for the individual patient and the condition based on sound medical judgement.

If desired, and for more effective distribution over a sustained period of time, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatine, polyvinylpyrrolidone, sucrose and acacia; (c) humectants, as for example, glycerol; (d) disintegrating agents, such as, agar-agar, calcium carbonate, potato or tapioca starch, alginic acid, certain complex solicates and sodium carbonate; (e) solution retarders, such as, paraffin; (f) absorption accelators, such as, quaternary ammonium compounds; (g) wetting agents, such as, cetyl alcohol and glyerol monostearate; (h) adsorbents, such as, kaolin and bentonite; and (i) lubricants, such as, talc, calcium stearate, magnesium stearate, solid polyethylene glycols, sodium lauryl sulfate or mixtures thereof. In the case of capsules, tablets and pills, the dosage forms may also comprise buffering agents.

Solid dosage forms such as tablets, dragees, capsules, pills and granules may be prepared with coatings and shells, such as enteric coatings and others well known in the art. They may contain pacifying agents, and may also be of such composition that they release the active compound in a certain part of the intestinal tract in a delayed manner.

Examples of embedding compositions which may be used are polymeric substances and waxes. The active compounds may also be microencapsulated with one or more of the above mentioned excipients.

Liquid dosage forms for oral administration include pharmaceutically acceptable emulsions, solutions, suspensions, syrups and elixers. In addition to the active compounds, the liquid dosage forms for oral administration may also contain inert diluents commonly used in the art, such as water or other solvents suitable for injestion, solubilizing agents and emulsifiers, such as, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances and the like.

Besides such inert diluents, these liquid dosage forms may also include adjuvants, such as wetting agents, emulsifying and suspending agents, sweetening, flavoring, and perfuming agents. Suspensions, in addition to the active compounds, may contain suspending agents, such as, ethoxylated isostearyl alcohols, polyoxyethylene sorbitol and sorbitan esters, microcrystalline cellulose, aluminum metahydroxide, bentonite, agar-agar and tragacanth, or mixture of these substances and the like. Compositions for rectal or vaginal administration may also be formulated with the appropriate known carriers such as cocoa butter or suppository waxes or other substances which are solid at ordinary room temperatures but liquid at body temperature which permits release of the drug in this manner.

Dosage forms for topical or transdermal administration of a compound of this invention further include ointments, pastes, creams, lotions, gels, powders, solutions, sprays, inhalents or transdermal patches. If a transdermal patch is utilized, the active component may be admixed under sterile conditions with a pharmaceutically acceptable carrier and any needed preservative, buffer or propellants as necessary. Compounds which absorb rapidly through the skin may need a formulation with absorption retarding agents or barriers. Ophthalmic formulations, eye ointments, powders and solutions are also contemplated.

The compounds of the invention may also be delivered in the form of liposomes which are known to be derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The liposome formulation may also contain other suitable excipients such as stabilizers, preservatives, excipients and the like. Phospholipids or lecithins are generally preferred. Prescott, ed., *Methods in Cell Biology*, vol. XIV, Academic Press, New York, N.Y. (1976) describes methods to form liposomes.

The compounds of the invention may also be coadministered with a peripherally acting anti-cholinergic agent such as N-methylscopolamine, N-methylatropine, propantheline, methantheline, glycopyrrolate, trimethaphan, pentolinium, mecamylamine or pempidine provided that the additional compounds do not affect the pain modulating or other targeted effect of the active ingredient. In addition, the compounds of the invention may be coadministered with opiate narcotics or pain relievers such as morphine wherein Applicants have shown that an improved pain relieving effect relative to morphine alone occurs when small doses of the compounds of the invention are administered with opiates such as morphine. This "improvement" occurs at doses of compound which are normally less effective in treating pain (e.g. 0.2 umol/kg,i.p. or less) with an increasing amount of morphine and may also occur at higher doses of the compounds of the invention with morphine. In addition or as an alternative to coadministration with morphine, coadministration may also occur with any known pain reliever or antiinflammatory as long as there are no contraindications or diminishment in pain treatment or relief. This coadministration thus includes combinations of the compounds of the invention and NSAIDS (including ibuprofen, (S)-ibuprofen, ibuprofen salts etc.).

Scheme 1 exemplifies the preparation of compounds of the invention, where P is a nitrogen protecting group such as Boc, Cbz, aryl substituted Cbz, trifluoroacetyl, benzenesulfonyl, aryl substituted benzensulfonyl and others commonly known in the art (see T. W. Greene and P. G. M. Wuts, *Protective Groups in Organic Synthesis,* 2nd edition, John Wiley & Sons, New York (1991); X is as defined above; in Scheme 1 R is Y, as defined above, or a group convertible to Y, in a manner described below wherein, for example, a halogen at the Y position is replaced in one or more steps with a $C_1$–$C_6$-alkyl, vinyl, propynyl or ethynyl group; * indicates a chiral center which may be R or S, depending on the starting material; and HA is an acid which will readily form a pharmaceutically acceptable salt with an amine, such as toluenesulfonic acid, methanesulfonic acid, naphthalenesulfonic acid, hydrogen chloride, benzoic acid, citric acid, or tartaric acid.

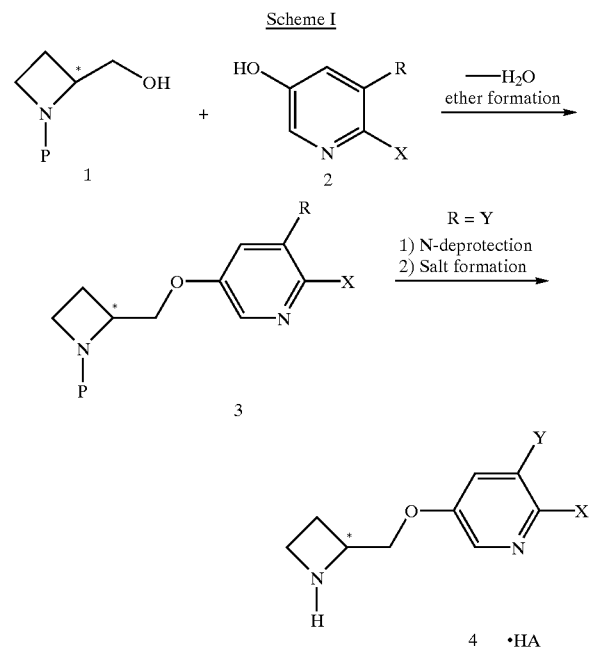

Scheme I

In Scheme 1, the ether forming reaction may be accomplished by various methods, for example: 1) (a) by conversion of the hydroxyl group of azetidine alcohol 1 to a leaving group by treatment with toluenesulfonyl chloride, methanesulfonyl chloride, or trifluoromethanesulfonic anhydride or the like in an inert solvent such as THF, dimethylformamide or dichloromethane in the presence of a base such as triethylamine or pyridine or the like; or alternatively, conducting the reaction in neat pyridine; (b) followed by treatment with a pyridinol of structure 2 under conditions sufficiently basic to cause removal of the phenolic proton of 2, for example with potassium hydroxide or sodium hydroxide in DMF, at a temperature from about 23° C. to about 120° C. as necessary to effect a convenient rate of reaction; alternatively, a salt of 2, preferably a potassium or cesium salt, can be pre-formed by treatment of 2 with potassium hydroxide or cesium hydroxide in a suitable solvent such as methanol, which can be evaporated and replaced with a solvent suitable for the coupling reaction as described above; (2) the ether forming reaction also may be accomplished by treatment of the reactants with a phosphine such as triphenylphosphine or tributylphosphine and an azodicarboxylate derivative, such as diethyl azodicarboxylate, di-tert-butyl azodicarboxylate, or 1,1'-(azodicarbonyl) dipiperidine in a suitable solvent, such as THF, benzene, or toluene or the like at a temperature of from about 0° C. to about 40° C. (the Mitsunobu reaction: see Hughes, *Organic Reactions*, 42, 335, 1992; Abreo, et al., J. Med. Chem. 1996, 39, 817).

One preferred coupling begins by cooling an isopropyl acetate solution of the Boc protected alcohol 1 to about 5° C. Triethylamine is added. Mesyl chloride is then added at a rate to keep the temperature below about 10° C. Then the solution is stirred for about 15 minutes and warmed to room temperature and stirred for another 4.5 hrs. An 8% sodium bicarbonate solution was added. The mesylated alcohol was isolated, dissolved in DMF and treated with sodium hydroxide the appropriate hydroxypyridine. The solution is heated to about 80° C. for about 6 hrs to form compound 3. Compound 3 is isolated, dissolved in ethanol and then deprotected with tosic acid at reflux temperature for 2 hrs to form the corresponding compound 4 as the tosylate salt.

The precise conditions of N-deprotection depend on the nature of the protecting group P, and are well described in suitable reference sources, such as Greene and Wuts (op. cit.) or computer databases such as the Synopsys Protecting Groups Database (Synopsys Scientific Systems, LTD., Leeds, UK). Conveniently, for P=Boc, the deprotection is effected by treatment of compound 3 with suitable mixtures (e.g. 1:1) of trifluoroacetic acid and dichloromethane, or with hydrogen chloride in an ether or alcohol solvent; for P=Cbz, by hydrogenolysis ($H_2$ gas, Pd catalyst, in an alcohol solvent such as methanol or ethanol, or other solvent such as ethyl acetate in which the starting material is soluble), or with trimethylsilyl iodide, optionally formed in situ by methods well known in the art, in a halocarbon solvent such as chloroform; for P=trifluoroacetyl, by treatment of 3 with a nucleophile such as a metal hydroxide, aqueous ammonia; or sodium borohydride; for P=arylsulfonyl, by treatment of 3 with sodium in liquid ammonia, or with sodium naphthalenide in an ether solvent such as dimethoxyethane, or with sodium amalgam in an alcohol solvent such as methanol, or by electrolysis.

The salt formation step consists of first isolating the free base of 4, for example, by extraction from an aqueous alkaline solution into an organic solvent, for example diethyl ether, dichloromethane, or ethyl acetate; drying the organic solvent with a suitable drying agent, for example sodium sulfate or magnesium sulfate; optionally removing the solvent and replacement with an alternative suitable solvent such as diethyl ether, ethyl acetate, or ethanol; and treatment of the solution with an acid HA, selected from the group of pharmaceutically acceptable species, as exemplified above.

In Scheme 2, preparing enantiomerically pure (R)-azetidine alcohol 1 (R=Cbz) from D-methionine is as described in Abreo, et al., op. cit. First, D-methionine in aqueous sodium hydroxide solution is treated with tosyl chloride to form N-tosyl-D-methionine, which is treated with MeI followed by 1N sodium hydroxide to afford α-(N-p-tosyl-amino)-γ-butyrolactone according to the method of Sugano and Miyoshi, *Bull. Chem. Soc. Japan,* 1973, 46, 669. Further conversion to azetidine-2-carboxylic acid is carried out by the procedure of Miyoshi, et al., *Chem. Lett.* 1973, 5–6. The lactone in ethanol is treated with gaseous HBr to form N-tosyl-g-bromonorvaline ethyl ester. The bromoester in DMF solution with about four equivalents of $H_2O$ is treated with NaOH to form (R)-N-tosylazetidine-2-carboxylic acid (may be contaminated by the (S)-enantiomer as determined by $^1$H-NMR analysis of the amide derivative with α-methylbenzylamine)(Abreo, et al., op. cit.) Treating the N-tosylazetidine-2-carboxylic acid with sodium in liquid ammonia affords azetidine-2-carboxylic acid, which is subsequently treated with N-(benzyloxycarbonyl)oxy succinimide according to Abreo, et al., to afford N-Cbz-azetidine-2-carboxylic acid. To remove contaminating (S)-enantiomer, the N-Cbz derivative in MeOH is treated with D-tyrosine hydrazide to form an insoluble salt of the (R)-enantiomer, which is collected by filtration. The optical rotation of the subsequently liberated free acid is $[\alpha]_D$ =+105.4 (c 4.0, $CHCl_3$). Treating the free acid with borane.THF affords 1 (R=Cbz). The S-enantiomer ((S)-1) may be synthesized analogously starting from L-methionine. If needed for enantiomeric enrichment, the product may be optically resolved with D-tyrosine-hydrazide in analogy to the procedure described above. Other protecting groups, for example Boc, are readily incorporated by standard methods, e.g. by reacting the intermediate or Cbz deprotected azetidine-2-carboxylic acid with an appropriate standard reagent under prescribed conditions (Greene and Wuts, see above.).

Scheme 2

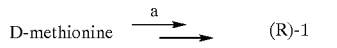

P = Boc, Cbz a. Abreo, et al., J. Med. Chem. 1996, 39, 817.

Alternatively, in accordance with Scheme 3, racemic azetidine-(2)-carboxylic acid 5 may be prepared from γ-butyrolactone according to Rodebaugh and Cromwell, *J. Het. Chem.,* 1969, 6, 435. The γ-butyrolactone is treated with bromine and catalytic phosphorus or phosphorus tribromide, then subsequently with benzyl alcohol and gaseous hydrogen chloride to afford benzyl α,γ-dibromobutyrate. The dibromide in a suitable solvent such as ethanol or acetonitrile is treated with one equivalent of benzhydrylamine to afford benzyl N-diphenylmethylazetidine-2-carboxylate. Hydrogenolysis over palladium catalyst, for example Pd(OH)$_2$ affords racemic 5. Resolution of the corresponding N-Cbz derivative is conducted according to Rodebaugh and Cromwell J. Het. Chem. 1969, 6, 993 to provide separately (R)- or (S)-N-Cbz-azetidine-2-carboxylic acid 6. Thus, treatment of a solution of compound 5 in aqueous alkali with benzylchloroformate affords racemic N-Cbz-azetidine-2-carboxylic acid. Treatment of a methanol solution of the racemate with L-tyrosine hydrazide causes precipitation of the R-enantiomer as an insoluble salt, which is further processed as described in the text accompanying Scheme 2. According to Rodebaugh and Cromwell, *J. Het. Chem.,* 1969, 6, 993, the pure (S)-enantiomer is obtained from the soluble fraction.

Scheme 3

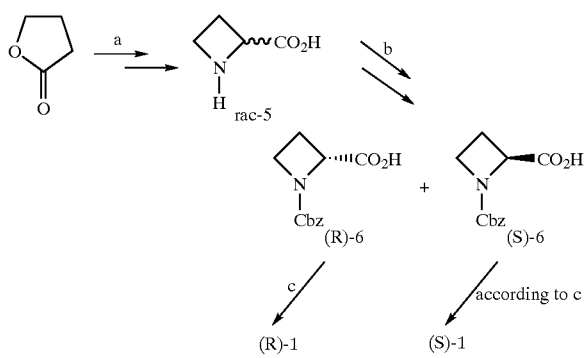

a. Rodebaugh and Cromwell, J. Het. Chem. 1969, 6, 435
b. Rodebaugh and Cromwell J. Het. Chem. 1969, 6, 993.
c. Abreo, et al., J. Med. Chem. 1996, 39, 817

Alternatively, in accordance with Scheme 4, (R)-1 may be prepared by a novel process starting from (R)-azetidinone 7, which is prepared from a diester of D-aspartic acid according to Baldwin, et al., Tetrahedron 1990, 46, 4733–48. Preferrably, excess RMgX consumes the triethylamine HCl salt formed during the desilylation. Thus, a solution of the free base of dibenzyl D-aspartate in diethyl ether is treated with trimethylsilyl chloride and triethylamine to afford an intermediate N-silyl derivative, which is treated with t-butylmagnesium chloride to afford 7. The trimethylsilyl group in this procedure may be replaced by alternative silyl groups e.g. a t-butyldimethylsilyl group as demonstrated by Baldwin, et al., which is removable with fluoride ion. Treatment of 7 with an appropriate reducing agent, for example diisobutylaluminum hydride (DIBAL), lithium aluminum hydride, aluminum hydride, mono- or dihalo aluminum hydride, or a mixture of aluminum trichloride and lithium aluminum hydride in an ether solvent at −20° C. to 40° C. effects reduction both of the 2-carbobenzyloxy group to hydroxymethyl and the azetidinone carbonyl to methylene. The scope of this novel conversion is intended to include other esters, for example C1–C6 alkyl esters, and also to include, as appropriate, stepwise reduction of the ester group and the azetidinone carbonyl. Preferably, the benzyl ester is hydrogenolyzed to th free acid prior to reduction of the carbonyl moieties. For example, treatment of 7 with sodium borohydride in methanol at room temperature according to Salzmann, et. al., (J. Am. Chem. Soc., 1980, 102, 6163–6165) or alternatively with lithium borohydride or calcium borohydride in ether or ether alcohol mixtures preferably at low temperature (−20° C. to 10° C.) affords selective reduction of the ester group to afford the corresponding azetidin-2-one-4-methanol (an alternative multistep route to this intermediate in the (S)-enantiomeric series is disclosed in Tanner and Somfai, Tetrahedron Lett. 1987, 28, 1211–1214). Subsequent reduction of the azetidinone carbonyl with an appropriate reducing agent, for example lithium aluminum hydride, aluminum hydride, mono- or dihalo aluminum hydride, or a mixture of aluminum trichloride and lithium aluminum hydride as described above provides the intermediate azetidine-2-methanol. Other methods of reducing the azetidinone carbonyl may be envisioned, e.g. conversion to a thioamide with $P_2S_5$ or Lawesson's reagent followed by reduction, for example, in the presence of nickel. N-protection of the intermediate azetidine-2-methanol is carried out using standard conditions, for example, treatment of the intermediate secondary amine with di-tert-butyl dicarbonate to afford the product (R)-1 (P=Boc). The process from 7 to (R)-1 (R=Boc) has been demonstrated in the case of a one-step reduction with lithium aluminum hydride in ether at 0° C. to ambient temperature with standard isolation (cf. Fieser and Fieser, Reagents for Organic Synthesis, vol. 1, p. 584) of the intermediate secondary amine followed by N-protection with Boc to proceed with a high degree of retention of chiral purity (>98% ee). Analogous to the preparation of (R)-1 starting from D-aspartic acid, (S)-1 may be prepared from L-aspartic acid.

Scheme 4

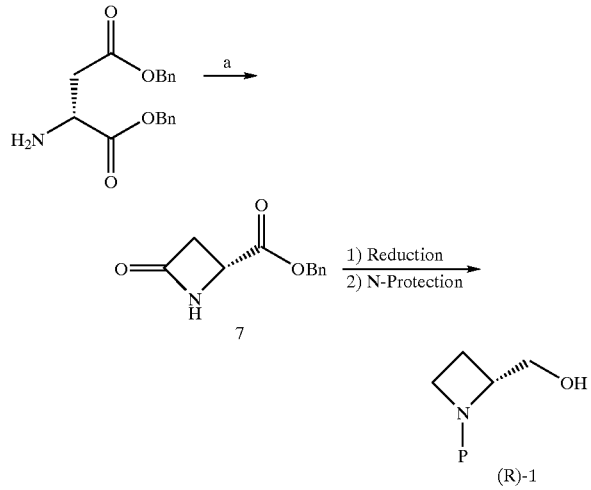

a. Baldwin, et al., Tetrahedron 1990, 46, 4733-48

Methods for preparation of various 5- and/or 6-substituted pyridin-3-ols 2 are as follows:

Pyridin-3-ol (2, X=R=H) is commercially available (e.g. Aldrich).

6-Methylpyridin-3-ol (2, X=Me, R=H) is commercially available (e.g. Aldrich).

5-Chloropyridin-3-ol (2, X=H, R=Cl) is commercially available.

5,6-Dichloropyridin-3-ol (2, X=R=Cl) and 5-bromo-6-chloropyridin-3-ol (2, X=Cl, R=Br) are prepared from commercially available (Aldrich) 2-hydroxy-5-nitropyridine according to Koch and Schnatterer, Synthesis, 1990, 499–501. Thus, treatment of 2-hydroxy-5-nitropyridine with, respectively, either potassium chlorate or bromine affords the respective 2-hydroxy-3-halo-5-nitropyridines, which are treated with phosphorus oxychloride in the presence of quinoline to provide the respective 2-chloro-3-halo-5-nitropyridines. Treatment with iron or tin under acidic conditions effects reduction of the nitro to afford the respective 5-amino-2-chloro-3-halopyridines. Diazotization of the intermediate with sodium nitrite in the presence of fluoroboric acid or alkyl nitrite in the presence of boron trifluoride affords an intermediate diazonium salt, which on heating with acetic anhydride affords the 5-acetoxy-2-chloro-3-halopyridine 8. A key step in the overall sequence is the conversion of a 3-amino group to the 3-hydroxy group under the conditions shown in Scheme 5.

Scheme 5

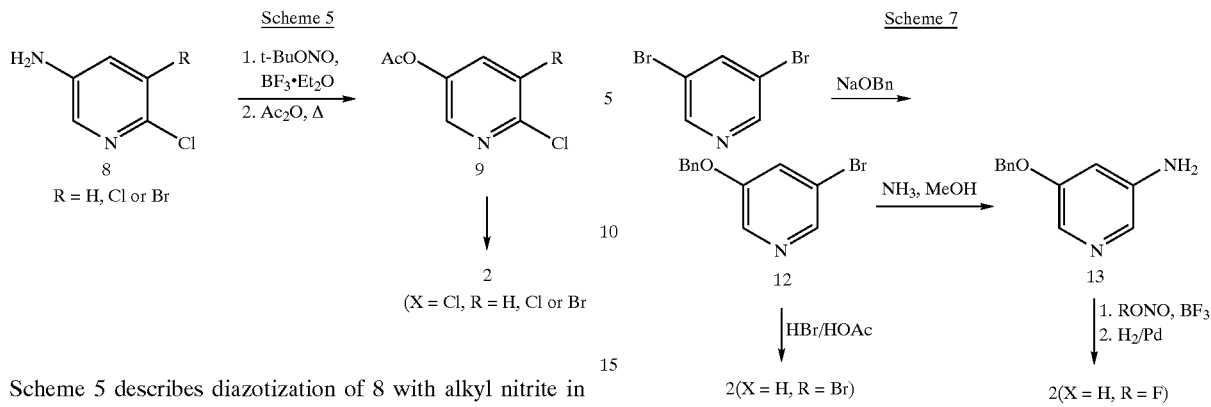

2
(X = Cl, R = H, Cl or Br

Scheme 5 describes diazotization of 8 with alkyl nitrite in the presence of boron trifluoride etherate to afford an intermediate diazonium salt, which on heating with acetic anhydride affords the 5-acetoxy-2-chloro-3-halo-pyridine 9. The diazonium intermediate may alternately be prepared using sodium nitrite under acid conditions as described in Koch and Schnatterer, *Synthesis*, 1990, 499–501. Hydrolysis or alcoholysis of the acetoxy group of 9 under mildly alkaline conditions affords 2 (X=Cl, R=Br or Cl).

6-Chloropyridin-3-ol (2, X=Cl, R=H) is prepared from commercially available 2-chloro-5-aminopyridine according to Effenberger, et al., *Chem. Ber.*, 1992, 125, 1131–1140, by treatment with sodium nitrite in the presence of aqueous sulfuric acid followed by heating with aqueous sulfuric acid and isolation by extraction, or preferably by a modified route according to the conditions shown in Scheme 5 where R=H.

5-Methyl-6-chloropyridin-3-ol is prepared from commercially available (Maybridge) 2-chloro-3-methyl-5-nitropyridine, by reduction of the nitro group (Fe, HOAc) followed by conditions analogous to those in Scheme 5.

Scheme 6

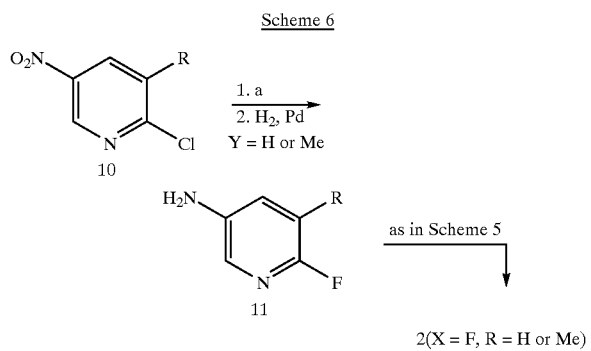

a. Clark and Macquarrie, Tet. Lett. 1987, 28, 111–114

In accordance with Scheme 6 (above), 6-fluoropyridin-3-ol (2, X=F, R=H) and 6-fluoro-5-methylpyridin-3-ol (2, X=F, R=Me) are prepared from the corresponding 3-amino compounds 11 under conditions analogous to those in Scheme 5. Compound 11 is prepared by catalytic reduction of the corresponding 3-nitropyridine derivative, which was prepared from commercially available 6-chloro derivative 10 according to Clark et al., Tet. Lett. 1987, 28, 111–114. Thus, for example, a solution of 10 in acetonitrile is heated with potassium fluoride in the presence of tetraphenylammonium bromide to afford 11.

Scheme 7

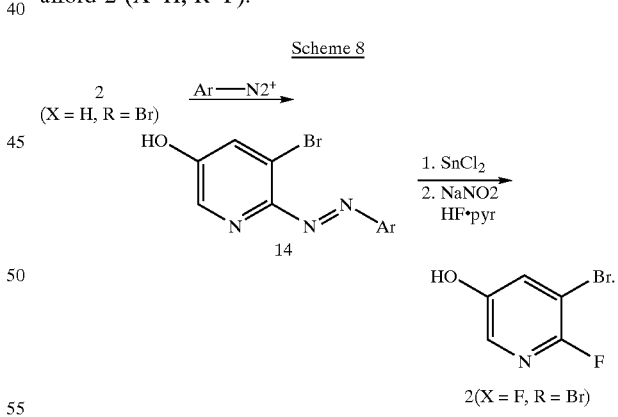

Intermediate 2 (from scheme 1) (X=H, R=F or Br) is prepared in accordance with Scheme 7. Commercially available 3,5-dibromopyridine is treated with the anion of benzyl alcohol, for example, with sodium benzylate in DMF at room temperature, affords the monobenzyloxy compound 12. Debenzylation of 12 by heating in 48% hydrogen bromide in acetic acid affords 2 (X=H, Y=Br). Treatment of a methanol solution of 12 with liquid ammonia followed by heating in a steel bomb at 120° C. to 150° C. for 16 to 48 hours in the presensce of a copper salt, for example copper (I) bromide, affords compound 13. Treatment of 13 with an alkyl nitrite, for example, t-butyl nitrite in the presence of borontrifluoride etherate in an inert solvent such as methylene chloride affords an intermediate diazonium tetrafluoroborate, which is heated at 50° C. to 90° C. in acetic anhydride, or preferably, in an inert solvent such as toluene to afford 3-benzyloxy-5-fluoropyridine. The benzyloxy compound is stirred under a hydrogen atmosphere in the presence of a palladium (0) catalyst, for example 10% palladium on charcoal, in a suitable solvent such as methanol, ethanol, or ethyl acetate at ambient temperature to afford 2 (X=H, R=F).

Scheme 8

2
(X = H, R = Br)

$Ar\text{---}N2^+$

HO
Br

14

1. SnCl$_2$
2. NaNO2
HF·pyr

HO
Br

2(X = F, R = Br)

Intermediate 2 (with X=F, R=Br) is prepared in accordance with Scheme 8. Compound 2 (X=H, R=Br), prepared as described in Scheme 7, is treated with an aryl diazonium salt, for example, commercially available p-nitrophenyldiazonium tetrafluoroborate to afford the diazo coupled product 14. Diazo reduction by treatment with, for example, tin chloride and hydrochloric acid in ethanol provides the intermediate 2-amino-3-bromo-5-hydroxypyridine, which is diazotized, and treated either concurrently or subsequently with fluoride ion to afford the fluoro compound 2 (X=F, R=Br). For example, treatment of the intermediate 2-amino-3-bromo-5-hydroxypyridine with sodium nitrite in the presence of HF.pyridine at 0° C. to 70° C. affords 2 (X=F, R=Br).

of aqueous acetic acid affords amino compound 15, which is converted to 2 (X=Me, R=Br) under conditions analogous to those in Scheme 5.

Scheme 10

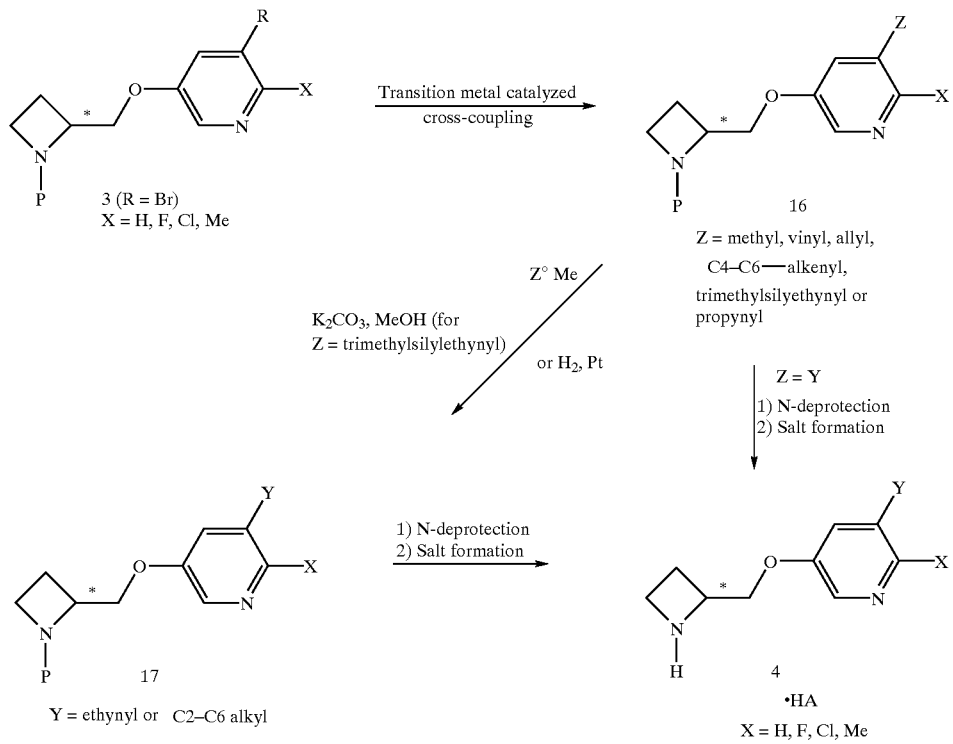

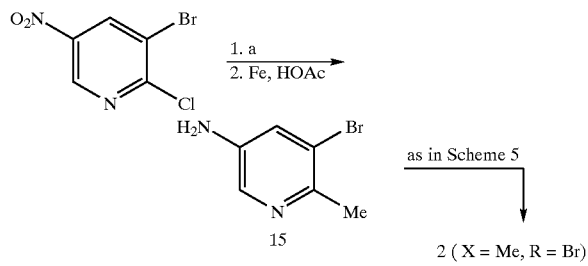

Scheme 9 a. Odashima et al., Bull Chem Soc Jpn 1993, 66, 797-803

In accordance with Scheme 9, intermediate 2 (X=Me, R=Br) is prepared from 3-bromo-2-chloro-5-nitropyridine (V. Koch and S. Schnatterer, *Synthesis*, 1990, 499–501) in a manner analogous to that described by Odashima et al. (*Bull. Chem. Soc. Japan*, 1993, 66, 797–803). The starting material is treated with the sodium salt of diethylmalonate followed by hydrolysis and decarboxylation to replace the 2-chloro substituent with a methyl group. Thus, heating an intimate mixture of 3-bromo-2-chloro-5-nitropyridine and diethyl sodiomalonate at 100° C. for about 1 hour, followed by heating the resultant mixture in the presence of 12 N sulfuric acid at reflux for about 16 hours affords the methylated product. Reduction of the nitro group, for example with iron or tin under acidic conditions, for example, in the presence Additional compounds of the invention are prepared in accordance with Scheme 10, where the starting materials 3 are prepared as described in Scheme 1, using the appropriate pyridinol 2, obtained, in turn, as described in Scheme 5 (for 2, X=Cl, R=Br); Scheme 7 (for 2, X=H, R=Br); Scheme 8 (for 2, X=F, R=Br); or Scheme 9 (for 2, X=Me, R=Br. The bromo substituent is then replaced by a transition metal-catalyzed cross-coupling reaction, which may occur under a variety of conditions depending on the nature of Z. Treatment of a bromo compound 3 (R=Br; preferably X=H or Me) in THF with one to three equivalents of methylmagnesium bromide in diethyl ether in the presence of (dppp) $NiCl_2$ at 40° C. to 70° C. affords 16 (Z=Me); when X=Cl or F, this method is less satisfactory than alternative methods disclosed in this specification. Treatment of a bromo compound 3 (R=Br) in toluene or benzene with an excess of vinyltri-n-butyltin or allyltri-n-butyltin and catalytic tetrakis (triphenylphosphine) palladium with heating at 80° C. to 110° C. affords compounds 16 (Z=vinyl or allyl). Treatment of a bromo compound 3 (R=Br) in toluene or benzene with an excess of trimethylsilylacetylene or propyne and catalytic tetrakis(triphenylphosphine) palladium in the presence of a copper salt, for example Cu(I)I, with heating at 80° C. to 110° C., optionally in a sealed tube, affords compounds 16 (Z=trimethylsilylethynyl or propyn-1-yl). Treatment of a bromo compound 3 (R=Br) in a nitrile solvent, for example acetonitrile or propionitrile, with an excess of a $C_4$–$C_6$-alk-1-ene in the presence of a catalytic amount of a palladium (II) salt, for example, palladium (II) acetate, a triaryl phosphine, for example tri-o-tolylphosphine, and a base, for example triethylamine, and heating, optionally in a sealed vessel, at 60° C. to 120° C. affords compounds 16 (Z=C$_4$–C$_6$-alkenyl). Preparation of compounds 17 wherein Y=ethynyl is accomplished by treatment of the corresponding compounds 16 (Z=trimethylsilylethynyl) with an excess of potassium carbonate in methanol at ambient temperature to 40° C. for from 1 to 24 hours. Preparation of compounds 17 wherein Y=C$_2$–C$_6$-alkyl is accomplished by stirring the corresponding compounds 16 (Z=vinyl, allyl, propynyl or C$_4$–C$_6$-alkenyl) under a hydrogen atmosphere in the presence of a platinum catalyst, for example, 5% platinum on charcoal, in a solvent such as methanol, ethanol, or ethyl acetate. Compounds 17 or compounds 16 (Z=Y) are converted to compounds of the invention by deprotection and salt formation using a method selected from those described with Scheme 1, for example, treatment with 1:1 trifluoroacetic acid/methylene chloride for N-deprotection of 16 or 17 (P=Boc).

As described above, the compounds of the invention are prepared from a process which comprises:
(1) contacting an azetidine of formula 1 wherein P is as recited above with a multisubstituted pyridyl compound of formula 2 with R and X as recited above to form, upon coupling and deprotection, a compound of formula I or a precursor to a compound of formula I wherein Y is chosen from C$_1$–C$_6$-alkyl, vinyl or ethynyl.

The term "contacting" means exposing 1 or a modified version of 1 which is selected from a compound of formula 1'

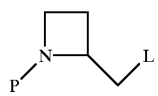

wherein L is a leaving group exeplified by toluenesulfonate, methanesulfonate, or trifluoromethanesulfonate, which is prepared by reacting compound 1 with toluenesulfonyl chloride, methanesulfonyl chloride or trifluoromethansulfonic anhydride in an inert solvent such as THF, dimethylformamide or dichloromethane in the presence of a base such as triethylamine or pyridine or in neat pyridine to a reactant selected from the multisubstituted pyridyl compound 2 or a derivative thereof under the conditions necessary to effect the coupling of 1 and 2 to result in, upon deprotection, the product. The preferred reaction conditions are typically in solution.

A "derivative thereof" as specified directly above is selected from a compound of formula 2 wherein the phenolic proton is abstracted (removed) to leave a nucleophilic anion or is selected from a potassium or cesium salt of a deprotonated derivative of formula 2. A derivative thereof is also selected from the Mitsunobu intermediate which is generated by exposing both compounds 1 and 2 to a phosphine such as triphenylphosphine or tributylphosphine and an azadicarboxylate such as diethyl azodicarboxylate, ditertbutyl azodicarboxylate or 1,1'-(azodicarbonyl)dipiperidine in suitable solvents such as THF, benzene, or toluene at a temperature of from about 0 to about 40 degrees Celcius.

More particularly, the present invention relates to a process for producing R-enantiomers which comprises,
(a) preparing a compound of formula 1 or a derivative 1' thereof with (R) stereochemistry at the 2-position on the azetidine ring;
(b) preparing a compound of formula 2 or a derivative 2' thereof;
(c) contacting the reactant formed in step (a) with the reactant formed in step (b) under suitable conditions to form a compound of formula 3;

(d) deprotecting the compound of formula 3 under suitable conditions to form the R-enantiomers.

Alternatively, steps (a')–(d') using the (S)-enantiomer in step (a) as above may be performed to form a compound of formula I which is the (S)-enantiomer at the 2-position of the azetidine.

The invention also relates to a process as described above further comprising a step (e) (or (e') in the case of the (S)-enantiomer) of adding an acid HA to the deprotected compound produced in step (d) (or (d')) to form a compound of formula 4 (or the (S)-enantiomer thereof in the case of (e')).

Biological Protocols

Compounds of the invention were subjected to in vitro assays against the nicotinic acetylcholine receptor as described below and were found to be effective binders to the receptor. Functional in vitro assays were also performed to assess the ability of the compounds to modulate nicotinic acetycholine receptor function related to ion flux, and neuroprotective actions. In addition, the compounds of the invention were assessed in known pain or analgesic animal models which are utilized to be predictive of analgesic properties in higher mammals, including humans, as well as antiinflammatory actions (Sheen, K. and Chung, J. M., *Brain Res.*, 610:62–68, 1993. The relevance of animal neuropathy models for chronic pain in humans is described by Seltzer (*Neurosciences*, 7: 211–220, 1995).

Compounds of the invention were found to be useful as nicotinic acetylcholine receptor binders and as effective analgesics. The tests described below show that the compounds of the invention are effective in animal models of pain. In addition to the compounds general analgesic properties, generally, some (R)-enantiomers relative to the (S)-enantiomers of the same chemical formula has an improved safety profile which is demonstrated in two ways (peripheral side effects related to activation of autonomic ganglionic-like receptors and peripheral side-effects related to activation of skeletal muscle-like nicotinic acetylcholine receptors). Data showing this improved safety profile are also presented below.

In vitro Protocols

Protocol for Determination of Nicotinic Acetylcholine Channel Receptor Binding Potencies of Ligands Binding of [$^3$H]-cytisine ([$^3$H]-CYT) to neuronal nicotinic acetylcholine receptors was accomplished using crude synaptic membrane preparations from whole rat brain (Pabreza et al., *Molecular Pharmacol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer. Homogenate (containing 125–150 μg protein) was added to triplicate tubes containing concentrations of test compound and [$^3$H]-CYT (1.25 nM) in a final volume of 500 μL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 μM (−)-nicotine and values were expressed as a percentage of total binding. IC$_{50}$ values were determined with the RS-1 (BBN) nonlinear least squares curve-fitting program and IC$_{50}$ values were converted to Ki values using the Cheng and Prusoff correction (Ki=IC$_{50}$/(1+[ligand]/Kd of ligand). Alternately, data were expressed as a percentage of the total specific binding. The binding data (shown in Table 1) suggest that the compounds of the present invention have high affinity for the neuronal nicotinic acetylcholine receptor.

TABLE 1

| Ex. | * | X | Y | [$^3$H] CYT Ki (nM) |
|---|---|---|---|---|
| 6 | R | H | H | 0.04 |
| 4 | R | Cl | H | 0.05 |
| 8 | R | F | H | 0.06 |
| 11 | R | H | F | 0.34 |
| 14 | R | H | Me | 0.18 |
| 16 | R | Cl | Cl | 0.06 |
| 18 | R | Cl | Br | 0.02 |
| 97* | R | H | H | 85 |
| 114 | R | H | Cl | 0.12 |
| 115 | R | Me | H | 0.07 |
| 118** | R | Me | H | 4.8 |
| 119 | R | OMe | H | 0.67 |
| 124 | R | Me | Br | 0.03 |
| 125 | R | F | Br | 0.04 |
| 127 | R | Cl | Me | 0.06 |
| 128 | R | Br | H | 0.17 |
| 129 | R | F | ethenyl | 0.09 |
| 7 | S | H | H | 0.04 |
| 19 | S | Cl | H | 0.04 |
| 9 | S | F | H | 0.16 |
| 20 | S | Me | H | 0.06 |
| 10 | S | H | F | 0.09 |
| 21 | S | H | Cl | 0.04 |
| 12 | S | H | Br | 0.26 |
| 13 | S | H | Me | 0.05 |
| 23 | S | H | Et | 0.11 |
| 24 | S | H | n-Pr | 0.05 |
| 22 | S | H | vinyl | 0.97 |
| 15 | S | Cl | Cl | 0.02 |
| 17 | S | Cl | Br | 0.02 |
| 25 | S | Cl | Me | 0.05 |
| 27 | S | Cl | Et | 0.04 |
| 28 | S | Cl | n-Pr | 0.03 |
| 29 | S | Cl | n-Bu | 0.16 |
| 26 | S | Cl | vinyl | 0.24 |
| 30 | S | Cl | ethynyl | 0.04 |
| 31 | S | F | Br | 0.03 |
| 32 | S | F | Me | 0.10 |
| 33 | S | F | Cl | 0.04 |
| 34 | S | Me | Br | 0.02 |
| 36 | S | Me | Et | 0.04 |
| 35 | S | Me | vinyl | 0.22 |
| 113 | S | CHF2 | H | 0.17 |
| 116** | S | F | H | 0.34 |
| 117** | S | Me | H | 0.17 |
| 120 | S | H | OEt | 0.04 |
| 121* | S | H | H | 2.3 |
| 122** | S | H | H | 0.10 |
| 123 | S | CN | H | 1.9 |
| 126 | S | F | Et | 0.07 |
| 130 | S | H | 3-propenyl | 0.04 |
| 131 | S | F | ethenyl | 0.13 |
| 132 | S | H | NO2 | 0.33 |

*compound also has a 2-chloro substitutent
**compound also has a 2-fluoro substituent Tissue isolates from Torpedo Californica electroplax model the properties of nicotinic acetylcholine receptors at the mammalian neuromuscular junction receptor. For that reason, binding of compounds was determined using a solid phase binding assay that measures the binding of [$^{125}$I] α-bungarotoxin (106 Ci/mmol) to tissue isolates. The wells of a 96-well microtiter plate (Immulon Removawells Strips, Dynatech, Chantilly, Va.) were coated with 0.5 µg of Torpedo membranes (ABS Inc., Wilmington, Del.) in 50 mM NaHCO$_3$ buffer, pH 9.6, for 12 hours at 4° C. Wells were then washed twice with phosphate buffered saline (PBS) and quenched for 1 hour with 5% bovine serum albumin (BSA). [$^{125}$I] α-bungarotoxin (~1.9 nM/100 µL 10 mM phosphate buffer, pH 7.4/0.2% BSA) was then added to the wells for 1 hour. For competition experiments, increasing concentrations of competitor (50 µL) were added to wells in triplicate followed immediately by 50 µL of [$^{125}$I] α-bungarotoxin and incubated for 1 hour. Non-specific binding was determined in the presence of 1 µM α-bungarotoxin. After incubation, wells were washed 5 times with PBS. Individual wells were placed in vials and radioactivity measured in a gamma counter (Model 5000, Beckman, Fullerton, Calif.).

The data in Table 2 demonstrate that the (R)-enantiomer of the compound of Example 4 remarkably has 12.8-fold reduced affinity (i.e. enhanced selectivity) for the neuromuscular junction nicotinic acetylcholine receptor, which contrasts with its equivalent activity at neuronal nicotinic acetylcholine receptors label by [$^3$H]-cytisine (Table 1). These data indicate that Example 4 would be safer and less likely to cause motoric or respiratory complications than its (S)-enantiomer.

TABLE 2

| Ex. | * | X | Y | Ki (nM) α-bungarotoxin |
|---|---|---|---|---|
| 19 | S | Cl | H | 1300 |
| 4 | R | Cl | H | 16,600 |

Protocol for the Determination of Ability of Nicotinic Acetylcholine Receptor Ligands to Activate Peripheral Ganglionic Receptors Cells of the IMR-32 human neuroblastoma clonal cell line (ATCC, Rockville, Md.) were maintained in a log phase of growth according to established procedures. Experimental cells were seeded at a density of 500,000 cells/mL into a 24-well tissue culture dish. Plated cells were allowed to proliferate for at least 48 hours before loading with 2 µCi/mL of $^{86}$Rb$^+$ (35 Ci/mmol) overnight at 37° C. The $^{86}$Rb$^+$ efflux assays were performed according to previously published protocols (Lukas, R. J., *J. Pharmacol. Exp. Ther.*, 265: 294–302, 1993) except serum-free Dulbecco's Modified Eagle's Medium was used during the $^{86}$Rb$^+$ loading, rinsing, and agonist-induced efflux steps. Data reflect the activation of $^{86}$Rb$^+$ flux at a concentration of 1 µM, and reflect the response as a percentage of the maximum response elicited by (S)-nicotine. The data are interpreted such that the larger the response, the more potent is the activation of peripheral ganglionic receptors, which is further interpreted to suggest that, in vivo, a more potent contribution to undesired effects will occur, for example, on the cardiovasular and/or gastrointestinal systems.

The data for activation of $^{86}$Rb$^+$ flux in the IMR-32 cell line for enantiomeric pairs of compounds of the invention are compared in Table 3. The data show that in the large majority of cases (5 of 6 listed), the (R)-enantiomer of each pair is less potent to activate $^{86}$Rb$^+$ flux. than the corresponding (S)-enantiomer. Therefore, it is expected that the (R)-enantiomers will be less potent to elicit undesired effects on peripheral autonomic nicotinic acetylcholine receptors of, for example, the cardiovascular or gastrointestinal systems.

TABLE 3

| Example # | * | X | Y | IMR-32 % maximal nicotine response at 1 μM Cmpd conc'n |
|---|---|---|---|---|
| 4 | R | Cl | H | 97 |
| 19 | S | Cl | H | 173 |
| 8 | R | F | H | 46 |
| 9 | S | F | H | 103 |
| 16 | R | Cl | Cl | 85 |
| 15 | S | Cl | Cl | 117 |
| 18 | R | Cl | Br | 93 |
| 17 | S | Cl | Br | 120 |
| 11 | R | H | F | 31 |
| 10 | S | H | F | 28 |
| 14 | R | H | Me | 15 |
| 13 | S | H | Me | 27 |

Protocol for Determination of Effectiveness of Nicotinic Acetylcholine Receptor Ligands as Agents to Prevent Neuronal Cell Death in the Spinal Cord (−)-Nicotine, ABT-418, ABT-089 and related nicotinic acetylcholine receptor ligants have properties indicative of neuroprotection in vitro and in vivo (Akaike, A., et al., *Brain Res.*, 644:181–187, 1994; Donnelly-Roberts et al., *Brain Res.*, 729:36–44, 1996; Marin, P., et al., *Neuroreport*, 5: 1977–1980, 1994; Martin, E. J., et al., *Drug Dev. Res.*, 31:135–141, 1994: Shimohama, S., et al., Annals New York Academy of Sciences, 356–361, 1996).

The effect of the compound of Example 4 to protect against neurotoxicity in one model relevant to neuropathic pain and spinal cord neurodegeneration is detailed below.

Primary spinal cord of mixed large and small diameter motoneuron cultures were prepared from Sprague-Dawley rats at day 13 of gestation as described by Regan and Choi (*J. Neuroscience*, 43:585–591, 1991). Cells were plated onto poly-L-lysine coated 96 well culture dishes at a density of about 50,000 cells per well in L15 medium containing 2% Horse Serum (HS)/33 mM glucose/2 mM glutamine/50 U/mL pen:strep/B27 supplement/10 mg/mL NGF. To eliminate fibroblasts and Schwann cells from the spinal cord cultures, antimitotic feed medium (L15 plus 10 mM uridine and 10 MM 5-fluro-2'-exoxyuridine with no HS) is used at day 3 for 2 days. Cultures were maintained at 36° C./10% $CO_2$.

After 7 days in vitro (DIV), cells were pretreated with test compound diluted in L-15 medium with B27 supplement for 2 hours. This pretreatment solution was replaced by HBSS (without magnesium, but containing 3 mM calcium chloride) containing substance P (SP) (30 μM) or glutamate (Glu) at 300 μM and co-applied with the-test compound for an additional 15 minutes. This compound/insult solution was removed and replaced with fresh L-15/B27 media for 24 hours. Neuronal damage was assessed by either 1) measuring the levels of the cytosolic enzyme lactate dehydrogenase (LDH) released into the medium by the damaged cells or 2) staining the cells with 4% Trypan blue for 5 min and morphologically assessing damage by light microscopy. LDH release was quantified using a Cytotox 96 assay kit (Promega; Madison, Wis.) as described previously (Donnelly-Roberts, op. cit.). Basal LDH release was typically between 6–9% of the LDH released following lysis of the cells with 0.8% Triton X-100, whereas insults usually resulted in a 2- to 3-fold increase over basal levels. In order to be able to compare from plate to plate, all values were normalized to the 30 μM SP-induced maximal LDH release (assigned 100%). These toxic events are receptor-mediated, because the effect of SP can be blocked by the SP receptor antagonist, spantide II (100 μM), and the Glu-induced toxicity blocked by the NMDA receptor antagonist, MK-801 (1 μM). However these induced toxicities are likely to be mechanistically distinct, since MK-801 cannot prevent SP-induced toxicity.

The results demonstrate that the compound of Example 4 has the potential to be more effective than NMDA receptor antagonists against a broader spectrum of neurotoxic events. In contrast to MK-801, compound of Example 4 reduces both SP and Glu-induced neurotoxicity with an $EC_{50}$ for neuroprotection of 10 μM (FIG. 1). However, the (S)-enantiomer, compound of Example 19, is 10-fold less potent as a neuroprotectant in spinal cord ($EC_{50}$=100 mM). This neuroprotective effect is blocked by selective nicotinic antagonists, mecamylamine (10 μM), methyllycaconitine, (MLA, 10 nM) and α-bungarotoxin (α-BTX, 1 nM) indicating a neuronal nicotinic receptor mechanism. These results suggest that compounds of formula I are effective in a method of treating or preventing neuronal cell death in mammals, including humans and thus are useful in the disorders associated therewith in the conditions associated with central and peripheral neuropathic pain which include AIDS, cancer, stroke, Parkinson's disease, diabetes, osteoarthritis, tissue trauma, surgical intervention or post-therapeutic neuralgia. The present invention thus includes a method of treating neurotoxicity or spinal cord neurodegeneration comprising administering a therapeutically effective amount of a compound of formula I to a patient in need of treatment thereof. The preferred compound is the R-enantiomer.

In vivo Protocols

Protocol for Determination of Effectiveness of Nicotinic Acetylcholine Receptor Ligands as Analgesic Agents in the Mouse Hot Plate Paradigm Separate groups of mice (n=8/group) were utilized for each dose group. All drugs were administered by the intraperitoneal route of administration. Animals were dosed 30 minutes prior to testing in the hot-plate. The hot-plate utilized was an automated hot-plate analgesia monitor (model # AHP16AN, Omnitech Electronics, Inc., Columbus, Ohio). The temperature of the hot-plate was maintained at 55° C. and a cut-off time of 180 seconds was utilized. Latency until the tenth jump was recorded as the dependent measure. An increase in the tenth jump latency relative to the control was considered an antinociceptive effect.

Table 4 shows the minimally effective dose (MED), among the doses tested, at which a significant antinociceptive effect, as defined above, was observed for compounds of the invention. The data show that the compounds of the invention generally show a significant antinociceptive effect at a dose between 0.062 to 62 μmol/kg, i.p.

Protocol for Determination of Effectiveness of Nicotinic Acetylcholine Receptor Ligands as Analgesic Agents in the Chung Model of Neuropathic Pain The Chung model of neuropathic pain is produced in rats (male, Sprague-Dawley) by unilateral ligation of L5 and L6 nerves which innervate the hindlimb (Kim and Chung, *Pain*, 1992, 50, 355–363. Following a sufficient recovery period, these animals show an apparent allodynic (withdrawal from a normally nonpainful stimulus) response to a tactile stimulus (i.e., VonFrey hairs). This response is quantitated by determining a 50% threshold response to different weight VonFrey hairs. The hairs are applied to the mid-plantar area of the hind paw ipsilateral to the ligations. The animals were tested repeatedly over the course of 120 min. A crossover design was used with each animal being tested after administration of saline and each dose of test compound on separate days. A significant increase in the 50% threshold after treatment with test compound relative to the 50% threshold after treatment with saline was considered an anti-allodynic effect.

An anti-allodynic effect is interpreted to demonstrate strong potential for the treatment of neuropathic pain. Selected compounds of the invention were tested in this model of neuropathic pain with results presented in Table 4. The table shows the minimally effective dose (MED), among the doses tested, at which the selected compounds effected a significant increase, relative to control subjects, in the 50% threshold response. The data indicate that seven out of the eight compounds tested showed a significant effect at at least one of the tested doses, and that the observed significant effects occurred in the dose range 0.19 to 0.62 $\mu$mol/kg, i.p.

TABLE 4

| Ex. | * | X | Y | MED Hot plate model ($\mu$mol/kg, i.p.) | MED Chung model ($\mu$mol/kg, i.p.) |
|---|---|---|---|---|---|
| 6 | R | H | H | NS | |
| 4 | R | Cl | H | 0.62 | 0.3 |
| 8 | R | F | H | 1.9 | 0.62 |
| 11 | R | H | F | NS | |
| 14 | R | H | Me | 62 | |
| 16 | R | Cl | Cl | 6.2 | 0.19 |
| 18 | R | Cl | Br | 0.62 | |
| 7 | S | H | H | 6.2 | |
| 19 | S | Cl | H | 0.62 | 0.3 |
| 9 | S | F | H | 0.62 | |
| 20 | S | Me | H | 0.62 | |
| 10 | S | H | F | 6.2 | 0.62 |
| 21 | S | H | Cl | NS | |
| 12 | S | H | Br | NS | |
| 13 | S | H | Me | NS | |
| 23 | S | H | Et | NS | |
| 24 | S | H | n-Pr | 62 | |
| 15 | S | Cl | Cl | 1.9 | NS |
| 17 | S | Cl | Br | 1.9 | 0.19 |
| 25 | S | Cl | Me | 0.062 | |
| 27 | S | Cl | Et | NS | |
| 28 | S | Cl | n-Pr | NS | |
| 29 | S | Cl | n-Bu | NS | |
| 26 | S | Cl | vinyl | 1.9 | |
| 30 | S | Cl | ethynyl | 6.2 | |
| 31 | S | F | Br | 6.2 | |
| 32 | S | F | Me | NS | |
| 34 | S | Me | Br | 0.62 | |
| 36 | S | Me | Et | NS | |
| 35 | S | Me | vinyl | NS | |
| 122** | S | H | H | — | 1.9 |

NS = no significant effect observed relative to saline controls at the doses tested.
**compound also has a 2-fluoro substitutent.

As shown in Table 4, some of the compounds in the (S) or (R) series did not show activity in the analgesic models. A method of treating or preventing pain, comprising administering a compound of formula I with X and Y as recited previously expressly excludes those specific (S) or (R) compounds shown above which had no activity in the pain models. Compounds which do show activity or which may show activity in later developed models of pain are included within the scope of the method claim. The compounds of formula I also have activity as modifiers of neuronal cell death and/or inflammation.

Protocols for Determination of Effectiveness of Nicotinic Acetylcholine Receptor Ligands in Interfering with Locomotor Activity in the Rotarod Apparatus Motor coordination was assessed using an accelerating rotarod apparatus (Omnitech Electronics, Inc., Columbus, Ohio). Locomotor activity was monitored under dim light in a 41×41 cm. open field using a photobeam activity system (San Diego Instruments, San Diego, Calif.). The mouse was placed on a 3.5 cm diameter rod which increased in speed from 0 to 40 rpm over 120 seconds. The time required for the mouse to fall from the rod was recorded with a maximum score of 120 seconds. Twenty-five min after receiving an i.p. injection, the mice were placed in the open field for 5 min. After removal from the open field (i.e., 30 min after injection), they were immediately tested on the rotarod. Body temperature was assessed using a probe inserted 3 cm into the rectum approximately 35 min after injection. (YSI Tele-Thermometer, Yellow Springs Instrument Co., Inc., Yellow Springs, Ohio). Diazepam (10.5 $\mu$mol/kg, i.p.) was used as a positive control.

The compound of Example 8 was tested in the activity, temperature and rotarod test and showed no rotarod effect until a dose of 19 was reached. In contrast, the compound of Example 9 showed impairments at 0.62 $\mu$mol/kg in 2 of 3 experiments. This demonstrates that the (R)-enantiomer (Example 8) had fewer motor coordination side effects than the (S)-enantiomer (Example 9).

Protocol for Determination of Effectiveness of Nicotinic Acetylcholine Receptor Ligands as Analgesic Agents in Combination with Opioids in the Mouse Hot Plate Paradigm In this set of experiments a non-effective dose of the compound of Example 4 was combined with subthreshold and effective doses of morphine. Compounds were co-mixed in a syringe, and co-administered via the intraperitoneal route 30 min prior to testing in the mouse hot-plate paradigm as indicated above. Separate groups of animals (n=7–8/group) were used for each dose group.

The results in FIG. 2 demonstrate that the compound of Example 4 combined with subthreshold doses of morphine can produce effective antinociceptive activity. In addition, combining non-effective doses of compound of Example 4 with effective doses of morphine results in enhanced antinociceptive activity.

Taken together, these results suggest that combination therapy of compounds disclosed within together with opioids may result in remarkably enhanced analgesic activity. It is conceivable that combination of these nicotinic acetylcholine ligands with other available analgesics may also result in added beneficial effects.

Protocol for Determination of Effectiveness of Nicotinic Acetylcholine Receptor Lipands as Analgesic Agents in the Chung Model of Neuropathic Pain Following Repeated Dosing Animals were surgically prepared as described above for the Chung model. For assessment of each test compound, two treatment groups (6 animals each) were established. One group was injected (i.p.) with test compound twice daily for 5 days, and the other group was injected on the same schedule with saline. Responses to von Frey hairs were assessed as described above both before, and 15 minutes after, injection on the first 2 days and also on the 5th day. The saline-treatment group was given saline for the first 4 days and on the morning of the 5th day, but received a challenge of the test compound in the afternoon of the fifth day. The results for test compounds as the compound of Example 4 and for morphine are shown in FIGS. 3 and 4, respectively, wherein light bars reflect responses before administration of test compound, and dark bars represent responses fifteen minutes following administration of test compound.

Significant anti-allodynic effects of compound of Example 4 were observed during each test session, and no differences in the anti-allodynic effects of this challenge with compound of Example 4 were noted between rats previously given b.i.d. injections of compound of Example 4 (0.3 µmol/kg, i.p) and rats previously given saline injections. This result indicates that the anti-allodynic effect of compound of the compound of Example 4 does not decrease following repeated dosing. In contrast, the effects of morphine (21 µmol/kg) in this model were significantly reduced after repeated b.i.d. dosing. This result indicates that the compound of Example 4 may have greater utility than morphine in alleviating chronic, neuropathic pain.

Protocol for Determination of Effectiveness of Nicotinic Acetylcholine Receptor Ligands as Analgesic Agents in the Formalin Model of Persistent Pain The test follows the protocol established in the literature (Tjølsen, et al., *Pain,* 1992, 51, 5–17). A 50 µL injection of 5% formalin, a potent chemical irritant, was made subcutaneously into the dorsal surface of one of the rear paws of male Sprague-Dawley rats. Rates of nociceptive behaviors (e.g., flinching, biting, licking, or elevating the paw) typically show a biphasic pattern over time, with a brief, initial period lasting about 5 min. following the formalin injection and a longer phase of responding beginning about 20 min. after the formalin injection. This second phase of responding is maximal at about 30–50 minutes after injection and appears to involve an inflammatory component. Nociceptive behaviors were recorded during this second phase of responding (30–50 minutes after formalin injection) using a time-sampling procedure (15 sec. of observation time for each rat during each minute). The test compound was administered orally to a group of seven rats at varying doses 15 minutes prior to formalin injection. Responses are compared to a similar group receiving saline.

The results in FIG. 5 demonstrate that the compound of Example 4 produced significant antinociceptive effects in this model of persistent pain after oral administration and indicate that this compound may have utility as an oral analgesic for the treatment of acute pain.

Protocol for Determination of Effectiveness of Nicotinic Acetylcholine Receptor Ligands as Analgesic Agents in the Paw Thermal Stimulator (Hotbox) Model For assessing nociceptive responses to an acute thermal stimulus, a commercially available paw thermal stimulator was utilized (Anesthesiology Research Laboratory, Department of Anesthesiology, University of California at San Diego, La Jolla, Calif.). This device has been previously described (Dirig, D. M. and Yaksh, T. L., *Pain,* 62: 321–328, 1995) and is based on the initial work of Hargreaves et al. (*Pain,* 32: 77–88, 1988). Rats were placed in Plexiglas cubicles that were located on a glass surface of the apparatus. The surface of the glass was maintained at 30° C. A thermal stimulus was applied to the bottom of the rear foot of the rat via a movable focused projection bulb. The stimulus current was maintained at 4.8 Amps. The latency until the animal moved its foot from the stimulus was recorded automatically by use of photodiode motion sensors. In the current studies, a 20 second cut-off was employed to limit possible tissue damage following exposure to the stimulus.

All studies began with a 20 min acclimation period. Following the acclimation period, a baseline measure was determined for each animal. Following determination of baseline, treatments were administered and measures were taken at various time points following treatment (e.g., 15, 30, and 45 min). For clarity, data were collapsed over time for statistical analysis (unless otherwise noted).

Stock solutions of compounds were prepared in absolute ethanol at a concentration of 62 µmol/ml. From this, solutions were made with 10% ethanol, and dosed by injection i.p. Compounds were tested in the dose range of from 0.62 to 6.2 µmol/kg.

For measurements, the following protocol was utilized. Six animals were used in each run. For any given measure (e.g., time point), one foot of each of the 6 animals was tested and then the process was repeated for the opposite foot. Mean values for the response were then computed based on the two scores.

Data from this experiment are given in the following table, and they indicate that selected compounds show analgesia at doses from 0.62 to 6.2 µmol/kg.

Table Showing
Analgesic Dose of Selected Compounds in Hotbox Model

| Compound of Example Number | analgesic dose (µmol/kg) |
|---|---|
| 54 | >6.2 |
| 71 | 0.62 |
| 72 | 0.62 |
| 75 | 6.2 |
| 79 | 0.62 |
| 80 | 0.62 |
| 81 | 0.62 |
| 92 | >6.2 |
| 95 | >6.2 |

Protocol for Determination of Anti-Inflammatory Effects of Nicotinic Acetylcholine Receptor Ligands Male Sprague-Dawley rats (Charles River, Portage, Mich.) weighing approximately 200 g are fasted 16 hours with free access to water. Adrenalectomized Sprague Dawley rats (Charles River, Portage, Mich.) used in selected studies are also fasted but given free access to saline. On the day of the experiment, rats are weighed, and the volume of each hindpaw is measured by water displacement using a Buxco plethysmograph. In these studies, all test agents are solubilized in sterile 0.9% saline, and administered by i.p. injection. At the time of challenge, 100 µl of a 1% carrageenan solution (Sigma) in sterile 0.9% saline is injected subcutaneously into the right hindpaw according to the method of Winter et al (Winter, C. A., et al., *Proc. Soc. Exp. Biol. Med.,* 111:544, 1962). After 2 hours (unless otherwise noted), left and right hindpaw volumes are remeasured for determination of edema.

Following injection of carrageenan into the footpad of a rat an acute inflammatory reaction occurs over the next 2–6 hours. The paw swells dramatically as evidenced by direct plethysmographic measurement of paw volumes. The increase in paw volume, through physical pressure on tendons and nerves, and local inflammation, sensitizes nociceptors (i.e. pain receptors) to cause hyperalgesia (i.e. an increased response to a noxious stimulus).

Compound of Example 4 reduces carrageenan-induced paw edema with an $ED_{30}$ of 0.21 µmol/kg, i.p. Moreover, compound of Example 4 is as efficacious as dexamethasone to reduce paw edema (panel A, FIG. 6). The effect of compound of Example 4 on paw edema is prevented by the nicotinic acetylcholine receptor antagonist, mecamylamine (panel B, FIG. 6). These data demonstrate that compound of Example 4 is active in a model used to establish anti-inflammatory effects, and that the effects are mediated by nicotinic acetylcholine receptors. In addition, the compounds of formula I with the variables as defined above in the method of treating pain should be active in a method of reducing or treating inflammation, as the above data suggest.

These data also suggest compounds of this invention would also have anti-inflammatory actions, and that the added benefit of reduction of inflammation of these nicotinic acetylcholine ligands may contribute to superior pain relief.

Protocol for Measurement of Cardiovascular Effects in Dogs

Male beagle dogs were anesthetized with pentobarbital (35 mg/kg, i.v.) followed by constant i.v. infusion of pentobarbital (5 mg/kg/h). The animals were ventilated with room air by means of a mechanical respiration pump. Blood pressure was measured using a dual tip micromanometer catheter (Millar, Model SPC-770, 7F) inserted into the heart left ventricle via the carotid artery. Compounds were injected into the right femoral vein via catheter. Hemodynamic variables were computed using XYZ Real Time Spreadsheet software on a signal processing workstation (Modular Instruments, Inc.). Sixty minutes were allowed following surgery to achieve a steady-state baseline for the measured variables. Test compounds were administered by i.v. bolus (10 nmol/kg) and compared for their relative ability to elicit changes in blood pressure and heart rate over a five minute data collection period.

Table Showing Cardiovascular effects of Example 1 vs. Example 19

| Assay | Compound of Example 19 | Compound of Example 1 |
| --- | --- | --- |
| Increase in Diastolic Blood Pressure (mm Hg), | 67.3 ± 3.2 | 23.2 ± 4.6 |
| Increase in Heart Rate (beats/min), | 26.0 ± 7.8 | 7.8 ± 2.9 |

The compound of Example 1 (the (R)-enantiomer of 5-(azetidinylmethoxy)-2-chloropyridine increased blood pressure approximately only ⅓ of that seen with compound of Example 19 (the (S)-enantiomer of 5-(azetidinylmethoxy)-2-chloropyridine). In addition, the compound of Example 1 increased the heart rate in the dogs only ⅓ of that seen for the compound of Example 19. These data suggest that the compound of Example 1 causes less robust effects on cardiovascular parameters than does the compound of Example 19 and is therefore a safer compound. That is, the (R)-isomer is safer than the (S)-isomer.

Prodrug Conversion in Dogs

Prodrugs of the form (R=ArCO, Z=Y=H, X=F) have been shown to convert rapidly to the active drug (R=Z=Y=H, X=F) following oral administration to dogs. Data are shown in the Table. In each case, peak plasma levels of parent (R=H) were observed within 0.6–0.8 hr, and at levels ($C_{max}$) consistent with an efficacious dose of the parent. The efficiency of conversion (F) varies from 27–61%. None of these compounds was active in a functional in vitro assay for activity at nicotinic receptors (K177 cell line), suggesting that in vivo activity results from conversion to the R=H form.

| R | $C_{max}$ (ng/ml) | $T_{max}$ (hr) | $t^{1/2}$ (hr) | $AUD_{0-}$ (ng · hr/ml) | F* (%) |
| --- | --- | --- | --- | --- | --- |
| PhCO | 6.31 | 0.6 | 1.8 | 18.89 | 27.3 |
| 4-NO$_2$C$_6$H$_4$CO | 6.01 | 0.8 | 1.9 | 18.76 | 27.1 |
| 4-MeOC$_6$H$_4$CO | 7.43 | 0.8 | 2.0 | 26.09 | 37.7 |

-continued

| R | $C_{max}$ (ng/ml) | $T_{max}$ (hr) | $t^{1/2}$ (hr) | $AUD_{0-}$ (ng · hr/ml) | F* (%) |
| --- | --- | --- | --- | --- | --- |
| 4-FC$_6$H$_4$CO | 3.25 | 0.8 | 1.6 | 9.35 | 13.5 |
| 4-ClC$_6$H$_4$CO | 4.54 | 0.8 | 2.5 | 18.61 | 26.9 |
| 4-MeC$_6$H$_4$CO | 7.05 | 0.8 | 2.4 | 29.85 | 43.1 |
| 4-MeO2CC$_6$H$_4$CO | 10.31 | 0.8 | 1.8 | 42.37 | 61.2 |

*bioavailability estimated from a 20 nmol/kg IV dose of (R = H) in a separate group of dogs Beagle dogs were fasted overnight prior to dosing but were permitted free access to water. Each of the prodrugs was administered to a group of three animals at a dose of 200 nmol/kg. The formulation was adminstered by oral gavage. The prodrugs were prepared as 200 nmol/ml (1 ml/kg) solutions in normal saline. Blood samples from a jugular vein of each dog prior to dosing and 0.17, 0.33, 0.5, 0.75, 1, 1.5, 2, 3, 4, 6 and 8 hours after drug administration. Plasma, separated from the red cells by centrifugation, was subjected to precolumn derivatization followed by HPLC with fluorescence detection for quantitation of active drug concentrations.

EXAMPLES

The following examples show how the specific examples were made from easily prepared or commericially available starting materials. The previous discussion on the preparation of compounds within the scope of this invention is also relevant with respect to general preparation of the starting reactants utilized to prepare the analgesics or compounds claimed and recited herein. The Examples presented in Tabular form are readily made according to the procedures described herein for the examples actually made. These examples are non-limiting and it is understood that compounds within the scope as recited herein are within the invention as well as uses thereof.

In this section some terms are specified in abbreviated form. These terms are as identified below adjacent to the abbreviation:

Boc, t-butyloxycarbonyl; Cbz, benzyloxycarbonyl; DMF, N,N-dimethylformamide; MED, minimally effective dose; THF, tetrahydrofuran; TFA, trifluoroacetic acid; TLC, thin layer chromatography; Ts, tosyl or p-toluenesulfonyl; OTs is tosylate or p-toluenesulfonate.

In terms of nomenclature as presented below in the examples, the compounds of this class have generally been designated as 3-pyridyl ethers with the 3-position of the pyridyl ring having the ether (O) functionality linking the methylene-azetidinyl moiety. However, when the pyridyl ring is di- or multi-substituted, the actual numbering on the pyridyl ring may change so that, for example, the compound of formula I is specifically described in Example 4 wherein the chloro substituent is at the 2-position of the pyridyl ring and the ether linkage is at the 5 position. One of ordinary skill in the art can readily identify the compounds.

Example 1

5-((2R)-Azetidinylmethoxy)-2-chloropyridine 1a. 5-((2R)-Azetidinylmethoxy)-2-chloropyridine A solution of (R)-1-t-butyloxycarbonyl-2-azetidinemethanol (36.5 g, 0.195 mol) in 195 mL of dichloromethane was treated with triethylamine (35.6 ml, 0.255 mol) and then p-toluenesulfonyl chloride (48.5 g, 0.254 mol). The resulting mixture was stirred at room temperature for 16 hours. A 10% solution of sodium hydroxide was added rapidly and the mixture stirred for one hour. After phase separation, the aqueous phase was extracted with additional dichloromethane, combined with the organic phase, washed with NaHCO$_3$ solution and brine, then dried (MgSO$_4$), filtered, and concentrated in vacuo to give 63.1 g of (R)-1-t-butyloxycarbonyl-2-toluensulfonyloxymethylazetidine (94.8%). Next, a solution of 2-chloro-5-hydroxypyridine (from Step 1g below, 24 g, 0.185 mol) in DMF (690 mL) was treated with ground KOH (17.95 g, 0.295 mol) and stirred for 30 minutes at 80° C. To this mixture was rapidly added (2R)-1-t-butyloxycarbonyl)-2-toluensulfonyloxymethylazetidine (63.1 g) dissolved in DMF (395 mL) and the mixture was stirred for 16 hours at 80° C. The mixture was concentrated in vacuo to remove the DMF and the resultant residue was diluted with water and extracted with EtOAc (3×). The organic extracts were combined, dried (MgSO$_4$), filtered and concentrated in vacuo to give 58.5 g of unpurified product. This material was chromatographed (silica gel, 25% EtOAc in hexane) to give 43.2 g of 5-(1-t-butyloxycarbonyl-(2R)-azetidinylmethyloxy)-2-chloropyridine as a clear oil (74%). A solution of 5-(1-t-butyloxycarbonyl-(2R)-azetidinylmethoxy)-2-chloropyridine (30 g, 0.1 mol) in 450 mL of dichloromethane at 0° C. was treated with 225 mL of trifluoroacetic acid dropwise over a 30 minute period. After two hours, the bulk of the solvent was removed in vacuo and the residue was diluted with ethyl acetate, washed with 1.0 M K$_2$CO$_3$ and brine, dried (Na$_2$SO$_4$) and concentrated in vacuo to give 19.1 g of a yellow oil. Flash silica gel chromatography (90:10 CHCl$_3$:MeOH then 90:10:0.5 CHCl$_3$:MeOH:NH$_4$OH) gave 16.5 g of the title compound (83% yield): MS (CI/NH$_3$) m/z: 199 (M+H)$^+$; $^1$H NMR (CDCl$_3$, 300 MHz) 67 2.21–2.43 (m, 2H), 3.42–3.50 (m, $^1$H), 3.69–3.78 (m, $^1$H), 3.98–4.07 (m, 2H), 4.25–4.34 (m, $^1$H), 7.22 (d, J=1.7 Hz, 2H), 8.07 (dd, 1.7, 2.0 Hz, $^1$H).

1b. Benzyl (R)-azetidin-2-one-4-carboxylate

To a flask under nitrogen containing dibenzyl (R)-aspartic acid (BACHEM, 6.5 g, 20.6 mmol) was added 82 mL of diethyl ether. The white heterogeneous mixture was cooled to 0° C., then 2.6 mL (2.23 g, 20.6 mmol) of chlorotrimethylsilane was added, followed by stirring for 15 minutes. Then 2.9 mL (2.08 g, 20.6 mmol) of triethylamine was added via syringe. The resultant white heterogeneous mixture was stirred for 1 hour and then quickly filtered through a medium fritted glass funnel filter under a stream of nitrogen. The cloudy white filtrate was placed under nitrogen and treated with 10.3 mL of 2 M t-butylmagnesium chloride in diethylether dropwise over a 20 minute period. The resultant light yellow homogeneous solution was allowed to slowly warm to room temperature overnight and then cooled to 0° C. To this was slowly added 50 mL of 2 N HCl that had been saturated with NH$_4$Cl. This biphasic mixture was transferred to a separatory funnel, the layers were separated, and then the aqueous phase was extracted with ethyl acetate and dichloromethane. The organic extracts were combined, washed with brine, dried (Na$_2$SO$_4$) and concentrated in vacuo to give 6.65 g of a yellow oil which solidified upon standing. The yellow solid was triturated with ethyl acetate and filtered to give 1.7 g of benzyl (R)-azetidin-2-one-4-carboxylate as a white crystalline solid. The mother liquors were combined, concentrated, triturated with diethyl ether, and filtered to give an additional 350 mg of the title compound. Combined yield 49%. MS (CI/NH$_3$) m/z: 206 (M+H)$^+$, 223 (M=NH$_4$)$^+$; $^1$H NMR (CDCl$_3$, 300 MHz) δ3.08 (ddd, J=2.2, 2.8, 15.1 Hz, $^1$H), 3.34 (ddd, J=1.5, 5.9, 15.1 Hz, $^1$H), 4.22 (dd, J=2.8, 5.9 Hz, $^1$H), 5.21 (s, 2H), 6.17 (s (br), $^1$H), 7.37 (m, 5H).

Step 1c. (R)-1-(t-butyloxycarbonyl)-2-azetidinemethanol

A dry round bottom flask was charged with 410 mg (2 mmol) of (R)-benzyl azetidin-2-one-4-carboxylate and 10 mL of dry tetrahydrofuran, then swept with nitrogen and cooled to 0° C. To this clear homogeneous solution was added 10 mL of 1 M LiAlH$_4$ in THF dropwise via syringe. After 76 hours, the reaction was cooled to 0° C. and 400 μL of distilled water was added slowly (vigorous gas evolution). The mixture was stirred for 15 minutes and then 400 μL of 15% NaOH was added and the mixture was stirred an additional 15 minutes. Finally, 800 μL of distilled water was added, the white heterogeneous reaction was allowed to warm to room temperature, and then filtered through a ½ inch plug of Celite and concentrated in vacuo to give 420 mg of a light yellow oil. A portion of this oil (310 mg) was treated with 4 mL CH$_2$Cl$_2$ followed by 460 mg di-tert-butyldicarbonate (2.1 mmol). This cloudy, light yellow mixture was stirred at room temperature for 4.5 hours and then concentrated in vacuo to yield 632 mg of a yellow oil. Flash chromatography (silica gel with 2:1 to 1:1 hexane: ethyl acetate) produced 167 mg of the title compound (61% yield): [α]$_D^{20}$ +22.3 (c 1.28, CHCl$_3$); MS (CI/NH$_3$) m/z: 188 (M+H)$^+$. $^1$H NMR (CDCl$_3$, 300 MHz) δ1.45 (s, 9H), 1.94 (m, $^1$H), 2.15 (m, $^1$H), 3.68–3.92 (m, 5H), 4.44 (m, $^1$H).

1d. (R)-1-t-butyloxycarbonyl-2-azetidinemethanol

An alternative to the procedures of Examples 1b–1c, (R)-1-t-butyloxycarbonyl-2-azetidinemethanol was prepared from γ-butyrolactone according to the procedure of Rodebaugh, R. M. and Cromwell, N. H., (*J. Heterocyclic Chem.*, 1969, 435). In this literature procedure, γ-butyrolactone was treated with bromine and catalytic phosphorus tribromide, then subsequently with benzyl alcohol and gaseous hydrogen chloride to afford benzyl α,γ-dibromobutyrate in 62% yield. This dibromide in ethanol was treated with one equivalent of benzhydrylamine and potassium carbonate at reflux for about 16 hours to afford benzyl N-diphenylmethylazetidine-2-carboxylate in 52% yield. Hydrogenolysis in MeOH over Pd(OH)$_2$ afforded racemic azetidine-2-carboxylic acid in 62% yield. Following the procedure of Rodebaugh, R. M. and Cromwell, N. H., (*J. Heterocyclic Chem.*, 1969, 993), racemic azetidine-2-carboxylic acid was converted to the N-Cbz derivative by treatment with benzyl chloroformate in aqueous NaOH at 0–5° C. Following isolation in quantitative yield, the Cbz derivative in methanol was treated with one equivalent of L-tyrosine hydrazide to precipitate the tyrosine hydrazide salt of (R)-azetidine-2-carboxylic acid in 77–87% yield. (R)-1-Cbz-azetidine-2-carboxylic acid was liberated from the salt by normal extractive procedures. Hydrogenolysis of the free acid by treatment of a methanol solution with hydrogen gas at 4 atm in the presence of 10% Pd/C for 19 h afforded (R)-azetidine-2-carboxylic acid, which was isolated in 88% yield by trituration with methanol. This product was treated with di-tert-butyl dicarbonate and N-methylmorpholine in dioxane/H$_2$O (1:1) to afford (R)-1-Boc-azetidine-2-carboxylic acid in quantitative yield. Treatment of a THF solution of (R)-1-Boc-azetidine-2-carboxylic acid with borane-methyl sulfide complex for 16 h at ambient temperature afforded the title compound in 92% yield.

1e. (R)-1-benzyloxycarbonyl-2-azetidinemethanol

The title compound was prepared from D-methionine following the procedure of Sugano and Miyoshi, Bull.

Chem. Soc. Japan 1973, 46, 669. D-methionine (29.84 g, 200 mmol) was dissolved in $H_2O$ (100 mL) and 1 N NaOH (200 mL, 200 mmol) was added to give a homogeneous solution. With cooling as necessary to maintain a temperature of ~20° C., p-toluenesulfonyl chloride was added (53.4 g, 280 mmol). Additional 1 N NaOH was added in small portions over 2 hours as needed to maintain the pH ~9 (total ca. 280 mL) and then the mixture was stirred at ambient temperature overnight. The mixture was acidified to pH 3–4 with 4.5 N HCl, then stored at −20° C. A crop of white crystals (26.1 g, 43%) was collected. An additional crop separated as an amber oil, which was collected and dried under vacuum to afford 24.8 g (41%). NMR and MS (m/z 321, $(M+NH4)^+$) of both crops were consistent with pure N-tosyl-D-methionine. The combined crops of N-tosyl-D-methionine (53.5 g, 176 mmol) were dissolved in HOAc (53 mL) and 88% $HCO_2H$ (106 mL), then methyl iodide (20 mL) was added and the mixture was allowed to stand in the dark overnight. The volatile components were evaporated under reduced pressure, and the residue was triturated repeatedly with ethyl ether to afford a semi-solid residue, which was dissolved in 1 N NaOH (180 mL). The solution was kept at 90° C. for 3 hours while maintaining pH 6–7 by addition of 3 N NaOH. The solution was acidified to pH 2–3 with 3 N HCl and a white precipitate was collected by filtration and dried to afford 28 g of α-(N-p-tosylamino)-γ-butyrolactone. Additional crops were obtained following storage of the mother liquors at −20° C. to afford an additional 8.3 g of product (combined yield 81%), mp 132–134° C. MS: m/z 273 $(M+NH_4^+)$, 291 $M+(NH_4)_2)^+$. Following the procedure of Miyoshi, et al., (*Chem. Lett.*, 1973, 5–6), a suspension of (R)-α-(N-p-tosylamino)-γ-butyrolactone (20 g) in EtOH (150 mL) was held at 65° C. while HBr(g) was bubbled into the mixture. After the mixture became homogeneous, slow bubbling of HBr was continued at 65° C. to maintain maximal saturation throughout the reaction. The volatile components were evaporated, then the residue was chromatographed (silica gel; 30% EtOAc/hexane) to afford 17.8 g (ca. 65%) of (R)-N-tosyl-γ-bromonorvaline ethyl ester as a slightly yellow oil. MS: $(CI/NH_3)$ m/z 301 $(M-HBr+NH_4)^+$; 381 $(M+NH_4)^+$; $M+(NH_4)_2)^+$. To N-tosyl-γ-bromonorvaline ethyl ester (24.24 g, 66.5 mmol) in DMF (725 mL) was added $H_2O$ (3.64 mL) followed by 60% NaH (8 g). The mixture was stirred at 10–20° C. for 20 min, after which the mixture was acidified with 1 N HCl, the solvents were evaporated, and $CH_2Cl_2$ was subsequently added and evaporated twice. Addition of 10% HCl precipitated the product, which was collected and recrystallized from EtOAc/petroleum ether to afford 12.3 g (72%) of (R)-N-tosylazetidine-2-carboxylic acid as white floculent crystals: mp 144–145° C.; $[\alpha]_D$ +146 (c 0.61, $CHCl_3$); MS $(CI/NH_3)$ m/z 273 $(M+NH_4)^+$. Further manipulations were carried out as described in Abreo, et al., *J. Med. Chem.* 1996, 39, 817–825. Analysis of enantiomeric purity was carried out by conversion to the α-methylbenzylamide, and evaluation by $^1H$-NMR, which indicated a ca. 4:1 mixture of enantiomers. This mixture (1.48 g, 5.8 mmol) was slurried in liquid $NH_3$ (25 mL) at −78° C. Sodium metal was added until a dark blue color persisted for 30 minutes and then solid ammonium chloride was added until the blue color disappeared. The cold bath was replaced with a water bath as the ammonia was allowed to evaporate. The remaining white solid was carefully dissolved in $H_2O$ (30 mL) and HOAc to adjust the mixture to pH 7.0. Then 1,4-dioxane (30 mL) and N-(benzyloxycarbonyloxy)succinimide (2.1 g, 8.7 mmol) were added and the mixture was stirred for 2 h. The biphasic mixture was partitioned between saturated $K_2CO_3$ and $Et_2O$ and the phases were separated. The aqueous phase was acidified with 12 N HCl and then extracted with $CH_2Cl_2$. The organic phase was dried ($MgSO_4$), concentrated, and chromatographed (silica gel; $CHCl_3$/MeOH/HOAc, 95:5:0.5) to afford a colorless oil (955 mg, 70%): MS $(CI/NH_3)$ m/z: 236 $(M+H)^+$; $^1H$ NMR ($CDCl_3$, 300 MHz) δ2.47–2.60 (m, 2H) 3.98–4.07 (m, 2H), 4.78–4.87 (m, $^1H$), 5.65 (s, 2H), 7.28–7.40 (m, 5H). The resultant 1-benzyloxycarbonyl azetidine-2-carboxylic acid (932 mg, 3.96 mmol) was dissolved in MeOH (20 mL) and L-tyrosine hydrazide (773 mg, 3.96 mmol) was added. The slurry was heated at reflux for 10 minutes, allowed to cool to ambient temperature and then filtered. The filter cake was dissolved in 6 M HCl and extracted with EtOAc (2×). The organic fractions were combined, dried ($MgSO_4$) and concentrated to give (R)-1-benzyloxycarbonyl azetidine-2-carboxylic acid as a colorless oil (403 mg, 55%): $[\alpha]_D^{20}$+104.7 (c 4.0, $CHCl_3$). The (R)-1-benzyloxycarbonyl azetidine-2-carboxylic acid (2.0 g, 8.6 mmol) in THF (35 mL) was cooled to 0° and 1.0 M $BH_3$.THF (12.9 mL, 12.9 mmol) was added dropwise. The mixture was allowed to warm to ambient temperature and stirred for 2.5 hours. A solution of 2 N HCl was carefully added and the heterogenous mixture was allowed to stir for 1 hour. The slurry was extracted with $CH_2Cl_2$ and the organic phase was dried ($MgSO_4$), concentrated, and chromatographed (silica gel; EtOAc/hexane, 1:1) to afford the title compound as a colorless oil (1.46 g, 77%): $[\alpha]_D^{20}$ 15.5 (c 1.2, $CHCl_3$). MS $(CI/NH_3)$ m/z: 222 $(M+H)^+$; $^1H$ NMR ($CDCl_3$, 300 MHz) δ1.93–2.08 (m, $^1H$) 2.18–2.29 (m, $^1H$), 3.72–4.01 (m, 4H), 4.47–4.58 (m, $^1H$), 5.12 (s, 2H), 7.30–7.41 (m, 5H).

1f. 5-acetoxy-2-chloropyridine

To a solution of 5-amino-2-chloropyridine (40.0 g, 0.311 mol, Aldrich) in 180 mL of 3:1 1,2-dimethoxyethane/$CH_2Cl_2$ at −10° C. was slowly added boron trifluoride diethyl etherate (76.5 mL, 0.662 mol). Then a solution of tert-butyl nitrite (44.4 mL, 0.373 mol) in 40 mL of 1,2-dimethoxyethane was slowly added over 15 min such that the reaction temperature remained below −5° C. The mixture was stirred for 10 min at −10° C. then warmed to 0° C. and stirred for an additional 30 min. Pentane was added and the solid was collected by suction filtration (cold pentane wash) to afford 69.1 g of the tetrafluoroborate diazonium salt. This was dissolved in 350 mL of acetic anhydride, warmed to 75° C. ($N_2$ evolution) and stirred for 3 h. The volatiles were removed in vacuo and the dark residue was diluted with $Et_2O$ and washed with saturated aqueous $NaHCO_3$. The aqueous phase was extracted with $Et_2O$. The combined ethereal extracts were washed with brine, dried ($MgSO_4$), and concentrated. Purification by chromatography (silica gel; hexane/EtOAc 90:10 to 70:30) afforded the title compound as a white solid (29.4 g, 55%): mp 45° C.; $^1H$ NMR ($CDCl_3$, 300 MHz) δ: 2.35 (s, 3H) 7.35 (d, J=8.5 Hz, $^1H$), 7.48 (dd, J=2.9, 8.5 Hz, $^1H$), 8.21 (d, J=2.9 Hz, $^1H$); MS $(CI/NH_3)$ m/z: 172, 174 $(M+H)^+$; 189, 191 $(M+NH_4)^+$ 1g. 2-chloro-5-hydroxypyridine 5-Acetoxy-2-chloropyridine (11.1 g, 64.7 mmol) from example 1f was dissolved in MeOH at ambient temperature and solid potassium carbonate (4.47 g, 32.4 mmol) was added. After stirring for 2 h, the volatiles were removed in vacuo and the residue was diluted with $Et_2O$ and $H_2O$. The aqueous phase was adjusted to pH 7 by the addition of 1 N aqueous HCl. The layers were separated and the aqueous phase was extracted twice with Et$_2$O. The combined organic extracts were dried (MgSO$_4$) and concentrated to provide the title compound as a white solid (8.03 g, 96%): mp 155° C.; $^1$H NMR (CD$_3$OD, 300 MHz) δ7.20–7.28 (m, 2H), 7.88 (m, $^1$H); MS (CI/NH$_3$) m/z: 130,132 (M+H)$^+$; 147,149 (M+NH$_4$)$^+$.

Example 2

5-((2R)-Azetidinylmethyloxy)-2-chloropyridine p-toluenesulfonate

A flask containing 5-((2R)-azetidinylmethyloxy)-2-chloropyridine from Example 1 (750 mg, 3.78 mmol) was charged with 15 mL absolute ethanol followed by p-toluenesulfonic acid monohydrate (718 mg, 3.78 mmol, Aldrich). This mixture was stirred at room temperature for 15 minutes and then concentrated in vacuo. The resulting off white crystalline solid was triturated with EtOAc, filtered, and placed in a vacuum oven overnight (~16 hours, ca. 15 mm Hg) to give the title compound as a white crystalline solid (1.38 g, 99%): mp 158–161° C.; $[\alpha]_D^{20}$+5.4° (c 1.05, MeOH); $^1$H NMR (DMSO-d$_6$, 300 MHz) δ8.88 (s (br), 2H), 8.19 (d, J=2.9 Hz, $^1$H), 7.46–7.58 (m, 4H), 7.11 (d, J=7.0 Hz, 2H), 4.73 (m, $^1$H), 4.42 (dd, J=7.0, 11.4 Hz, $^1$H), 4.33 (dd, J=3.3, 11.4 Hz, $^1$H), 3.86–3.97 (m, 2H), 2.35–2.55 (m, 2H); MS (CI/NH$_3$) m/z: 199 (M+H)$^+$; 216 (M+NH$_4$)$^+$.

Example 3

5-((2R)-Azetidinylmethyloxy)-2-chloropyridine benzoate

A flask containing 5-((2R)-azetidinylmethyloxy)-2-chloropyridine from Example 1 (780 mg, 3.93 mmol) was charged with 16 mL of absolute ethanol and swept with nitrogen. To this solution was added benzoic acid (480 mg, 3.93 mmol). After 1 hour, the mixture was concentrated in vacuo to give a thick yellow oil. This oil was treated with 10 mL diethyl ether with stirring for ten minutes which gave a fine white crystalline precipitate. The solid was filtered off and washed with diethylether and placed in a vacuum oven overnight (~20° C., ca. 15 mm Hg) to give the title compound (1.1 g, 88%): mp 102–104° C.; $[\alpha]_D^{20}$ +5.35 (c 1.03, MeOH); $^1$H NMR (CDCl$_3$, 300 MHz) δ8.02 (d, J=2.7 Hz, $^1$H), 7.92 (m, 2H), 7.33–7.50 (m 5H), 7.10 (m, 2H), 4.64 (m, 2H), 4.23 (m, 2H), 3.91 (m, 2H), 2.44–2.65 (m, 2H); MS (CI/NH$_3$) m/z: 199 (M+H)$^+$; 216 (M+NH$_4$)$^+$.

Example 4

5-((2R)-Azetidinylmethyloxy)-2-chloropyridine hydrochloride 5-((2R)-Azetidinylmethyloxy)-2-chloropyridine from Example 1 (478 mg, 2.4 mmol) was slurried in Et$_2$O (100 mL) and HCl saturated in Et$_2$O was added slowly at ambient temperature until no further solid precipitated. The solvent was removed and the yellow solid was recrystallized from MeOH/Et$_2$O to afford the title compound as a fine white powder (365 mg, 64%): mp 116–117° C.; MS (CI/NH$_3$) m/z: 199/201 (M+H)$^+$; $^1$H NMR (D$_2$O, 300 MHz) δ2.65–2.76 (m, 2H), 4.03–4.21 (m, 2H), 4.42 (d, J=4.1 Hz, 2H), 4.92–5.00 (m, $^1$H), 7.47 (d, J=8.8 Hz, $^1$H), 7.56 (dd, J=3.0, 8.8 Hz, $^1$H), 8.15 (d, J=3.0 Hz, $^1$H). Anal. Calcd for C$_9$H$_{12}$Cl$_2$N$_2$O: C, 45.98; H, 5.14; N, 11.91; Found: C, 46.03; H, 5.06; N, 11.76. $[\alpha]_D^{20}$ +8.6 (c 0.52, MeOH).

Example 5

5-((2R)-Azetidinylmethyloxy)-2-chloropyridine dihydrochloride

To a flask containing 5-((2R)-azetidinylmethyloxy)-2-chloropyridine from Example 1 (25.0 g, 0.126 mol) in dichloromethane at 0° C. was added an excess of a saturated solution of HCl in diethylether. After addition was complete, the white heterogeneous mixture was concentratred in vacuo. Recrystalliztion from methanol and diethyl ether provided the title compound (30.5 g, 89%) as a white, hygroscopic solid: mp 113–115. $[\alpha]_D^{20}$ +11.8 (c 0.84, MeOH); $^1$H NMR (D$_2$O, 300 MHz) δ2.65–2.76 (m, 2H), 4.03–4.21 (m, 2H), 4.42 (d, J=4.1 Hz, 2H), 4.95 (m, $^1$H), 7.47 (d, J=8.8 Hz, $^1$H), 7.56 (dd, J=3.0, 8.8 Hz, $^1$H), 8.15 (d, J=3.0 Hz, $^1$H). Anal. Calcd for C$_9$H$_{13}$Cl$_3$N$_2$O: C, 37.78; H, 4.72; N, 9.79. Found: C, 37.50; H, 4.70; N, 9.55.

Example 6

(R)-3-(2-Azetidinylmethyloxy)pyridine dihydrochloride

Diethyl azodicarboxylate (1.2 mL, 7.9 mmol) was added to a stirred solution of triphenylphosphine (2.1 g, 7.9 mmol) in THF (60 mL) at 0° C. After 15 minutes, (R)-1-(benzyloxycarbonyl)-2-azetidinemethanol (1.46 g, 6.6 mmol, Step 1e above) in THF (6.6 mL) was added to the reaction vessel followed by 3-hydroxypyridine (690 mg, 7.3 mmol, Aldrich). After stirring for 18 h at ambient temperature the solvent was removed and the residue was dissolved in CH$_2$Cl$_2$ and washed with saturated K$_2$CO$_3$, dried (MgSO$_4$), concentrated and chromatographed (silica gel; EtOAc/hexane, 1:2) to afford a mixture (2.8 g) of (R)-1-(benzyloxycarbonyl)-3-((2-azetidinylmethyl)oxy)pyridine and triphenylphosphine oxide: MS (CI/NH$_3$) m/z: 299 (M+H)$^+$. A sample (1.6 g) of this mixture was dissolved in EtOH (25 mL) and stirred in the presence of 10% Pd/C (320 mg) under an atmosphere of H$_2$ (1 atm) for 4 h. The reaction was filtered, concentrated and chromatographed (silica gel; CHCl$_3$/MeOH/NH$_4$OH, 90:10 to 90:10:0.5) to afford the free base of the title compound as an amber oil (465 mg, overall yield 75%): $[\alpha]_D^{20}$ +5.8 (c 1.6, CHCl$_3$); MS (CI/NH$_3$) m/z: 165 (M+H)$^+$; $^1$H NMR (CDCl$_3$, 300 MHz) δ2.22–2.46 (m, 2H), 3.45–3.51 (m, $^1$H), 3.73 (dd, J=7.7, 8.5 Hz, $^1$H), 4.00–4.10 (m, 2H), 4.26–4.35 (m, $^1$H), 7.21–7.24 (m, 2H), 8.22 (dd, J=2.9, 3.0 Hz, $^1$H), 8.33 (dd, J=1.5, 2.2 Hz, $^1$H). The (R)-3-((2-azetidinylmethyl)oxy)pyridine (450 mg, 2.74 mmol) was slurried in Et$_2$O (20 mL) and MeOH (~2 mL), then Et$_2$O saturated with HCl gas was added at ambient temperature. The solvent was removed and the remaining solid recrystallized from MeOH/Et$_2$O to afford the title compound as a deliquescent white solid (206 mg, 31%): mp 138–140° C.; $[\alpha]_D^{20}$ +9.8 (c 0.5, MeOH). MS (CI/NH$_3$) m/z: 165 (M+H)$^+$; $^1$H NMR (D$_2$O, 300 MHz) δ2.71 (dd, J=8.5, 17.3 Hz, 2H) 4.05–4.21 (m, 2H), 4.57 (d, J=4.4 Hz, 2H), 4.96–5.03 (m, $^1$H), 7.99 (dd, J=5.7, 9.0 Hz, $^1$H), 8.21 (ddd, J=1.2, 2.8, 9.0 Hz, $^1$H), 8.46 (d, J=5.7 Hz, $^1$H), 8.59 (d, J=2.8 Hz, $^1$H); Anal. Calcd for C$_9$H$_{12}$N$_2$O.2 HCl.0.2 H$_2$O: C, 44.90; H, 6.03; N, 11.64. Found: C, 44.90; H, 5.98; N, 11.54.

Example 7

(S)-3-(2-Azetidinylmethyloxy)pyridine dihydrochloride 7a. (S)-3-((2-Azetidinylmethyl)oxy)pyridine dihydrochloride An ice-cooled solution of 1-butyloxycarbonyl-2-(S)-azetidinemethanol (2.8 g, 15.0 mmol, Step 7c below) in THF (40 mL) was stirred under a nitrogen atmosphere. To this was added DEAD (3.54 mL, 22.46 mmol) followed by triphenylphosphine (4.78 g, 22.5 mmol) and the mixture was stirred 10 minutes. 3-Hydroxypyridine (2.14 g, 22.5 mmol) was then added to the reaction with additional tetrahydrofuran (40 mL). After 18 h, additional 3-hydroxypyridine (0.10 g, 1.05 mmol) was added and the reaction stirred 24 hours longer. When all starting azetidine alcohol was consumed, the reaction mixture was concentrated in vacuo. The crude mixture was then acidified (pH<2) with a 10% solution of potassium hydrogen sulfate (80 mL), and washed with ethyl acetate (3×75 mL). The aqueous portion was then basified with a saturated solution of potassium carbonate (pH=10) and products extracted with ethyl acetate (4×75 mL). These extracts were dried (MgSO$_4$), filtered and concentrated in vacuo to a red-brown oil (1.84 g, 50% yield). Purification by flash silica gel chromatography Rf=0.19, (ethyl acetate:hexane=2:1) afforded the coupled product as a light yellow oil in 25% yield; MS (CI/NH$_3$) m/z 265 (M+H)$^+$, 282 (M+NH$_4$)$^+$; $^1$H NMR (CDCl$_3$) δ: 8.36–8.35 (dd, J=3.7 Hz, J=0.7 Hz, $^1$H), 8.24–8.22 (dd, J=4.0 Hz, J=1.5 Hz, $^1$H), 7.25–7.22 (m, 2H), 4.56–4.48 (m, $^1$H), 4.36–4.31 (dd, J=10 Hz, J=4.9 Hz, $^1$H), 4.17–4.12 (dd, J=10 Hz, J=2.9 Hz, $^1$H), 3.92–3.87 (dd, J=8.2 Hz, J=6.8 Hz, 2H), 2.42–2.25 (m, 2H), 1.42 (s, 9H). To an ice-cooled solution of the compound from above (286 mg, 1.08 mmol) in absolute ethanol (4 mL), was added a hydrogen chloride saturated ethanol solution (4 mL), under nitrogen. The reaction mixture was stirred 18 hours while gradually warming to room temperature. The reaction mixture was then concentrated in vacuo, the product dissolved in absolute ethanol and triturated with diethyl ether. Two recrystallizations from ethanol and diethyl ether yielded pure title compound as a white powder (174 mg, 87 mmol, 81% yield): mp 135–137° C.; [α]$_D$ −5.0 (c 0.4, MeOH); MS (CI/NH$_3$) m/z 165 (M+H)$^+$, 182 (M+NH$_4$)$^+$. $^1$NMR (D$_2$O, 300 MHz) δ: 8.60–8.59 (d, J=2.9 Hz, $^1$H), 8.48–8.46 (d, J=5.8 Hz, $^1$H), 8.25–8.21 (ddd, J=9.0 Hz, J=2.6 Hz, J=1.1 Hz, $^1$H), 5.05–4.97 (m, $^1$H), 4.59–4.57 (d, J=4.0 Hz, 2H), 4.22–4.05 (m, 2H), 2.77–2.67 (dd, J=16.9 Hz, J=8.45 Hz, 2H). Anal. calcd. for C$_9$H$_{12}$N$_2$O.2.7 HCl.0.2 H$_2$O: C, 40.60; H, 5.71; N, 10.52. Found: C, 40.75; H, 5.76; N, 10.51.

7b. 1-butyloxycarbonyl-2-(S)-azetidine carboxylic acid

To an ice-cooled solution of 2-(S)-azetidinecarboxylic acid (10.2 g, 100 mmol, Aldrich) in 300 mL of 1:1 water/1,4-dioxane was added di-tert-butyl dicarbonate (28.5 g, 131 mmol), followed by 4-methylmorpholine (11.7 g, 115 mmol). The reaction mixture was warmed to ambient temperature and stirred for 18 hours. The reaction mixture was then poured into a ice cooled saturated solution of sodium bicarbonate (250 mL) and washed with ethyl acetate. The aqueous phase was then acidified with potassium hydrogen sulfate (pH=1) and the product extracted with ethyl acetate. These organic extracts were dried (Na$_2$SO$_4$), filtered and concentrated in vacuo to afford the title compound as a white semi-solid: MS (CI/NH$_3$) m/z 202 (M+H)$^+$, 219 (M+NH$_4$)$^+$; $^1$H NMR (CDCl$_3$, 300 MHz) δ10.0 (br s, $^1$H), 4.81–4.76 (t, J=15 Hz, $^1$H), 3.99–3.83 (m, 2H), 2.62–2.38 (m, 2H), 1.48 (s, 9H).

7c. 1-t-butyloxycarbonyl-(2S)-azetidinemethanol

To an ice-cooled solution of the compound from Step 7b (9.39 g, 46.7 mmol) in THF (100 mL) was added borane.THF complex (1 M, 210 mL, 4.50 eq.) under nitrogen. The reaction was gradually warmed to room temperature and stirred for 48 hours. A 10% aqueous potassium hydrogen sulfate solution (60 mL) was added gradually, and the volatile components were then evaporated in vacuo. The remaining slurry was extracted with EtOAc. The organic extracts were washed with a saturated solution of aqueous sodium hydrogen carbonate, dried (MgSO$_4$), filtered and concentrated in vacuo, providing the title compound as a colorless oil (8.4 g, 96%): MS (CI/NH$_3$) m/z 188 (M+H)$^+$; $^1$H NMR (CDCl$_3$, 300 MHz) δ4.49–4.40 (ddd, J=9.0 Hz, J=9.0 Hz, J=3.0 Hz, $^1$H), 3.95–3.68 (m, 4H), 2.23–2.12 (m, $^1$H), 1.99–1.87 (m, $^1$H), 1.46 (s, 9H).

Example 8

5-(2R)-Azetidinylmethyloxy)-2-fluoropyridine dibenzoate

8a. 5-(2R)-Azetidinalmethyloxy)-2-fluoropyridine dibenzoate

To a solution of triphenylphosphine (0.8 g, 3.0 mmol) in THF (20 mL) was added diethyl azodicarboxylate (4.7 mL, 3.0 mmol) at 0° C., and the mixture was stirred for 0.5 h. 1-t-butyloxycarbonyl-2-(R)-azetidinemethanol (0.51 g, 2.7 mmol, from Example 1c above) and 2-fluoro-5-hydroxypyridine (0.32 g, 2.8 mmol, Step 8e below) were then added. The mixture was allowed to warm slowly to room temperature and stirred overnight. The solvent was removed and the residue was chromatographed (silica gel; hexane/EtOAc, 9:1 to 7:3) to provide 0.80 g of the coupled product: MS (CI/NH$_3$) m/z 283 (M+H)$^+$, 300 (M+NH$_4$)$^+$; $^1$H NMR (CDCl$_3$, 300 MHz) δ1.42 (m, 9H), 3.33 (m, $^1$H),3.89 (t, J=7.31 Hz,1H), 4.11 (m $^1$H), 4.31 (m, $^1$H), 4.51 (m, $^1$H), 6.85 (m, $^1$H), 7.38 (m, $^1$H), 7.87 (m, $^1$H). The 6-fluoro-3-(1-t-butyloxycarbonyl-2-(R)-azetidinylmethoxy)pyridine (760 mg, 2.70 mmol) was combined with TFA (2 mL) in methylene chloride (2 mL) at 0° C., and the solution was stirred for 30 minutes. The volatile components were then removed under vacuum. The residue was basified with saturated aqueous NaHCO$_3$ and extracted with methylene chloride. The organic extract was dried over MgSO$_4$ and concentrated. The residue was chromatographed (silica gel-:methylene chloride:methanol:NH$_4$OH 10:1:0.1) to afford of the free base of the title compound (240 mg, 49%). The base was converted to the dibenzoic acid salt by treatment with benzoic acid in ether to give the title compound (235 mg, 42%): mp 76–80° C.; [α]$_D^{2.9}$ (c 1, MeOH); MS (CI/NH$_3$) m/z 183 (M+H)$^+$; $^1$H NMR (D$_2$O, 300 MHz) δ2.23 (m, $^1$H), 2.34 (m, $^1$H), 3.49(m, $^1$H), 3.66 (m, $^1$H), 4.14 (m, $^1$H), 4.35 (m, $^1$H), 7.12 (dd, J=2.44, 8.81 Hz, $^1$H), 7.45 (m, 4H), 7.56 (m, 2H), 7.63 (m, $^1$H), 7.93 (m, 3H); Anal. Calcd. for C$_9$H$_{11}$N$_2$OF.2 C$_6$H$_5$COOH: C, 64.78 H, 5.44; N, 6.57. Found: C, 64.65; H, 5.48; N, 6.45.

8b. 2-fluoro-5-nitropyridine

2-Chloro-5-nitropyridine (100 g, 0.656 mol, Aldrich), potassium fluoride (84.1 g, 1.45 mol, Aldrich), tetraphenylphosphonium bromide (95.3 g, 0.227 mol, Aldrich), and acetonitrile (1.5 L) were combined and heated at reflux until consumption of the 2-chloro-5-nitropyridine was complete. The volume of the mixture was reduced to 750 mL, diluted with 2 L of ether, filtered and concentrated. The resultant residue was triturated with hot hexane, and the combined hexane extracts were concentrated to give of the title compound (48 g, 54%): $^1$H NMR (CDCl$_3$, 300 MHz) δ7.15 (dd, J=3, 6 Hz, $^1$H), 8.64 (m, $^1$H), 9.15 (d, J=1.6 Hz, $^1$H).

8c. 3-Amino-6-fluoropyridine

2-Fluoro-5-nitropyridine (52.4 g, 368 mmol, from Step 8b above) was combined with 5% Pd/C (100 mg, Aldrich) in EtOH (100 mL) and the mixture was stirred under a $H_2$ atmosphere for 4 days. The mixture was filtered and concentrated. The crude product was chromatographed (silica gel; hexane/EtOAc, 9:1 to 1:1) to give 30.9 g (75%) of the title compound: $^1$H NMR (DMSO-$d_6$, 300 MHz) δ6.74 (dd, J=3, 6 HzH, $^1$H), 7.11 (m, $^1$H), 7.26 (t, J=1 Hz, $^1$H), MS (CI/$NH_3$) m/z 113 (M+H)$^+$, 130 (M+$NH_4$)$^+$.

8d. 3-acetoxy-6-fluoropyridine

A solution of 3-amino-6-fluoropyridine (5.0 g, 45 mmol, from Step 8c above) dissolved in DME (30 mL) was added to a cooled solution (−15° C.) of boron trifluoride etherate (12.2 mL, 99 mmol). tert-Butyl nitrite (6.3 mL, 54 mmol) was then added at a rate which maintained the temperature below 0° C. After 10 minutes at −10° C. the reaction was warmed to 5° C. and stirred for 30 min. Pentane (150 mL) was then added to the reaction mixture, and the resultant solid was collected by suction filtration, washed with cold ether, air dried, and dissolved in acetic anhydride (75 mL). The solution was heated to 105° C. until nitrogen evolution ceased. The solvent was removed in vacuo, and the residue was suspended in saturated aqueous $Na_2CO_3$ (200 mL) and extracted with ethyl ether (2×150 mL). The combined organic extracts were dried ($MgSO_4$) and concentrated. Purification by chromatography (silica gel; hexane/EtOAc, 9:1 to 7:3) afforded the title compound (2.25 g, 33%): $^1$H NMR (CDCl$_3$ 300 MHz) δ2.32 (s, 3H), 6.96 (d, J=3, 9 Hz, $^1$H), 7.59 (m, $^1$H), 8.03 (dd, J=0.5, 1 Hz, $^1$H); MS (CI/$NH_3$) m/z 156 (M+H)$^+$, 171 (M+$NH_4$)$^+$.

8e. 2-Fluoro-5-hydroxypyridine 5-acetoxy-2-fluoropyridine (2.26 g, 14.6 mmol, from step 8d above) was dissolved in 20% aqueous NaOH (15 mL). After stirring at ambient temperature for 1 hour the solution was neutralized by addition of concentrated HCl. The aqueous mixture was extracted with ethyl acetate. The combined organic extracts were dried ($MgSO_4$), and the solvent was evaporated. Purification by chromatography (silica gel; CHCl$_3$/MeOH, 98:2) afforded 1.31 g (79%) of the title compound: MS m/z: 114 (M+H)$^+$, 131 (M+$NH_4$)$^+$; $^1$H NMR (CDCl$_3$, 300 MHz) δ6.84 (dd, J=1.85, 5.14 Hz, $^1$H), 7.43 (m, 1 H), 7.81(t, J=2.84 Hz, $^1$H).

Example 9

5-(2S)-Azetidinylmethyloxy)-2-fluoropyridine dibenzoate

Following the procedures of Example 8, replacing the 1-t-butyloxycarbonyl-2-(R)-azetidinemethanol thereof with 1-t-butyloxycarbonyl-2-(S)-azetidinemethanol, the title compound was prepared: mp 76–80° C.; MS (CI/$NH_3$) m/z 183 (M+H)$^+$; $^1$H NMR (D$_2$O, 300 MHz) δ2.65 (m, 2H), 4.11 (m, 2H), 4.38 (d, J=4.39 Hz 2H), 4.92 (m, $^1$H), 7.09 (dd, J=2.83, 9.28 Hz, $^1$H), 7.50(m, 4H), 7.56 (m, 2H), 7.63 (m, $^1$H), 7.92 (m, 4H). Anal. Calcd for $C_9H_{11}N_2OF.2$ $C_6H_5CO_2H$: C, 64.78; H, 5.44; N, 6.57. Found: C, 64.55; H, 5.46; N, 6.59.

Example 10

5-((2S)-Azetidinylmethyloxy)-3-fluoropyridine dihydrochloride

10a. 5-((2S)-Azetidinylmethyloxy)-3-fluoropyridine dihydrochloride

A solution of 3-fluoro-5-hydroxypyridine (500 mg, 4.43 mmol, as prepared in step 10f below) in dimethylformamide (20 mL) was treated with ground KOH (400 mg, 7.10 mmol) and stirred for 30 minutes at 80° C. To this mixture was rapidly added the 1-(t-butyloxycarbonyl)-(2S)-p-toluenesulfonyloxymethylazetidine (1.05 g, 4.39 mmol, as prepared in Step 10b below) dissolved in dimethylformamide (5 mL) and the reaction mixture was subsequently stirred for 16 h at 80° C. The mixture was concentrated to remove the dimethylformamide and the resultant residue diluted with water and extracted with EtOAc (3×). The organic extracts were combined, dried (MgSO$_4$), filtered and concentrated in vacuo. This material was purified by flash chromatography (silica gel; hexane/EtOAc, 10:1) to give 5-fluoro-3-(1-t-butyloxycarbonyl-(2S)-azetidinylmethoxy)pyridine (692 mg, 56%): $^1$H NMR (CDCl$_3$, 300 MHz) δ1.40 (s, 9H), 2.30 (m, 2H), 3.92 (m, 2H), 4.16 (m, $^1$H), 4.40 (m, $^1$H), 4.54 (m, $^1$H), 7.05 (m, $^1$H), 8.20 (m, 2H); MS (CI/$NH_3$) m/z: 283 (M+H)$^+$. To 5-fluoro-3-(1-Boc-(2S)-azetidinylmethoxy) pyridine from above (320 mg, 1.14 mmol) was added HCl/Et$_2$O in methylene chloride at 0° C., and the solution was stirred for 2 h. The solvent was removed and the residue was recrystallized from EtOH/Et$_2$O to afford the title compound (250 mg): mp 165–167° C.; $[α]_D^{25}$ 27.8 (c 0.56, MeOH); $^1$H NMR (D$_2$O, 300 MHz) δ2.70 (m, 2H), 4.10 (m, 2H), 4.50 (d, J=4.5 Hz, 2H), 5.01 (m, $^1$H), 7.80 (tt, J=3 Hz, $^1$H), 8.42 (dd, J=3, 6 Hz, 2H); MS (CI/$NH_3$) m/z 183 (M+H)$^+$, 200 (M+$NH_4$)$^+$.

10b. (S)-1-t-butyloxycarbonyl-2-toluensulfonyloxymethylazetidine

A solution of(2S)-1-t-butyloxycarbonyl-2-azetidinemethanol (22.6 g, 0.121 mol) in 40 mL of pyridine was treated with p-toluenesulfonyl chloride (27.6 g, 0.145 mol). The resulting mixture was stirred at room temperature for 16 hours, diluted with CH$_2$Cl$_2$ and washed sequentially with 1 N aqueous HCl, H$_2$O, saturated aqueous K$_2$CO$_3$, and brine. The organic phase was dried (Na$_2$SO$_4$) and concentrated. Purification by chromatography (silica gel; Hexane/EtOAc, 80:20) afforded 32.8 g of a white solid which was recrystallized from CH$_2$Cl$_2$/hexane to afford the title compound as thin white needles: mp 59–60° C.; $^1$H NMR (CDCl$_3$, 300 MHz) δ1.37 (s, 9H), 2.15–3.28 (m, 2H), 2.44 (s, 3H), 3.74–3.81 (m, 2H), 4.13 (dd, J=3.1, 10.2 Hz, $^1$H), 4.23–4.34 (m, 2H), 7.35 (d, J=8.1 Hz, 2H), 7.80 (d, J=8.2 Hz, 2H); MS (CI/$NH_3$) m/z: 242 (M+H)$^+$.

10c. 3-benzyloxy-5-bromopyridine

NaH (60% in mineral oil) (40.9 g 1.0225 mol) in 800 mL of DMF was cooled to 0° C., and benzyl alcohol (105 mL 1.014 mol) was added slowly. The reaction mixture was stirred for 1 hour at 20° C., then 3,5-dibromopyridine (200.4 g, 846 mmol) was added and the mixture was stirred for 16 hours. The mixture was quenched with saturated NH$_4$Cl (500 mL), diluted with water and extracted with Et$_2$O. The combined Et$_2$O extracts were washed with 50% brine and dried (MgSO$_4$). The solvent was evaporated in vacuo and the crude product was recrystallized from Et$_2$O to afford the title product (161 g, 72%): mp 63–68° C.; $^1$H NMR (CDCl$_3$, 300 MHz) δ8.37–8.27 (m, 2H), 7.5–7.35 (m, 6H), 5.1 (s, $^1$H); MS (CI/$NH_3$) m/z 264, 266 (M+H)$^+$.

10d. 3-amino-5-benzyloxypyridine

The product of Example 10c above (41.3 g 156 mmol), copper(I) bromide (22.43 g 156 mmol), MeOH (275 mL ), and liquid NH$_3$ (50 mL ) were combined in a stainless steel reactor and heated to 130° C. for 24 hours. The mixture was allowed to cool to ambient temperature, then concentrated.

The residue was suspended in 300 mL of saturated aqueous Na$_2$CO$_3$ and extracted with CH$_2$Cl$_2$. The combined CH$_2$Cl$_2$ solutions were washed with brine, dried (MgSO$_4$), and concentrated. The crude product was chromatographed (silica gel; hexane/EtOAc, 9:1 to 7:3) to afford the title compound (15.6 g, 50%): $^1$H NMR (CDCl$_3$, 300 MHz) δ: 8.21–8.29 (m, 2H), 7.44–1.26 (m, 6H), 5.10 (s, 2H); MS (CI/NH$_3$) m/z 201 (M+H)$^+$.

10e. 3-fluoro-5-benzyloxypyridine

To boron trifluoride etherate (9.3 mL, 75 mmol) cooled to −15° C. under N$_2$ was added the product of Example 10d (10 g, 50 mmol) dissolved in DME (100 mL). tert-Butyl nitrite (7.8 mL, 65 mmol) was added at a rate which kept the temperature below −5° C. After 10 minutes at −10° C. the reaction was warmed to 5° C. and stirred for 30 minutes. Pentane (200 mL) was then added to the reaction mixture, and the solid was collected by suction filtration, washed with cold ether, and then dissolved in acetic anhydride (150 mL). The resulting solution was heated to 70° C. until N$_2$ evolution stopped. The solvent was removed in vacuo, and the residue was suspended in saturated aqueous Na$_2$CO$_3$ and extracted with diethyl ether. The ether solution was dried (Na$_2$SO$_4$) and concentrated. The crude product was chromatographed (silica gel; hexane/EtOAc, 6:1) to yield 2.0 g of the title compound: $^1$H NMR (CDCl$_3$, 300 MHz) δ: 5.17 (s, 2H), 7.04 (tt, J=3 Hz, $^1$H), 7.41(m, 5H), 8.15 (d, J=3 Hz, $^1$H), 8.25 (d, J=3 Hz, $^1$H); MS (CI/NH$_3$) mn/z 204 (M+H)$^+$, 221 (M+NH$_4$)$^+$.

10f 3-fluoro-5-hydroxypyridine

The product of Example 10e (2.0 g, 9.85 mmol) in MeOH (50 mL) was stirred under an atmosphere of H$_2$ in the presence of 10% Pd/C (50 mg) for 4 hours. The mixture was filtered and concentrated to afford 1.1 g (93%) of the title compound as white solid: $^1$H NMR (300 MHz) δ: 7.78 (tt, J=3 Hz, $^1$H), 8.38 (d, J=3 Hz, $^1$H), 8.56 (d, J=3 Hz, $^1$H), 10.72 (b, $^1$H); MS (CI/NH$_3$) m/z 114 (M+H)$^+$, 131 (M+NH$_4$)$^+$.

Example 11

5-((2R)-Azetidinylmethyloxy)-3-fluoropyridine dibenzoate

The procedure of Example 10a was followed, replacing the 1-t-butyloxycarbonyl-2(S)-p-toluensulfonyloxymethylazetidine with the corresponding (R) isomer (Example 1c) to give the free amine compound (65%): $^1$H NMR (CDCl3, 300 MHz) δ: 1.42 (s, 9H), 2.30 (m, 2H), 3.92 (m, 2H), 4.16 (dd, J=3 Hz, $^1$H), 4.38 (m, $^1$H), 4.58 (m, $^1$H), 7.05 (tt, J=3 Hz, $^1$H), 8.20 (dd, J=3 Hz, 2H); MS (CI/NH3) m/z 283 (M+H)$^+$. To 5-(N-Boc-(2R)-azetidinylmethyloxy)-3-fluoropyridine from above (692 mg, 2.45 mmol) was added HCl/Et$_2$O in methylene chloride at 0° C., and the solution was stirred for 2 hours. The solvent was removed and the residue was recrystallized from EtOH/Et$_2$O to afford the title compound (365 mg): mp 163–165° C.; [α]$_D^{25}$ −30.0 (c 0.51, MeOH); $^1$H NMR (D$_2$O, 300 MHz) δ2.72 (m, 2H), 4.15 (m, 2H), 4.52 (d, J=4.5 Hz, 2H), 4.98 (m, $^1$H), 7.40 (d, J=12 Hz, $^1$H), 8.42 (b, 2H); MS (CI/NH$_3$) m/z 183 (M+H)$^+$, 200 (M+NH4)$^+$. Anal. Calcd for C$_9$H$_{12}$FClN$_2$O.0.3HCl: C, 47.08; H, 5.40; N, 12.20. Found: C, 47.25; H, 4.90; N, 12.04.

Example 12

5-((2S)-Azetidinylmethyloxy)-3-bromopyridine dihydrochloride 12a. 5-((2S)-Azetidinylmethyloxy)-3-bromopyridine dibenzoate Triphenylphosphine (4.01 g, 15.3 mmol) and DEAD (2.43 mL, 15.3 mmol) were dissolved in 30 mL of THF at 0° C., and the mixture was stirred for 10 minutes. Samples of 1-t-butyloxycarbonyl-2-(S)-azetidinemethanol (2.86 g, 15.3 mmol, Step 7c above) and 3-bromo-5-hydroxypyridine. (1.51 g, 10.2 mmol, Step 10c above) were added, and the mixture was stirred for 40 hours at room temperature. The volatile components were removed under vacuum, and the residue was triturated with hexane. The separated hexane fraction was concentrated, and the residue was chromatographed (silica gel; hexane/ether, 10:1 to 10:2) to afford 5-bromo-3-((1-t-butyloxycarbonyl-(2S)-azetidinyl)methoxy)pyridine as a colorless oil (1.669 g): $^1$H NMR (CDCl$_3$, 300 MHz) δ1.42 (s, 9H), 2.31 (m, 2H), 3.89 (m, 2H), 4.12 (m, $^1$H), 4.322 (m, $^1$H), 4.52 (m, $^1$H), 7.43 (m, $^1$H), 8.29 (m, 2H); MS (CI/NH$_3$) m/z 344 (M+H)$^+$. The 5-bromo-3-(2-(1-BOC-2-(S)-azetidinyl)methoxy)pyridine was treated with with 4 M HCl in dioxane to give the free base of the title compound. This was converted to the dihydrochloride salt and recrystallized from methanol/ether to provide the title compound: mp 163–165° C.; [α]$^{25}_D$ −5.1 (c 0.57, methanol); $^1$H NMR (D$_2$O, 300 MHz) δ8.36 (d, J=1.8 Hz, $^1$H), 8.32 (d, J=2.6 Hz, $^1$H), 7.84 (dd, J=1.8, 2.6 Hz, $^1$H), 4.98–4.90 (m, $^1$H), 4.43 (d, J=4.0 Hz, 2H), 4.20–4.02 (m, 2H), 2.67 (q, J=8.5 Hz, 2H); MS (CI/NH$_3$) m/z 243/246 (M+H)$^+$, 260/262 (M+NH$_4$)$^+$. Anal. calcd for C$_9$H$_{13}$N$_2$OBrCl$_2$: C, 34.21; H, 4.15; N, 8.86. Found: C, 34.18; H, 4.17; N, 8.89.

12b. 3-Bromo-5-hydroxypyridine

3-Benzyloxy-5-bromopyridine from Example 10c was heated at reflux with 48% HBr/HOAc (60 mL) for 16 hours. The reaction was quenched with excess NaHCO$_3$, the basic mixture was extracted with ethyl acetate, and the extract was dried over Na$_2$SO$_4$. The solvent was removed, and the residue was chromatographed (silica gel; MeOH/CCl$_4$, 1/10) to afford the title compound: $^1$H NMR (CDCl$_3$, 300 MHz) δ8.27 (d, J=1.8 Hz, $^1$H), 8.23 (d, J=2.6 Hz, $^1$H), 7.44 (dd, J=1.8, 2.6 Hz, $^1$H); MS (CI/NH3) m/z 174, 176 (M+H)$^+$, 191, 193 (M+NH$_4$)$^+$.

Example 13

5-Methyl-3-((2S)-Azetidinylmethyloxy)pyridine dibenzoate

To a solution of 5-bromo-3-(1-t-butyloxycarbonyl-(2S)-azetidinylmethoxy)pyridine (400 mg, 1.20 mmol, Step 12a above) in THF (10 mL) at 0° C. was added a catalytic amount of [1,3-bis(diphenylphosphino)-propane]nickel(II) chloride (3.8 mg) followed by MeMgBr (0.8 mL of a 3.0 M solution in THF, Aldrich). The mixture was refluxed for 3 hours, cooled to ambient temperature, and quenched with saturated aqueous ammonium chloride. The volatile components were evaporated and the residue was diluted with CH$_2$Cl$_2$ and saturated aqueous ammonium chloride. The organic extract was dried over MgSO$_4$ and concentrated. The residue was chromatographed (silica gel; CH$_2$Cl$_2$/MeOH, 10:0.2 to 10:0.5) to afford the 5-methyl-3-(1-t-butyloxycarbonyl-(2S)-azetidinylmethyloxy)pyridine as an oil (177 mg, 53%): $^1$H NMR (CDCl$_3$, 300 MHz) δ1.42 (s, 9H), 2.20–2.40 (m, 2H), 3.90 (t, J=8.33 Hz, 2H), 4.14 (m, $^1$H), 4.31 (m, $^1$H), 4.51 (m, $^1$H), 7.04 (s, $^1$H), 8.06 (s, $^1$H), 8.18 (d, J=3.33 Hz, $^1$H); MS (CI/NH$_3$) m/z 279 (M+H)$^+$. To a solution of the above product (170 mg, 0.6 mmol) in CH$_2$Cl$_2$ (2 mL) at 0° C. was added TFA (1.0 mL). After stirring for 30 minutes the solution was basified with 15% aqueous NaOH and extracted with CH$_2$Cl$_2$. The combined organic extracts were dried over MgSO4 and concentrated. The crude product was chromatographed (silica gel;

CH$_2$Cl$_2$/MeOH, 10:1) to afford 5-methyl-3-(azetidinyl-(2S)-methoxyl)pyridine as an oil (93 mg, 64%): $^1$H NMR (CDCl$_3$, 300 MHz) δ2.28 (m, $^1$H), 2.36 (s, 3H), 2.39 (m, $^1$H), 3.43 (m, $^1$H), 3.65 (q, J=3.33 Hz, $^1$H), 3.98–4.02 (m, 2H), 4.22 (m, $^1$H), 7.12(m, $^1$H), 8.04 (s, $^1$H), 8.14 (d, J=3.33 Hz, $^1$H); MS (CI/NH$_3$) m/z: 179 (M+H)$^+$. The above product was slurried in Et$_2$O and HCl in Et$_2$O was added dropwise. The solvent was removed and the resultant solid was recrystallized from MeOH/Et$_2$O to afford the title compound as a light yellow, very hygroscopic solid: $^1$H NMR (D$_2$O, 300 MHz) δ2.36 (s, 3H), 2.67 (q, J=8.33 Hz, 2H), 4.04–4.21 (m, 2H), 4.40 (d, J=3.40 Hz, 2H), 4.90 (m, $^1$H), 7.40 (s, $^1$H), 8.04 (s, $^1$H), 8.14 (s, $^1$H). MS (CI/NH3) m/z: 179 (M+H+)$^+$. Anal. Calcd. for C$_{10}$H$_{14}$N$_2$O.1.5HCl: C, 51.57; H, 6.71; N, 12.03. Found: C, 51.53; H, 6.86; N, 12.03.

Example 14

5-Methyl-3-((2R)-azetidinylmethyloxy)pyridine hydrochloride

Following the procedures of Example 12a, replacing the 1-t-butyloxycarbonyl-(2S)-azetidinemethanol thereof with 1-t-butyloxycarbonyl(2R)-azetidinemethanol (from Example 1d), 5-bromo-3-(1-t-butyloxycarbonyl-(2R)-azetidinylmethoxy)pyridine was prepared. Following the procedures of Example 13, replacing 5-bromo-3-(1-t-butyloxycarbonyl-(2S)-azetidinylmethoxy)pyridine thereof with the enantiomeric 5-bromo-3-(1-t-butyloxycarbonyl-(2R)-azetidinylmethoxy)pyridine, the title compound was prepared as a white solid: [α]$_D$ –5.38 (c 0.93, MeOH); $^1$H NMR (D$_2$O) δ2.40 (s, 3H), 2.70 (q, 2H, J=9.30 Hz), 4.04–4.20 (m, 2H), 4.42 (d, 2H, J=5.0 Hz), 4.95–5.00 (m, $^1$H), 7.45 (s, $^1$H), 8.08 (s, $^1$H), 8.15 (s, $^1$H); MS (CI/NH3): m/z 179 (M+H$^+$), 196 (M+NH$_4^+$). Anal. Calcd for C$_{10}$H$_{14}$N$_2$O.1.5 HCl: C, 51.57; H, 6.71; N, 12.03. Found: C, 51.53; H, 6.86; N, 12.03.

Example 15

5-((2S)-azetidinylmethoxy)-2,3-dichloropyridine hydrochloride

15a. 5-((2S)-azetidinylmethoxy)-2,3-dichloropyridine hydrochloride

A solution of triphenylphosphine (2.6 g, 9.94 mmol) and diethyl azodicarboxylate (1.6 mL, 9.94 mmol) in THF (16 mL) was stirred at 0° C. for 15 minutes. 1-t-Butyloxycarbonyl-2-(S)-azetidinemethanol (1.55 g, 8.28 mmol, from step 7c above) and 5,6-dichloro-3-pyridinol (1.5 g, 9.1 mmol) were then added. The reaction mixture was allowed to warm slowly to room temperature and stir overnight. The solvent was removed, and the residue was redissolved in methylene chloride. The solution was washed with saturated aqueous K$_2$CO$_3$ and brine, dried over MgSO$_4$ and concentrated. The residue was chromatographed (silica gel; ethyl acetate:hexane, 1:5) to afford the 5,6-dichloro-3-(1-t-butyloxycarbonyl-2-(S)-azetidinylmethoxy)pyridine (1.08 g): MS (CI/NH$_3$) m/z 333 (M+H)$^+$; $^1$H NMR (CDCl$_3$, 300 MHz) δ1.42 (s, 9H), 2.22–2.42 (m, 2H), 3.85–3.92 (m, 2H), 4.12 (dd, J=2.7, 10.1 Hz, $^1$H), 4.30–4.40 (m, $^1$H), 4.48–4.56 (m, $^1$H), 7.41 (d, J=2.8 Hz, $^1$H), 7.97 (d, J=2.8 Hz, $^1$H). To a solution of 5,6-dichloro-3-(1-t-butyloxycarbonyl-2-(S)-azetidinylmethoxy)-pyridine (1.06 g, 3.11 mmol) in CH$_2$Cl$_2$ (10 mL) at 0° C. was added TFA (10 mL). The solution was allowed to warm to room temperature while stirring for 45 minutes. The volatile components were then removed under vacuum. The residue was treated with saturated K$_2$CO$_3$ solution, then extracted with methylene chloride. The organic extract was dried over MgSO$_4$ and concentrated. The residue was chromatographed (silica gel; MeOH/CHCl$_3$/NH$_4$OH, 1:10:0 to 1:10:0.05) to afford the free base of the title compound (475 mg, 64% yield): mp 59–60° C.; MS (CI/NH$_3$) m/z 233 (M+H)$^+$; $^1$H NMR (CDCl$_3$, 300 MHz) δ2.21–2.44 (m, 2H), 3.45 (m, $^1$H), 3.73 (dd, J=8.4, 15.8 Hz, $^1$H), 3.98–4.08 (m, 2H), 4.28 (m, $^1$H), 7.37 (d, J=2.8 Hz, $^1$H), 8.01 (d, J=2.8 Hz, $^1$H). The base (336 mg) was slurried in ether and converted to the hydrochloride salt by treatment with saturated HCl in ether. Recrystallization from methanol/ether gave the title compound (317 mg, 81% yield): mp 181–182° C.; MS (CI/NH$_3$) m/z 233 (M+H)$^+$; $^1$H NMR (D$_2$O, 300 MHz) δ2.65–2.74 (m, 2H), 4.03–4.21 (m, 2H), 4.44 (d, J=4.4 Hz, $^1$H), 4.95 (m, $^1$H), 7.79 (d, J=2.9 Hz, $^1$H), 8.13 (d, J=2.9 Hz, $^1$H). Anal. Calcd. for C$_9$H$_{11}$N$_2$OCl$_2$.1.0 HCl: C, 40.10; H, 4.11; N, 10.39. Found: C, 39.89; H, 4.08; N, 10.25.

15b. 5-amino-2,3-dichloropyridine

The procedure of Koch and Schnatterer, Synthesis,1990, 499–501 was followed. To 2-hydroxy-5-nitropyridine (70.0 g, 0.5 mol) in 12 N hydrochloric acid was added dropwise a solution of potassium chlorate (21.4 g, 0.18 mol) in H$_2$O (300 mL) at a rate such that the temperature remained ≦60° C. The mixture was allowed to stir for a further 30 minutes at ca. 50° C., then allowed to cool to ambient temperature, then was further cooled in an ice bath. The yellow solid was collected by filtration, washed with cold H$_2$O, and dried under vacuum at 50° C. to afford 3-chloro-2-hydroxy-5-nitropyridine (72.4 g, 83%) as a yellow powder. To phosphorus oxychloride (37.4 mL, 0.4 mol) at 0° C. was added quinoline (23.6 mL, 0.2 mol), followed by 3-chloro-2-hydroxy-5-nitropyridine (70 g, 0.4 mol) from above. The mixture was heated at 120° C. for 2.5 hours, during which time it became a dark liquid. After cooling to 100° C., H$_2$O (150 mL) was added cautiously, and the mixture was cooled to 0° C. The precipitated solid was collected by filtration, washed with cold H$_2$O, and dried under vacuum at 50° C. to afford 2,3-dichloro-5-nitropyridine (68.6 g, 89%). To 2,3-dichloro-5-nitropyridine (68.5 g, 0.39 mol) in a mixture of H$_2$O (800 mL) and acetic acid (160 mL) were added bits of metallic iron with stirring until the starting material was consumed (TLC analysis). The mixture was filtered, and the filter cake was washed repeatedly with EtOAc. The aqueous filtrate was extracted with EtOAc and the organic fractions were combined and concentrated. The residue was chromatographed (silica gel; MeOH: CHCl$_3$, 0.5:99.5 to 1:99) to afford the title compound (44.5 g, 70%) as a light orange powder: MS (CI/NH$_3$) m/z 163 and 165 (M+H$^+$), 180 and 182 (M+NH$_4$)$^+$.

15c. 5-acetoxy-2,3-dichloropyridine

To a flask containing boron trifluoride etherate (11.3 mL, 91.9 mmol) at –15° C. was added dropwise a solution of the compound of Example 15b (10.0 g, 61.3 mmol) in dimethoxyethane (20 mL). Then a solution of t-butyl nitrite (8.7 mL, 73.5 mmol) in dimethoxyethane (61 mL) was added at such a rate that the internal temperature remained –5° C. The mixture was stirred at about 5° C. for 0.75 hours, then pentane (200 mL) was added. The mixture was filtered and the filter cake was washed with cold diethyl ether, then allowed to dry to afford 15.0 g of a light orange solid. This material was heated gradually to 70° C. in the presence of acetic anhydride and held at this temperature until gas evolution ceased, and then for an addition 0.5 hour. The mixture was allowed to cool to ambient temperature, concentrated in vacuo then diluted with diethyl ether. The solution was washed with H$_2$O, then the organic phase was dried (MgSO$_4$) and concentrated. The residue was chromatographed (silica gel; ethyl acetate:hexane, 1:9) to afford the title compound (9.2 g, 73%) as a clear yellow oil: MS (CI/NH$_3$) 206 and 208 (M+H$^+$).

15d. 5,6-dichloro-3-pyridinol

The product of Example 15c (9.15 g, 44.4 mmol) was treated with 2 N potassium hydroxide solution (67 mL, 133 mmol), and the mixture was stirred for 18 hours. The mixture was diluted with H$_2$O and treated with acetic acid to pH 6–7. The solid precipate was collected by filtration and washed with H$_2$O, then dried at 50° C. to afford 5.4 g (94%) of the title compound as a white solid: MS (CI/NH$_3$) 164, 166, 168 (M+H$^+$).

Example 16

5-((2R)-azetidinylmethoxy)-2,3-dichloropyridine hydrochloride

Following the procedures of Example 15a, replacing the 1-BOC-(2s)-azetidinemethanol thereof with 1-t-butyloxycarbonyl-(2R)-azetidinemethanol (3 mmol) (from Step 1d), the title compound was prepared (212 mg, 83% yield): mp 166–168° C.; [α]$^{25}_D$ 9.5 (c 0.55, MeOH); MS (CI/NH$_3$) m/z 233, 235, 237 (M+H)$^+$; $^1$H NMR (D$_2$O, 300 MHz) δ2.65–2.74 (m, 2H), 4.03–4.20 (m, 2H), 4.44 (d, J=4.4 Hz, 1H), 4.91–5.00 (m, 1H), 7.79 (d, J=2.7 Hz, 1H), 8.13 (d, J=2.7 Hz, 1H). Anal. Calcd. for C$_9$H$_{11}$N$_2$OCl$_2$.1.0 HCl: C, 40.10; H, 4.11; N, 10.39. Found: C, 40.01; H, 4.02; N, 10.33.

Example 17

5-((2S)-azetidinylmethoxy)-3-bromo-2-chloropyridine hydrochloride

To a solution of diethyl azodicarboxylate (1.52 mL, 9.6 mmol) in THF (56 mL) was added triphenylphosphine (2.52 g, 9.6 mmol) at 0° C., and the reaction mixture was stirred for 0.5 hour. 1-t-butyloxycarbonyl-(2S)-azetidinemethanol (1.44 g, 7.7 mmol, Step 7c) and 5-bromo-6-chloropyridin-3-ol (1.4 g, 6.4 mmol; prepared from 2-hydroxy-5-nitropyridine according to V. Koch and S. Schnatterer, Synthesis 1990, 499–501) were then added. The reaction mixture was allowed to warm slowly to room temperature and stirred overnight. Solvent was removed, and the residue was chromatographed (silica gel; chloroform:methanol, 100:1) to afford 5-bromo-6-chloro-3-(1-t-butyloxycarbonyl-2-(S)-azetidinylmethoxy)pyridine: MS (CI/NH$_3$) m/z 377, 379 (M+H)$^+$. To a solution of the product from above (360 mg, 0.95 mmol) in methylene chloride at 0° C. was added TFA, and the mixture was stirred for 30 minutes. The volatile components were then removed under vacuum. The residue was neutralized with NaHCO$_3$, then extracted with methylene chloride, which was dried over MgSO$_4$ and concentrated. The residue was chromatographed (silica gel; methylene chloride:methanol:NH$_4$OH, 10:1:0.1) to afford to give the free base of the title compound. The base was converted to the salt by treatment with hydrogen chloride in ether to give the title compound (224 mg): mp 168–169° C.; [α]$_D^{25}$ −4.81 (c 0.13, MeOH); $^1$H NMR (D$_2$O, 300 MHz) δ2.69 (dd, J=7.0, 8.5, 2H), 4.06–4.20 (m, 3H), 4.43 (d, J=4.5, 2H), 4.95 (m, 1H), 7.94 (d, J=3.0, 1H), 8.17 (d, J=3.0, 1H); MS (CI/NH$_3$) m/z 277, 279 (M+H)$^+$. Anal. Calcd for C$_9$H$_{10}$N$_2$OBrCl.0.9 HCl: C, 34.83; H, 3.54; N, 9.03. Found: C, 34.85; H, 3.56; N, 8.82.

Example 18

5-((2R)-azetidinylmethoxy)-3-bromo-2-chloropyridine hydrochloride

A solution of triphenylphosphine (1.10 g, 4.20 mmol) and diethyl azodicarboxylate (0.65 mL, 4.2 mmol) in THF (10 mL) was stirred at 0° C. for 0.5 hours followed by addition of a solution containing (R)-azetidinol (0.6 g, 3.2 mmol, from Step 1d above) and 5-bromo-6-chloropyridin-3-ol (0.80 g, 3.8 mmol, prepared as described in Example 17) in THF (5 mL). The mixture was warmed to room temperature over 24 hours, then concentrated. The residue was triturated with a mixture of hexane/Et$_2$O and filtered to remove the triphenylphosphine oxide. The filtrate was concentrated, and the crude product was chromatographed (silica gel; hexane/EtOAc, 60:40) to give the 5-(1-t-butyloxycarbonyl-(2R)-azetidinylmethoxy)-3-bromo-2-chloropyridine as an oil (1.10 g, 91%). The product from above was then dissolved in CH$_2$Cl$_2$ (30 mL) and cooled at 0° C. TFA (excess) was added and the mixture was warmed to room temperature over 1 hour. The solution was then concentrated, and saturated Na$_2$CO$_3$ solution (30 mL) was added followed by extraction with EtOAc and CH$_2$Cl$_2$. The combined organic extracts were dried (Na$_2$SO$_4$), and concentrated to give the free base of the title compound (0.83 g, 100%). A solution containing the free base (0.34 g, 1.2 mmol) was dissolved in CH$_2$Cl$_2$ (10 mL) and cooled to 0° C. followed by dropwise addition of a solution of HCl in Et$_2$O until the mixture became cloudy. The solvent was removed and the product was recrystallized from EtOH/CH$_2$Cl$_2$/Et$_2$O to afford the title compound as a white solid (0.34 g, 81%): mp 175° C.; [α]$_D^{23}$ 7.2 (c 0.5, MeOH); $^1$H NMR (D$_2$O, 300 MHz) δ2.65–2.73 (q, 2H), 4.03–4.20 (m, 2H), 4.43 (d, J=4.2 Hz, 2H), 4.92–4.98 (m, 1H), 7.93 (d, J=2.7 Hz, 1H), 8.17 (d, J=2.7 Hz, 1H); MS (CI/NH$_3$) m/z: 277 (M+H)$^+$; Anal. Calcd for C$_9$H$_{11}$Cl$_2$BrN$_2$O.0.1 H$_2$O: C, 34.23; H, 3.57; N, 8.87. Found: C, 34.26; H, 3.36; N, 8.68.

Example 19

5-((2S)-Azetidinylmethyloxy)-2-chloropyridine dihydrochloride

A 950 mg (5.1 mmol) sample of 1-t-butyloxycarbonyl-2-(S)-azetidinemethanol, prepared as in Example 7c above, and 550 mg (4.25 mmol) of 2-chloro-5-hydroxypyridine (Example 1g above) were added to a solution of triphenylphosphine and DEAD (5.1 mmol each) in 20 mL of THF, according to the procedure of Example 12a, to give 1.09 g of 3-(1-t-butyloxycarbonyl-(2S)-azetidinylmethoxy)-6-chloropyridine: [α]$_D^{25}$ −67.3 (c1.1, CHCl$_3$); $^1$H NMR (DMSO-d$_6$, 300 MHz) δ8.14 (d, J=3.3 Hz, 1H), 7.48 (dd, J=8.8, 3.3 Hz, 1H), 7.37 (d, J=8.8 Hz, 1H), 4.47–4.42 (m, 1H), 4.36 (dd, J=11.0, 4.4 Hz, 1H), 4.20 (dd, J=11.0, 3.3 Hz, 1H), 3.77 (t, J=7.7 Hz, 2H), 2.36–2.29 (m, 1H), 2.19–2.12 (m, 1H), 1.36 (s, 9H); MS (CI/NH$_3$) m/z: 299/301 (M+H)$^+$. A portion of this material (1.02 g) was stirred with 10 mL of 4.5 N HCl at room temperature for 30 minutes. The solvent was removed, and the residue was recrystallized from methanol/ether, to afford 340 mg of the title compound: mp 113–115° C.; $^1$H NMR (D$_2$O, 300 MHz) δ: 8.15 (d, J=3.0 Hz, 1H), 7.57 (dd, J=8.9, 3.0 Hz, 1H), 7.47 (d, J=8.9 Hz, 1H), 4.98–4.89 (m, 1H), 4.42 (d, J=4.4 Hz, 2H), 4.19–4.02 (m, 2H), 2.68 (q, J=8.5 Hz, 2H); MS (CI/NH$_3$) m/z: 299/301 (M+H)$^+$. Anal. Calcd for C$_9$H$_{13}$N$_2$OCl$_3$: C, 39.80; H, 4.82; N, 10.32; Found C, 40.12; H, 4.84; N, 10.35.

Example 20

5-((2S)-Azetidinylmethyloxy)-2-methylpyridine dihydrochloride

An ice-cooled solution of the compound from Example 7c (0.232 g, 1.24 mmol) was allowed to react with 5-hydroxy-2-methylpyridine (Aldrich, 0.142 g, 1.30 mmol) under the conditions of Example 15a, to yield the 2-methyl-5-(1-t-butoxycarbonyl-(2S)-azetidinylmethoxy)pyridine (0.123 g, 36%) after purification on silica gel (ethyl acetate/hexane 2:1): MS (CI/NH$_3$) m/z: 279 (M+H)$^+$; $^1$H NMR (CDCl$_3$, 300 MHz) δ8.22 (d, J=2.6 Hz, $^1$H), 7.20 (dd, J=8.5, 3.0 Hz, $^1$H), 7.08 (d, J=8.5 Hz, $^1$H), 4.50 (m, $^1$H), 4.29 (m, $^1$H), 4.13 (dd, J=9.9, 2.9 Hz, $^1$H), 3.89 (t, J=7.75 Hz, 2H), 2.51 (s, 3H), 2.37–2.28 (m, 2H), 1.41 (s, 9H). This material (0.12 g, 0.44 mmol) was treated with saturated ethanolic HCl (5 mL) for 18 h. The volatiles were removed in vacuo, and the solid was washed with Et$_2$O, evaporated to dryness and recrystallized (EtOH/Et$_2$O) to yield the title compound (0.074 g, 63%) as a white solid: mp 141–144° C.; [α]$_D^{24}$ −7.89 (c 0.19, MeOH); MS (CI/NH$_3$) m/z: 179 (M+H)$^+$; $^1$H NMR (D$_2$O, 300 MHz) δ8.33 (d, J=2.9 Hz, $^1$H), 7.89 (dd, J=9.0, 2.8 Hz, $^1$H), 7.64 (d J=8.8 Hz, $^1$H), 4.97 (m, $^1$H), 4.48 (d, J=4.4 Hz, 2H), 4.21–4.04 (m, 2H), 2.70 (q, J=8.5 Hz, 2H), 2.62 (s, 3H); Anal. calcd for C$_{10}$H$_{16}$Cl$_2$N$_2$O.H$_2$O: C, 44.62; H, 6.74; N, 10.41. Found: C, 44.55; H, 7.02; N, 10.50.

Example 21

5-((2S)-Azetidinylmethyloxy)-3-chloropyridine dihydrochloride

An ice-cooled solution of the compound from Example 7c (0.242 g, 1.20 mmol) was allowed to react with 3-chloro-5-hydroxypyridine (0.187 g, 1.40 mmol) under the conditions of Example 15a, to afford 5-((1-t-butyloxycarbonyl-2-(S)-azetidinyl)methoxy)-3-chloropyridine (0.137 g, 88%) after purification by chromatography (silica gel; ethyl acetate/hexane, 2:1): MS (CI/NH$_3$) m/z: 299 (M+H)$^+$; $^1$H NMR (CDCl$_3$, 300 MHz) δ8.25 (d, J=1.38 Hz, $^1$H), 8.21 (br. s, $^1$H), 7.29 (t, J=2.2 Hz, $^1$H), 4.52 (m, $^1$H), 4.34 (m, $^1$H), 4.13 (dd, J=10.3, 2.9 Hz, $^1$H), 3.91–3.86 (m, 2H), 2.51 (s, 3H), 2.38–2.29 (m, 2H), 1.43 (s, 9H). A portion of this material (0.13 g, 0.44 mmol) was treated with saturated ethanolic HCl (5 mL) for 16 h. The volatiles were removed in vacuo, and the solid was recrystallized (EtOH/Et$_2$O) to afford the title compound (0.094 g, 80%) as a white solid: mp 156–157° C.; [α]$_D^{23}$ −3.23 (c 0.16, MeOH); MS (CI/NH$_3$) m/z: 199 (M+H)$^+$, 216 (M+NH$_4$)$^+$; $^1$H NMR (D$_2$O, 300 MHz) δ8.41 (d, J=5.1 Hz, $^1$H), 8.39 (d, J=4.4 Hz, $^1$H), 7.94 (t, J=2.1 Hz, $^1$H), 4.97 (m, $^1$H), 4.50 (d, J=4.0 Hz, 2H), 4.20–4.03 (m, 2H), 2.69 (q, J=8.45 Hz, 2H); Anal. calcd for C$_9$H$_{13}$Cl$_3$N$_2$O.0.5 H$_2$O: C, 38.53; H, 5.03; N, 9.98. Found: C, 38.51; H, 5.16; N, 9.96.

Example 22

5-Vinyl-3-((2S)-Azetidinylmethyloxy)lpyridine dihydrochloride

5-Bromo-3-(2-(1-t-butyloxycarbonyl-2-(S)-azetidinyl)methoxy)pyridine (1.37 g, 3.99 mmol, Step 12a above) in toluene (30 mL) was mixed with vinyltributyltin (1.44 mL, 4.79 mmol, Aldrich), tetrakis(triphenylphosphine)palladium (0) (140 mg, 0.200 mmol). The mixture was stirred at 100° C. overnight, cooled to ambient temperature, then the volatile components were removed in vacuo. Purification by chromatography (silica gel; hexane/EtOAc, 5:1 to 1:1) afforded the vinyl-substituted pyridine as an oil (1.06 g, 92%): MS (CI/NH$_3$) m/z: 291(M+H)$^+$; $^1$H NMR (CDCl$_3$, 300 MHz) δ1.40 (s, 9H), 2.30–2.42 (m, 2H), 3.87 (t, J=7.72 Hz, 2H), 4.11 (dd, J=2.94, 9.92 Hz, $^1$H), 4.35 (m, $^1$H), 4.53 (m, $^1$H), 5.80 (d, J=12.67 Hz, $^1$H), 5.83 (d, J=19.33 Hz, $^1$H), 6.68 (dd, J=12.67, 19.33 Hz, $^1$H), 7.29 (t, J=2.67 Hz, $^1$H), 8.24 (d, J=3.30 Hz, $^1$H). A portion of this material (191 mg, 0.66 nmol) was dissolved in CH$_2$Cl$_2$ (2 mL) at 0° C. and TFA (1.8 mL) was added. After stirring for 30 min, the solution was basified with 15% aqueous NaOH and extracted with CH$_2$Cl$_2$. The combined organic extracts were dried over MgSO$_4$ and concentrated. Purification by chromatography (silica gel; CH$_2$Cl$_2$/MeOH/NH$_4$OH, 10:0.4 to 10:1:0.3) afforded the free amine of the title compound as an oil (101 mg, 81%)L: MS (CI/NH$_3$) m/z: 191 (M+H)$^+$; $^1$H NMR (CDCl$_3$, 300 MHz) δ2.44–2.56 (m, 2H), 3.72 (m, $^1$H), 3.88 (m, $^1$H), 4.16 (m, 2H), 4.54 (m, $^1$H), 5.40 (d, J=11.03 Hz, $^1$H), 5.82 (d, J=17.65 Hz, $^1$H), 6.66 (dd, J=11.0, 17.65 Hz, $^1$H), 7.26 (m, $^1$H), 8.18 (d, J=3.33 Hz, $^1$H), 8.22 (d, J=1.67 Hz, $^1$H). The amine was slurried in Et$_2$O and a solution of 1.0 M HCl in Et$_2$O was added dropwise. The solvent was removed and the product was recrystallized from MeOH/Et$_2$O to afford a the title compound a yellow hygroscopic powder: mp 88–90° C.; [α]$_D^{23}$ +2.58° (c 0.62, MeOH); MS (CI/NH$_3$) m/z: 191 (M+H+)$^+$; $^1$H NMR (D$_2$O, 300 MHz) δ2.64–2.76 (m, 2H), 4.04–4.20 (m, 2H), 4.49 (d, J=4.1 Hz, 2H), 4.96 (m, $^1$H), 5.58 (d, J=11.0 Hz, $^1$H), 6.04 (d, J=17.7 Hz, $^1$H), 6.83 (dd, J=11.0, J=17.7 Hz, $^1$H), 7.85 (t, J=1.9 Hz, 1H), 8.33 (d, J=14.3 Hz, $^1$H); Anal. Calcd for C$_{11}$H$_{14}$N$_2$O.1.8 HCl: C, 51.64; H, 6.22; N, 10.95. Found: C, 51.59; H, 5.92; N, 10.75.

Example 23

5-Ethyl-3-((2S)-Azetidinylmethyloxy)lpyridine hydrochloride 5-(N-t-Butyloxycarbonyl-(2S)-azetidinylmethoxy)-3-bromopyridine (1.37 g, 3.99 mmol, Example 12a above) in toluene (30 mL) was mixed with vinyltributyltin (1.44 mL, 4.79 mmol), tetrakis(triphenylphosphine)palladium(0) (140 mg, 0.20 mmol). The reaction mixture was stirred at 100° C. for 16 hours. Solvent was removed under reduced pressure and the resultant residue was chromatographed (silica gel; hexane/EtOAc, 5:1 to 1:1) to afford 3-vinyl-5-(N-t-butyloxycarbonyl-(S)-azetidinyl-2-methoxy)pyridine as an oil (1.06 g, 92%): MS (CI/NH$_3$) m/z: 291(M+H)$^+$; $^1$H NMR (CDCl$_3$, 300 MHz) δ1.40 (s, 9H), 2.30–2.42 (m, 2H), 3.87 (t, J=7.7 Hz, 2H), 4.11 (dd, J=2.9, 9.9 Hz, $^1$H), 4.35 (m, $^1$H), 4.53 (m, $^1$H), 5.80 (d, J=12.7 Hz, $^1$H), 5.83 (d, J=19.3 Hz, $^1$H), 6.68 (dd, J=12.6, 19.3 Hz, $^1$H), 7.29 (t, J=2.7 Hz, $^1$H), 8.24 (d, J=3.3 Hz, $^1$H). A suspension of 5% Pt on carbon (54 mg, Aldrich) and 3-vinyl-5-(1-t-butyloxycarbonyl-(2S)-azetidinylmethoxy)pyridine (540 mg, 1.87 mmol) in MeOH (10 mL) at room temperature was placed under an atmosphere of hydrogen for 16 h. Removal of the catalyst by filtration and concentration of the solvent afforded 3-ethyl-5-(N-t-butyloxycarbonyl-(2S)-azetidinyl-2-methoxy)pyridine as an oil (480 mg, 88%): MS (CI/NH$_3$) m/z: 293 (M+H)$^+$; $^1$H NMR (CDCl$_3$, 300 MHz) δ1.25 (t, J=8.3 Hz, 3H), 1.42 (s, 9H), 2.20–2.40 (m, 2H), 2.64 (q, J=8.3 Hz, 2H), 3.88 (t, J=8.3 Hz, 2H), 4.12 (dd, J=3.3, 8.0 Hz, $^1$H), 4.32 (m, $^1$H), 4.51 (m, $^1$H), 7.08 (t, J=3.3 Hz, $^1$H), 8.08 (d, J=1.7 Hz, $^1$H), 8.16 (d, J=2.3 Hz, $^1$H). To a solution of the product from above (479 mg, 1.64 mmol) in CH$_2$Cl$_2$ (6 mL) at 0° C. was added TFA (5.5 mL). After 30 min the solution was basified with 15% aqueous NaOH and extracted with CH$_2$Cl$_2$ (3×). The organic extract was dried over MgSO$_4$, filtered and concentrated. Purification by chromatography (silica gel; $CH_2Cl_2$/MeOH/$NH_4OH$, 10:0.4:0 to 10:1:0.3) afforded the free base of the title compound as an oil (228 mg, 72%): MS (CI/NH3) m/z: 193 (M+H)$^+$; $^1$H NMR (CDCl$_3$, 300 MHz) δ1.24 (t, J=8.3 Hz, 3H), 2.20–2.48 (m, 2H), 2.62 (q, J=8.3 Hz, 2H), 3.46–3.54 (m, 2H), 3.64 (q, J=8.7 Hz, $^1$H), 4.06 (t, J=5.7 Hz, 2H), 7.16 (t, J=2.7 Hz, $^1$H), 8.07 (d, J=1.7 Hz, $^1$H), 8.13 (d, J=3.3 Hz, $^1$H). The free amine was dissolved in Et$_2$O and HCl in Et$_2$O was added dropwise carefully. The solvent was then removed, and the salt was recrystallized from MeOH/Et$_2$O to afford a the title compound as a white hygroscopic solid: $[\alpha]_D^{25}$ +3.85° (c 3.64, MeOH); MS (CI/NH$_3$) m/z: 193 (M+H)$^+$; $^1$H NMR (D$_2$O, 300 MHz) δ1.23 (t, J=7.8 Hz, 3H), 3.84–3.90 (m, 3H), 4.37 (dd, J=3.4, 11.2 Hz, 2H), 4.54 (dd, J=7.5, 11.2 Hz, $^1$H), 4.64–4.60 (m, 2H), 4.92 (m, $^1$H), 7.62 (s, $^1$H), 8.26(s, $^1$H). Anal. Calcd for $C_{11}H_{16}N_2O$.1.8 HCl: C, 51.23; H, 6.96; N, 10.86. Found: C, 51.03; H, 6.70; N, 10.96.

Example 24

5-Propyl-3-((2S)-azetidinylmethyloxy)]pyridine hydrochloride

To a solution of 5-(N-t-butyloxycarbonyl-(2S)-azetidinylmethoxy)-3-bromopyridine (1.50 g, 4.37 mmol, Example 12a above) in THF (30 mL) at 0° C. was added [1,3-bis(diphenylphosphino)-propane]nickel(II) (14.0 mg) followed by propylmagnesium chloride (5.50 mL of a 2 M solution in diethyl ether, Aldrich). The reaction mixture was refluxed for 3 h, cooled to ambient temperature and then quenched with saturated aqueous ammonia chloride. The desired product was extracted with CH$_2$Cl$_2$. The organic phase was dried over MgSO$_4$, filtered and concentrated. The residue was chromatographed (silica gel; hexane/EtOAc, 10:1 to 1:1) to afford 5-propyl-3-(N-t-butyloxycarbonyl-(2S)-azetidinylmethoxy)pyridine as an oil (292 mg, 22%): MS (CI/NH$_3$) m/z: 307 (M+H)$^+$; $^1$H NMR (CDCl$_3$, 300 MHz) δ0.95 (t, J=8.3 Hz, 3H), 1.42 (s, 4.5H), 1.46 (s, 4.5H), 1.60–1.70 (m, 2H), 2.22–2.40 (m, 2H), 2.56 (t, J=8.3 Hz, 2H), 3.70–3.80 (m, 2H), 3.90 (m, $^1$H), 4.13 (m, $^1$H), 4.51 (m, $^1$H), 7.04 (s, $^1$H), 8.06 (s, $^1$H), 8.18 (d, J=3.3 Hz, $^1$H). To a 0° C. solution of 5-propyl-3-(N-t-butyloxycarbonyl-(2S)-azetidinylmethoxy)pyridine (290 mg, 0.950 mmol) in CH$_2$Cl$_2$ (3 mL) was added TFA (3 mL). After stirring for 30 min the reaction mixture was basified with 15% aqueous NaOH and extracted with CH$_2$Cl$_2$ (3×). The combined organic extracts were dried over MgSO$_4$, filtered and concentrated. Purification by chromatography (silica gel; CH$_2$Cl$_2$/MeOH, 10:0.5) afforded the free base of the title compound as an oil (103 mg, 53%): MS (CI/NH$_3$) m/z: 207 (M+H)$^+$; $^1$H NMR (CDCl$_3$, 300 MHz) δ0.94 (t, J=8.3 Hz, 3H), 1.58–1.70 (m, 2H), 2.30–2.48 (m, 2H), 2.55 (t, J=8.3 Hz, 2H), 3.57 (m, $^1$H), 3.76 (q, J=8.3 Hz, $^1$H), 4.04–4.10 (m, 2H), 4.39 (m, 1H), 7.03 (t, J=3.0 Hz, $^1$H), 8.04 (s, $^1$H), 8.14 (d, J=3.3 Hz, $^1$H). The free base was dissolved in Et$_2$O and a saturated solution of HCl in Et$_2$O was added dropwise carefully. The solvent was removed, and the resultant solid was recrystallized from MeOH/Et$_2$O to afford the title compound as a yellow hygroscopic solid: mp 79–80° C.; MS (CI/NH$_3$) m/z: 207 (M+H)$^+$; $^1$H NMR (D$_2$O, 300 MHz) δ1.01 (t, J=3.05 Hz, 3H), 1.68–1.80 (m, 2H), 2.62–2.78 (m, 2H), 2.80 (t, J=7.1 Hz, 2H), 4.04–4.21 (m, 3H), 4.44–4.60 (m, 2H), 7.40 (s, $^1$H), 8.04 (s, $^1$H), 8.14 (s, $^1$H). Anal. Calcd for $C_{12}H_{18}N_2O$.2 HCl.H$_2$O: C, 48.49; H, 7.46; N, 9.43. Found: C, 48.35; H, 7.23; N, 9.48.

Example 25

2-Chloro-3-methyl-5-(2-(S)-azetidinylmethoxy) pyridine citrate 25a. 2-Chloro-3-methyl-5-(2-(S)-azetidinylmethoxy) pyridine citrate To a solution of triphenylphosphine (0.55 g, 2.09 mmol) and (S)-1-t-butyloxycarbonyl-2-azetidinemethanol (0.39 g, 2.09 mmol, Example 7c) in THF (5 mL) at 0° C. was added 2-chloro-3-methyl-5-hydroxypyridine (0.20 g, 1.39 mmol, Step 25b below). The mixture was allowed to warm to ambient temperature, then diethyl azodicarboxylate (0.33 mL, 2.09 mmol) was added dropwise, and the mixture was stirred for 16 hours. The solvent was removed in vacuo, and the residue was diluted with hexane and sonicated for 30 minutes. The resulting precipitate was separated by filtration and washed with hexane. The hexane was removed in vacuo and the residue was chromatographed (silica gel; hexane/EtOAc, 1:1) to give a product that was contaminated with triphenylphosphine oxide.

To a solution of the product from above in methylene chloride (6 mL) at 0° C. was added trifluoroacetic acid (6 mL). The mixture was stirred at 0° C. for 40 minutes then allowed to warm to room temperature and stir for an additional 30 minutes. Then saturated K$_2$CO$_3$ was added and the mixture was extracted with CH$_2$Cl$_2$. The organic layer was then dried (MgSO$_4$) and concentrated. The residue was purified (silica gel; 1% NH$_4$OH/10% MeOH/EtOAc) to give 0.12 g (27%) of 2-chloro-3-methyl-5-(2S)-pyrrolidinylmethoxy)pyridine as a pale yellow oil: MS (CI/NH$_3$) m/z: 213 (M+H)$^+$; $^1$H NMR (CDCl$_3$, 300 MHz) δ2.34 (s, 3H), 2.34–2.55 (m, 2H), 3.64 (m, $^1$H), 3.84 (q, J=9 Hz, $^1$H), 4.03–4.98 (m, 2H), 4.45 (m, $^1$H), 7.16 (d, J=3.0 Hz, $^1$H), 7.93 (d, J=3.0 Hz, $^1$H).

The product from above was dissolved in ethanol and treated with citric acid (108 mg) in ethanol. The solvent was removed in vacuo. The resulting salt was triturated with diethyl ether and dried under vacuum to give a white powder: mp 125–127° C.; $[\alpha]_D^{25}$ −4.2 (c 1.0, MeOH); MS (CI/NH$_3$) m/z: 213 (M+H)$^+$; $^1$H NMR (D$_2$O, 300 MHz) δ: 2.27 (d, J=10.5 Hz, $^1$H), 2.36 (s, 3H), 2.41–2.91 (m, 8H), 4.0–4.21 (m, 2H), 4.40 (d, J=5 Hz, $^1$H), 4.93 (m, $^1$H), 7.48 (d, J=3.1 Hz, $^1$H), 7.97 (d, J=3.0 Hz, $^1$H). Anal. Calcd for $C_{10}H_{13}N_2OCl$.1.2 $C_6H_8O_7$.H$_2$O: C, 44.79; H, 5.38; N, 6.07. Found: C, 44.85; H, 5.29; N, 5.91

25b. 2-chloro-3-methyl-5-hydroxypyridine

2-Chloro-3-methyl-5-nitropyridine (3.2 g, 18.5 mmol; Maybridge Chemical Co.) was dissolved in a mechanically stirred solution of H$_2$O/HOAc (60 mL, 5:1). Iron powder was added over a 5 h period, maintaining the temperature below 40° C., and stirring was continued until starting material had be consumed. The reaction mixture was filtered, and the filter cake was washed with EtOAc. The aqueous filtrate was extracted with EtOAc, and the combined organic fractions were washed with saturated NaHCO$_3$ solution, dried (MgSO$_4$) and concentrated. The residue was chromatographed (silica gel; CHCl$_3$/MeOH, 98:2) to afford 5-amino-2-chloro-3-methylpyridine as an orange solid (2.34 g, 89%): MS (CI/NH$_3$) m/z: 143 (M+H)$^+$; NMR (DMSO-d$_6$, 300 MHz) δ2.17 (s, 3H), 5.40 (br s, 2H), 6.90 (d, J=2.2 Hz, $^1$H), 7.54 (d, J=2.2 Hz, $^1$H).

To a solution of boron trifluoride diethyl etherate (5.8 mL, 47.5 mmol) in DME (18 mL) at −14° C. was added dropwise a solution of 5-amino-2-chloro-3-methylpyridine (4.5 g, 31.7 mmol) in DME (60 mL). The mixture was stirred for 15 minutes and then a solution of t-butyl nitrite (4.5 mL, 38 mmol) in DME (60 mL) was added dropwise. The mixture was stirred for 1 hour at 0° C., then pentane (100 mL) was added to give a solid. The solid was collected by filtration and dried to give the title compound (6.9 g): $^1$H NMR (MeOH-d$_4$, 300 MHz) δ2.58 (s, 3H), 8.86 (d, J=2.1 Hz, $^1$H), 9.41 (d, J=2.4 Hz, $^1$H).

A solution of the above solid (2.49 g) in acetic anhydride (20 mL) was heated at 70° C. for 4 hours. The solvent was then evaporated under reduced pressure and H$_2$O (200 mL) was added. The solution was adjusted to pH 9 with solid K$_2$CO$_3$ following by extraction with EtOAc. The organic layer was then washed with H$_2$O and brine, dried (Na$_2$SO$_4$), and concentrated. The residue was chromatographed (silica gel; hexane/EtOAc, 50:50) to give 5-acetoxy-2-chloro-3-methylpyridine as an oil (1.45 g, 76%): $^1$H NMR (CDCl$_3$, 300 MHz) δ2.32 (s, 3H), 2.39 (s, 3H), 7.37 (dd, J=1.5, 1.5 Hz, $^1$H), 8.06 (d, J=2.7, $^1$H); MS (CI/NH$_3$) m/z 186 (M+H)$^+$, 203 (M+NH$_4$)$^+$.

The acetate obtained above (1.25 g, 6.7 mmol) was hydrolyzed with 2 N aqueous potassium hydroxide solution. The solution was adjusted to pH 6.0 with acetic acid followed by extraction with ethyl acetate. The organic layer was washed with H$_2$O and brine, dried (MgSO$_4$), and concentrated. The residue was chromatographed (silica gel; hexane/EtOAc, 50:50) to give the title compound as an oil (1.2 g, 100%): $^1$H NMR (CDCl$_3$, 300 MHz) δ2.36(s, 3H), 7.19 (d, J=3.0 Hz, $^1$H), 7.89 (d, J=3.0 Hz, $^1$H); MS (CI/NH$_3$) m/z 144 (M+H)$^+$, 146 (M+3H)$^+$, 161(M+H+NH4)$^+$, 163(M+2H+NH4)$^+$.

Example 26

2-Chloro-3-vinyl-5-((2S)-azetidinylmethoxy) pyridine hydrochloride

To 5-bromo-6-chloro-3-(1-t-butyloxycarbonyl-2-(S)-azetidinylmethoxy)pyridine from Example 17 above (1.00 g, 2.65 mmol) in toluene (30 mL) was added tetrakis (triphenylphosphine)palladium(0) (93 mg, 0.081 mmol) and vinyltributyltin (0.93 mL, 3.18 mmol). The mixture heated at 95° C. overnight, then the volatile components were removed in vacuo. The residue was chromatographed (silica gel; CH$_2$Cl$_2$/MeOH, 100:2) to afford 2-chloro-3-vinyl-5-(1-t-butyloxycarbonyl-(2S)-azetidinylmethoxy)pyridine as an oil (720 mg, 84%): $^1$H NMR (CDCl$_3$, 300 MHz) δ1.42 (s, 9H), 2.33 (m, 2H), 3.89 (t, J=8.5 Hz, 2H), 4.14 (m, $^1$H), 4.36 (m, $^1$H), 4.52 (m, $^1$H), 5.50 (d, J=10.9 Hz, $^1$H), 5.80 (d, J=17 Hz, $^1$H), 6.98 (dd, J=17.6 Hz, J=11.2 Hz, $^1$H), 7.44 (d, J=2.7 Hz, $^1$H), 8.02 (d, J=2.7 Hz, $^1$H); MS (CI/NH3) m/z: 325 (M+H)$^+$. This product was treated with TFA in CH$_2$Cl$_2$ to give, following extractive work-up, the free base of the title compound. The free amine was converted to the hydrochloride salt by treatment with a solution of HCl in diethyl ether to give the title compound as a light yellow hygroscopic solid: mp 121° C. (dec); MS (CI/NH$_3$): m/z 225 (M+H$^+$), 242 (M+NH$_4^+$). Anal. Calcd for C$_{11}$H$_{13}$ClN$_2$O.1.1 HCl: C, 49.90; H, 5.37; N, 10.58. Found: C, 49.84; H, 5.25; N, 10.27.

Example 27

2-Chloro-3-ethyl-5-((2S)-azetidinylmethoxy) pyridine hydrochloride

A suspension of 5% Pt on carbon and 2-chloro-3-vinyl-5-(1-t-butyloxycarbonyl-(2S)-azetidinylmethoxy)pyridine (Example 26 above, 440 mg, 1.36 mmol) in MeOH (10 mL) were stirred overnight under an atmosphere of hydrogen (balloon). The mixture was filtered and the filtrate was concentrated to afford 2-chloro-3-ethyl-5-(1-t-butyloxycarbonyl-(2S)-azetidinylmethoxy)pyridine as a colorless oil (219 mg, 51%): $^1$H NMR (CDCl$_3$, 300 MHz) δ1.25 (t, J=7.5 Hz, 3H), 1.42 (s, 9H), 2.32 (m, 2H), 2.71 (q, J=7.5 Hz, 2H), 3.89 (t, J=7.8 Hz, 2H), 4.12 (dd, J=3.0, 9.8 Hz, 1H), 4.30 (m, $^1$H), 4.50 (m, 1H), 7.16 (d, J=3.1 Hz, 1H), 7.94 (d, J=3.0 Hz, 1H); MS (CI/NH$_3$) m/z 327 (M+H)$^+$. To a solution of the product from above (216 mg, 0.66 mmol) in CH$_2$Cl$_2$ (2 mL) at 0° C. was added trifluoroacetic acid (1.8 mL). The solution was allowed to warm to room temperature, then adjusted to pH 11 with aqueous 10% NaOH, and extracted with CH$_2$Cl$_2$. The organic extract was dried over MgSO$_4$ and concentrated. The residue was chromatographed (silica gel; CH$_2$Cl$_2$/MeOH, 100:3 to 100:15) to afford the free base of the title compound as an oil (60 mg, 40%): $^1$H NMR (CDCl$_3$, 300 MHz) δ1.22 (m 3H), 2.38 (m, 2H), 2.71 (q, J=7.5 Hz, 2H), 3.57 (m, 1H), 3.80 (m, 1H), 4.08 (m, 2H), 4.38 (m, 1H), 7.15 (d, J=2.4 Hz, 1H), 7.92 (d, J=3.0 Hz; 1H); MS (CI/NH$_3$) m/z: 227 (M+H)$^+$. The free base was dissolved in THF and treated with 1 M HCl in Et$_2$O to afford the hydrochloride salt, which was triturated with Et$_2$O and dried under vacuum to afford the title compound as a white solid: mp 102–104° C.; [α]$_D^{23}$ −9.68 (c 0.62, MeOH); $^1$H NMR (D$_2$O) δ1.24 (t, J=7.5 Hz, 3H), 2.71 (m, 4H), 4.11 (m, 2H), 4.42 (d, J=4 Hz, 2H), 4.95 (m, 1H), 7.51 (d, J=3 Hz, 1H), 8.00 (d, J=3 Hz, 1H). Anal. Calcd. for C$_{11}$H$_{15}$N$_2$OCl1.1 HCl: C, 49.52; H, 6.08; N, 10.50. Found: C, 49.63; H, 5.89; N, 10.20.

Example 28

2-Chloro-3-propyl-5-((2S)-azetidinylmethoxy) pyridine hydrochloride

2-Chloro-3-bromo-5-(1-t-butyloxycarbonyl-(2S)-azetidinylmethoxy)pyridine (1.20 g, 3.18 mmol, from Example 17 above) in toluene (10 mL) was mixed with allyltributyltin (1.98 mL, 6.36 mmol) and tetrakis (triphenylphosphine)palladium(0) (305 mg). The reaction mixture was stirred at 100° C. for 16 hours. The solvent was removed under vacuum and the resultant residue was chromatographed (silica gel; hexane/EtOAc, 5:1) to afford 2-chloro-3-(3-propenyl)-5-(1-t-butyloxycarbonyl-(S)-azetidinyl-2-methoxy)pyridine as an oil (947 mg, 88%): MS (CI/NH$_3$) m/z: 339 (M+H)$^+$; $^1$H NMR (CDCl$_3$, 300 MHz) δ1.40 (s, 9H), 2.20–2.40 (m, 2H), 3.45 (d, J=6.60 Hz, 2H), 3.89 (t, J=7.72 Hz, 2H), 4.11 (dd, J=2.94, 9.92 Hz, $^1$H), 4.30 (m, $^1$H), 4.51 (m, $^1$H), 5.10–5.20 (m, 2H), 5.93 (m, $^1$H), 7.17 (d, J=2.94 Hz, $^1$H), 7.98 (d, J=3.31 Hz, $^1$H). A suspension of the product above (945 mg, 2.79 mmol) and 5% Pt on carbon (500 mg) in MeOH (10 mL) were stirred under an atmosphere of hydrogen for 16 hours. The catalyst was filtered and the solvent was removed in vacuo to afford the desired product (770 mg, 81%) as an oil. MS (CI/NH3) m/z: 341 (M+H)$^+$; $^1$H NMR (CDCl$_3$, 300 MHz): δ0.99 (t, J=7.5 Hz, 3H), 1.42 (s, 9H), 1.60–1.74 (m, 2H), 2.20–2.40 (m, 2H), 2.65 (t, J=7.5 Hz, 2H), 3.89 (t, J=7.5 Hz, 2H), 4.11 (dd, J=3.1, 9.8 Hz, 1H), 4.32 (m, 1H), 4.50 (m, 1H), 7.14 (d, J=2.7 Hz, 1H), 7.95 (d, J=3.1 Hz, 1H,). The product from above (759 mg, 2.22 mmol) was dissolved in CH$_2$Cl$_2$ (4 mL) and TFA (3 mL) was added at 0° C. After stirring for 30 min, the reaction was warmed to room temperature slowly. The reaction mixture was then basified with 15% aqueous NaOH and extracted with CH$_2$Cl$_2$. The combined organic extracts were dried over MgSO4, filtered and concentrated. The crude product was chromatographed (silica gel; CH$_2$Cl$_2$/MeOH, 10:0.4 to 10:1:0.3 CH$_2$Cl$_2$/MeOH/NH$_4$OH) to afford the free base of the title compound as an oil (193 mg, 50%): MS (CI/NH$_3$) m/z: 241 (M+H)$^+$; $^1$H NMR (CDCl$_3$, 300 MHz) δ0.98 (t, J=7.35 Hz, 3H), 1.58–1.70 (m, 2H), 2.60–2.70 (m, 4H, 3.96–4.10 (m, 2H), 4.24–4.32 (m, 2H), 4.79 (m, 1H), 7.16 (d, J=3.4 Hz, 1H), 7.91 (d, J=2.9 Hz, 1H). The free base from above was dissolved in Et$_2$O and HCl in Et$_2$O was added dropwise. The solvent was removed and the product recrystallized from MeOH/Et$_2$O to afford a white hygroscopic solid: mp 148–150° C.; [α]$_D$ −8.54 (c 2.67, MeOH); MS (CI/NH$_3$) m/z: 241 (M+H)$^+$; $^1$H NMR (D$_2$O, 300 MHz) δ0.95 (t, J=7.1 Hz, 3H), 1.60–1.74 (m, 2H), 2.71 (t, J=8.1 Hz, 4H), 4.04–4.22 (m, 2H), 4.41 (d, J=4.1 Hz, 2H), 4.97 (m, 1H), 7.48 (d, J=3.1 Hz, $^1$H), 8.00 (d, J=3.1 Hz, $^1$H); Anal. Calcd for C$_{12}$H$_{17}$N$_2$OCl.1.6 HCl.0.1 H$_2$O: C, 47.90; H, 6.30; N, 9.31. Found: C, 47.97; H, 5.91; N, 9.14.

Example 29

3-Butyl-2-chloro-5-((2S)-azetidinylmethoxy) pyridine hydrochloride

2-Chloro-3-bromo-5-(1-t-butyloxycarbonyl-(2S)-azetidinylmethoxy)-pyridine (1.00 g, 2.70 mmol, from Step 17 above) in toluene (10 mL) was added Pd(OAc)$_2$ (67 mg, Aldrich) and tri-o-tolylphoshine (335 mg, Aldrich). 1-Butene was bubbled through the mixture for 20 minutes. The reaction mixture was stirred at 100° C. in sealed tube for 16 hours, cooled to ambient temperature, then the volatile components were removed under reduced pressure. The residue was chromatographed (silica gel; hexane/EtOAc, 5:1 to 2:1) to afford an oil (715 mg, 76%): MS (CI/NH$_3$) m/z: 353 (M+H)$^+$; $^1$H NMR (CDCl$_3$, 300 MHz) δ1.13 (t, J=7.4 Hz, 3H) 1.42 (s, 9H), 2.20–2.50 (m, 4H), 3.89 (t, J=7.7 Hz, 2H), 4.09 (m, 1H), 4.28 (m, 1H), 5.00 (m, 1H), 5.54 (m, 1H), 7.14 (d, J=2.9 Hz, 1H), 7.96 (d, J=3.0 Hz, 1H). A suspension of the 2-chloro-3-butenylpyridine from above (420 mg, 1.19 mmol) and 5% Pt on carbon (40 mg) in MeOH (10 mL) was placed under an atmosphere of hydrogen (balloon) for 16 hours. The catalyst was filtered and the solvent was removed in vacuo to afford the desired product (310 mg, 74%): MS (CI/NH$_3$) m/z: 355 (M+H)$^+$; $^1$H NMR (CDCl$_3$, 300 MHz) δ0.96(t, J=7.5 Hz, 3H), 1.42 (s, 9H), 1.56–1.60 (m, 4H), 2.22–2.40 (m, 2H), 2.67 (t, J=7.8 Hz, 2H), 3.84–3.94 (m, 2H), 4.12 (m, 1H), 4.32 (m, 1H), 4.50 (m, 1H), 7.14 (d, J=7.1 Hz, 1H), 7.94 (t, J=7.1 Hz, 1H). The product from above (310 mg, 0.87 mmol) was dissolved in CH$_2$Cl$_2$ (2 mL) at 0° C. and TFA (1.2 mL) was added. After stirring for 30 min, the reaction mixture was basified with 15% aqueous NaOH and extracted with CH$_2$Cl$_2$. The combined organic extracts were dried over MgSO$_4$, filtered and concentrated. The crude product was chromatographed (silica gel; CH$_2$Cl$_2$/MeOH/NH$_4$OH, 10:0.4:0 to 10:1:0.3) to afford the free base of the title compound as an oil (165 mg, 75%): MS (CI/NH$_3$) m/z: 255 (M+H)$^+$; $^1$H NMR (CDCl$_3$, 300 MHz) δ0.95 (t, J=7.1 Hz, 3H), 1.32–1.44 (m, 2H), 2.54–2.66 (m, 4H), 2.38–2.56 (m, 2H), 2.67 (t, J=7.8 Hz, 2H), 3.67 (m, 1H), 3.86 (m, 1H), 4.04–4.20 (m, 2H), 4.49 (m, 1H), 7.15 (d, J=3.1 Hz, 1H), 7.91 (d, J=2.7 Hz, 1H). The free base was dissolved in Et$_2$O and HCl in Et$_2$O was added dropwise carefully. The solvent was removed and the resultant salt was recrystallized from MeOH/Et$_2$O to afford the title compound as a white solid: mp. 88–90° C.; [α]$_D$ −8.00 (c 1.92, MeOH); MS (CI/NH$_3$) m/z: 255 (M+H)$^+$; $^1$H NMR (D$_2$O, 300 MHz) δ0.93 (t, J=7.3 Hz, 3H), 1.35–1.42 (m, 2H), 1.58–1.68 (m, 2H), 2.60–2.78 (m, 4H), 4.02–4.22 (m, 2H), 4.41 (d, J=4.1 Hz, 2H), 4.97 (m, 1H), 7.50 (s, 1H), 8.00 (d, J=2.6 Hz, 1H). Anal. Calcd for C$_{13}$H$_{19}$N$_2$OCl.1.5 HCl.0.1 H$_2$O: C, 50.17; H, 6.70; N, 9.00. Found: C, 50.27; H, 6.95; N, 8.89.

Example 30

2-Chloro-3-ethynyl-5-((2S)-azetidinylmethoxy) pyridine hydrochloride

2-Chloro-3-bromo-5-(1-t-butyloxycarbonyl-(2S)-azetidinylmethoxy)pyridine (1.00 g, 2.65 mmol, from Step 17 above) was mixed with trimethylsilylacetylene (0.45 mL, 3.18 mmol), tetrakis(triphenylphosphine)palladium(0) (305 mg), copper(I) iodide (50 mg) and triethylamine (1 mL) in toluene (20 mL). The reaction mixture was stirred at 100° C. for 16 hours. The solvent was removed and the residue was chromatographed (silica gel; hexane/EtOAc, 5:1 to 2:1) to afford the trimethylsilylethynyl-substituted pyridine as an oil (770 mg, 74%): MS (CI/NH3) m/z: 395 (M+H)$^+$; $^1$H NMR (CDCl$_3$, 300 MHz) δ1.43 (s, 9H), 2.20–2.40 (m, 2H), 3.80–3.92 (m, 2H), 4.12 (m, $^1$H), 4.32 (m, $^1$H), 4.49 (m, $^1$H), 7.38 (d, J=3.1 Hz, $^1$H), 8.05 (d, J=3.0 Hz, $^1$H). Solid K$_2$CO$_3$ (293 mg, 2.12 mmol) was added to a solution of the product from above (760 mg, 1.93 mmol) in MeOH (20 mL). The reaction mixture was stirred at ambient temperature for 2 hours, then diluted with EtOAc and washed with H$_2$O. The organic layer was dried over MgSO$_4$ and concentrated to afford the ethynyl-substituted pyridine (610 mg, 98%): MS (CI/NH$_3$) m/z: 323 (M+H)$^+$; $^1$H NMR (CDCl$_3$, 300 MHz) δ1.42 (s, 9H), 2.20–2.40 (m, 2H), 3.46 (s, 1H), 3.84–3.92 (m, 2H), 4.07 (m, 1H), 4.33 (m, 1H), 4.52 (m, 1H), 7.41 (d, J=2.9 Hz, 1H), 8.08 (d, J=2.9 Hz, 1H). The product from above (605 mg, 1.88 mmol) was dissolved in CH$_2$Cl$_2$ (2 mL) and TFA (2 mL) was added at 0° C. After stirring for half hour, the reaction was warmed to room temperature slowly. Then the mixture was basified with 15% aqueous NaOH and extracted with CH$_2$Cl$_2$. The combined organic extracts were dried over MgSO$_4$ and concentrated. The crude product was chromatographed (silica gel; CH$_2$Cl$_2$/MeOH/NH$_4$OH, 10:0.4:0 to 10:1:0.3) to afford the free base of the title compound as an oil (265 mg, 64%): MS (CI/NH3) m/z: 223 (M+H)$^+$; $^1$H NMR (CDCl$_3$, 300 MHz) δ2.20–2.40 (m, 2H), 3.45 (m, 1H), 3.74 (m, 1H), 3.98–4.06 (m, 2H), 4.25 (m, 1H), 7.38 (d, J=2.9 Hz, 1H), 8.08 (d, J=3.0 Hz, 1H). The free base from above was dissolved in Et$_2$O and HCl in Et$_2$O was added dropwise carefully. The solvent was removed and the product recrystallized from MeOH/Et$_2$O to afford a brown hygroscopic solid: mp. 90° C. (dec.); MS (CI/NH$_3$) m/z: 223 (M+H)$^+$; $^1$H NMR (D$_2$O, 300 MHz) δ2.71 (q, J=8.2 Hz, 2H), 4.04–4.22 (m, 2H), 4.44 (d, J=4.1 Hz, 2H), 4.92–5.00 (m, 1H), 7.77 (d, J=3.5 Hz, 1H), 8.19 (d, J=3.1 Hz, 1H). Anal.Calcd for C$_{11}$H$_{11}$N$_2$OCl.1.1 HCl.0.5 H$_2$O: C, 48.60; H, 4.63; N, 10.30. Found: C, 48.70; H, 4.81; N, 10.01.

Example 31

5-((2S)-azetidinylmethoxy)-3-bromo-2-fluoropyridine dibenzoic acid salt 31a. 5-((2S)-azetidinylmethoxy)-3-bromo-2-fluoropyridine dibenzoate To a solution of diethyl azodicarboxylate (0.7 mL, 4.4 mmol) in THF (25 mL) was added triphenylphosphine (1.19 g, 4.4 mmol) at 0° C., and the reaction mixture was stirred for 0.5 hour. 1-t-Butyloxycarbonyl-(2S)-azetidinemethanol (0.85 g, 4.5 mmol, Example 7c) and 5-bromo-6-fluoropyridin-3-ol (0.75 g, 4.0 mmol, Step 31d) were then added. The reaction mixture was allowed to warm slowly to room temperature and stirred overnight. The solvent was removed, and the residue was chromatographed (silica gel, hexane/ethyl acetate, 5:1) to afford 5-bromo-6-fluoro-3-(1-t-butyloxycarbonyl-(2S)-azetidinylmethoxy)pyridine (1.02 g, 72.3%): MS (CI/NH$_3$) m/z 362, 379 (M+H)$^+$, (M+NH$_4$$^+$); $^1$H NMR (CDCl$_3$ 300 MHz) δ7.82 (m, 1H), 7.60 (dd, J=3.1, 7.1 Hz 1H), 4.51 (m, 1H), 4.35 (m, 1H), 4.11 (dd, J=3.1, 10.2 Hz, 1H), 3.88 (m, 2H), 2.33 (m, 2H), 1.45 (s, 9H). To a solution of the product from above (0.70 g, 1.9 mmol) in CH$_2$Cl$_2$ (2 mL) at 0° C. was added TFA (2 mL). After 30 min the volatile components were removed under vacuum, the residue was diluted with saturated aqueous NaHCO₃ extracted with methylene chloride. The organic extract was dried over MgSO₄ and concentrated. The residue was chromatographed (silica gel; methylene chloride:methanol:NH₄OH 10:1:0.1) to afford to give 282 mg (56%) of the free base of the title compound. The base was converted to the salt by treatment with benzoic acid in ether to give the title compound (207 mg): MS (CI/NH₃) m/z 261, 278 (M+H)⁺, (M+NH₄⁺); ¹H NMR (D₂O, 300 MHz) δ2.69 (dd, J=7.0, 8.5, 2H), 4.11 (m, 1H), 4.40 (d, J=4.4, 1H), 4.63 (m, 1H), 4.95 (m, 1H), 7.53 (m, 8H), 7.93 (m, 7H). Anal. Calcd for C₉H₁₀N₂OBrF.2 C₆H₅COOH: C, 54.67; H, 4.39; N, 5.54. Found: C, 54.45; H, 4.25; N, 5.58.

31b. 3-Bromo-2-(4-nitrophenylazo)-5-hydroxypyridine

5-Bromo-3-pyridinol from Example 12b (8.7 g, 0.050 mmol) and KOH (1.1 g, 19.6 mmol) were dissolved in water (200 mL). A suspension of p-nitrobenzenediazonium tetrafluoroborate (11.8 g, 0.50 mol, prepared as described in *J. Org. Chem.*, 44: 1572–15783 (1979)) was added. The reaction was stirred for 1 hour, diluted with acetic acid (50 mL) and filtered. The crude product was allowed to air dry, then chromatographed (silica gel; chloroform/methanol, 95:5–90:10) to provide the title compound (5.45 g, 34% yield): MS (CI/NH₃) m/z 323, 325 (M+H)⁺; NMR (DMSO-d₆, 300 MHz) δ8.48–8.43 (m, 2H), 8.21 (d, J=2.4 Hz, 1H), 8.09–8.06 (m, 2H), 7.72 (d, J=2.4 Hz, 1H).

31c. 2-Amino-3-bromo-5-hydroxypyridine

The compound from 31b above (5.0 g, 15.8 mmol) and tin chloride (25 g, 111 mmol) were suspended in concentrated HCl and ethanol (150 mL), and the mixture was heated at reflux for 1 hour. The mixture was cooled to 0° C., then filtered. The filtrate was neutralized with sodium bicarbonate (180 g) and extracted with ethyl acetate. The organic extracts were washed with brine, dried (MgSO₄) and concentrated. The residue was chromatographed (silica gel; chloroform/methanol/NH₄OH, 95:5:0.5–90:10:1) to afford the title compound (3.3 g, 34% yield): MS (CI/NH₃) m/z 189, 191 (M+H)⁺; ¹H NMR (DMSO-d₆, 300 MHz) δ7.57 (d, J=2.6 Hz, 1H), 7.43 (d, J=2.6 Hz, 1H).

31d. 3-Bromo-2-fluoro-5-hydroxypyridine

The compound from 31c (3.0 g, 15.9 mmol) was dissolved in HF.pyridine (50 mL). The solution was cooled to 0° C. and stirred under nitrogen, then sodium nitrite (1.09 g, 15.8 mmol) was added in portions over 20 minutes. The mixture was heated to 50° C. for 1 hour, cooled to 0° C. and basified with 20% aqueous NaOH. The aqueous phase was washed with methylene chloride (5×100 mL), neutralized with HCl, and extracted with ethyl acetate (5×100 mL). The organic extracts were dried (MgSO₄), filtered and concentrated in vacuo, yielding the title compound as a tan solid: MS (CI/NH₃) m/z 192, 194 (M+H)⁺. ¹H NMR (DMSO-d₆, 300 MHz) δ9.38 (d, J=2.6 Hz, 1H), 9.20 (d, J=2.6 Hz, 1H).

Example 32

5-((2S)-azetidinylmethoxy)-3-methyl-2-fluoropyridine benzoate

32a. 5-((2S)-azetidinylmethoxy)-3-methyl-2-fluoropyridine benzoate

The procedure of Example 6 was followed, substituting 2-fluoro-5-hydroxy-3-methylpyridine (Example 32e below) and (S)-1-benzyloxycarbonyl-2-azetidinemethanol (Example 7c above) for 3-hydroxypyridine and (R)-1-benzyloxycarbonyl-2-azetidinemethanol, respectively to afford 6-fluoro-5-methyl-3-(1-benzyloxycarbonyl-(2S)-azetidinylmethoxy)pyridine in 60% yield: MS (CI/NH₃) m/z 331 (M+H)⁺ 348 (M+NH₄)⁺; ¹H NMR (CDCl₃ 300 MHz) δ7.63 (br s, 1H), 7.29 (m, 5H), 7.18 (br s, 1H), 5.05 (m, 2H), 4.59 (m, 1H), 4.3 (br s, 1H), 4.09 (m, 1H), 3.99 (m, 1H), 2.26–2.05 (m, 2H), 2.05 (s, 3H). The benzyloxycarbonyl group of the above product was removed by hydrogenolysis (10% Pd/C, MeOH, 1 atmosphere hydrogen), and the salt was prepared by treatment of the free amine with benzoic acid in Et₂O to give the title compound as an off-white solid (53%): mp 104–108° C.; [α]_D −5.55 (c 0.55, MeOH); ¹H NMR (DMSO) δ7.90 (m, 2H), 7.70 (s, 1H), 7.51–7.48 (m, 2H), 7.42–7.39 (t, J=7.2 Hz, 2H), 4.27 (m, 1H), 4.17 (dd, J=7.3, 10.4 Hz, 1H), 4.08 (dd, J=4.9, 10.4 Hz, 1H), 3.79 (m, 1H), 3.47 (m, 1H), 2.35 (m, 1H), 2.19 (s, 3H), 2.16 (m, 1H); MS (CI/NH₃): m/z 197 (M+H), 214 (M+NH₄)⁺. Anal. Calcd for C₁₀H₁₃N₂OF.C₇H₆O₂: C, 64.14; H, 6.02; N, 8.80. Found: C, 63.90; H, 6.10; N, 8.70.

32b. 2-fluoro-3-methyl-5-nitropyridine

2-Chloro-3-methyl-5-nitropyridine (15.0 g, 86.9 mmol; from Maybridge Chemical Co.), KF (12 g, 258 mmol), and tetraphenylphosphonium bromide (20 g, 47.7 mmol) were combined in 200 mL of acetonitrile and heated at reflux for 4 days. The mixture was diluted with Et₂O (500 mL), filtered, and the solution was concentrated. The residue was triturated with hot hexane, then the combined hexane solutions were concentrated to give 8.4 g (60%) of the title compound: ¹H NMR (DMSO-d₆, 300 MHz) δ8.95 (dd, J=1.6 Hz, 1H), 8.43 (m, 1H), 2.42 (s, 1H); MS (CI/NH₃) m/z: 157 (M+H)⁺.

32c. 3-Amino-6-fluoro-5-methylpyridine

2-Fluoro-3-methyl-5-nitropyridine (from Step 32b above) was combined with 100 mg of 5% Pd/C in EtOH (100 mL), and the mixture was stirred under an atmosphere of hydrogen for 16 hours. The mixture was filtered and concentrated. The crude product was chromatographed (silica gel; CHCl₃/MeOH, 99:1 to 94:6) to yield 5.2 g (78%) of the title compound: ¹H NMR (DMSO-d₆, 300 MHz) δ7.26 (t, J=2.7 Hz, 1H), 6.95 (dd, J=8.1 Hz, 1H), 5.11 (br, s, 2H), 2.10 (s, 3H); MS (CI/NH₃) m/z: 127 (M+H)⁺, 144 (M+NH₄)⁺.

32d. 3-acetoxy-6-fluoro-5-methylpyridine

To boron trifluoride etherate (10 mL, 81 mmol) at −15° C. under N₂ was added the product of step 32c (5.1 g, 40 mmol) in DME (30 mL). tert-Butyl nitrite (5.5 mL, 46 mmol, Aldrich) was added at a such a rate that the temperature remained below 0° C. Additional DME (25 mL) was then added. After 10 minutes at −10° C. the reaction was warmed to 5° C. and stirred for 30 minutes. Pentane (400 mL) was then added to the reaction mixture, the solid was collected by suction filtration, washed with cold ether, air dried, and dissolved in 100 mL acetic anhydride. The resulting solution was heated to 77±5° C. for 1 hour. The solvent was removed in vacuo, and the residue was suspended in saturated aqueous Na₂CO₃ (200 mL) and extracted with ethyl ether. The ether solution was dried (MgSO₄) and concentrated. The crude product was chromatographed (silica gel; hexane/EtOAc 9:1 to 7:3) to yield 3.62 g (53%) of the title compound: MS m/z: 170 (M+H)⁺, 187 (M+NH₄)⁺; ¹H NMR (CDCl₃ 300 MHz) δ7.8 (m, 1H) 7.34 (m, 1H), 2.32 (s, 3H), 2.29 (s, 3H).

32e. 2-Fluoro-5-hydroxy-3-methylpyridine

The product of step 32d (3.6 g, 21.3 mmol) was dissolved in 20% aqueous NaOH (25 mL). After complete consumption of the starting material the solution was neutralized by addition of HCl. The aqueous mixture was extracted with ethyl acetate. The organic extracts were dried (MgSO4), and the solvent was evaporated. The crude product was triturated with hexane to yield 2.35 g (87%) of the title compound: MS (CI/NH$_3$) m/z: 128 (M+H)$^+$, 145 (M+NH$_4$)$^+$; $^1$H NMR (CDCl$_3$, 300 MHz) δ: 7.61(t, J=2.2 Hz, 1H), 7.17 (m, 1 H), 2.25 (s, 3H).

Example 33

5-((29)-azetidinylmethoxy)-3-chloro-2-fluoropyridine tosylate

33a. 5-((2S)-azetidinylmethoxy)-3-chloro-2-fluoropyridine tosylate

Following the procedures of Example 10, replacing 3-fluoro-5-hydroxypyridine thereof with 3-chloro-2-fluoro-5-hydroxypyridine (3.0 mmol), 5-(1-t-butyloxycarbonyl-(2S)-azetidinylmethoxy)-3-chloro-2-fluoropyridine was prepared (668 mg, 70%) as a colorless oil: [α]$_D$ −56.6 (c 2.7, CH$_2$Cl$_2$); $^1$H NMR (CDCl$_3$) δ1.43 (s, 9H), 2.24–2.40 (m, 2H), 3.84–3.91 (m, 2H), 4.12 (dd, J=2.7, 11.2 Hz, 1H); 4.36 (m, 1H); 4.50 (m, $^1$H), 7.46 (dd, J=3.1, 7.5 Hz, 1H), 7.78 (dd, J=2.0, 2.7 Hz, 1H); MS (CI/NH$_3$) m/z: 317, 319 (M+H)$^+$. A solution of the above compound (780 mg, 2.46 mmol) was stirred in a 1:1 solution of CH$_2$Cl$_2$/TFA at 0° C. After 30 minutes the reaction solution was concentrated, and the residue was diluted with CH$_2$Cl$_2$ and washed with saturated K$_2$CO$_3$. The organic extract was dried (Na$_2$SO$_4$) and concentrated. Chromatography (silica gel; 90:10:1 CH$_2$Cl$_2$/MeOH/NH$_4$OH) afforded 407 mg (76%) of the free base of the title compound: MS (CI/NH$_3$) m/z: 217, 219 (M+H)$^+$. The free amine (387 mg, 1.79 mmol) was dissolved in MeOH (5 mL) and p-toluenesulfonic acid monohydrate (340 mg, 1.79 mmol) was added. The solution was concentrated and the solid was recrystallized from MeOH/hexane to afford the title compound as a white solid: mp 99° C.; $^1$H NMR (D$_2$O) δ2.40 (s 3H), 2.69 (q, J=8.5 Hz, 2H), 4.05–4.18 (m, 2H), 4.41 (d, J=4.3 Hz, 2H), 4.94 (m, 1H), 7.37 (d, J=8.0 Hz, 2H), 7.69 (d, J=8.0 Hz, 2H), 7.82 (dd, J=3.1, 7.31 Hz, 1H), 7.87 (m, 1H); MS (CI/NH$_3$): m/z 217, 219 (M+H)$^+$, 234, 236 (M+NH$_4$)$^+$; Anal. Calcd for C$_9$H$_{10}$N$_2$OFCl.C$_7$H$_8$O$_3$S: C, 49.42; H, 4.67; N, 7.20. Found: C, 49.14; H, 4.56; N, 6.98.

33b. 3-Chloro-2-(4-nitrophenylazo)-5-hydroxypyridine

To a solution of 5-chloro-3-pyridinol (20.0 g, 0.154 mol, Aldrich) and KOH (13.0 g, 0.232 mol) in 300 mL of water at 0° C. was added p-nitrobenzenediazonium tetrafluoroborate (36.6 g, 0.154 mol, Aldrich). After 1 hour, 50 mL of glacial acetic acid was added, and the bright red precipitate was filtered and air-dried. Chromatography (silica gel; CH$_2$Cl$_2$/MeOH, 95:5–90:10) afforded the title compound as a bright red solid (28.8 g, 67%): $^1$H NMR (DMSO-d$_6$, 300 MHz) δ7.14 (d, J=2.4 Hz, 1H), 7.89 (d, J=2.4 Hz, 1H), 8.00 (m, 2H), 8.39 (m, 2H); MS (CI/NH$_3$) m/z: 279, 281 (M+H)$^+$.

33c. 2-Amino-3-Chloro-5-hydroxypyridine

To a suspension of the diazo compound from Step 33b (8.82 g, 31.7 mmol) and copper(I) chloride (9.40 g, 95.0 mmol Aldrich) in MeOH (150 mL) at 0° C. was added potassium borohydride portion wise (12.0 g, 221 mmol, nitrogen evolution). The dark mixture was allowed to warm to ambient temperature, stirred for 1 hour, then filtered and concentrated. The residue was dissolved in glacial acetic acid (75 mL) and 30% HBr/HOAC was added (75 mL). The mixture was filtered (HOAc wash), and the filtrate was concentrated to provide 8.64 g (89%) of the unpurified title compound as the dihydrobromide salt: $^1$H NMR (DMSO-d$_6$, 300 MHz) δ5.40 (br s, 1H), 7.16 (d, J=2.6 Hz, 1H), 7.56 (d, J=2.2 Hz, 1H), 8.25 (br s, 2H); MS (CI/NH$_3$) m/z: 145, 147 (M+H)$^+$.

33d. 3-chloro-2-fluoro-5-hydroxypyridine

To a 0° C. solution of compound from Step 33c (11.8 g, 38.4 mmol) dissolved in HF.pyridine (100 g, Aldrich) was added sodium nitrite (2.92 g, 42.3 mmol) in portions. The reaction mixture was warmed to 50° C. for 1 hour, then cooled to 0° C. and basified with 20% aqueous NaOH. The aqueous phase was washed with EtOAc, neutralized with 1 N aqueous HCl, and extracted with ethyl acetate. The latter extracts were dried (MgSO$_4$), filtered and concentrated in vacuo. Purification by chromatography (silica gel; hexane/EtOAc, 50:50) afforded 1.49 g (25%) of the title compound as a tan solid: $^1$H NMR (DMSO-d$_6$, 300 MHz) δ7.54 (m, 1H), 7.67 (m, 1H); 10.44 (s, 1H); MS (CI/NH$_3$) m/z 148, 150 (M+H)$^+$.

Example 34

5-Bromo-6-methyl-3-((2S)-azetidinylmethoxy) pyridine dihydrochloride

34a. 5-Bromo-6-methyl-3-((2S)-azetidinylmethoxy) pyridine dihydrochloride

Triphenylphosphine (6.3 g, 24 mmol) was dissolved in THF (100 mL), cooled to 0° C. and treated with DEAD (3.8 mL, 24 mmol) for 15 minutes. Then the 5-bromo-6-methyl-3-pyridinol (3 g, 16 mmol, see Step 34e below) and 1-t-butyloxycarbonyl-(2S)-azetidinemethanol (3.4 g, 18 mmol, from Step 7c) were added, and the mixture was allowed to warm slowly to ambient temperature. After 3 days, the solvent was evaporated, and the residue was chromatographed (silica gel; hexanes/EtOAc, 4:1) to provide the title compound as an oil, contaminated with hydrazine byproduct derived from the DEAD: MS (CI/NH$_3$) m/z: 357 (M+H)$^+$, 279. The product from above (0.40 g, 1.12 mmol) was dissolved in methylene chloride (4 mL) and treated with TFA (2 mL) at 0° C. for 1 hour. The solution was concentrated, and the residue was diluted with saturated aqueous bicarbonate and extracted with methylene chloride. The organic extract was washed with H$_2$O, and dried (MgSO$_4$). Evaporation of the solvent provided 0.25 g (76%) of neutral product, which was dissolved in ether and treated with 1 N HCl in ether. The resulting solid was collected and washed with fresh ether to provide 151 mg (41%) of the title compound: mp 153–155° C.; [α]$_D$ −7.4 (c 0.54, MeOH); $^1$H NMR (CD$_3$OD) δ2.63–2.76 (m, 2H), 2.78 (s, 3H), 4.04–4.18 (m, 2H), 4.50–4.63 (m, 2H), 4.88–4.96 (m, 1H), 8,50 (d, J=2 Hz, 1H), 8.10 (d, J=2 Hz, 1H); MS (CI/NH3): m/z 257 (M+H)$^+$, 274 (M+NH$_4$)$^+$; Anal. Calcd for C$_{10}$H$_{13}$N$_2$OBr.2 HCl: C, 36.39; H, 4.58; N, 8.49. Found: C, 36.31; H, 4.66; N, 8.41.

34b. 3-bromo-2-methyl-5-nitropyridine

A solution of diethyl malonate (17.6 mL, 0.116 mol) in diethyl ether (250 mL) at ambient temperature was treated with sodium hydride (80% in mineral oil, 3.5 g, 0.116 mol), and the mixture was stirred for 1 hour. Then 3-bromo-2-chloro-5-nitropyridine (25 g, 105 mmol; prepared from 2-hydroxy-5-nitropyridine according to the procedure of V. Koch and S. Schnatterer, *Synthesis* 1990, 499–501) was added in portions over 5 minutes. After the mixture had stirred for 1 hour, the solvent was evaporated, and the residue was heated at 100° C. for 1 hour. After the mixture had cooled, 12 N $H_2SO_4$ was added, and the mixture was heated at reflux for about 16 hours. The mixture was allowed to cool to ambient temperature, then further cooled as it was treated with 50% NaOH to give an alkaline pH. The resulting solution was extracted with $CHCl_3$ (3×), and the organic extracts were washed with $H_2O$, dried ($MgSO_4$) and evaporated to afford 17.1 g of the title compound as a red oil: $^1H$ NMR ($CDCl_3$, 300 MHz) δ2.81 (s, 3H), 8.61 (d, J=2 Hz, 1H), 9.26 (d, J=2 Hz, 1H).

34c. 5-amino-3-bromo-2-methylpyridine

The compound of Example 34b above (17.1 g, 78.8 mmol) was dissolved in HOAc (50 mL) and water (150 mL) and treated with iron powder (13.3 g, 236 mmol) added in portions over 2 hours. The mixture was filtered, and the filter cake was washed with EtOAc. The layers were separated, and the aqueous phase was extracted with EtOAc. The combined organic fractions were washed with 1 M sodium bicarbonate and water, then dried ($MgSO_4$) and concentrated to afford 12.65 g (86%) of the title compound: MS ($CI/NH_3$) m/z: 187 $(M+H)^+$, 204 $(M+NH_4)^+$.

34d 5-Acetoxy-3-bromo-2-methylpyridine

The compound of Example 34c (12.6 g, 67 mmol) was treated with t-butyl nitrite and $BF_3·OEt_2$ followed by acetic anhydride according to the procedure of Example 1f. The crude product was chromatographed (silica gel; hexanes/EtOAc, 4:1) to afford the title compound (12.0 g, 58%): MS ($CI/NH_3$) m/z: 230 $(M+H)^+$.

34e. 3-bromo-5-hydroxy-2-methylpyridine

The product of Example 34d was stirred with 15% aqueous NaOH (75 mL) at 0° C., and the mixture was allowed to warm to ambient temperature. After 1 hour, the mixture was acidified with 6 N aqueous HCl with cooling, and the resulting suspension was extracted with EtOAc. The EtOAc was washed with $H_2O$, dried ($MgSO_4$) and concentrated to provide 7.0 g (95%) of the title compound: $^1H$ NMR ($CDCl_3$, 300 MHz) δ2.59 (s, 3H), 7.46 (d, J=2Hz, 1H), 8.10 (d, J=2Hz, 1H); MS ($CI/NH_3$) m/z: 188 $(M+H)^+$, 207 $(M+NH_4)^+$.

Example 35

6-Methyl-5-vinyl-3-((2S)-azetidinylmethoxy) pyridine hydrochloride

5-Bromo-6-methyl-3-(1-t-butyloxycarbonyl-(2S)-azetidinylmethoxy)pyridine (0.95 g, 2.7 mmol, Step 34a above) was treated with vinyl tributyltin (1.62 mL, 5.56 mmol) and tetrakis(triphenylphosphino)palladium(0) (0.29 g, 0.25 mmol) in toluene (30 mL) at 90° C. overnight. The reaction was cooled to ambient temperature and chromatographed on silica gel with 2:1 hexane-EtOAc eluent to provide 6-methyl-5-vinyl-3-(1-t-butyloxycarbonyl-(2S)-azetidinylmethoxy)pyridine (0.49 g, 60%): MS (CI/NH3) m/z: 305 $(M+H)^+$; $^1H$ NMR (300 MHz, $CDCl_3$) δ1.42 (s, 9H), 2.22–2.38 (m, 2H), 2.52 (s, 3H), 3.91 (dt, J=2, 6 Hz, 2H), 4.13 (dd, J=3, 10 Hz, 1H), 4.30–4.36 (m, 1H), 4.49–4.55 (m, 1H), 5.40 (dd, J=1, 11 Hz, 1H), 5.64 (dd, J=1, 17 Hz, 1H), 6.84 (dd, J=11, 17 Hz, 1H), 7.32 (d, J=3 Hz, 1), 8.13 (d, J=3 Hz, 1H). The product from above (0.47 g,1.53 mmol) was treated with 8 mL of 1:1 TFA-methylene chloride at 0° C. for 2 hours. The volatile components were evaporated in vacuo, and the residue was diluted with saturated aqueous sodium bicarbonate and extracted with $CH_2Cl_2$. The combined organic layers were washed with water and dried over $MgSO_4$ to provide the product (277 mg, 89% yield). Half of the sample was dissolved in ether and treated with 1 M HCl in ether to provide 85 mg of the title compound as an off-white solid: mp 154–155° C.; $[α]_D$ −8.9 (c 0.45, MeOH); $^1H$ NMR ($CD_3OD$) δ2.63–2.77 (m, 2H), 2.74 (s, 3H), 4.08–4.16 (m, 2H), 4.52–4.64 (m, 2H), 4.85–4.95 (m, 1H), 5.80 (d, J=11 Hz, 1H), 6.15 (d, J=17 Hz, 1H), 7.02 (dd, J=11, 17 Hz, 1H), 8.36 (d, J=2 Hz), 1H, 8.48 (d, J=2 Hz, 1H); MS ($CI/NH_3$) m/z; 205 $(M+H)^+$; Anal. Calcd for $C_{12}H_{16}N_2O.2.1$ HCl: C, 51.32; H, 6.50; N, 9.97. Found: C, 51.60; H, 6.21; N, 9.82.

Example 36

6-Ethyl-6-methyl-3-((2S)-azetidinylmethoxy) pyridine hydrochloride

6-Methyl-5-vinyl-3-(1-t-butyloxycarbonyl-(2S)-azetidinylmethoxy)pyridine (0.26 g, 0.86 mmol, from Example 35 above) was dissolved in MeOH (15 mL) and treated with 10% Pd/C (50 mg) and 1 atm hydrogen gas. After 1 day, the catalyst was removed, the solvent evaporated, and the residue was chromatographed (silica gel; hexanes-EtOAc, 1:1) to provide 5-ethyl-6-methyl-3-(1-t-butyloxycarbonyl-2-(S)-azetidinylmethoxy)pyridine (0.12 g, 45%): MS ($CI/NH_3$) m/z: 307 $(M+H)^+$; $^1H$ NMR (300 MHz, $CDCl_3$) δ1.23 (t, J=7 Hz, 3H), 1.42 (s, 9H), 2.23–2.38 (m, 2H), 2.47 (s, 3H), 2.60 (q, J=7 Hz, 2H), 3.86–3.93 (m, 2H), 4.12 (dd, J=3, 9 Hz, 1H), 4.29 (dd, J=5,10 Hz, 1H), 4.43–4.53 (m, 1H), 7.04 (d, J=3 Hz, 1H), 8.05 (d, J=3 Hz, 1H). The product from above (0.26 g, 0.85 mmol) was treated with 10 mL of 1:1 TFA-methylene chloride at 0° C. for 1 hour. The residue was diluted with saturated sodium bicarbonate and extracted into $CHCl_3$. The organic layer was washed with water, dried over $MgSO_4$, and evaporated to provide of the free base of the title compound (132 mg, 75%). This was dissolved in ether and treated with 1 M HCl in ether and the resulting salt collected by filtration to provide the title compound (52 mg, 25%). The mother liquor was evaporated to further provide 73 mg of the title compound: mp 150–153° C.; $[α]_D$ −7.6 (c 0.62, MeOH); $^1H$ NMR (300 MHz, $CD_3OD$) δ1.34 (t, J=7 Hz, 3H), 2.63–2.76 (m, 2H), 2.72 (s, 3H), 4.04–4.19 (m, 2H), 4.49–4.63 (m, 2H), 4.88–4.97 (m, $^1H$), 8.14 (d, J=2 Hz, 1H), 8.40 (d, J=2 Hz, 1H); MS ($CI/NH_3$): m/z 207 $(M+H^+)$. Anal. Calcd for $C_{12}H_{18}N_2O.2HCl.0.1\ H_2O$: C, 51.29; H, 7.25; N, 9.97. Found: C, 51.21; H, 7.14; N, 9.77.

Examples 37–53

R-enantiomers of Formula I, with X and Y defined as shown in Table 5, are prepared, each according to the procedure used for preparation of the corresponding (S)-enantiomer as presented in Table 5, and using the corresponding N-protected (R)-2-azetidinemethanol as a starting material in place of the N-protected (S)-2-azetidinemethanol.

| Ex. | X | Y | Using procedure of Example: |
|---|---|---|---|
| 37 | Me | H | 20 |
| 38 | H | Cl | 21 |
| 39 | H | Br | 12 |
| 40 | H | Et | 23 |
| 41 | H | n-Pr | 24 |
| 42 | H | vinyl | 22 |
| 43 | Cl | Me | 25 |
| 44 | Cl | Et | 27 |
| 45 | Cl | n-Pr | 28 |
| 46 | Cl | n-Bu | 29 |
| 47 | Cl | vinyl | 26 |
| 48 | Cl | ethynyl | 30 |
| 49 | F | Br | 31 |
| 50 | F | Me | 32 |
| 51 | Me | Br | 34 |
| 52 | Me | Et | 36 |
| 53 | Me | vinyl | 35 |

Example 54

1-(N-BOC-L-Alanyl) prodrug of 5-(2R)-azetidinylmethoxy)-2-fluoropyridine

To a solution of 5-(2R)-azetidinylmethoxy)-2-fluoropyridine (from Example 8, 102 mg, 0.60 mmol) in THF (20 mL) was added N-BOC-L-alanine (106 mg, 1.0 eq), 1-(dimethylaminopropyl)-3-ethylcarbodiimide HCl (107 mg, 1.0 eq), and 4-(dimethylamino)pyridine (68 mg, 1.0 eq), and the resulting mixture was stirred at 20–25° C. for approximately 2 hours. The volatiles were removed under vacuum, and the residue purified by chromatography on silica gel, eluting with 10%MeOH/$CH_2Cl_2$. The product was obtained as a yellow oil (155 mg, 73%): $^1$H NMR (300 MHz, $CDCl_3$) δ7.85 (m, 1H), 7.37 (ddd, J=3, 7, 10 Hz, 1H), 6.84 (dd, J=3, 9 Hz, 1H), 5.0–5.2 (m, 1H), 4.0–4.7 (br m, 5H), 3.49 (d, J=6 Hz, 1H), 2.47 (m, 2H), 1.41 (s, 9H), 1.29 (d, J=7 Hz, 3H); MS (CI/$NH_3$) m/e 354, 298, 254; $[\alpha]_D^{20}$ −49.78° (c=0.10, $CH_2Cl_2$); Analysis calc'd for $C_{17}H_{24}N_3O_4F.0.55 H_2O$: C, 56.20; H, 6.96; N, 11.57; found: C, 56.23; H, 7.03; N, 11.26.

Example 55

1-(N-acetyl-L-phenylalanyl) prodrug of 5-(2R)-azetidinylmethoxy)-2-fluoropyridine The title compound was prepared according to the procedure of Example 54, except replacing the N-BOC-L-alanine thereof with N-acetyl-L-phenylalanine. The product was obtained as a colorless oil in 56% yield: $^1$H NMR (300 MHz, $CDCl_3$) δ7.81 (m, 1H), 7.1–7.4 (m, 6H), 6.84 (m, 1H), 6.12 (m, 1H), 4.4–5.0 (m, 2H), 3.5–4.2 (m, 3H), 2.97 (m, 3H), 2.0–2.2 (m, 2H), 1.96 (s, 3H); MS (CI/$NH_3$) m/e 372; $[\alpha]_D^{20}$ −46.21° (c=0.20, $CH_2Cl_2$); Analysis calc'd for $C_{20}H_{22}N_3O_3F$: C, 64.68; H, 5.97; N, 11.31; found: C, 64.44; H, 5.99; N, 11.06.

Example 56

1-(N-acetyl-L-alanyl) prodrug of 5-(2R)-azetidinylmethoxy)-2-fluoropyridine

The title compound was prepared according to the procedure of Example 54, except replacing the N-BOC-L-alanine thereof with N-acetyl-L-alanine. The product was obtained as a colorless oil in 78% yield: $^1$H NMR (300 MHz, $CDCl_3$) δ7.85 (m, 1H), 7.37 (m, 1H), 6.86. m (1), 6.2 (m, 1H), 4.4–4.8 (m, 3H), 3.9–4.4 (m, 3H), 2.48 (m, 2H), 1.96 (s, 3H), 1.30 (d, J=7 Hz, 3H); MS (CI/$NH_3$) m/e 296, 183; $[\alpha]_D^{20}$ −86.72° (c=0.15, $CH_2Cl_2$); Analysis calc'd for $C_{14}H_{18}N_3O_3F.0.4 H_2O$: C, 56.58; H, 6.26; N, 13.89; found: C, 55.66; H, 6.38; N, 13.93.

Example 57

1-(N-BOC-L-phenylalanyl) prodrug of 5-(2R)-azetidinylmethoxy)-2-fluoropyridine

The title compound was prepared according to the procedure of Example 54, except replacing the N-BOC-L-alanine thereof with N-BOC-L-phenylalanine. The product was obtained as a pale oil in 98% yield: $^1$H NMR (300 MHz, $CDCl_3$) δ7.83 (m, 1H), 7.30 (m, 5H), 7.15 (m, 1H), 6.83 (dd, J=3, 5 Hz, 1H), 5.18 (m, 1H), 4.46 (m, 2H), 4.25 (m, 1H), 3.6–4.2 (m, 2H), 2.96 (m, 3H), 2.13 (m, 2H), 1.41 (s, 9H); MS (CI/$NH_3$) m/e 430, 330; $[\alpha]_D^{20}$ 36.72° (c=0.15, $CH_2Cl_2$); Analysis calc'd for $C_{23}H_{28}N_3O_4F.0.1 H_2O$: C, 64.05; H, 6.59; N, 9.74; found: C, 64.03; H, 6.28; N, 9.73.

Example 58

1-(monomethyl phthalyl) prodrug of 5-(2R)-azetidinylmethoxy)-2-fluoropyridine

The title compound was prepared according to the procedure of Example 54, except replacing the N-BOC-L-alanine thereof with monomethyl phthalate. The product was obtained as a colorless oil in 99% yield: 1H NMR (300 MHz, $CDCl_3$) δ7.96 (m, 2H), 7.52 (m, 3H), 7.22 (m, 1H), 6.87 (m, 1H), 4.1–4.9 (m, 3H), 3.91 (s, 3H), 3.78 (m, 2H), 2.44 (m, 2H); MS (DCI/$NH_3$) m/e 345; $[\alpha]_D^{20}$ −18.21° (c=0.20, $CH_2Cl_2$); Analysis calc'd for $C_{18}H_{17}N_2O_4F.0.55 H_2O$: C, 61.03; H, 5.15; N, 7.91; found: C, 61.09; H, 5.12; N, 7.90.

Example 59

1-(N-Acetyl-D-phenylalanlyl) prodrug of 5-(2R)-azetidinylmethoxy)-2-fluoropyridine The title compound was prepared according to the procedure of Example 54, except replacing the N-BOC-L-alanine thereof with N-acetyl-D-phenylalanine. The product was obtained as a white foam in 97% yield: $^1$H NMR (300 MHz, $CDCl_3$) δ7.82 (m, 1H), 7.2–7.5 (m, 6H), 6.87 (m, 1H), 6.27 (m, 1H), 4.6–5.0 (m, 2H), 3.8–4.2 (m, 3H), 3.54 (m, 1H), 2.9–3.1 (m, 2H), 2.01 (s, 3H), 1.8–2.4 (m, 2H); MS (DCI/$NH_3$) m/e 372; $[\alpha]_D^{20}$ +56.67° (c=0.15, $CH_2Cl_2$); Analysis calc'd for $C_{20}H_{22}N_3O_3F.0.45 H_2O$: C, 63.30; H, 6.08; N, 11.07; found: C, 63.29; H, 5.93; N, 11.09.

Example 60

1-(N-Acetyl-D-alanyl) prodrug of 5-(2R)-azetidinylmethoxy)-2-fluoropyridine

The title compound was prepared according to the procedure of Example 54, except replacing the N-BOC-L-alanine thereof with N-acetyl-D-alanine. The product was obtained as a pale yellow oil in 86% yield: $^1$H NMR (300 MHz, $CDCl_3$) δ7.86 (m, 1H), 7.36 (m, 1H), 6.85 (m, 1H), 6.26 (m, 1H), 4.71 (m, 1H), 4.1–4.6 (m, 5H), 2.47 (m, 2H), 1.98 (s, 3H), 1.22 (d, J=7 Hz, 3H); MS (DCI/$NH_3$) m/e 296; $[\alpha]_D^{20}$ +95.67° (c=0.30; $CH_2Cl_2$); Analysis calc'd for $C_{14}H_{18}N_3O_3F.0.40 H_2O$: C, 55.58; H, 6.26; N,13.89; found: C, 55.57; H, 6.30; N, 13.80.

Example 61

1-(4-(Diethylaminomethyl)benzoyl) prodrug of 5-(2R)-azetidinylmethoxy)-2-fluoropyridine The title compound was prepared according to the procedure of Example 54, except replacing the N-BOC-L- alanine thereof with 4-(dimethylaminomethyl)benzoic acid. The product was obtained as a pale yellow oil in 59% yield: $^1$H NMR (300 MHz, CDCl$_3$) δ7.90 (m, 1H), 7.54 (m, 2H), 7.38 (m, 4H), 6.83 (m, 1H), 4.88 (m, 1H), 4.1–4.6 (m, 3H), 3.60 (br s, 2H), 2.50 (m, 6H), 1.03 (d, J=7 Hz, 6H); MS (DCI/NH$_3$) m/e 372; $[\alpha]_D^{20}$ +97.00° (c=0.60, CH$_2$Cl$_2$); Analysis calc'd for C$_{21}$H$_{26}$N$_3$O$_2$F.0.3 H$_2$O: C, 66.93; H, 7.11; N, 11.15; found: C, 66.99; H, 7.13; N, 11.17.

Example 62

1-(N-BOC-D-phenylalanyl) prodrug of 5-(2R)-azetidinylmethoxy)-2-fluoropyridine The title compound was prepared according to the procedure of Example 54, except replacing the N-BOC-L-alanine thereof with N-BOC-D-phenylalanine. The product was obtained as a colorless oil in 79% yield: $^1$H NMR (300 MHz, CDCl$_3$) δ7.82 (m, 1H), 7.31 (m 3), 7.19 (m, 3H), 6.87 (m, 1H), 5.25 (m, 1H), 4.62 (m, 1H), 3.7–4.4 (m, 4H), 3.53 (m, 1H), 2.95 (m, 2H), 1.8–2.4 (m, 2H), 1.37 & 1.44 (s, 9H); MS (DCI/NH$_3$) m/e 430, 274, 330; $[\alpha]_D^{20}$ +33.20° (c=0.20, CH$_2$Cl$_2$); Analysis calc'd for C$_{23}$H$_{28}$N$_3$O$_4$F.0.65 H$_2$O: C, 62.61; H, 6.69; N, 9.52; found: C, 62.64; H, 6.66; N, 9.36.

Example 63

1-(N-BOC-D-alanyl) prodrug of 5-(2R)-azetidinylmethoxy)-2-fluoropyridine

The title compound was prepared according to the procedure of Example 54, except replacing the N-BOC-L-alanine thereof with N-BOC-D-alanine. The product was obtained as a colorless oil in 99% yield: $^1$H NMR (300 MHz, CDCl$_3$) δ7.87 (m, 1H), 7.36 (ddd, J=3, 6, 9 Hz, 1H), 6.85 (dd, J=3, 9 Hz, 1H), 5.20 (m, 1H), 4.72 (m, 1H), 4.53 (m, 1H), 4.1–4.3 (m, 4H), 2.46 (m, 2H), 1.43 (s, 9H), 1.20 (d, J=7 Hz, 3H); MS (DCI/NH$_3$) m/e 354, 298, 254; $[\alpha]_D^{20}$ +79.20° (c=0.52, CH$_2$Cl$_2$); Analysis calc'd for C$_{17}$H$_{24}$N$_3$O$_4$F.0.25 H$_2$O: C, 57.05; H, 6.90; N, 11.74; found: C, 57.09; H, 6.91; N, 11.58.

Example 64

1-(2-oxo-tetrahydrofuran-4-(S)-carboxoyl) prodrug of 5-(2R)-azetidinylmethoxy)-2-fluoropyridine The title compound was prepared according to the procedure of Example 54, except replacing the N-BOC-L-alanine thereof with S-4-carboxybutyrolactone. The product was obtained as a colorless oil in 65% yield: $^1$H NMR (300 MHz, CDCl$_3$) δ7.86 (m, 1H), 7.37 (m, 1H), 6.86 (m, 1H), 4.7–5.1 (m, 2H), 4.0–4.6 (m, 4H), 2.43 (m 6); MS (CI/NH$_3$) m/e 295, 199, 174, 123; $[\alpha]_D^{20}$ +94.0° (c=0.30, CH$_2$Cl$_2$); Analysis calc'd for C$_{14}$H$_{15}$N$_2$O$_4$F.0.4 H$_2$O: C, 55.77; H, 5.28; N, 9.24; found: C, 55.88; H, 5.39; N, 9.28.

Example 65

1-(2-oxo-tetrahydrofuran-4-(R)-carboxoyl) prodrug of 5-(2R)-azetidinylmethoxy)-2-fluoropyridine The title compound was prepared according to the procedure of Example 54, except replacing the N-BOC-L-alanine thereof with R-4-carboxybutyrolactone. The product was obtained as a pale yellow oil in 63% yield: $^1$H NMR (300 MHz, CDCl$_3$) δ7.88 (m, 1H), 7.37 (m, 1H), 6.86 (m, 1H), 4.86 (m, 1H), 4.76 (m, 1H), 4.60 (m, 1H), 4.32 (t, J=8 Hz, 2H), 4.11 (m, 1H), 2.50 (m, 6H); MS (DCI/NH$_3$) m/e 295; $[\alpha]_D^{20}$ +77.50° (c=0.16, CH$_2$Cl$_2$); Analysis calc'd for C$_{14}$H$_{15}$N$_2$O$_4$F.0.4 H$_2$O: C, 55.77; H, 5.28; N, 9.29; found: C, 55.82; H, 5.34; N, 9.21.

Example 66

1-(2-(hydroxymethyl)benzoyl) prodrug of 5-(2R)-azetidinylmethoxy)-2-fluoropyridine The title compound was prepared according to the procedure of Example 54, except replacing the N-BOC-L-alanine thereof with 2-hydroxymethylbenzoic acid. The product was obtained as a pale oil in 44% yield: $^1$H NMR (300 MHz, CDCl$_3$) δ7.94 (m 1), 7.37 (m, 5H), 6.87 (m, 1H), 4.90 (m, 1H), 4.71 (m, 1H), 4.60 (br d, J=11 Hz, 1H), 4.43 (br d, J=11 Hz, 1H), 4.18 (m, 2H), 3.99 (m 1), 2.50 (m, 2H); MS (DCI/NH$_3$) m/e 317, 200, 183, 169, 152; $[\alpha]_D^{20}$ −12.18° (c=0.12, CH$_2$Cl$_2$); Analysis calc'd for C$_{17}$H$_{17}$N$_2$O$_3$F.0.1 H$_2$O: C, 64.18; H, 5.45; N, 8.81; found: C, 64.24; H, 5.39; N, 8.73.

Example 67

1-(L-phenylalanyl) prodrug of 5-(2R)-azetidinylmethoxy)-2-fluoropyridine

BF$_3$.Et$_2$O (103 mg, 1.0 eq) was added to a solution of the 1-(N-BOC-L-phenylalanyl) prodrug of 5-(2R)-azetidinylmethoxy)-2-fluoropyridine (from Example 57, 310 mg, 0.70 mmol) in methylene chloride (20 mL). The reaction was stirred at room temperature for 1 h, then quenched with 5% NaHCO$_3$ and extracted into methylene chloride (100 mL), and dried over MgSO$_4$. The solvent was removed under vacuum, and the residue purified by chromatography on silica gel, eluting with 10% MeOH/CH$_2$Cl$_2$. The product was obtained as a colorless oil in 53% yield: $^1$H NMR (300 MHz, CDCl$_3$) δ7.84 (m, 1H), 7.26 (m, 6H), 6.84 (dd, J=3, 9 Hz, 1H), 4.53 (m, 1H), 4.46 (dd, J=5, 10 Hz, 1H), 4.16 (dd, J=3, 10 Hz, 1H), 3.93 (q, J=8 Hz, 1H), 3.42 (m, 1H), 3.14 (m, 1H), 2.91 (dd, J=8, 13 Hz, 1H), 2.82 (dd, J=7, 13 Hz, 1H), 2.23 (m, 1H), 2.09 (m, 1H); MS (DCI/NH$_3$) m/e 330, 120; $[\alpha]_D^{20}$ −52.71° (c=0.30, CH$_2$Cl$_2$); Analysis calc'd for C$_{18}$H$_{20}$N$_3$O$_2$F.0.5 H$_2$O: C, 63.86; H, 6.26; N, 12.42; found: C, 63.77; H, 6.08; N, 12.40.

Example 68

1-(L-alanyl) prodrug of 5-(2R)-azetidinylmethoxy)-2-fluoropyridine

This compound was obtainied by deprotection of 1-(N-BOC-L-alanyl) prodrug of 5-(2R)-azetidinylmethoxy)-2-fluoropyridine (from example 54) according to the procedure described in Example 67. The product was obtained as a colorless oil in 26% yield: $^1$H NMR (300 MHz, CDCl$_3$) δ7.87 (m, 1H), 7.37 (m, 1H), 6.96 (dd, J=3, 9 Hz, 1H), 4.69 (m, 1H), 4.55 (m, 1H), 4.20 (m, 2H), 4.06 (m, 1H), 3.38 (q, J=7 Hz, 1H), 2.47 (m, 2H), 1.23 (d, J=7 Hz, 3H); MS (DCI/NH$_3$) m/e 254; $[\alpha]_D^{20}$ −31.62° (c=0.05, CH$_2$Cl$_2$); Analysis calc'd for C$_{12}$H$_{16}$N$_3$O$_2$F.1.15 H$_2$O: C, 52.60; H, 6.73; N, 15.34; found: C, 52.58; H, 6.56; N, 15.27.

Example 69

1-(D-phenylalanyl) prodrug of 5-(2R)-azetidinylmethoxy)-2-fluoropyridine

This compound was obtained by deprotection of 1-(N-BOC-D-phenylalanyl) prodrug of 5-(2R)-azetidinylmethoxy)-2-fluoropyridine (from example 62) according to the procedure described in Example 67. The product was obtained as a colorless oil in 53% yield: $^1$H NMR (300 MHz, CDCl$_3$) δ7.84 (m, 1H), 7.35 (m, 1H), 7.22 (m, 5H), 6.87 (m, 1H), 4.67 (m, 1H), 4.31 (m, 1H), 4.10 (m, 2H), 3.6–4.0 (m, 2H), 2.88 (m, 2H), 2.40 (m, 1H), 2.24 (m, 1H); MS (DCI? NH$_3$) m/e 330; [α]$_D^{20}$ +20.75° (c=0.27, CH$_2$Cl$_2$); Analysis calc'd for C$_{18}$H$_{20}$N$_3$O$_2$F.0.5 H$_2$O: C, 63.89; H, 6.26; N, 12.42; found: C, 63.92; H, 6.06; N, 12.48.

Example 70

1-(D-alanyl) prodrug of 5-(2R)-azetidinylmethoxy)-2-fluoropyridine

This compound was obtained by deprotection of the 1-(N-BOC-D-alanyl) prodrug of 5-(2R)-azetidinylmethoxy)-2-fluoropyridine (from example 63) according to the procedure described in Example 67. The product was obtained as a colorless oil, which was treated with 1 eq of p-toluenesulfonic acid in ethanol to form the tosylate salt as a colorless semisolid (17%): $^1$H NMR (300 MHz, CD$_3$OD) δ7.90. m (1), 7.70 (d, J=8 Hz, 2H), 7.59 (m, 1H), 7.23 (d, J=8 Hz, 2H), 7.00 (dd, J=3,9 Hz, 1H), 4.76 (m, 1H), 4.55 (m, 1H), 4.39 (m, 1H), 4.21 (m, 2H), 4.02 (m, 1H), 2.52 (m, 2H), 2.37 (s, 3H), 1.34 (d, J=7 Hz, 3H); MS (DCI/NH$_3$) m/e 254, 183, 141; [α]$_D^{20}$ +11.10° (c=0.05, EtOH); Analysis calc'd for C$_{12}$H$_{16}$N$_3$O$_2$F.C$_7$H$_8$O$_3$S: C, 52.42; H, 5.75; N, 7.64; found: C, 53.31; H, 5.77; N, 7.34.

Example 71

1-(N-succinimidylmethyl) prodrug of 5-(2R)-azetidinylmethoxy)-2-fluoropyridine 5-(2R)-Azetidinylmethoxy)-2-fluoropyridine tosylate (from Example 8, 150 mg, 0.42 mmol) was combined with succinimide (47 mg, 1.1 eq) and K$_2$CO$_3$ (88 mg, 1.5 eq). Ethanol (20 mL) was added, followed by aqueous formalin (36%, 110 mg, 3.2 eq). The mixture was stirred at 40–45° C. for 2–3 hours, then cooled to 25° C. and concentrated to a white solid. This was purified on silica gel with 1% MeOH/EtOAc to provide the title compound as a colorless oil (70 mg, 59%): $^1$H NMR (300 MHz, CDCl$_3$) δ7.86 (m, 1H), 7.41 (ddd, J=3, 6, 9 Hz, 1H), 6.85 (dd, J=3, 9 Hz, 1H), 4.34 (AB quartet, J=13 Hz, 2H), 4.02 (m, 2H), 3.76 (m, 1H), 3.43 (dt, J=3, 8 Hz, 1H), 3.24 (m, 1H), 2.76 (s, 4H), 2.11 (m, 1H), 2.02 (m, 1H); MS (DCI/NH$_3$) m/e 294 ((M+1)), 183; Analysis calc'd for C$_{14}$H$_{16}$N$_3$O$_3$F.0.5 H$_2$O: C, 55.62; H, 5.67; N, 13.90; found: C, 55.76; H, 5.61; N, 13.92.

Example 72

1-(N-phthalimidylmethyl) prodrug of 5-(2R)-azetidinylmethoxy)-2-fluoropyridine 5-(2R)-Azetidinylmethoxy)-2-fluoropyridine tosylate (from Example 8) was combined with phthalimide by the procedure described in Example 71 to give the title compound: m.p. 97–100°; $^1$H NMR (300 MHz, CDCl$_3$) δ7.88 (m, 2H), 7.76 (m, 3H), 7.33 (ddd, J=3, 6, 9 Hz, 1H), 6.82 (dd, J=3, 9 Hz, 1H), 4.54 (s, 2H), 4.05 (m, 2H), 3.82 (m, 1H), 3.45 (m, 1H), 3.28 (q, J=8 Hz, 1H), 2.13 (m, 1H), 2.00 (m, 1H); MS (DCI/NH$_3$) m/e 342 (M+1), 183; Analysis calc'd for C$_{18}$H$_{16}$N$_3$O$_3$F.0.50 H$_2$O: C, 61.70; H, 4.89; N, 11.99; found: C, 61.68; H, 4.93; N, 11.87.

Example 73

1-(N-(2-hydroxybenzoyl)aminomethyl) prodrug of 5-(2R)-azetidinylmethoxy)-2-fluoropyridine 5-(2R)-Azetidinylmethoxy)-2-fluoropyridine tosylate (from Example 8) was combined with salicylamide by the procedure described in Example 71 to give the title compound: $^1$H NMR (300 MHz, CDCl$_3$) δ7.80 (dd, J=2, 3 Hz, 1H), 7.40 (t, J=8 Hz, 1H), 7.28 (m, 2H), 6.99 (d, J=8 Hz, 1H), 6.78 (m, 3H), 4.39 (dd, J=6, 12 Hz, 1H), 4.24 (dd, J=5, 12 Hz, 1H), 4.05 (m, 2H), 3.80 (m, 1H), 3.45 (q, J=6 Hz, 1H), 3.27 (q, J=8 Hz, 1H), 2.12 (m, 2H); MS (DCI/NH$_3$) m/e 332 ((M+1)), 183, 155, 138; Analysis calc'd for C$_{17}$H$_{18}$N$_3$O$_3$F.0.50 H$_2$O: C, 59.99; H, 5.62; N, 12.34; found: C, 59.78; H, 5.67; N, 12.06.

Example 74

1-(2,5-dihydro-2-oxo-furan-4-yl) prodrug of 5-(2R)-azetidinylmethoxy)-2-fluoropyridine A mixture of 5-(2R)-azetidinylmethoxy)-2-fluoropyridine tosylate (from Example 8, 200 mg, 0.56 mmol), tetronic acid (84 mg, 1.5 eq), potassium carbonate (77 mg, 1 eq), and absolute ethanol (2 mL) was heated in a sealed tube at 45–50° C. for 2–3 hours. The mixture was filtered, and the filtrate was concentrated under vacuum. The product was purified by chromatography on silica gel, eluting with 2% MeOH/CH$_2$Cl$_2$, to provide the title compound (86 mg, 56%): m.p. 93° (EtOAc/Et$_2$O); $^1$H NMR (300 MHz, CDCl$_3$) δ7.85 (dd, J=2, 3 Hz, 1H), 7.36 (ddd, J=3, 6, 9 Hz, 1H), 6.90 (dd, J=3, 9 Hz, 1H), 4.67 (m, 4H), 4.18 (m, 2H), 4.08. dt (5, J=9 Hz, 1H), 3.95 (m, 1H), 2.68 (m, 1H), 2.39 (m, 1H); MS (APCI) m/e 265 ((M+1)); Analysis calc'd for C$_{13}$H$_{13}$N$_2$O$_3$F: C, 59.08; H, 4.95; N, 10.60; found: C, 58.90; H, 4.88; N, 10.52.

Example 75

1-(5,5-dimethyl-3-oxocyclohexenyl) prodrug of 5-(2R)-azetidinylmethoxy)-2-fluoropyridine The title compound was prepared in 65% yield from 5-(2R)-azetidinylmethoxy)-2-fluoropyridine tosylate (from Example 8) by reaction with 5,5-dimethyl-1,3-cyclohexanedione according to the procedure of Example 74. $^1$H NMR (300 MHz, CDCl$_3$) δ7.85 (dd, J=2, 3 Hz, 1H), 7.35 (ddd, J=3, 6, 9 Hz, 1H), 6.87 (dd, J=3, 9 Hz, 1H), 5.02 (m, 1H), 4.62 (m, 1H), 4.29 (m, 1H), 4.15 (m, 1H), 4.05 (m, 1H), 3.91 (m, 1H), 2.59 (m, 1H), 2.37 (m, 1H), 2.14 (br s, 2H), 2.09 (m, 2H), 1.05 (s, 3H), 1.03 (s, 3H); MS (CDI/NH$_3$) m/e 305 ((M+1)); Analysis calc'd for C$_{17}$H$_{21}$N$_2$O$_2$F.0.75 H$_2$O: C, 64.23; H, 7.13; N, 8.81; found: C, 63.89; H, 7.03; N, 8.73.

Example 76

1-(3-oxocyclohexenyl) prodrug of 5-(2R)-azetidinylmethoxy)-2-fluoropyridine

The title compound was prepared in 77% yield from 5-(2R)-azetidinylmethoxy)-2-fluoropyridine tosylate (from Example 8) by reaction with 5,5-dimethyl-1,3-cyclohexanedione according to the procedure of Example 74. $^1$H NMR (300 MHz, CDCl$_3$) δ7.84 (dd, J=2, 3 Hz, 1H), 7.35 (ddd, J=3, 6, 9 Hz, 1H), 6.87 (dd, J=3, 9 Hz, 1H), 5.01 (m, 1H), 4.61 (m, 1H), 4.26 (m, 1H), 4.13 (m, 1H), 4.04 (m, 1H), 3.92 (m, 1H), 2.58 (m, 1H), 2.37 (m, 1H), 2.27 (m, 4H), 1.94 (m, 2H); MS (DCI/NH$_3$) m/e 277 ((M+1)); Analysis calc'd for C$_{15}$H$_{17}$N$_2$O$_2$F.0.75 H$_2$O: C, 62.16; H, 6.43; N, 9.66; found: C, 62.15; H, 6.30; N, 9.67.

Example 77

1-(2,2-bis(ethoxycarbonyl)ethenyl) prodrug of 5-(2R)-azetidinylmethoxy)-2-fluoropyridine The title compound was prepared in 81% yield from 5-(2R)-azetidinylmethoxy)-2-fluoropyridine tosylate (from Example 8) by reaction with diethyl ethoxymethylenemalonate according to the procedure of Example 74 and warming for 20 hours. $^1$H NMR (300 MHz, CDCl$_3$) δ7.85 (m, 1H), 7.67 (br s, 1H), 7.36 (ddd, J=3, 6, 9 Hz, 1H), 6.87 (dd, J=3, 9 Hz, 1H), 4.79 (m, 1H), 4.29 (m, 1H), 4.17 (m, 6H), 4.02 (m, 1H), 2.58 (m, 1H), 2.26 (m, 1H), 1.30 (t, J=7 Hz, 3H), 1.26 (t, J=7 Hz, 3H); MS (DCI/NH$_3$) m/e 353 (M+1); Analysis calc'd for C$_{17}$H$_{21}$N$_2$O$_5$F: C, 57.94; H, 6.00; N, 7.95; found: C, 57.63; H, 6.05; N, 7.77.

Example 78

1-(ethoxycarbonyl) prodrug of 5-(2R)-azetidinylmethoxy)-2-fluoropyridine

To a solution of 5-(2R)-azetidinylmethoxy)-2-fluoropyridine tosylate (from Example 8, 0.2 g, 0.56 mmol) in CH$_2$Cl$_2$ (10 mL) and 10 ml of NaHCO$_3$ solution was added ethyl chloroformate (0.064 g, 0.59 mmol). The reaction mixture was stirred at room temperature for 2 hours. The organic layer was separated, dried (MgSO$_4$) and evaporated. The residue was chromatographed on silica gel eluting with 1:1 EtOAc:hexane to yield 0.09 g (63%) of the title compound: $^1$H NMR (300 MHz, CDCl$_3$) δ7.87 (m, 1H), 7.28 (ddd, J=3, 6, 9 Hz, 1H), 6.86 (dd, J=3, 9Hz, 1H), 4.59 (m, 1H), 4.26 (m, 1H), 4.14 (m, 1H), 4.10 (q, J=7 Hz, 2H), 3.96 (t, J=8 Hz, 2H), 2.38 (m, 2H), 1.22 (t, J=7 Hz, 3H); MS (DCI/NH$_3$) m/e 255; Analysis calc'd for C$_{12}$H$_{15}$N$_2$O$_3$F: C, 56.69; H, 5.95; N, 11.02; found: C, 56.40; H, 5.78; N, 10.92.

Example 79

1-(phenoxycarbonyl) prodrug of 5-(2R)-azetidinylmethoxy)-2-fluoropyridine

The title compound was prepared in 83% yield from 5-(2R)-azetidinylmethoxy)-2-fluoropyridine tosylate (from Example 8) by the procedure of Example 78, except substituting phenyl chloroformate for the ethyl chloroformate thereof. $^1$H NMR (300 MHz, CDCl$_3$) δ7.90 (dd, J=2, 3 Hz, 1H), 7.35 (m, 3H), 7.18 (m, 1H), 7.06 (br d, J=8 Hz, 2H), 6.86 (dd, J=3, 9 Hz, 1H), 4.73 (m, 1H), 4.46 (dd, J=4, 10 Hz, 1H), 4.12 (m, 3H), 2.48 (m, 2H); MS (DCI/NH$_3$) m/e 303; Analysis calc'd for C$_{16}$H$_{15}$N$_2$O$_3$F: C, 63.57; H, 5.00; N, 9.27; found: C, 63.82; H, 4.86; N, 8.99.

Example 80

1-(4-nitrophenoxycarbonyl) prodrug of 5-(2R)-azetidinylmethoxy)-2-fluoropyridine The title compound was prepared in 82% yield from 5-(2R)-azetidinylmethoxy)-2-fluoropyridine tosylate (from Example 8) by the procedure of Example 78, except substituting 4-nitrophenyl chloroformate for the ethyl chloroformate thereof: m.p. 68–70°; $^1$H NMR (300 MHz, CDCl$_3$) δ8.22 (m, 2H), 7.91 (m, 1H), 7.39 (ddd, J=3, 6, 9 Hz, 1H), 7.27 (m, 2H), 6.88 (dd, J=3, 9 Hz, 1H), 4.76 (m, 1H), 4.47 (m, 1H), 4.19 (m, 3H), 2.52 (m, 2H); MS (DCI/NH$_3$) m/e 348; [α]$_D^{20}$ 11.18° (c=0.004, CH$_2$Cl$_2$); Analysis calc'd for C$_{16}$H$_{14}$N$_3$O$_5$F: C, 55.33; H, 4.06; N, 12.10; found: C, 54.95; H, 4.00; N, 11.96.

Example 81

1-(4-methoxyphenoxycarbonyl) prodrug of 5-(2R)-azetidinylmethoxy)-2-fluoropyridine The title compound was prepared in 65% yield from 5-(2R)-azetidinylmethoxy)-2-fluoropyridine tosylate (from Example 8) by the procedure of Example 78, except substituting 4-methoxyphenyl chloroformate for the ethyl chloroformate thereof: m.p. 60–61°; $^1$H NMR (300 MHz, CDCl$_3$) δ7.90 (m, 1H), 7.40 (ddd, J=3, 6, 9 Hz, 1H), 6.97 (br d, J=9 Hz, 2H), 6.86 (m, 3H), 4.72 (m, 1H), 4.46 (dd, J=4, 10 Hz, 1H), 4.15 (m, 3H), 3.77 (s, 3H), 2.48 (m, 2H); MS (DCI/NH$_3$) m/e 333; [α]$_D^{20}$ 9.11° (c=0.0047, CH$_2$Cl$_2$); Analysis calc'd for C$_{17}$H$_{17}$N$_2$O$_4$F: C, 61.44; H, 5.16; N, 8.43; found: C, 61.39; H, 5.11; N, 8.22.

Example 82

1-(4-(methoxycarbonyl)phenoxycarbonyl) prodrug of 5-(2R)-azetidinylmethoxy)-2-fluoropyridine The title compound was prepared in 84% yield from 5-(2R)-azetidinylmethoxy)-2-fluoropyridine tosylate (from Example 8) by the procedure of Example 78, except substituting 4-(methoxycarbonyl)phenyl chloroformate for the ethyl chloroformate thereof: mp 90–92° C.; $^1$H NMR (300 Mhz, CDCl$_3$) δ8.13 (m, 2H), 7.9 (m, 1H), 7.4 (m, 1H), 7.15 (d, 2H), 6.88 (dd, 1H), 4.73 (m, 1H), 4.48 (m, 1H), 4.18 (m, 3H), 3.9 (s, 3H), 2.5 (m, 2H); MS (CI/NH$_3$) m/e 361 (M+1), 378 (M+NH$_4$).

Example 83

1-(4-methylphenoxycarbonyl) prodrug of 5-(2R)-azetidinylmethoxy)-2-fluoropyridine The title compound was prepared in 96% yield from 5-(2R)-azetidinylmethoxy)-2-fluoropyridine tosylate (from Example 8) by the procedure of Example 78, except substituting 4-methylphenyl chloroformate for the ethyl chloroformate thereof: mp 68–70° C.; $^1$H NMR (300 MHz, CDCl$_3$) δ7.9 (m, 1H), 7.4 (m, 1H), 7.12 (d, 2H), 6.93 (d, 2H, 6.86 (dd, 1H), 4.71(m, 1H), 4.45 (m, 1H), 4.13(m, 3H), 2.47 (m, 2H), 2.3 (s, 3H); MS (CI/NH$_3$) m/e 317 (M+1), 334 (M+NH$_4$).

Example 84

1-(4-fluorophenoxycarbonyl) prodrug of 5-(2R)-azetidinylmethoxy)-2-fluoropyridine The title compound was prepared in 72% yield from 5-(2R)-azetidinylmethoxy)-2-fluoropyridine tosylate (from Example 8) by the procedure of Example 78, except substituting 4-fluorophenyl chloroformate for the ethyl chloroformate thereof: $^1$H NMR (300 MHz, CDCl$_3$) δ7.9 (m, 1H), 7.4 (m, 1H), 7.2 (d, 4H), 6.88 (dd, 1H), 4.73 (m, 1H), 4.48 (m, 1H), 4.18 (m, 3H), 2.5 (m, 2H); MS (CI/NH$_3$) m/e 321 (M+1), 338 (M+NH$_4$).

Example 85

1-(4-chlorophenoxycarbonyl) prodrug of 5-(2R)-azetidinylmethoxy)-2-fluoropyridine The title compound was prepared in 85% yield from 5-(2R)-azetidinylmethoxy)-2-fluoropyridine tosylate (from Example 8) by the procedure of Example 78, except substituting 4-chlorophenyl chloroformate for the ethyl chloroformate thereof: 1$^1$H NMR (300 MHz, CDCl$_3$) δ7.9 (m, 1H), 7.4 (m, 1 H), 7.3 (m, 2H), 7.02 (m, 2H), 6.87 (dd, 1H), 4.73 (m, 1H), 4.47 (m, 1H), 4.17 (m, 3H), 2.5 (m, 2H); MS (CI/NH$_3$) m/e 337 (M+1), 354 (M+NH$_4$).

Example 86

1-(2,6-dimethylphenoxycarbonyl) prodrug of 5-(2R)-azetidinylmethoxy)-2-fluoropyridine The title compound was prepared in 43% yield from 5-(2R)-azetidinylmethoxy)-2-fluoropyridine tosylate (from Example 8) by the procedure of Example 78, except substituting 2,6-dimethylphenyl chloroformate for the ethyl chloroformate thereof: $^1$H NMR (300 MHz, CDCl$_3$) δ7.9 (m, 1H), 7.4 (m, 1H), 7.03 (s, 3H), 6.88 (dd, 1H), 4.73 (m, 1H), 4.5 (m, 1H), 4.18 (m, 3H), 2.5 (m, 2H), 2.15 (bs, 6H); MS (CI/NH$_3$) m/e 331 (M+1), 348 (M+NH$_4$).

Example 87

1-(2-methylphenoxycarbonyl) prodrug of 5-(2R)-azetidinylmethoxy)-2-fluoropyridine The title compound was prepared as a colorless oil in quantitative yield from 5-(2R)-azetidinylmethoxy)-2-fluoropyridine tosylate (from Example 8) by the procedure of Example 78, except substituting 2-methylphenyl chloroformate for the ethyl chloroformate thereof: 1H NMR (CDCl$_3$) δ8.13 (m, 2H), 7.9 (m, 1H), 7.4 (m, 1H), 7.15 (d, 2H), 6.88 (dd, 1H), 4.73 (m, 1H), 4.5 (m, 1H), 4.18 (m, 3H), 2.5 (m, 2H), 2.15 (s, 3H); MS (CI/NH$_3$) m/e 317 (M+1), 334 (M+NH$_4$).

Example 88

1-(1-acetoxy-1-methyl)ethoxycarbonyl) prodrug of 5-(2R)-azetidinylmethoxy)-2-fluoropyridine 88a. Isopropenyl p-nitrophenyl carbonate Isopropenyl chloroformate (5.0 g, 41.5 mmol) was added to an ice cold suspension of p-nitrophenol (6.3 g, 45.6 mmol) in chloroform (100 mL). To the stirred reaction mixture, pyridine (3.32 g, 41.5 mmol) was added dropwise over 20 minutes. After stirring at ice bath temperature for 15 minutes, the reaction mixture was allowed to warm up and stirred at room temperature for 16 hours. The reaction mixture was washed with water, 1N HCl, ice-cold 1% aqueous sodium hydroxide, water and brine. The organic layer was dried (MgSO$_4$) and the solvent was evaporated. The solid residue was subsequently crystallized from hexane to provide the title compound (7.8 g, 84% yield): $^1$H NMR (CDCl$_3$, 300 MHz) δ2.05 (s, 3H), 4.82 (t, 1H, J=1.0 Hz), 4.96 (d, 1H, J=2.0 Hz), 7.40–7.46 (m, 2H), 8.27–8.32 (m, 2H).

88b. 2-Chloro2-propyl p-nitrophenyl carbonate

The isopropenyl carbonate from step 88a (7.5 g, 33.6 mmol) was dissolved in a mixture of ethyl ether (100 mL) and chloroform (100 mL). The mixture was cooled to 0° C. and then bubbled with HCl gas. After standing at room temperature for 16 hours the mixture was purged with nitrogen to remove the excess HCl, and the solvent was evaporated to give the title compound (8.0 g, 92%): $^1$H NMR (CDCl$_3$, 300 MHz) δ2.11 (s, 6H), 7.39–7.44 (m, 2H), 8.27–8.32 (m, 2H).

88c. 2-Acetoxy-2-propyl p-nitrophenyl carbonate

A mixture of 2-chloro-2-propyl p-nitrophenyl carbonate (8.0 g, 30.8 mmol) and mercuric acetate (11.0 g, 34.6 mmol) in dichloromethane (400 mL) was stirred at room temperature for 72 hours. The reaction mixture was washed with brine containing a few drops of sodium bicarbonate solution and then with aqueous sodium bicarbonate. The organic layer was dried (MgSO$_4$) and evaporated to afford an oil (5.4 g, 62%). $^1$H NMR (CDCl$_3$, 300 MHz) δ1.93 (s, 6H), 2.10 (s, 3H), 7.37–7.42 (m, 2H), 8.26–8.31 (m, 2H).

88d. 1-(1-acetoxy-1-methyl)ethoxycarbonyl) prodrug of 5-(2R)-azetidinylmethoxy)-2-fluoropyridine A solution of 3-(2-(R)-azetidinylmethoxy-6-fluoropyridine (from Example 8, 0.30 g, 1.65 mmol) and the 2-acetoxy-2-propyl p-nitrophenyl carbonate from step 88c (0.49 g, 1.73 mmol) in dimethylformamide (6 mL) was stirred at room temperature for 24 hours. The reaction mixture was diluted with water (25 mL) and extracted with ethyl acetate. The organic layer was washed with water, ice cold 1% aqueous sodium hydroxide, 1N HCl water and brine, and then dried (MgSO$_4$) and concentrated. The residuewas chromatographed to afford an light yellow oil (0.175 g, 33%): $^1$H NMR (300 MHz, CDCl$_3$) δ7.88 (s, 1H), 7.40 (m, 1H), 6.86 (dd, J=3.7, 8.8 Hz, 1H), 4.57 (m, 1H), 4.34 (m, 1H), 4.14 (m, 1H), 3.95 (t, J=7.5 Hz, 2H), 2.34–2.44 (m, 2H), 2.01 (s, 3H), 1.98 (s, 3H), 1.79 (s, 3H); MS (DC/NH$_3$) m/e 327 ((M+1)); [α]$_D^{20}$ +74.5° (c=0.2, MeOH); Analysis calc'd for C$_{15}$H$_{19}$N$_2$O$_5$F: C, 54.81; H, 5.60; N, 8.26; found: C, 55.21; H, 5.87; N, 8.58.

Example 89

1-((5-methyl-2-oxo-1,3-dioxol-4-en-4-yl)methoxycarbonyl) prodrug of 5-(2R)-azetidinylmethoxy)-2-fluoropyridine A sample of 5-(2R)-azetidinylmethoxy)-2-fluoropyridine (from Example 8 (0.13 g, 0.7 mmol) ) and (5-methyl-2-oxo-1,3-dioxol-4-en-4-yl)methyl p-nitrophenyl carbonate (prepared according to J. Alexander, et al., J. Med. Chem. 1996, 39, 480–486) (0.21 g, 0.73 mmol) in DMF (2 ml) was stirred at room temperature for 16 hours. The reaction mixture was diluted with water and extracted with EtOAc. The organic layer was washed with with water, 1N HCl, 2% sodium carbonate and brine. It was dried over MgSO$_4$ and evaporated. The residue was chromatographed on silica gel eluting with 30% EtOAc/hexane to yield 0.17 g (72%) of product: $^1$H NMR (300 MHz, CDCl$_3$) δ7.86 (m, 1H), 7.36 (ddd, J=3, 6, 9 Hz, 1H), 6.87 (dd, J=3, 9 Hz, 1H), 4.80 (m, 2H), 4.61 (m, 1H), 4.36 (m, 1H), 4.11 (dd, J=3, 10 Hz, 1H), 3.99 (m, 2H), 2.42 (m, 2H), 2.15 (s, 3H); MS (DCI/NH$_3$) m/e 339, 183; [α]$_D^{20}$ +6.43° (c=0.0042, CH$_2$Cl$_2$); Analysis calc'd for C$_{15}$H$_{15}$N$_2$O$_6$F: C, 53.26; H, 4.47; N, 8.28; found: C, 53.52; H, 4.58; N, 8.15.

Example 90

1-((5-methyl-2-oxo-1,3-dioxol-4-en-4-yl)methoxycarbonyl) prodrug of 5-(2R)-azetidinylmethoxy)-2-fluoropyridine The title compound was prepared in 61% yield from 5-(2R)-azetidinylmethoxy)-2-fluoropyridine (from Example 8) by the procedure of Example 450, except substituting 5-phenyl-2-oxo-1,3-dioxolan-4-ylmethyl p-nitrocarbonate (J. Alexander et al., J. Med. Chem. 1996, 39, 480–486) for the (5-methyl-2-oxo-1,3-dioxol-4-en-4-yl)methyl p-nitrophenyl carbonate thereof: $^1$H NMR (300 MHz, CDCl$_3$) δ7.85 (m, 1H), 7.59 (m, 2H), 7.44 (m, 3H), 7.35 (m, 1H), 6.84 (dd, J=3, 9 Hz, 1H), 5.09 (m, 2H), 4.63 (m, 1H), 4.37 (m, 1H), 4.11 (dd, J=3, 10 Hz, 1H), 4.03 (m, 2H), 2.44 (m, 2H); MS (DCI/NH$_3$) m/e 401, 194; [α]$_D^{20}$ +3.07° (c=0.0035, CH$_2$Cl$_2$); Analysis calc'd for C$_{20}$H$_{17}$N$_2$O$_6$F: C, 60.00; H, 4.28; N, 7.00; found: C, 59.81; H, 4.30; N, 6.98.

Example 91

1-((pyrrolidin-1-yl)carbonyl) prodrug of 5-(2R)-azetidinylmethoxy)-2-fluoropyridine A solution of 5-(2R)-azetidinylmethoxy)-2-fluoropyridine (from Example 8, 0.09 g, 0.49 mmol) and pyrrolidine carbonyl chloride (0.073 g, 0.54 mmol) in toluene (10 mL)

was refluxed for 5 hours. The reaction mixture was evaporated and partitioned in $CH_2Cl_2/H_2O$. The organic layer was dried ($MgSO_4$) and concentrated. The residue was chromatographed on silica gel, eluting with EtOAc to yield 0.07 g (51%) of product: $^1$H NMR (300 MHz, CDCl$_3$) δ7.86 (m, 1H), 7.38 (m, 1H), 6.85 (m, 1H), 4.5–4.8 (m, 2H), 3.8–4.2 (m, 3H), 3.33 (m, 4H), 2.36 (m, 2H), 1.84 (m, 4H); MS (DCI/NH$_3$) m/e 280, 169; $[\alpha]_D^{20}$ +6.57° (c=0.0026, $CH_2Cl_2$); Analysis calc'd for $C_{14}H_{18}N_3O_2F.0.75\ H_2O$: C, 57.42; H, 6.71; N, 14.35; found: C, 57.51; H, 6.43; N, 14.36.

Example 92

1-((pyrrolidin-1-yl)carbonyl) prodrug of 5-(2R)-azetidinylmethoxy)-2-fluoropyridine The title compound was prepared in 46% yield from 5-(2R)-azetidinylmethoxy)-2-fluoropyridine (from Example 8) by the procedure of Example 91, except substituting diethylcarbamyl chloride for the pyrrolidine carbonyl chloride thereof: 1H NMR (300 MHz, CDCl$_3$) δ7.87 (m, 1H), 7.39 (ddd, J=3, 6, 9 Hz, 1H), 6.82 (dd, J=3, 9 Hz, 1H), 4.72 (m, 1H), 4.20 (dd, J=5, 10 Hz, 1H), 4.10 (dd, J=3, 10 Hz, 1H), 3.96 (m, 1H), 3.84 (m, 1H), 3.18 (m, 4H), 2.33 (m, 2H), 1.09 (t, J=7 Hz, 6H); MS (DCI/NH$_3$) m/e 282; $[\alpha]_D^{20}$ 2.66° (c=0.005, $CH_2Cl_2$); Analysis calc'd for $C_{14}H_{20}N_3O_2F$: C, 59.77; H, 7.17; N, 14.94; found: C, 59.65; H, 7.04; N, 14.90.

Example 93

1-(acetyl) prodrug of 5-(2R)-azetidinylmethoxy)-2-fluoropyridine 5-(2R)-azetidinylmethoxy)-2-fluoropyridine (from Example 8, 162 mg, 0.89 mmole), acetic anhydride (0.12 mL, 1.26 mmole), TEA (0.2 mL 1.47 mmole), and $CH_2Cl_2$ (30 mL) were combined under $N_2$ and stirred for 16 hours. The solution was extracted with sat. aq. $Na_2CO_3$ (30 mL), brine (2×30 mL) and dried ($MgSO_4$).The solvent was evaporated under vacuum and the crude product was chromatographed (silica gel; hexane/EtOAc 9:1 to 7:3) to yield 160 mg (80%) of the title compound: $^1$H NMR (DMSO-d$_6$, 300 MHz) δ: 1.74 (s, 3H), 2.16 (m, H), 2.40 (m, 1H), 3.86 (br s, 2H), 4.25 (dd,J=3.5, 10.5, 1H), 4.36 (d,J=4.5,10.5 1H), 4.58 (br s, 1H), 7.01 (dd, J=3.5, 8.5, 1H), 7.57 (m, 1H), 7.90 (m, 1H); MS (CI/NH$_3$) m/e 225 (M+H)$^+$ 242 (M+NH$_4$)$^+$; $[\alpha]_D$ +91.7 (c 1, MeOH); Anal. calcd. for $C_{11}H_{13}FN_2O_2.0.2\ C_4H_8O_2$. C, 58.6 H, 6.08;N, 11.58; found: C, 58.27; H, 6.04; N, 11.63.

Example 94

1-(t-butyloxycarbonyl) prodrug of 5-(2R)-azetidinylmethoxy)-2-fluoropyridine

A solution of 5-(2R)-azetidinylmethoxy)-2-fluoropyridine (from Example 8, 0.12 g, 0.7 mmol), di-t-butyl-dicarbonate (0.23 g, 1 mmol) and DMAP (0.13 g, 1 mmol) in $CH_2Cl_2$ (10 mL) was stirred at room temperature for 16 hours. The mixture was evaporated and the residue chromatographed on silica gel eluting with EtOAc/hexane 1:1 to yield 0.14 g (71%) of product: $^1$H NMR (300 MHz, CDCl$_3$) δ7.87 (m, 1H), 7.38 (ddd, J=3, 6, 9 Hz, 1H), 6.85 (dd, J=3, 9 Hz, 1H), 4.50 (m, 1H), 4.31 (m, 1H), 4.12 (dd, J=3, 10 Hz, 1H), 3.89 (t, J=8 Hz, 2H), 2.33 (m, 2H), 1.42 (s, 9H); MS (DCI/NH$_3$) m/e 283, 227; Analysis calc'd for $C_{14}H_{19}N_2O_3F$: C, 59.56; H, 6.78; N, 9.92; found: C, 59.34; H, 6.65; N, 9.88.

Example 95 disulfide prodrug dimer of 1-(3-thiopropionyl) 5-(2R)-azetidinylmethoxy)-2-fluoropyridine To a solution of 3,3'-dithiodipropionic acid (100 mg, 0.48 mmol) and triethylamine (53 mg, 0.53 mmol) in THF (1.0 mL) at –78° C. was added isobutyl chloroformate (68 mg, 0.51 mmol) dropwise with stirring. After stirring at –78° C. for 1 hour, 5-(2R)-azetidinylmethoxy)-2-fluoropyridine (from Example 8, 175 mg, 0.96 mmol) was added to the reaction mixture. The resultant solution was allowed to warm to 25° C. and stirred for 3 hours. After all of the starting material was consumed, the organic solvent was evaporated under vacuum. The residue was purified by column silica gel chromatography eluting with ethyl acetate: hexane (1:1) to provide the title compound (102 mg, 21%). $^1$H NMR (300 MHz, CDCl$_3$) δ2.32–2.65 (m, 8H), 2.79–2.97 (m, 4H), 3.89–4.27 (m, 6H), 4.50 (dd, J=4.4 Hz, 9.8H, 2H), 4.61–4.83 (m, 1H), 6.85 (dd, J=3.8 Hz, 8.2H, 2H), 7.37 (m, 2H), 7.87 (m, 2H); MS (DCI/NH$_3$) m/e 539 (M+1); $[\alpha]_D^{20}$ 101° (c=0.10, MeOH); Analysis calc'd for $C_{24}H_{28}N_4O_2F_2S_2.0.5\ CHCl_3$: C, 51.96; H, 5.07; N, 9.89; found: C, 52.13; H, 5.40; N, 10.25.

Example 96

1-(S-(phenylmethyl)cysteinoyl) prodrug of 5-(2R)-azetidinylmethoxy)-2-fluoropyridine To a solution of S-benzyl-N-Cbz-(L)-cysteine and triethylamine in THF at –78° C. was added isobutyl chloroformate dropwise with stirring. After stirring at –78° C. for 1 hour, 5-(2R)-azetidinylmethoxy)-2-fluoropyridine (from Example 8, 175 mg, 0.96 mmol) was added to the reaction mixture. The resultant solution allowed to warm to 25° C. and stirred for 3 hours. After all of the starting material was consumed, the organic solvent was evaporated under vacuum. The residue was N-deprotected and purified by column silica gel chromatography eluting with ethyl acetate: hexane (1:1) to provide the title compound. $^1$H NMR (300 MHz, CDCl$_3$) δ7.16–7.40 (m, 6H), 7.86 (m, 1H), 6.84 (m, 1H), 4.66 (m, 1H), 4.51 (m, 1H), 4.04–4.22 (m, 2H), 3.96 (m, 1H), 3.75 (s, 2H), 3.38 (m, 1H), 2.74 (m, 1H), 2.58 (m, 1H), 2.34–2.48 (m, 2H), 1.63–2.04 (m, 2H); MS (DCI/NH$_3$) m/e 376 (M+1)$^+$; $[\alpha]_D^{20}$ +110° (c=0.05, MeOH); Analysis calc'd for $C_{19}H_{22}N_3O_2FS.0.1\ H_2O$: C, 60.49; H, 5.93; N, 11.14; found: C, 60.11; H, 6.01; N, 10.80.

Example 97

2-Chloro-3-(2-(R)-azetidinylmethoxy)pyridine tosylate 97a. 2-Chloro-3-(1-Boc-2-(R)-azetidinylmethoxy) pyridine The procedures of examples 10c and 10d were used, substituting Boc-(R)-hydroxymethylazetidine for the Boc-(S)-hydroxymethylazetidine used in step 10c, and 2-chloro-3-hydroxypyridine for 3-fluoro-5-hydroxypyridine in step 10d. The title compound was obtained as an oil (535 mg, 93%): $^1$H NMR (CDCl$_3$, 300 MHz) δ1.40 (s, 9H), 2.40 (m, 2H), 3.90–4.00(m, 2H), 4.16 (m, 1H), 4.55 (m, 2H), 7.20 (m, 1H), 7.35 (m, 1H), 8.00 (m, 1H); MS (CI/NH$_3$) m/z: 299 (M+H)$^+$.

97b. 2-Chloro-3-(2-(R)-azetidinylmethoxy)pyridine tosylate

The product of of Example 459a (530 mg, 1.78 mmol) was treated according the the procedure of example 407b. The residue was chromatographed (silica gel; CHCl$_3$/MeOH, 95:5 to 90:10) to afford the free base of the title compound as white solid, which was converted to the salt by treatment with p-toluenesulfonic acid in ethanol to give the title compound (398 mg). mp 102–104° C.; $[\alpha]^{25}_D$=+5.78° (c=0.74, MeOH); $^1$H NMR (DMSO, 300 MHz) δ2.28 (s, 3H), 2.52 (m, 2H), 2.62 (m, 1H), 3.98 (m, 2H), 4.42 (d, J=3 Hz, 2H), 4.78 (br, 1H), 7.18 (d, J=9 Hz, 2H), 7.45 (d, J=6 Hz, 1H), 7.52 (d, J=9 Hz, 2H), 7.64 (dd, J=3, 9 Hz, 1H), 8.05 (dd, J=3, 6 Hz, 1H), 8.90 (br, 1H); MS (APCI) m/z 199 (M+H)$^+$, 231 (M+H+MeOH)$^+$. Anal. calcd. for $C_9H_{11}ClN_2O.1.2$ TsOH.0.5 H2O: C, 50.45; H, 5.25; N, 6.76. Found: C, 50.30; H, 5.15; N, 6.56.

Example 98

6-Fluoro-3-(1-methyl-2-(R)-azetidinylmethoxy) pyridine tosylate

98a. 1-Cbz-2-(R)-azetidinemethyl-p-toulenesulfonate

To a solution of 1-Cbz-2-(R)-azetidinemethanol (30.76 g, 218.8 mmol) in methylene chloride (75 mL) at 0° C. was added triethylamine (25.2 mL 179 mmol) and p-tolenesulfonyl chloride (34.46 g 181 mmol). The mixture was stirred for 16 hours and filtered, then the filtrate was washed with 2N sodium hydroxide (50 mL), 2N HCl (50 mL), brine and dried (MgSO$_4$). The solvent was evaporated under vacuum, and the crude product was chromatographed (silica gel; hexane/EtOAc 9:1 to 6:4) to yield 44.1 g (78.8 %) of the title compound. $^1$H NMR (CDCl$_3$, 300 MHz) δ: 2.21–2.43 (m, 3H), 2.45 (s,3H), 3.84–3.92 (m, 2H), 4.13 (m, 1H), 4.36 (m, 1H), 4.58 (m, 1H), 5.0 (br. s 2H), 7.26–7.27 (m, 7H). MS (CI/NH$_3$) m/e 376 (M+H)$^+$ 393 (M+NH$_4$)$^+$. Anal. calcd. for $C_{19}H_{21}NO_5S$. C, 60.78 H, 5.64;N, 3.73. Found: C, 60.40 H, 5.82; N, 3.75. $[\alpha]_D$ +53.06 (c 1.0, CHCl$_3$).

98b. 6-Fluoro-3-(1-Cbz-2-(R)-azetidinylmethoxy) pyridine

The procedure of example 10d was used, substituting the product of step 98a for t-butoxycarbonyl-(S)-toluensulfonyoxymethylazetidine and 2-fluoro-5-hydroxypyridine from Example 8 for 3-fluoro-5-hydroxypyridine. The product was obtained as a colorless oil: $^1$H NMR (dmso-d$_6$, 300 MHz) δ: 2.21 (m, 1H), 2.38 (m, 1H), 3.87 (t, J=7 Hz, 2H), 4.19 (dd, J=4, 11 Hz, 1H), 4.34 (dd J=4, 11 Hz, 1H), 4.54 (m, 1H), 5.01 (m, 2H), 6.97 (dd, J=3, 9 Hz, 1H), 7.28 (m, 5H), 7.50 (m, 1H), 7.85 (m, 1H). MS (CI/NH$_3$) m/e 317 (M+H)$^+$. Anal. calcd. for $C_{17}H_{17}FNO_3$. C, 64.55; H, 5.42; N, 8.86. Found: C, 64.57; H, 5.44; N, 8.83. $[60]_D$ +74.6 (c 1.1, CHCl$_3$).

98c. 6-Fluoro-3-(1-methyl-2-(R)-azetidinylmethoxy) pyridine tosylate

6-Fluoro-3-(1-Cbz-2-(R)-azetidinylmethoxy)pyridine from Example 98b (1 g, 3.16 mmol) was combined with 10% Pd-C (50 mg) and paraformaldehyde (1 g) in ethanol (10 mL), and the mixture was stirred under hydrogen (1 atm) for 16 hours. The mixture was filtered and concentrated. The residue was taken up in ethyl acetate, treated with p-toluenesulfonic acid, and the resulting salt was crystallized from ethyl acetate-ether to provide the title compound (813 mg, 74%): m.p. 121–125°; $^1$H NMR (500 MHz, D$_2$O) δ7.91 (m, 1H), 7.69 (d, J=8.4 Hz, 2H), 7.66 (m, 1H), 7.37 (d, J=7.9 Hz, 2H), 7.10 (dd, J=2.7, 8.6 Hz, 1H), 4.86 (m, 1H), 4.45 (dd, J=2.4, 11.6 Hz, 1H), 4.37 (dd, J=5.5, 11.6 Hz, 1H), 4.27 (m, 1H), 4.00 (q, J=10.2 Hz, 1H), 2.99 (s, 3H), 2.67 (m, 1H), 2.62 (m, 1H), 2.40 (s, 3H); $^{19}$F NMR (471 MHz, D$_2$O) δ−78.38; MS (CI/NH$_3$) m/e 197 (M+H)$^+$; Analysis calc'd for $C_{17}H_{21}N_2O_4FS$: C, 55.42; H, 5.75; N, 7.60; found: C, 55.07; H, 5.79; N, 7.40.

Example 99

6-Fluoro-3-(1-ethyl-2-(R)-azetidinylmethoxy) pyridine tosylate

The title compound was prepared in 27% yield by the procedure of example 98 c starting with acetaldehyde in place of paraformaldehyde: m.p. 106–109°; $^1$H NMR (500 MHz, D$_2$O) δ7.91 (m, 1H), 7.69 (d, J=8.0 Hz, 2H), 7.66 (m, 1H), 7.37 (d, J=7.9 Hz, 2H), 7.11 (dd, J=2.8, 8.4 Hz, 1H), 4.82 (m, 1H), 4.43 (m, 2H), 4.23 (m, 1 H), 3.98 (q, J=9.7 Hz, 1H), 3.42 (m, 1H), 3.30 (m, 1H), 2.64 (m, 2H), 2.40 (s, 3H), 1.24 (t, J=7.3 Hz, 3H), $^{19}$F NMR (471 MHz, D$_2$O) δ−78.38; MS (CI/NH$_3$) m/e 211 (M+H)$^+$; Analysis calc'd for $C_{18}H_{23}N_2O_4FS$: C, 56.53; H, 6.06; N, 7.32; found: C, 56.28; H, 5.97; N, 7.20.

Example 100

6-Fluoro-3-(1-propyl-2-(R)-azetidinylmethoxy) pyridine tosylate

The title compound was prepared in 40% yield by the procedure of example 98c starting with propanal in place of paraformaldehyde: m.p. 93–95°; $^1$H NMR (500 MHz, D$_2$O) δ7.92 (m, 1H), 7.70 (d, J=8.5 Hz, 2H), 7.66 (m, 1H), 7.38 (d, J=8.0 Hz, 2H), 7.11 (dd, J=2.5, 9.2 Hz, 1H), 4.84 (m, 1H), 4.44 (m, 2H), 4.23 (m, 1H), 4.01 (m, 1H), 3.34 (m, 1H), 3.20 (m, 1H), 2.63 (q, J=8.5 Hz, 2H), 2.40 (s, 3H), 1.66 (m, 2H), 0.96 (t, J=7.8 Hz, 3H); $^{19}$F NMR (471 MHz, D$_2$O) δ−78.35; MS (CI/NH$_3$) m/e 225 (M+H)$^+$; Analysis calc'd for $C_{19}H_{25}N_2O_4FS$: C, 57.56; H, 6.36; N, 7.07; found: C, 57.37; H, 6.13; N, 6.82.

Example 101

6-Fluoro-3-(1-(1-methylethyl)-2-(R)-azetidinylmethoxy)pyridine tosylate

The title compound was prepared in 22% yield by the procedure of example 98c starting with acetone in place of paraformaldehyde: m.p. 93–95°; $^1$H NMR (500 MHz, D$_2$O) δ7.88 (m, 1H), 7.68 (d, J=8.4 Hz, 2H), 7.64 (m, 1H), 7.35 (d, J=7.9 Hz, 2H), 7.09 (dd, J=2.6, 8.5 Hz, 1H), 4.85 (m, 1H), 4.39 (m, 2H), 4.14 (m, 1H), 4.02 (q, J=9.5 Hz, 1H), 3.58 (hept, J=6.7 Hz, 1H), 2.58 (m, 2H), 2.38 (s, 3H), 1.31 (d, J=6.7 Hz, 3H), 1.25 (d, J=6.7 Hz, 3H); $^{19}$F NMR (471 MHz, D$_2$O) δ−78.42; MS (CI/NH$_3$) m/e 225 (M+H)$^+$; Analysis calc'd for $C_{19}H_{25}N_2O_4FS.0.1 CH_3OH$: C, 57.19; H, 6.29; N, 6.77; found: C, 56.98; H, 6.38; N, 6.94.

Example 102

6-Fluoro-3-(1-butyl-2-(R)-azetidinylmethoxy) pyridine tosylate

The title compound was prepared in 83% yield by the procedure of example 98c starting with butanal in place of paraformaldehyde: m.p. 93–97°; $^1$H NMR (500 MHz, D$_2$O) δ7.91 (m, 1H), 7.69 (d, J=8.1 Hz, 2H), 7.65 (m, 1H), 7.37 (d, J=8.5 Hz, 2H), 7.10 (dd, J=3, 9 Hz, 1H), 4.81 (m, 1H), 4.42 (br, 2H), 4.23 (m, 1H), 4.00 (m, 1H), 3.35 (m, 1H), 3.25 (m, 1H), 2.62 (m, 2H), 2.40 (s, 3H), 1.61 (m, 2H), 1.37 (m, 2H), 0.91 (t, J=7.3 Hz, 3H); $^{19}$F NMR (471 MHz, D$_2$O) δ−78.32; MS (CI/NH$_3$) m/e 239 (M+H)$^+$; Analysis calc'd for $C_{20}H_{27}N_2O_4FS$: C, 58.52; H, 6.63; N, 6.82; found: C, 58.23; H, 6.68; N, 6.72.

Example 103

6-Fluoro-3-(1-(2-methylpropyl)-2-(R)-azetidinylmethoxy)pyridine tosylate

The title compound was prepared in 43% yield by the procedure of example 98c starting with isobutyraldehyde in place of paraformaldehyde: m.p. 103–104°; $^1$H NMR (500 MHz, D$_2$O) δ7.91 (br, 1H), 7.69 (d, J=8.6 Hz, 2H), 7.66 (m, 1H), 7.37 (d, J=7.9 Hz, 2H), 7.11 (dd, J=3, 9 Hz, 1H), 4.86 (m, 1H), 4.44 (br, 2H), 4.26 (m, 1H), 4.04 (m, 1H), 3.30 (m, 1H), 3.07 (dd, J=9.2, 12.8 Hz, 1H), 2.62 (m, 2H), 2.40 (s, 3H), 2.04 (m, 1H), 0.98 (d, J=7.3 Hz, 3H), 0.96 (d, J=7.3 Hz, 3H); $^{19}$F NMR (471 MHz, D$_2$O) δ-78.3; MS (DCI/NH$_3$) m/e 239 (M+H)$^+$; Analysis calc'd for C$_{20}$H$_{27}$N$_2$O$_4$FS: C, 58.52; H, 6.63; N, 6.82; found: C, 58.36; H, 6.58; N, 6.77.

Example 104

6-Fluoro-3-(1-pentyl-2-(R)-azetidinylmethoxy)pyridine tosylate

The title compound was prepared in 64% yield by the procedure of example 472c starting with pentanal in place of paraformaldehyde: m.p. 77–79°; $^1$H NMR (500 MHz, D$_2$O) δ7.90 (br, 1H), 7.69 (d, J=7.9 Hz, 2H), 7.65 (m, 1H), 7.37 (d, J=8.6 Hz, 2H), 7.11 (dd, J=2.6, 8.5 Hz, 1H), 4.82 (m, 1H), 4.42 (br s, 2H), 4.23 (m, 1H), 4.01 (m, 1H), 3.35 (m, 1H), 3.23 (m, 1H), 2.62 (q, J=8.5 Hz, 2H), 2.40 (s, 3H), 1.62 (m, 2H), 1.31 (m, 4H), 0.86 (m, 3H); $^{19}$F NMR (471 MHz, D$_2$O) δ-78.3; MS (CI/NH$_3$) m/e 253 (M+H)$^+$; Analysis calc'd for C$_{21}$H$_{29}$N$_2$O$_4$FS: C, 59.41; H, 6.89; N, 6.60; found: C, 59.25; H, 6.81; N, 6.48.

Example 105

6-Fluoro-3-(1-methyl-2-(S)-azetidinylmethoxy)pyridine tosylate

105a. 6-Fluoro-3-(1-Cbz-2-(S)-azetidinylmethoxy)pyridine

The procedure of example 98 was followed, except substituting 1-Cbz-2-(S)-azetidinemethanol for the 1-Cbz-2-(R)-azetidinemethanol thereof. The product was obtained as a clear oil: $^1$H NMR (dmso-d$_6$, 300 MHz) δ: 2.21 (m, 1H), 2.38 (m, 1H), 3.87 (t, J=7 Hz, 2H), 4.19 (dd, J=4, 11 Hz, 1H), 4.34 (dd J=4, 11 Hz, 1H), 4.54 (m, 1H), 5.01 (m, 2H), 6.97 (dd, J=3, 9 Hz, 1H), 7.28 (m, 5H), 7.50 (m, 1H), 7.85 (m, 1H). MS (CI/NH$_3$) m/e 317 (M+H)$^+$. Anal. calcd. for C$_{17}$H$_{17}$FNO$_3$: C, 64.55; H, 5.42; N, 8.86. Found: C, 64.37; H, 5.30; N, 8.83. [α]$_D$ -74.7 (c 1.0, CHCl$_3$).

105b. 6-Fluoro-3-(1-methyl-2-(S)-azetidinylmethoxy)pyridine tosylate

The title compound was prepared by the procedure of example 98c, except substituting 6-fluoro-3-(1-Cbz-2-(S)-azetidinylmethoxy)pyridine for the R enantiomer thereof. The product was obtained as a white solid: mp 124–126° C.; [α]$_D$=+15.93 (c 0.5, MeOH); $^1$H NMR (300 MHz, D$_2$O) δ7.92 (s, 1H), 7.68 (m, 3H), 7.38 (d, 2H, J=8.0 Hz), 7.11 (dd, 1H, J=2.5,8.5 Hz), 4.8 (br s, 1H), 4.45 (m, 2H), 4.27 (br s, 1H), 4.02 (br s, 1H), 2.99 (s, 3H), 2.68 (m, 2H), 2.40 (s, 3H); MS (CI/NH$_3$); m/z 197 (M+H)$^+$. Anal. Calcd for C$_{10}$H$_{13}$FN$_2$O.TsOH: C, 55.42; H, 5.75; N, 7.60. Found: C, 55.33; H, 5.74; N, 7.59.

Example 106

6-Fluoro-3-(1-ethyl-2-(S)-azetidinylmethoxy)pyridine tosylate

The title compound was prepared in 47% yield by the procedure of example 105b, substituting acetaldehyde for the paraformaldehyde therein. The product was obtained as a white solid: m.p. 101–103°; $^1$H NMR (500 MHz, D$_2$O) δ7.91 (m, 1H), 7.69 (d, J=8 Hz, 2H), 7.66 (m, 1H), 7.37 (d, J=8 Hz, 2H), 7.11 (dd, J=9, 2 Hz, 1H), 4.80 (m, 1H), 4.44 (m, 2H), 4.23 (m, 1H), 3.98 (m, 1H), 3.42 (1), 3.30 (dq, J=12, 7 Hz, 1H), 2.63 (br q, J=8 Hz, 2H), 2.40 (s, 3H), 1.24 (t, J=7 Hz, 3H); $^{19}$F NMR (471 MHz, D$_2$O) δ-78.36; MS (DCI/NH$_3$) m/e 211 (M+1)$^+$; Analysis calc'd for C$_{18}$H$_{23}$N$_2$O$_4$FS: C, 56.53; H, 6.06; N, 7.32; found: C, 56.54; H, 6.05; N, 7.26.

Example 107

6-Fluoro-3-(1-propyl-2-(S)-azetidinylmethoxy)pyridine tosylate

The title compound was prepared in 74% yield by the procedure of example 105b, substituting propanal for the paraformaldehyde thereof. The product was obtained as a white solid: m.p. 95–104°; $^1$H NMR (500 MHz, D$_2$O) δ7.90 (m, 1H), 7.68 (d, J=8 Hz, 2H), 7.65 (m, 1H), 7.36 (d, J=8 Hz, 2H), 7.10 (dd, J=9, 2 Hz, 1H), 4.81 (m, 1H), 4.41 (m, 2H), 4.23 (m, 1H), 4.00 (q, J=10 Hz, 1H), 3.34 (m, 1H), 3.20 (m, 1H), 2.62 (m, 2H), 2.39 (s, 3H), 1.65 (m, 2H), 0.95 (t, J=7 Hz, 3H); $^{19}$F NMR (471 MHz, D$_2$O) δ-78.34; MS (CI/NH$_3$) m/e 225 (M+1)$^+$; Analysis calc'd for C$_{19}$H$_{25}$N$_2$O$_4$FS: C, 57.56; H, 6.36; N, 7.07; found: C, 57.51; H, 6.27; N, 6.90.

Example 108

6-Fluoro-3-(1-butyl-2-(S)-azetidinylmethoxy)pyridine tosylate

The title compound was prepared in 82% yield by the procedure of example 105b, substituting butanal for the paraformaldehyde thereof. The product was obtained as a white solid: m.p. 88–93°; $^1$H NMR (500 MHz, D$_2$O) δ7.90 (m, 1H), 7.69 (d, J=8 Hz, 2H), 7.65 (m, 1H), 7.37 (d, J=8 Hz, 2H), 7.10 (dd, J=9, 2 Hz, 1H), 4.81 (m, 1H), 4.42 (m, 2H), 4.22 (m, 1H), 4.00 (q, J=9 Hz, 1H), 3.37 (m, 1H), 3.25 (m, 1H), 2.62 (m, 2H), 2.40 (s, 3H), 1.61 (m, 2H), 1.37 (hex, J=7 Hz, 2H), 0.91 (t, J=7 Hz, 3H); $^{19}$F NMR (471 MHz, D$_2$O) δ-78.31; MS (CI/NH$_3$) m/e 239 (M+1)$^+$; Analysis calc'd for C$_{20}$H$_{27}$N$_2$O$_4$FS: C, 58.52; H, 6.63; N, 6.82; found: C, 58.28; H, 6.64; N, 6.60.

Example 109

6-Fluoro-3-(1-(2-methylpropyl)-2-(S)-azetidinylmethoxy)pyridine tosylate

The title compound was prepared in 83% yield by the procedure of example 105b, substituting isobutyraldehyde for the paraformaldehyde. The product was obtained as a white solid: m.p. 104–106°; $^1$H NMR (500 MHz, D$_2$O) δ7.91 (m, 1H), 7.70 (d, J=8 Hz, 2H), 7.66 (m, 1H), 7.37 (d, J=8 Hz, 2H), 7.11 (dd, J=9, 2 Hz, 1H), 4.86 (m, 1H), 4.45 (m, 2H), 4.25 (m, 1H), 4.05 (m, 1H), 3.29 (m, 1H), 3.07 (dd, J=13, 9 Hz, 1H), 2.62 (m, 2H), 2.40 (s, 3H), 2.05 (m, 1H), 0.97 (t, J=7 Hz, 6H); $^{19}$F NMR (471 MHz, D$_2$O) δ-78.29; MS (DCI/NH$_3$) m/e 239 ((M+1)$^+$); Analysis calc'd for C$_{20}$H$_{27}$N$_2$O$_4$FS: C,58.52; H, 6.63; N, 6.82; found: C, 58.36; H, 6.68; N, 6.73.

Example 110

6-Fluoro-3-(1-pentyl-2-(S)-azetidinylmethoxy)pyridine tosylate

The title compound was prepared in 49% yield by the procedure of example 105b, substituting pentanal for the paraformaldehyde thereof. The product was obtained as a white solid: m.p. 71–73°; $^1$H NMR (500 MHz, $D_2O$) δ7.91 (m, 1H), 7.69 (d, J=8 Hz, 2H), 7.66 (m, 1H), 7.37 (d, J=8 Hz, 2H), 7.11 (m, 1H), 4.82 (m, 1H), 4.43 (m, 2H), 4.23 (m, 1H), 3.99 (m, 1H), 3.36 (m, 1H), 3.24 (m, 1H), 2.62 (m, 2H), 2.40 (s. 3), 1.63 (m, 2H), 1.32 (m, 4H), 0.87 (m 3); $^{19}$F NMR (471 MHz, $D_2O$) δ–78.31; MS (DCI/$NH_3$) m/e 253 ((M+1)$^+$); Analysis calc'd for $C_{21}H_{29}N_2O_4FS$: C, 59.41; H, 6.89; N, 6.60; found: C, 59.13; H, 6.86; N, 6.53.

Example 111

6-Fluoro-3-(1-(1 1-dimethylpropyl)-2-(R)-azetidinylmethoxy)pyridine tosylate 111a. 5-[1-(1,1-Dimethyl-2-propynyl)-(2S)-azetidinylmethoxy]-2-fluoro-pyridine To a solution of 5-((2S)-azetidinylmethyloxy)-2-fluoropyridine (530 mg, 2.91 mmol) and 3-chloro-3-methyl-1-butyne (0.654 mL, 5.82 mmol) in THF (6 mL) at room temperature was added a catalytic amount of copper(I) chloride (14 mg, 0.15 mmol), resulting in formation of a precipitate. The mixture was stirred for 1 hour, diluted with $Et_2O$ and washed with 1 N aqueous HCl. The layers were separated, and the aqueous phase was basified with 15% aqueous NaOH (pH=12) and extracted with $CH_2Cl_2$. The $CH_2Cl_2$ extracts were dried ($Na_2SO_4$) and concentrated. Purification by chromatography (silica gel; 98:2 $CH_2Cl_2$/MeOH) afforded 290 mg (40%) of the title compound as a light yellow oil: $[\alpha]_D^{23}$ –93.8 (c 1.03, $CH_2Cl_2$); $^1$H NMR ($CDCl_3$) δ1.21 (s, 3H), 1.29 (s, 3H), 2.02 (m, 1H), 2.14 (m, 1H), 2.39 (s, 1H), 3.23–3.29 (m, 2H), 3.90–4.06 (m, 3H), 6.85 (dd, J=1.7, 8.8 Hz, 1H), 7.32 (m, 1H), 7.82 (dd, J=1.7, 3.1 Hz, 1H); MS (CI/$NH_3$) m/z 249 (M+H$^+$).

111b. 5-[1-(1,1-Dimethyl-2-propynyl)-(2S)-azetidinylmethoxy]-2-fluoro-pyridine tosylate To a solution of 5-[1-(1,1-dimethyl-2-propynyl)-(2S)-azetidinylmethoxy]-2-fluoropyridine (58 mg, 0.23 mmol) from step 111a above in EtOH (3 mL) was added p-toluenesulfonic acid.monohydrate (44 mg, 0.23 mmol). The solution was stirred for 1 hour, then the volatiles were removed under vacuum. The solid was triturated with $Et_2O$ then dried under high vacuum to afford 93 mg (95%) of the the title compound as a white solid: mp 155–157° C.; $^1$H NMR ($D_2O$) δ1.55 (s, 3H), 1.62 (s, 3H), 2.40 (s, 3H), 2.55 (m, 2H), 3.26 (s, 1H), 4.06 (m, 1H), 4.21 (m, 1H), 4.42 (d, J=4.0 Hz, 2H), 5.05 (m, 1H), 7.10 (dd, J=2.6, 8.8 Hz, 1H), 7.38 (d, J=8.1 Hz, 2H), 7.67 (m, 1H), 7.70 (d, J=8.5 Hz, 2H), 7.91 (m, 1H); MS (CI/$NH_3$) m/z 249 (M+H$^+$). Anal. Calcd for $C_{14}H_{17}FN_2O.C_7H_8O_3S$: C, 59.98; H, 5.99; N, 6.66. Found: C, 59.78; H, 5.91; N, 6.52.

111c. 5-[1-(1,1-Dimethylpropyl)-(2S)-azetidinylmethoxy]-2-fluoropyridine

A suspension of 5-[1-(1,1-dimethyl-2-propynyl)-(2S)-azetidinylmethoxy]-2-fluoropyridine from step 111b above (210 mg, 0.846 mmol) and 10% palladium on activated carbon (20 mg) in MeOH (10 mL) was stirred under an atmosphere of hydrogen (balloon) for 18 hours. The catalyst was removed by filtration through a pad of Celite ($CH_2Cl_2$ wash), and the organic solution was concentrated to afford 206 mg of a yellow oil. Purification by chromatography (silica gel, 90:10 $CH_2Cl_2$eOH) afforded 190 mg (89%) of the title compound as a colorless oil: $[\alpha]_D^{23}$ –40.9 (c 1.13, $CH_2Cl_2$); $^1$H NMR ($CDCl_3$) δ0.84 (t, J=7.1 Hz, 3H), 0.92 (s, 3H), 0.94 (s, 3H), 1.30 (q, J=7.1 Hz, 2H), 1.95 (m, 1H), 2.07 (m, 1H), 3.10–3.35 (m, 2H), 3.82 (m, 1H), 3.92–4.05 (m, 2H), 6.84 (m, 1H), 7.31 (m, 1H), 7.81 (dd, J=2.4, 2.9 Hz, 1H); MS (CI/$NH_3$) m/z 253 (M+H$^+$).

111d. 5-[1-(1,1-Dimethylpropyl)-(2S)-azetidinylmethoxy]-2-fluoropyridine tosylate The free amine (84 mg, 0.33 mmol) from step 111c above was dissolved in EtOH (3 mL) and p-toluenesulfonic acid-.monohydrate (63 mg, 0.33 mmol) was added. The solution was stirred for 2 hours, then the volatiles were removed under vacuum. The solid was triturated with $Et_2O$ then dried under high vacuum to afford 145 mg (95%) of the the title compound as a white solid: mp 84–86° C.; $^1$H NMR ($D_2O$) δ0.95 (t, J=7.3 Hz, 3H), 1.31 (s, 3H), 1.37 (s, 3H), 1.68 (m, 2H), 2.40 (s, 3H), 2.54 (q, J=8.6 Hz, 1H), 4.02 (m, 1H), 4.15 (m, 1H), 4.43 (m, 2H), 4.97 (m, 1H), 7.11 (dd, J=2.4, 9.2 Hz, 1H), 7.38 (d, J=7.9 Hz, 2H), 7.67 (m, 1H), 7.70 (d, J=8.6 Hz, 2H), 7.91 (dd, J=1.2, 3.1 Hz, 1H); MS (CI/$NH_3$) m/z 253 (M+H$^+$); Anal. Calcd for $C_{14}H_{21}FN_2O.1.2$ $C_7H_8O_3S$: C, 58.62; H, 6.72; N, 6.10. Found: C, 58.62; H, 6.81; N, 6.45.

Example 112

6-Fluoro-3-(1-(1,1-dimethylpropyl)-2-(R)-azetidinylmethoxy)pyridine tosylate

Following the procedures of Example 111a and b, except replacing the 5-(2S)-azetidinylmethyloxy)-2-fluoropyridine thereof with 5-(2R)-azetidinylmethyloxy)-2-fluoropyridine, 5-[1-(1,1-dimethyl-2-propynyl)-(2R)-azetidinylmethoxy]-2-fluoropyridine was prepared in 21% yield. Following the procedures of Example 111c and d, replacing 5-[1-(1,1-dimethyl-2-propynyl)-(2S)-azetidinylmethoxy]-2-fluoropyridine thereof with the enantiomeric material 5-[1-(1,1-eimethyl-2-propynyl)-(2R)-azetidinylmethoxy]-2-fluoropyridine, the title compound was prepared as a white solid: mp 67–70° C.; $^1$H NMR ($D_2O$) δ0.95 (t, J=7.3 Hz, 3H), 1.31 (s, 3H), 1.37 (s, 3H), 1.67 (m, 2H), 2.40 (s, 3H), 2.54 (q, J=8.5 Hz, 1H), 4.02 (m, 1H), 4.15 (m, 1H), 4.43 (m, 2H), 4.96 (m, 1H), 7.11 (dd, J=3.0, 9.2 Hz, 1H), 7.38 (d, J=8.5 Hz, 2H), 7.67 (m, 1H), 7.70 (d, J=7.9 Hz, 2H), 7.92 (dd, J=1.8, 3.1 Hz, 1H); MS (CI/$NH_3$) m/z 253 (M+H$^+$); Anal. Calcd for $C_{14}H_{21}FN_2O.C_7H_8O_3S.0.8$ $H_2O$: C, 57.46; H, 7.03; N, 6.38. Found: C, 57.46; H, 6.95; N, 6.27.

Example 113

6-Difluoromethyl-3-((1-methyl-2-(S)-azetidinyl)methoxy)pyridine citrate 113a. 6-Hydroxymethyl-3-((1-t-butoxycarbonyl-2-(S)-azetidinyl)methoxy)pyridine A sample of (S)-1-t-butoxycarbonyl-2-azetidinemethanol (1.64 g, 8.18 mmol) and 1.05 g (6.29 mmol) of 6-acetyloxymethyl-3-hydroxypyridine, prepared as described by Deady and Dayhe, *Aust. J. Chem.*, 2565:36 (1983), were reacted with triphenylphosphine (540 mg, 2.06 mmol) and DEAD (0.33 mL, 2.06 mmol) in THF (25 mL) according to the procedure of Example 2a. The product was stirred in methanol (4 mL) containing KOH (450 mg) at room temperature for 4 hours, then neutralized and concentrated. The residue was purified by chromatography (silica gel; 1:1 ether:hexane and ethyl acetate) to give title compound (240 mg, 41% for two steps). MS (DCI/$NH_3$) m/e: 295 (M+H)$^+$. $^1$H NMR ($CDCl_3$, 300 MHz) δ: 1.42 (s, 9H), 2.24–2.48 (m, 2H), 3.84–3.96 (m, 2H), 4.18 (dd, J=2.6, 11

Hz, 1H), 4.40 (m, 1H), 4.53 (m, 1H), 4.82 (s, 2H), 7.36 (d, J=8.5 Hz, 1H), 7.51 (m 1H), 8.31 (d, J=3.0 Hz, 1H).

113b. 6-Difluoromethyl-3-((1-t-butoxycarbonyl-2-(S)-azetidinyl)methoxy)pyridine To a sample of the compound of step 113a above (127 mg, 0.43 mmol) in phosphoric acid (3 mL) was added dicyclohexylcarbodiimide (310 mg, 1.5 mmol), and the solution was stirred at 25° C. for 2 hours. The solid was filtered and the filtrate was then washed with saturated $NaHCO_3$. The organic layer was dried ($MgSO_4$), filtered, and the solvent was removed. The residue (110 mg) was used for next reaction without further purification. MS ($DCI/NH_3$) m/e: 293 $(M+H)^+$. To the crude product (110 mg, 0.38 mmol) in methylene chloride (3 mL) was added triethylamine (0.1 mL), and the solution was cooled to −78° C. To this solution was added DAST (42 μL, 0.39 mmol), then the solution was stirred at −78–0° C. for 1.5 hours. The reaction mixture was warmed to room temperature, and the reaction was quenched by the addition of saturated $NaHCO_3$. The mixture was extracted with chloroform, the solvent was removed, and the residue was chromatographed (silica gel; EtOAc/hexane, 1:1) to give the title compound (52 mg, 44%). MS (DCI/$NH_3$) m/e: 315 $(M+H)^+$. $^1$H NMR ($CDCl_3$, 300 MHz) δ: 1.55 (s, 9H), 2.34 (s, 3H), 2.11–2.44 (m, 2H), 3.90 (t, J=7.8 Hz, 2H), 4.17 (dd, J=2.9, 10 Hz, 1H), 4.36 (m, 1H), 4.53 (m, 1H), 6.62 (t, J=55.5 Hz, 1H), 7.36 (dd, J=2.5, 8.6 Hz), 7.57 (d, J=8.5 Hz, 1H), 8.36 (d, J=3.0 Hz, 1H).

113c. 6-Difluoromethyl-3-((1-methyl-2-(S)-azetidinyl)methoxy)pyridine citrate The compound obtained from step 113b above was treated with p-toluenesulfonic acid (64.6 mg, 0.34 mmol) in methylene chloride (3 mL). The resultant mixture was refluxed for 6 hours. The solvent was removed under reduced pressure. The residue was triturated with ether several times to give a white very hygroscopic solid (102 mg). MS ($CI/NH_3$) m/e: 215 $(M+H)^+$, 232 $(M+NH_4)^+$. $^1$H NMR ($CDCl_3$, 300 MHz) δ: 2.38 (s, 3H), 2.69 (q, J=8.5 Hz, 2H), 4.03–4.11 (m, 2H), 4.45 (d, J=4.4 Hz, 2H), 4.96 (m, 1H), 6.79 (t, J=55.5 Hz, 1H), 7.35 (d, J=7.5 Hz, 2H), 7.60 (dd, J=2.7, 8.5 Hz, 1H), 7.68 (d, J=8.2 Hz, 2H), 7.72 (d, J=8.8 Hz, 1H), 8.39 (d, J=3.0 Hz, 1H). Anal. Calcd for $C_{10}H_{12}F2N_2O.2.5 C_7H_8SO_3.2 H_2O$: C, 48.52; H, 5.33; N, 4.12. Found: C, 48.46; H, 5.27 N, 4.10. $[α]_D^{25}$=1° (c0.28, MeOH).

Example 114

3-(2-(R)-Azetidinylmethoxy)-5-chloropyridine tosylate

114a. 3-(1-t-butoxycarbonyl-2-(R)-azetidinylmethoxy)-5-chloropyridine

To a solution of 5-chloro-3-hydroxypyridine (0.3 g, 2.6 mmol) in DMF was added KOH (0.2 g, 3.8 mmol) at room temperature. 1-t-Butoxycarbonyl-2-(R)-azetidinylmethyl tosylate (0.8 g, 2.4 mmol, from example 10d) was then added, and the reaction mixture was stirred at 80° C. for 16 hours. The DMF was removed by washing with $H_2O$/brine (1:1) in EtOAc. The organic layer was dried, concentrated and chromatographed (silica gel; hexane/EtOAc, 5:1 to 1:1) to afford an oil (0.6 g, 87%): $^1$H NMR ($CDCl_3$, 300 MHz) δ1.43 (s, 9H), 2.21–2.40 (m, 2H), 3.89 (t, 2H, J=8 Hz), 4.12 (m, 1H), 4.36 (m, 1H), 4.52 (m, 1H), 7.29 (m, 1H), 8.20 (d, 1H, J=2 Hz), 8.25 (d, 1H, J=3 Hz); MS ($CI/NH_3$) m/z 299 $(M+H)^+$.

114b. 3-(2-(R)-Azetidinylmethoxy)-5-chloropyridine tosylate

To a solution of 3-(1-t-butoxycarbonyl-2-(R)-azetidinylmethoxy)-5-chloropyridine (0.6 g, 2.1 mmol) in $CH_2Cl_2$ (4 mL) was added TFA (3 mL) at 0° C. The reaction mixture was allowed to stir at 0° C.–25° C. After 30 minutes, it was basified with 15% NaOH and extracted with $CH_2Cl_2$. The organic solvent was dried ($MgSO_4$), concentrated and chromatographed (silica gel; $CH_2Cl_2$/MeOH, 10:0.4 to 10:1) to afford an oil (0.4 g, 93%): $^1$H NMR ($CDCl_3$, 300 MHz) δ2.44–2.64 (m, 2H), 3.80 (m, 1H), 3.98 (m, 1H), 4.08 (m, 1H), 4.24 (m, 1H), 4.61 (m, 1H), 7.26 (m, 1H), 8.23 (m, 1H); MS ($CI/NH_3$) m/z 199 $(M+H)^+$. The free base was converted to the salt with TsOH. white solid: mp 100–102° C.; $^1$H NMR ($D_2O$, 300 MHz) δ2.38 (s, 3H), 2.60–2.78 (m, 2H), 4.00–4.20 (m, 2H), 4.39–4.43 (m, 2H), 4.98 (m, 1H), 7.36 (d, 2H, J=8 Hz), 7.60 (m, 1H), 7.67 (d, 2H, J=8 Hz), 8.20–8.24 (m, 2H); MS ($CI/NH_3$) m/z 199 $(M+H)^+$. Anal. Calcd for $C9H11ClN2O.TsOH.0.5 H_2O$: C, 50 59;H, 5.31;N, 7.37. Founf: C, 50.91; H, 5.02; N, 7.00. $[α]_D^{25}$ 9.3° (c 0.4, MeOH).

Example 115

6-Methyl-3-(2-(R)-azetidinylmethoxy)pyridine

The title compound was prepared by the procedure of example 17, substituting 1-t-butoxycarbonyl-2-(R)-azetidinemethanol for the (S) enantiomer therein, and substituting 6-methyl-3-pyridinol for the 3-bromo-2-chloro-5-hydroxypyridine. After deprotection and conversion to the HCl salt as in example 17a, a white solid was obtained: mp 134–136° C.; $^1$H NMR ($D_2O$ 300 MHz) δ2.48 (s, 3H), 2.69 (m, 2H), 4.12 (m, 2H), 4.41 (d, J=4 H z, 2H), 4.95 (hept, J=4 Hz, 1H), 7.32 (d, J=9 Hz, 1H), 7.47 (dd, J=3, 9 Hz, 1H), 8.20 (d, J=3 Hz, 1H); MS ($DCI/NH_3$) m/e 179 $(M+H)^+$. Anal. calcd. for $C_{10}H_{14}N_2O.HCl.H_2O$: C, 54.13; H, 7.18; N, 12.62. Found: C, 53.85; H, 6.98; N, 12.38.

Example 116

2.6-Difluoro-3-(2-(S)-azetidinylmethoxy)pyridine tosylate

116a. 3-Hydroxy-2 6-difluoropyridine

To a solution of 2,6-difluoropyridine (6.7 mL, 73.8 mmole) in THF (100 mL, cooled to −78° C.) was added a 2M solution of LDA in heptane/THF/ethylbenene (38 mL, 76 mmol). The mixture was stirred at −78° C. for 1 hour, and trimethyl borate (6.8 mL, 89.7 mmol) was added. The mixture was stirred for 1 hour and allowed to warm to 20° C., then the reaction was quenched with HOAc (10 mL). The solution was made basic with 20% aq NaOH (20 mL), $H_2O_2$ (50%, 200 mL) was added, and the mixture stirred for 16 hours. The mixture was neutralized by addition of HCl (2M, aq) and extracted with EtOAc. The combined EtOAc extracts were dried ($MgSO_4$). The solvent was evaporated under vacuum, and the crude product was chromatographed (silica gel; hexane/EtOAc 9:1 to 6:4) to yield 2.7g (28% ) of the title compound. $^1$H NMR ($DMSO$-$d_6$, 300 MHz) δ: 6.75 (dd, J=3.0, 5.5 Hz, 1H), 7.48 (m, 1H). MS ($DCI/NH_3$) m/e 149 $(M+NH_4)^+$.

116b. 2,6-diFluoro-3-(1-Cbz-2-(S)-azetidinylmethoxy)pyridine 2, 6-DiFluoro-3-hydroxypyridine from Example 116a (2 g, 15.26 mmole), 1-Cbz-2-(S)-azetidinemethyl tosylate (5.73 g 15.26 mmole, prepared in example 105), and KOH (1.4 g 24.9 mmole) were combined in DMF (15 mL) and heated at 90° C. for one hour, cooled to 20° C. and poured into brine (100 mL). The resulting mixture was extracted with ether. The combined Et$_2$O extracts were washed with 50% brine and dried (MgSO$_4$). The solvent was evaporated in vacuo and the crude product was chromatographed (silica gel; hexane/EtOAc 95:5 to 6:4) to yield 1.75 g (34%) of the title compound. $^1$H NMR (DMSO-d$_6$, 120° C. 300 MHz) δ: 2.22 (m, 1H), 2.42 (m, 1H), 3.85–3.90 (m, 2H), 4.23 (m, 1H), 4.40 (m, 1H), 4.54 (m, 1H), 5.01 (s, 1H), 6.93 (dd, J=3.0, 5.5, 1 H), 7.29 (m, 5H), 7.77 (m, 1H).MS (DCI/NH$_3$) m/e 335 (M+H)$^+$, 352 (M+NH$_4$)$^+$. Anal. calcd. for C$_{17}$H$_{16}$F$_2$N$_2$O$_3$,: C, 61.07; H, 54.82; N, 8.38. Found: C, 61.10; H, 4.84; N, 7.90.

116c. 2,6-diFluoro-3-(2-(S)-azetidinylmethoxy) pyridine tosylate 2,6-Difluoro-3-(1-Cbz-2-(S)-azetidinylmethoxy)pyridine from Example 116b (640 mg, 1.9 mmol) was combined with 10% Pd on C (50 mg) and p toluenesulfonic acid monohydrate (1.1 g, 5.7 mmole) in 30 mL of EtOH, and the mixture was stirred under an H$_2$ atmosphere for 16 hours. The mixture was concentrated, triturated with ether and then recrystallized from ethyl acetate/ether to yield 231 mg (32.4%) of the title compound: mp 140–143° C. $^1$H NMR (D$_2$O 300 MHz) δ: 2.40 (s, 3H), 2.69 (m, 2H), 4.12 (m, 2H), 4.46 (d, J=4.5, 2H), 4.94 (m, 1H), 7.01 (m, 1H), 7.38 (d,J=8.0, 2H), 7.70 (d,J=8.0, 2H), 7.81 (m, 1H). MS (DCI/NH$_3$) m/e 201 (M+H)$^+$, 218 (M+NH$_4$)$^+$. Anal. calcd. for C$_9$H$_{10}$F$_2$N$_2$O.C$_7$H$_8$O$_3$S: C, 51.61; H, 4.87; N, 7.52. Found: C, 51.37; H, 4.89; N, 7.40. [α]$_D$ –1.44 (c 1, MeOH).

Example 117

2-Fluoro-6-methyl-3-(2-(S)-azetidinylmethoxy) pyridine tosylate

117a. 3-Hydroxy-6-methal-2-nitropyridine

5-Hydroxy-2-methylpyridine (23.6 g, 216 mmole)was dissolved in conc. H$_2$SO$_4$ (50 mL) and cooled to 0° C. Fuming HNO$_3$ (50 mL) was added over one hour. The solution was stirred at room temperature for one hour, poured onto ice (400 g), and filtered. The solids were dissolved in EtOAc washed with brine (100 mL). The organic extracts were dried (MgSO$_4$), and the solvent was evaporated to yield 12.1 g (36.3% ) of the title compound. mp 102–105° C. $^1$H NMR (DMSO-d$_6$, 300 MHz) δ: 2.44 (s, 3H), 7.52 (d, J=8.5 Hz, 1H), 7.58 (d J=8.5 Hz, 1H). MS (ESI-Q1MS) m/e 153(M–H)$^+$. Anal. calcd. for C$_6$H$_6$N$_2$O$_3$ C, 46.76; H, 3.92; N, 18.18. Found: C, 46.65; H, 3.98; N, 18.10.

117b. 2-Amino-3-hydroxy-6-methylpyridine

3-Hydroxy-6-methyl-2-nitropyridine from Example 117a (10.5 g, 68 mmole) was combined with 10% Pd/C (100 mg) in EtOH (100 mL), and the mixture was stirred under a H$_2$ atmosphere for 16 hours. The mixture was filtered and concentrated to yield 8.40 g (99% ) of the title compound. mp 141–145° C. $^1$H NMR (DMSO-d$_6$, 300 MHz) δ: 2.14 (s, 3H), 6.22 (d, J=7.5 Hz, 1H), 6.71 (d J=7.5 Hz, 1H). MS (DCI/NH$_3$) m/e 125 (M+H)$^+$, 142 (M+NH$_4$)$^+$.

117c. 2-Fluoro-3-hydroxy-6-methylpyridine

2-Amino-3-hydroxy-6-methylpyridine from Example 117b (8.35 g, 67.25 mmol) was dissolved in aquious HF (48% 100 mL) and cooled to –5° C. NaNO$_2$ (5.2 g, 75.4 mmol) was added at a rate that maintained the temperature below 0° C. After the addition was complete, the solution was heated to 30° C. After 30 minutes, the solution was cooled to 0° C., and the solution was neutralized by addition of NaOH (20% aq) The aqueous mixture was extracted with ethyl acetate. The organic extracts were dried (MgSO$_4$), and the solvent was evaporated. The crude product was chromatographed (silica gel; hexane/EtOAc 1:1) to yield 4.68 g (54.7% ) of the title compound. mp 133–135° C. $^1$H NMR (DMSO-d$_6$, 300 MHz) δ: 2.29 (s, 3H), 6.98 (d, J=8 Hz, 1H), 7.26 (dd J=8 Hz, 1H). MS (DCI/NH$_3$) m/e 128(M+H)$^+$, 145 (M+NH$_4$)$^+$. Anal. calcd. for C$_6$H$_6$FNO C, 56.69; H, 4.76; N, 11.02. Found: C, 56.72; H, 4.73; N, 11.03.

117d. 2-Fluoro-6-methyl-3-(1-Cbz-2-(S)-azetidinylmethoxy)pyridine

2-Fluoro-3-hydroxy-6-methylpyridine from Example 117c (Ig 7.87 mmole), 1-Cbz-2-(S)-azetidinemethyl tosylate (2.37 g 7.5 mmole, prepared as for example 105) and KOH (0.66 g 11.76 mmole) were combined in DMF (25 mL) and heated at 90° C. for one hour, cooled to 20° C. and poured into brine (100 mL). The resulting mixture was extracted with ether. The combined Et$_2$O extracts were washed with 50% brine and dried (MgSO$_4$). The solvent was evaporated under vacuum, and the crude product was chromatographed (silica gel; hexane/EtOAc 3:1) to yield 1.31 g (53%) of the title compound. $^1$H NMR (DMSO-d$_6$, 120° C. 300 MHz) δ: 2.26 (m, 1H), 2.33 (s, 3H), 2.48 (m, 1H), 3.82–3.88 (m, 2H), 4.19 (q, J=3, 1H), 4.35 (q, J=4.5, 1H), 4.53 (m, 1H), 5.01 (s, 2H), 7.01 (d, J=8, 1H), 7.28 (m, 5H), 7.43 (m, 1H). MS (DCI/NH$_3$) m/e 331 (M+H)$^+$, 348 (M+NH$_4$)$^+$. Anal. calcd. for C$_{18}$H$_{19}$FN$_2$O$_3$ C, 65.44; H, 5.8; N, 8.48. Found: C, 65.04; H, 5.86; N, 8.44; [α]$_D$ –70.38 (c 1, MeOH).

117e. 2-Fluoro-6-methyl-3-(2-(S)-azetidinylmethoxy)pyridine tosylate

2-Fluoro-6-methyl-3-(1-Cbz-2-(S)-azetidinylmethoxy) pyridine from Example 117d (714 mg, 2.16 mmol) was combined with 10% Pd/C (50 mg) and p-toluenesulfonic acid monohydrate (830 mg, 4.36 mmole) in 30 mL of EtOH, and the mixture was stirred under an H$_2$ atmosphere for 16 hours. The mixture was filtered, concentrated, the residue was triturated with ether, and the product was recrystallized from ethyl acetate/ether to yield 480 mg (60%) of the title compound. mp 141–143° C. $^1$H NMR (D$_2$O 300 MHz) δ: 2.40 (s, 6H), 2.65–2.71 (m, 2H), 4.07–4.16 (m, 2H), 4.43(d, J=4.5, 2H), 4.81–95 (m, 1H), 7.16 (d, J=8.0, 1H), 7.37 (d,J=8.0, 2H), 7.55 (dd, J=8.0, 2.5, 1H), 7.70 (d,J=8.0, 2H). MS (DCI/NH$_3$) m/e 197 (M+H)$^+$ 214 (M+NH$_4$)$^+$. Anal. calcd. for C$_{10}$H$_{13}$FN$_2$O.C$_7$H$_8$S: C, 55.42; H, 5.75; N, 7.60. Found: C, 55.27; H, 5.69; N, 7.44. [α]$_D$ –3.2 (c 1, MeOH).

Example 118

2-Fluoro-6-methyl-3-(2-(R)-azetidinylmethoxy) pyridine tosylate

118a. 2-Fluoro-6-methyl-3-(1-Cbz-2-(R)-azetidinylmethoxy)pyridine

2-Fluoro-3-hydroxy-6-methylpyridine from Example 117c (0.5 g 3.47 mmole), 1-Cbz-2-(R)-azetidinemethyl tosylate (1.1 g 3.9 mmole) from example 98a and KOH (0.3 g 5.33 mmole) were combined in DMF (5 mL) and heated at 80° C. for two hours, cooled to rt and poured into saturated NH$_4$Cl (100 mL). The resulting mixture was extracted with ether, and the combined Et$_2$O extracts were washed with 50% brine and dried (MgSO$_4$). The solvent was evaporated under vacuum, and the crude product was chromatographed (silica gel; hexane/EtOAc 9:1 to 7:3) to yield 592 mg (51.7%) of the title compound. $^1$H NMR (DMSO-d$_6$, 120° C. 300 MHz) δ2.22 (m, 1H), 2.33 (s, 3H), 2.41 (m, 1H), 3.83–3.88 (m, 2H), 4.19 (q, J=3, 1H), 4.35 (q, J=5, 1H), 4.53 (m, 1H), 5.01 (s, 2H), 7.01 (d, J=8, 1H), 7.28 (m, 5H), 7.43 (m, 1H). MS (CI/NH$_3$) m/e 331 (M+H)$^+$ 348 (M+NH$_4$)$^+$. Anal. calcd. for C$_{18}$H$_{19}$FN$_2$O$_3$ C, 65.44; H, 5.8; N, 8.48. Found: C, 65.19 H, 5.95; N, 8.69; [α]$_D$ +68.15 (c 1, MeOH).

118b. 2-Fluoro-6-methyl-3-(2-(R)-azetidinylmethoxy)pyridine tosylate

2-Fluoro-6-methyl-3-(1-Cbz-2-(R)-azetidinylmethoxy)pyridine from step 118a (500 mg, 1.51 mmol) was combined with 10% Pd/C (50 mg) and p toluenesulfonic acid monohydrate (600 mg, 3.15 mmole) in 30 mL of EtOH, and the mixture was stirred under an H$_2$ atmosphere for 16 hours. The mixture was filtered, concentrated, the residue was triturated with ether, and the product was recrystallized from ethyl acetate/ether to yield 270 mg (50%) of the title compound. mp 158–160° C. $^1$H NMR (D$_2$O 300 MHz) δ2.40 (s, 6H), 2.65–2.70 (m, 2H), 4.07–4.18 (m, 2H), 4.42 (d, J=4.5, 2H), 4.91–95 (m, 1H), 7.15 (d, J=8.0, 1H), 7.37 (d,J=8.0, 2H), 7.55 (dd, J=8.0, 2.0, 1H), 7.69 (d,J=8.5, 2H). MS (DCI/NH$_3$) m/e 197 (M+H)$^+$ 214 (M+NH$_4$)$^+$. Anal. calcd. for C$_{10}$H$_{13}$FN$_2$O.C$_7$H$_8$O$_3$S.0.4 H$_2$O: C, 54.36; H, 5.85; N, 7.46. Found: C, 54.48; H, 5.81; N, 7.28; [α]$_D$ +2.05 (c 1, MeOH).

Example 119

6-Methoxy-3-(2(R)-azetidinylmethoxy)pyridine

119a. 5-acetoxy-2-methoxypyridine

To 47.6 mL of boron trifluoride etherate (387 mmol, Aldrich) cooled to −10° C. under N$_2$ was added 24 g (193 mmol, Aldrich)) of 5-amino-2-methoxypyridine dissolved in 100 mL of dimethoxyethane. Then tert-butyl nitrite (20.2 mL, 193 mmol, Aldrich) was added at a rate which kept the temperature below 0° C. After 1 hour at −10° C. pentane (400 mL) was then added to the reaction mixture, the pentane solution was decanted, and the residue was washed with cold ether and dissolved in 200 mL of acetic anhydride. The resulting solution was heated to 100° C.±5° C. for 1 hour. The solvent was removed under vacuum, and the residue was suspended in saturated aqueous Na$_2$CO$_3$(200 mL) and extracted with ethyl ether (3×200 mL). The ether solution was dried (MgSO$_4$), the solvent was removed in vacuo, and the residue was chromatographed on silica gel, eluting with 95:5 to 80:20 hexane:ethyl acetate to give 7.3 (20.7%) g of the title compound. MS (CI/NH$_3$) m/e: 168 (M+H)+, 185 (M+NH$_4$)+. $^1$H NMR (CDCl$_3$ 300 MHz) δ.2.30 (s, 3H), 3.92 (s, 3H), 6.75 (d, J=9.0 Hz 1H), 7.35 (dd, J=2.5,9.0 1H), 7.95 (d, J=3.0 Hz 1H). Anal. calcd. for C$_8$H$_9$NO$_3$ C, 57.48; H, 5.43; N, 8.38. Found: C, 57.46; H, 5.40; N, 7.99.

119b. 2-methoxy-5-hydroxypyridine

The product of Example 119a (6.8 g, 40.7 mmol) was dissolved in 20% aqueous NaOH (50 mL) at 0° C., and the solution was warmed to room temperature and stirred for 3 hours. The solution was neutralized by addition of HCl, and the aqueous mixture was extracted with ethyl acetate. The organic extracts were washed with water and brine, then dried (MgSO$_4$), and the solvent was evaporated to yield 5.05 g (99%). The product was recrystalized from ethyl acetate/hexane to yield 3.6 g (70.6%) of the title compound. mp 80–82° C.; MS m/e: 126 (M+H)$^+$; 143 (M+NH$_4$)$^+$. $^1$H NMR (CDCl$_3$, 300 MHz) δ3.88 (s, 3H), 6.69 (d, 1H, J=9.0 Hz),7.23 (dd, 1H, J=3.0, 9.0 Hz), 7.78 (d, 1H, J=3.0 Hz). Anal. calcd. for C$_6$H$_7$NO C, 57.59; H, 5.64; N, 11.19. Found: C, 57.55; H, 5.62; N, 11.13.

119c. 6-methoxy-3-(1-Cbz-2-(R)-azetidinylmethoxy)pyridine

3-Hydroxy-6-methoxypyridine from Example 119b (514 mg, 4.1 mmole), 1-Cbz-2-(R)-azetidinemethyl tosylate (1.2 g, 3.26 mmole) from Example 98a and KOH (335 mg 6 mmole) were combined in DMF (10 mL) and heated at 80° C. for 3 hours, cooled to rt and poured into Na$_2$CO$_3$ (100 mL). The resulting mixture was extracted with ether, and the combined Et$_2$O extracts were washed with 50% brine and dried (MgSO$_4$). The solvent was evaporated under vacuum, and the crude product was chromatographed (silica gel; hexane/EtOAc, 9:1 to 7:3) to yield 672 mg (67.2% ) of the title compound. 1H NMR (DMSO-d$_6$, 120° C. 300 MHz) δ2.20 (m, 1H), 2.37 (m, 1H), 2.82 (s, 3H), 3.82–3.88 (m, 2H), 4.13 (m, 1H), 4.27 (m, 1H), 4.52 (m, 1H), 5.02 (s, 1H), 6.67 (d, J=11, 1H), 7.26–7.32 (m, 6H), 7.83 (d,J=3, 1H). MS (DCI/NH$_3$) m/e 331 (M+H)$^+$, 348 (M+NH$_4$)$^+$. Anal. calcd. for C$_{18}$H$_{20}$N$_2$O$_4$ C, 65.84; H, 6.14; N, 8.53. Found: C, 65.98; H, 6.23; N, 8.51.

119d. 6-methoxy-3-(2-(R)-azetidinylmethoxy)pyridine 6-methoxy-3-(1-Cbz-2-(R)-azetidinylmethoxy)pyridine from Example 119c (300 mg, 0.91 mmol) was combined with 10% Pd/C (50 mg) in 30 mL of EtOH, and the mixture was stirred under an H$_2$ atmosphere for 16 hours. The mixture was filtered and concentrated. The crude free base was converted to the salt by treatment with p toluenesulfonic acid in ethyl acetate. The mixture was concentrated, the residue was triturated with ether, and the product was recrystalized from ethyl acetate/ether to give 167 mg (33.9%) of the title compound: mp 139–142° C.; $^1$H NMR (D$_2$O 300 MHz) δ2.39 (s, 6H), 2.60–2.70 (m, 2H), 2.98 (s, 3H), 4.04–4.15 (m, 2H), 4.36 (d, J=4.5, 2H), 4.95 (m, 1H), 7.08 (d, J=9.0, 1H), 7.36 (d, J=8.0, 4H), 7.68 (d, J=8.0, 4H), 7.75 (dd, J=3.5, 9.5, 1H), 7.91 (d, J=3.0, 1H); MS (DCI/NH$_3$) m/e 195 (M+H)$^+$. Anal. calcd. for C$_{10}$H$_{14}$N$_2$O$_2$.2C$_7$H$_8$O$_3$S: C, 53.52; H, 5.61; N, 5.20. Found: C, 53.24; H, 5.68; N, 5.07. [α]$_D$ +3.55(c 1, MeOH).

Example 120

5-Ethoxy-3-(2-(S)-azetidinylmethoxy)pyridine tosylate

120a. 3-Benzyloxy-5-bromopyridine

NaH (60% in mineral oil) (40.9 g, 1.03 mol) in 800 mL of DMF was cooled to 0° C. and benzyl alcohol (105 mL, 1.02 mol) was added slowly. The reaction mixture was stirred for 1 hour at 20° C., then 3,5-dibromopyridine (200.4 g, 846 mmol) was added and the mixture was stirred for 16 hours. The mixture was quenched with saturated NH$_4$Cl (500 mL), diluted with 400 mL of water and extracted with Et$_2$O. The combined Et$_2$O extracts were washed with 50% brine and dried (MgSO$_4$). The solvent was evaporated under vacuum, and the crude product was recrystallized from Et$_2$O to afford 161 g (72%) of the title product: mp 63–68° C.; $^1$H NMR (CDCl$_3$, 300 MHz) δ5.1 (s, 1H), 7.35–7.50 (m, 6H), 8.27–8.37 (m, 2H); MS (CI/NH$_3$) m/z: 264, 266 (M+H)$^+$.

120b. 3-Amino-5-benzyloxypyridine

The product of step 120a (41.3 g, 156 mmol), copper (I) bromide (22.43 g, 156 mmol), MeOH (275 mL), and liquid NH$_3$ (50 mL) were combined in a stainless steel reactor and heated to 130° C. for 24 hours. The mixture was allowed to cool to ambient temperature, then concentrated. The residue was suspended in 300 mL of saturated aqueous Na$_2$CO$_3$ and extracted with CH$_2$Cl$_2$. The combined CH$_2$Cl$_2$ extracts were washed with brine, dried (MgSO$_4$), and concentrated. The crude product was chromatographed (silica gel; hexane/EtOAc, 9:1 to 7:3) to afford 15.6 g (50%) of the title compound: $^1$H NMR (CDCl$_3$, 300 MHz) δ5.10 (s, 2H), 7.30–7.45 (m, 6H), 8.20–8.30 (m, 2H); MS (CI/NH$_3$) m/z: 201 (M+H)$^+$.

120c. 3-Acetoxy-5-benzyloxypyridine

To boron trifluoride etherate (9.3 mL, 75 mmol) cooled to −15° C. under N$_2$ was added the product of Step 120b (10 g, 50 mmol) dissolved in DME (100 mL). Tert-butyl nitrite (7.8 mL, 65 mmol) was added at a rate which kept the temperature below −5° C. After 10 minutes at −10° C., the reaction was warmed to 5° C. and stirred for 30 min. Pentane (200 mL) was then added to the reaction mixture, and the solid was collected by suction filtration, washed with cold Et$_2$O, and dissolved in acetic anhydride (150 mL). The resulting solution was heated to 70° C. until N$_2$ evolution stopped. The solvent was removed under vacuum, and the residue was suspended in saturated aqueous Na$_2$CO$_3$ (150 mL) and extracted with Et$_2$O. The Et$_2$O extract was dried (Na$_2$SO$_4$) and concentrated. The crude product was chromatographed (silica gel; hexane/EtOAc, 6:1) to yield 2.0 g of the title compound: $^1$H NMR (CDCl$_3$, 300 MHz) δ2.35 (s, 3H), 5.15 (s, 2H), 7.15 (t, 1H, J=3 Hz), 7.35–7.42 (m, 5H), 8.15 (d, 1H, J=3 Hz), 8.30 (d, 1H, J=3 Hz); MS (CI/NH$_3$) m/z: 244 (M+H)$^+$, 261 (M+NH$_4$)$^+$.

120d. 3-Benzyloxy-5-hydroxypyridine

The product of Step 120c (2 g, 8.4 mmol) was dissolved in methanol (15 mL), and K$_2$CO$_3$ (600 mg, 4.34 mmol) was added. After consumption of the starting material, the solution was neutralized by addition of aqueous 1N HCl. The mixture was extracted with Et$_2$O, and the organic extracts were dried (Na$_2$SO$_4$) and concentrated. The crude product was triturated with hexane to provide the title compound (1.3 g, 82%) as white solid: $^1$H NMR (DMSO, 300 MHz) δ5.15 (s, 2H), 6.80 (t, 1H, J=3 Hz), 7.35–7.42 (m, 5H), 7.75 (d, 1H, J=3 Hz), 7.85 (d, 1H, J=3 Hz), 9.95 (br s, 1H); MS (CI/NH$_3$) m/z: 202 (M+H)$^+$, 219 (M+NH$_4$)$^+$.

120e. 5-Benzyloxy-3-(1-Boc-2-(S)-azetidinylmethoxy)pyridine

1-Boc-2-(S)-azetidinylmethanol (36.5 g, 0.195 mol) was dissolved in 195 mL of CH$_2$Cl$_2$ followed by addition of triethylamine (35.6 ml, 0.255 mol) and toluenesulfonyl chloride (48.5 g, 0.254 mol). The resulting mixture was stirred at room temperature for 16 hours. A 10% solution of NaOH was added rapidly, and the mixture was stirred for one hour. After phase separation, the aqueous phase was extracted with additional CH$_2$Cl$_2$, combined with the organic phase, and then washed with NaHCO$_3$ solution and brine. The resulting solution was dried (MgSO$_4$), filtered, and concentrated under vacuum to give 63.1 g of Boc-(S)-toluensulfonyloxymethylazetidine (94.8%).

Next, a solution of 3-benzyloxy-5-hydroxypyridine (350 mg, 1.74 mmol, from step 120d) in DMF (20 mL) was treated with ground KOH (154 mg, 2.74 mmol) and stirred for 30 minutes at 80° C. To this mixture was rapidly added the Boc-(S)-toluensulfonyloxymethylazetidine (585 mg, 1.74 mmol) dissolved in DMF (5 mL), and the mixture was stirred for 16 hours at 80° C. The mixture was concentrated under vacuum to remove the DMF, and the residue was diluted with water and extracted with EtOAc. The organic extracts were combined, dried (Na$_2$SO$_4$), filtered, and concentrated under vacuum to give 800 mg of crude product. This material was purified by chromatography (silica gel; hexane/EtOAc, 10:1) to give the title compound (575 mg, 90%): $^1$H NMR (CDCl$_3$, 300 MHz) δ1.40 (s, 9H), 2.26–2.30 (m, 2H), 3.90–2.94 (m, 2H), 4.16 (m, 1H), 4.35 (m, 1H), 4.54 (m, 1H), 5.10 (s, 2H), 6.95 (s, 1H), 7.40–7.46 (m, 5H), 8.20 (br s, 2H), MS (CI/NH$_3$) m/z: 371 (M+H)$^+$.

120f. 5-hydroxy-3-(1-Boc-2-(S)-azetidinylmethoxy)pyridine

The product of step 120e (5.0 g, 13.51 mmol) in MeOH (25 mL) was stirred under an atmosphere of H$_2$ in the presence of 10% Pd/C (200 mg) for 4 hours. The mixture was filtered and concentrated to afford 3.4 g (92%) of the title compound as colorless oil: $^1$H NMR (CDCl3, 300 Hz) δ1.40 (s, 9H), 2.30 (m, 2H), 3.90 (t, J=9 Hz, 2H), 4.10 (m, 1H), 4.30 (m, 1H), 4.50 (m, 1H), 6.85 (m, 1H), 7.85 (m, 1H), 7.95 (m, 1H). MS (CI/NH$_3$) 281 (M+H)$^+$.

120g. 5-Ethoxy-3-(1-Boc-2-(S)-azetidinylmethoxy)pyridine

A solution of 5-hydroxy-3-(1-Boc-2-(S)-azetidinylmethoxy)pyridine (500 mg, 1.78 mmol, from step 120f) in dimethylformamide (15 mL) was treated with ground KOH (170 mg, 1.7 mmol) and stirred for 30 minutes at room temperature. To this mixture was rapdily added ethyl p-toluenesulfonate (430 mg, 2.14 mmol), and the resultant was stirred at 80° C. overnight. The mixture was concentrated to remove the dimethylformamide, and the residue was diluted with water and extracted with EtOAc. The organic extracts were combined, dried (MgSO$_4$), filtered and concentrated under vacuum to give 1.0 g of unpurified product. This material was purified by chromatography (silica gel: hexane/EtOAc, 1:1) to give 537 mg (98%) of the title compound. $^1$H NMR (CDCl$_3$, 300 MHz) δ: 1.40 (s, 9H), 1.42 (t, J=6 Hz, 3H), 2.30 (m, 2H), 3.92 (t, J=9 Hz, 2H), 4.05 (q, J=6 Hz, 2H), 4.16 (m, 1H), 4.30 (m, 1H), 4.54 (m, 1H), 6.80 (m, 1H), 7.95 (m, 2H). MS (CI/NH$_3$) m/e: 309 (M+H)$^+$.

120h. 5-Ethoxy-3-(2-(S)-azetidinylmethoxy)pyridine

To the 5-ethoxy-3-(2-(1-Boc-2-(S)-azetidinylmethoxy)pyridine from step 120g (540 mg, 1.75 mmol) was added trifluoroacetic acid (1.5 mL) in methylene chloride (15 mL) at 0° C. The solution was stirred for 2 hours, allowed to warm to room temperature, then adjusted to pH 11 with aqueous 10% NaOH, and extracted with CH$_2$Cl$_2$. The organic layer was dried over MgSO$_4$ and concentrated. The residue was chromatographed (silica gel; CHCl$_3$:MeOH, 95:5) to afford the free base of the title compound (300 mg, 82%). $^1$H NMR (CDCl$_3$, 300 MHz) δ: 1.42 (t, J=6 Hz, 3H), 2.18 (m, 2H), 2.95 (m, 1H), 3.58 (m, 2H), 4.02 (m, 2H), 4.15 (q, J=6 Hz, 2H), 6.75 (t, J=3 Hz, 1H), 7.95 (t, J=3 Hz, 2H). MS (CI/NH$_3$) m/e: 209 (M+H)$^+$.

120i. 5-Ethoxy-3-(2-(S)-azetidinylmethoxy)pyridine tosylate

The compound from step 120h (100 mg, 0.484 mmol) was converted to the salt by treatment with p-toluenesulfonic acid in ethanol to give the title compound (125 mg): mp 105° C. (dec); [a]$^{25}{}_D$ =−6.8° (c=0.47, MeOH); $^1$H NMR (CDCl$_3$, 300 MHz) δ1.40 (t, J=6 Hz, 3H), 2.35 (s, 3H), 2.50 (m, 2H), 3.95 (q, J=6 Hz, 2H), 4.15 (m, 2H), 4.38 (d, J=3 Hz, 2H), 4.98 (br, 1H), 6.95 (t, J=3 Hz, 1H), 7.10 (d, J=6 Hz, 2H), 7.65 (d, J=6 Hz, 2H), 7.90 (d, J=3 Hz, 1H), 8.02 (d, J=3 Hz, 1H); MS (CI/NH$_3$) m/z 209 (M+H)$^+$. Anal. calcd. for C$_{11}$H$_{16}$N$_2$O$_2$.1.2 TsOH.0.8 H$_2$O: C, 54.28; H, 6.39N, 6.53. Found: C, 54.60; H, 6.29; N, 6.20.

Example 121

2-Chloro-3-(2-(S)-azetidinylmethoxy)pyridine hydrochloride 121a. 2-chloro-3-(1-BOC-2-(S)-azetidinylmethoxy) pyridine To a solution of triphenylphosphine (1.73 g, 6.6 mmol) in THF (26 mL) was added diethyl azodicarboxylate (1.04 mL, 6.6 mmol) at 0° C., and the reaction mixture was stirred for 15 minutes. 1-BOC-2-(S)-azetidinemethanol (1.03 g, 5.5 mmol) and 2-chloro-3-pyridinol (785 mg, 6.0 mmol, Aldrich Chemical Co.) were then added. The reaction mixture was allowed to warm slowly to room temperature and stir overnight. Solvent was removed, and the residue was dissolved in ethyl acetate. The solution was washed with saturated aqueous K$_2$CO$_3$ and brine, dried over MgSO$_4$ and concentrated. The residue was chromatographed on a silica gel column, eluting with ethyl acetate:hexane (1:4 to 1:1) to afford the title compound (611 mg). MS (DCI/NH$_3$) m/z 299 (M+H)$^+$.

121b. 2-chloro-3-(2-(S)-azetidinylmethoxy)pyridine hydrochloride

To 2-chloro-3-(1-BOC-2-(S)-azetidinylmethoxy)pyridine from step 121a (469 mg, 1.66 mmol) was added TFA (5 mL) in methylene chloride (5 mL) at 0° C., and the mixture was stirred for 30 minutes. The volatile components were then removed under vacuum. The residue was treated with saturated K$_2$CO$_3$ solution, then extracted with methylene chloride, which was dried over MgSO$_4$ and concentrated. The residue was chromatographed on a silica gel column, eluting with chloroform:methanol:NH$_4$OH (10:1:0–10:1:0.5) to afford the free base of the title compound (217 mg). The base (156 mg) was dissolved in methylene chloride (3 mL) and then converted to the salt by treatment with saturated HCl in ether to give the title compound (142 mg). mp 155–156° C. MS (DCI/NH$_3$) m/z 199, 201 (M+H)$^+$, 216 (M+NH$_4$)$^+$. $^1$H NMR (D$_2$O, 300 MHz) δ2.7–2.79 (m, 2H), 4.13–4.24 (m, 2H), 4.44–4.58 (m, 2H), 4.98 (m, 1H), 7.45 (dd, J=4.8, 8.1 Hz, 1H), 7.59 (dd, J=1.5, 8.2 Hz, 1H), 8.03 (dd, J=1.4, 4.5 Hz, 1H). Anal. Calcd. for C$_9$H$_{11}$N$_2$OCl.1.0 HCl: C, 45.98; H, 5.14; N, 11.91. Found: C, 45.76; H, 5.09; N, 11.64.

Example 122

2-Fluoro-3-(2(S)-azetidinylmethoxy)pyridine hydrochloride 122a. 2-Fluoro-3-hydroxypyridine 2-Amino-3-hydroxypyridine (8.25 g, 75 mmol; from Aldrich) was dissolved in hydrogen fluoride-pyridine (100 g, Aldrich) and cooled to 0° C. Then sodium nitrite (5.4 g 78 mmol) was added over 30 min. The solution was stirred for an additional 30 minutes and then slowly poured into 300 mL of 25% NaOH at 0° C. The aqueous mixture was filtered and then extracted with CH$_2$Cl$_2$ (6×75 mL). The aqueous solution was adjusted to pH 6 with 20% aq NaOH and extracted with EtOAc (6×100 mL), then the combined EtOAc extracts were dried over MgSO$_4$ and concentrated. The residue was chromatographed (silica gel; hexane/EtOAc, 9:1 to 6:4) to afford 3.93 g of the title compound $^1$H NMR (CDCl$_3$, 300 MHz) δ7.75(m, 1H), 7.37 (m, 1H), 7.11 (m, 1H). MS (DCI/NH$_3$) m/z 114 (M+H)$^+$, 131 (M+NH$_4$)$^+$.

122b. 2-Fluoro-3-(1-Cbz-2-(S)-azetidinylmethoxy) pyridine

The procedure of example 17a was followed, substituting 2-fluoro-3-hydroxypyridine and 1-Cbz-2-(S)-azetidinemethanol for 5-bromo-9-chloropyridine-3-ol and 1-BOC-2-(S)-azetidinemethanol, respectively. Yield: 56%. $^1$H NMR (DMSO-d$_6$, 130° C., 300 MHz): δ7.72 (m. 1H), 7.55 (m, 1H), 7.30–7.20 (m, 5H), 7.17 (m, 1H), 5.01 (s, 1H), 4.56 (m, 1H), 4.41 (dd, J=11.11, 1H), 4.5 (dd, J=10.68, 1H), 3.90–3.85 (t, J=7.26, 2H), 2.42 (m, 1H), 2.25 (m, 1H). MS (DCI/NH$_3$) m/z 334 (M+H)$^+$, 317 (M+NH$_4$)$^+$.

122c. 2-Fluoro-3-(2-azetidinylmethoxy)pyridine hydrochloride

2-Fluoro-3-(1-Cbz-2-(S)-azetidinylmethoxy)pyridine (step 122b, 1.1 g, 34.8 mmol) was combined with 100 mg of 5% Pd/C in EtOH (25 mL) and the mixture was stirred under an H$_2$ atmosphere for 16 hours. The mixture was filtered and concentrated, and the crude product was chromatographed (silica gel; CHCl$_3$, 99:1 to 94:6) to afford 480 mg (76%) of the free base. The base was converted to the salt by treatment with 1M hydrogen chloride in ether. The salt was recrystallized three times from EtOH/EtOAc/Et$_2$O to give 150 mg of the title compound $^1$H NMR (D$_2$O 300 MHz) δ7.81 (m. 1H), 7.67 (m, 1H), 7.35 (m, 1H), 4.97 (m, 1H), 4.5–4.48 (t, J=2.04 Hz, 2H), 4.21–4.06 (m, 2H), 2.75–2.66 (tt, J=6.95 Hz, 2H). MS (DCI/NH$_3$) m/z 183 (M+H)$^+$, 200 (M+NH$_4$)$^+$ Anal. Calcd. for C$_9$H$_{11}$N$_2$OF.HCl.0.3 H$_2$O: C, 48.24; H, 5.67; N, 12.50. Found: C,48.30: H, 5.56; N, 12.15.

Example 123

6-Cyano-3-(2(S)-azetidinylmethoxy)pyridine hydrochloride 123a. 3-amino-6-bromopyridine A mixture of 2-bromo-5-nitropyridine (30.75 g, 151.5 mmol), water (250 mL), and acetic acid (110 mL) was heated to 45° C. Iron powder (24.5 g, 439 mmol) was added at a rate which kept the temperature below 53° C., then the mixture was stirred at 48° C.±5° C. for one hour. The mixture was cooled to room temperature and filtered through diatomaceous earth filter aid, washing with ethyl acetate. The layers were separated and the aqueous phase was extracted with ethyl acetate. The combined organic fractions were washed with saturated Na$_2$CO$_3$ and brine, dried over MgSO$_4$, and the solvent was removed in vacuo. The residue was chromatographed (silica gel, hexane:EtOAc, 100:0 to 50:50) to give 20.4 g of the title compound: MS (CI/NH$_3$) m/e: 173 (M+H)$^+$, 190 (M+NH$_4$)$^+$; $^1$H NMR (CDCl$_3$ 300 MHz) δ6.86–6.90 (dd, 1H, J=8.5, 2.4 Hz) 7.21–7.23 (d, 1H, J=8.2 Hz) 7.85–7.86 (d, 1H, J=3 Hz).

123b. 3-acetoxy-6-bromopyridine

To 25.6 mL of boron trifluoride etherate (208 mmol, Aldrich) cooled to −15° C. under N$_2$ was added 18 g (104 mmol) of 3-amino-6-bromopyridine (from Step 123a above) dissolved in 35 mL of dimethoxyethane. Then t-Butyl nitrite (14.7 mL, 125 mmol, Aldrich) was added at a rate which kept the temperature below 0° C. Dimethoxyethane (65 mL) and methylene chloride (60 mL) were then added to aid stirring. After 10 minutes at −10° C. the mixture was allowed to warm to 5° C. and stirred for 30 minutes. Pentane (400 mL) was then added to the reaction mixture, the solid was collected by suction filtration, washed with cold ether, air dried, and dissolved in 125 mL of acetic anhydride. The resulting solution was heated to 100° C.±5° C. for 1 hour. The solvent was removed in vacuo, and the residue was suspended in saturated aqueous $Na_2CO_3$, and extracted with ethyl ether. The ether solution was dried over $MgSO_4$, the solvent was removed in vacuo, and the residue was chromatographed on silica gel, eluting with 100:0 to 60:40 hexane:ethyl acetate to give 13.6 g of the title compound: 1H NMR (CDCl$_3$ 300 MHz) δ8.20 (m, 1H).7.51 (d, J=8.5 Hz 1H),7.38 (dd, J 2.9, 7.5 Hz, 1H), 2.35 (s, 3H). MS (CI/NH$_3$) m/e: 216 (M+H)$^+$, 233 (M+NH$_4$)$^+$.

123c. 2-Bromo-5-hydroxypyridine

The product of Example 123b (12.8 g, 60 mmol was dissolved in 15% aqueous NaOH (50 mL) at 0° C., and the solution was allowed to warm to room temperature and stirred for 60 minutes. After complete consumption of the starting material the solution was neutralized by addition of HCl. The aqueous mixture was extracted with ethyl acetate. The organic extracts were washed with water and brine, then dried (MgSO$_4$), and the solvent was evaporated to yield 9.8 g of the title compound: $^1$H NMR (CDCl$_3$, 300 MHz) δ7.12–7.16 (dd, 1H, J=3.2 Hz),7.36–7.39 (d, 1H, J=8.5Hz), 8.04–8.05 (d, 1H, J=2.4 Hz). MS m/e: 174 (M+H)$^+$ 123d. 6-Bromo-3-(1-BOC-2-(S)-azetidinylmethoxy) pyridine The product of Example 123c was coupled to 1-BOC-2-(S)-azetidinemethanol using the procedure described in Example 17a. $^1$H NMR (CDCl$_3$, 300 MHz): 1.42 (s, 9H), 2.20–2.43 (m, 2H), 4.88 (t, J=8.0 Hz, 2H), 4.17 (dd, J=3.0, 9.0 Hz, 1H), 4.30–4.39 (m, 1H), 4.43–4.58 (m,1H), 7.42 (t, J=2.0 Hz, 1H), 8.25–8.32 (m, 2H). MS (DCI/NH$_3$) m/e: 343 (M+H)$^+$, 360 (M+NH$_4$)$^+$.

123e. 6-Cyano-3-(1-BOC-2-(S)-azetidinylmethoxy) pyridine

To the product of Example 123d (1.22 g, 3.60 mmol) in degassed DMF (10 mL) were added zinc cyanide (0.295 g, 2.50 mmol) and tetrakis(triphenylphosphine)palladium(0) (0.249 g, 0.20 mmol) and the mixture was heated at 80° C. for 5 hours. The mixture was cooled to room temperature and poured into saturated sodium bicarbonate. The aqueous layer was extracted with EtOAc (400 mL), dried (MgSO$_4$) and concentrated in vacuo. The crude product was chromatographed (silica gel; EtOAc/hexane 1/1) to afford a colorless oil (0.784 g, 75%): $^1$H NMR (CDCl$_3$, 300 MHz) δ1.42 (s, 9H), 2.22–2.42 (m, 2H), 3.82–3.87 (m, 2H), 3.18 (dd, J=3.0, 9.0 Hz, 1H), 4.38–4.45 (m, 1H), 4.48–4.60 (m, 1H), 7.32–7.58 (m, 1H), 7.62 (d, J=11.5 Hz, 1H), 8.42 (d, J=4.0 Hz, 1H). MS (DCI/NH$_3$) m/e: 290 (M+H)$^+$, 307 (M+NH$_4$)$^+$.

123f. 6-Cyano-3-(2(S)-azetidinylmethoxy)pyridine hydrochloride

The product of Example 123e was deprotected and converted to the hydrochloride salt according to the procedure described in Example 17b: $^1$H NMR (CDCl$_3$) δ2.66–2.74 (m, 2H), 4.02–4.19 (m, 2H), 4.50 (d, 2H, J=4.4 Hz), 4.84–4.99 (m, 1H), 7.63 (dd, 1H, J=3.0, 11.5 Hz), 7.97 (d, 1H, J=8.8 Hz), 8.48 (d, 1H, J=3.0 Hz). MS (CI/NH3): m/z 190.00 (M+H$^+$), 207.00 (M+NH$_4$$^+$); Anal. Calcd. for $C_{10}H_{11}N_3O.1.0$ HCl.0.1 Et$_2$O.0.1 H$_2$O: C, 53.18; H, 5.66; N, 17.89. Found: C, 53.07; H, 5.46; N, 17.87.

Example 124

3-(2-(R)-azetidinylmethoxy)-5-bromo-6-methylpyridine tosylate 124a. 5-Bromo-6-methyl-3-(1-BOC-2-(R)-azetidinylmethoxy)pyridine A mixture of 5-bromo-3-hydroxy-6-methylpyridine (1.10 g, 5.85 mmol) and KOH (0.52 g, 9.28 mmol) in DMF (20 mL) was heated at 80° C. for 1 h, and a solution of 1-BOC-2-(R)-toluenesulfonyloxymethylazetidine (2.0 g, 5.86 mmol) in DMF (10 mL) was added. The reaction mixture was heated at 80° C. overnight. After cooling to room temperature, the brown solution was diluted with EtOAc (150 mL), washed with distilled water and brine, dried (Na$_2$SO$_4$), and concentrated under vacuum. The crude product was chromatographed (silica gel; 1:1 EtOAc:hexane) to afford a colorless oil (1.1 8 g, 56%): $^1$H NMR (CDCl$_3$, 300 MHz) δ1.43 (s, 9H), 2.30 (m, 2H), 2.59 (s, 3H), 3.88 (t, 2H, J=7.5 Hz), 4.10 (dd, 1H, J=7.2 Hz), 4.29 (m, 1H), 4.50 (m, 1H), 7.44 (d, 1H, J=2.7 Hz), 8.18 (d, 1H, J=2.7 Hz); MS (DCI/NH$_3$) m/z 357 (M)$^+$.

124b. 3-(2-(R)-azetidinylmethoxy)-5-bromo-6-methylpyridine

A solution of the compound from Example 124a (0.5 g, 1.40 mmol) in CH$_2$Cl$_2$ (6 mL) was cooled to 0° C. with an ice-bath, and trifluoroacectic acid (3 mL) was added dropwise via a dropping addition funnel. The reaction mixture was stirred at 0° C. for 2 hours. The mixture was concentrated under vacuum, and the resulting residue was taken up in EtOAc (40 mL) and washed with 1M aqueous K$_2$CO$_3$. The basic aqueous washes were combined, saturated with brine and back extracted several times with EtOAc to recover the desired product. The combined organic extracts were dried (Na$_2$SO$_4$) and concentrated under vacuum. The crude product was chromatographed (silica gel; 80:19:1 CH$_2$Cl$_2$:MeOH:NH$_4$OH) to afford a colorless oil (0.33 g, 92%): $^1$H NMR (CDCl$_3$, 300 MHz) δ2.30 (m, 3H), 2.57 (s, 3H), 3.48 (m, 1H), 3.71 (q, 1H, J=8.0 Hz), 4.01 (m, 2H), 4.28 (m, 1H), 7.41 (d, 1H, J=2.7 Hz), 8.15 (d, 1H, J=2.7 Hz); MS (DCI/NH$_3$) m/z 257 (M)$^+$.

124c. 3-(2-(R)-azetidinylmethoxy)-5-bromo-6-methylpyridine tosylate

To a solution of 5-bromo-6-methyl-3-(2-(R)-azetidinylmethoxy)pyridine (0.32 g, 1.24 mmol) from Example 124b in EtOH (5 mL) was added p-toluenesulfonic acid monohydrate (0.23 g, 1.21 nmmol). The reaction mixture was stirred at rt for 30 min and concentrated under vacuum. The residue was taken up in MeOH (2 mL) and triturated with ether. The precipitate was collected by filtration and dried to give a white solid (0.48 g, 91%): mp 142–144° C.; $[α]_D^{23}$ +5.2 (c 0.5, MeOH); $^1$H NMR (D$_2$O, 300 MHz) δ2.39 (s, 3H), 2.55 (s, 3H), 2.67 (q, 2H, J=8.5 Hz), 4.09 (m, 2H), 4.37 (d, 2H, J=4.4 Hz), 4.92 (m, 1H), 7.35 (d, 2H, J=7.7 Hz), 7.68 (d, 2H, J=8.5 Hz), 7.75 (d, 1H, J=2.8 Hz), 8.16 (d, 1H, J=2.7 Hz); MS (DCI/NH$_3$) m/z 257 (M)$^+$.

Anal. Calcd for $C_{10}H_{13}BrN_2O \cdot TsOH$: C, 47.56; H, 4.93; N, 5.62. Found: C, 47.42; H, 5.13; N, 6.59.

Example 125

5-bromo-6-fluoro-3-(2-(R)-azetidinylmethoxy)pyridine

The free base of the title compound was prepared according to the procedures detailed in Example 31, replacing 1-tert-butyloxy-(2S)-azetidinemethanol thereof with the enantiomeric material, 1-tert-butyloxy-(2R)-azetidinemethanol. The tosylate salt was prepared by adding an equivalent of para-toluenesulfonic acid monohydrate to an ethanolic solution of 5-((2R)-azetidinylmethoxy)-3-bromo-2-fluoropyridine. The volatile components were removed in vacuo and the residue was triturated with $Et_2O$ then dried under vacuum to afford the title compound as a white solid: mp 238–240° C.; $[\alpha]_D^{21}$ 8.4 (c 0.5, MeOH); $^1$H NMR (DMSO-$d_6$) δ2.29 (s, 3H), 2.39 (m, 1H), 2.52 (m, 1H), 3.93 (m, 2H), 4.36 (m, 1H), 4.43 (m, 1H), 4.73 (m, 1H), 7.11 (d, 2H, J=7.9 Hz), 7.48 (d, 2H, J=7.9 Hz), 8.00 (m, 1H), 8.08 (dd, 1H, J=2.4,4.9 Hz), 8.85 (br s, 2H); MS (CI/NH$_3$) m/z 261,263 (M+H)$^+$. Anal. Calcd for $C_9H_{10}BrFN_2O \cdot 1.7$ TsOH·0.5 H$_2$O: C, 44.17; H, 4.44; N, 5.10. Found: C, 44.07; H, 4.08; N, 4.70.

Example 126

5-ethyl-6-fluoro-3-(2-(S)-azetidinylmethoxy)pyridine

126a. 3-Bromo-2-fluoro-5-nitropyridine

3-Bromo-2-chloro-5-nitropyridine (119 g, 0.500 mol, prepared according to V. Koch and S. Schnatterer, *Synthesis*, 1990, 497–498), potassium fluoride (79.5 g, 1.37 mol), and tetraphenylphosphonium bromide (109 g, 0.260 mol) were combined in acetonitrile (1.5 L) and heated at reflux for 4 days until GLC indicated complete consumption of the 3-bromo-2-chloro-5-nitropyridine. The volume of the mixture was reduced to 750 mL in vacuo, then the residual liquid was diluted with 2 L of ether. The mixture was filtered and the filtrate concentrated. The residue was triturated with hot hexane, and the combined hexane extracts were concentrated to give 62.8 g (54%) of the title compound: $^1$H NMR (DMSO-$d_6$ 300 MHz) δ9.14 (m, 2H).

126b. 5-Amino-3-bromo-2-fluoropyridine

To a solution of 3-bromo-2-fluoro-5-nitropyridine from Step 126a above (5.0 g, 23 mmol) in MeOH (100 mL) was added tin(II) chloride dihydrate. The mixture was heated at reflux for 3 hours, then cooled to ambient temperature and concentrated in vacuo. The residue was diluted with saturated aqueous NaHCO$_3$ and EtOAc resulting in formation of an emulsion which was filtered. The filtrate was poured into a separatory funnel and the layers were separated. The aqueous phase was extracted with EtOAc. The combined organic extracts were washed with brine, dried (MgSO$_4$), and concentrated. Purification by chromatography (silica gel; hexane/EtOAc, 70:30) afforded 3.61 g (83%) of the title compound as a yellow solid: mp 91–92° C.; $^1$H NMR (CDCl$_3$, 300 MHz) δ7.15 (dd, J=2.5, 7.5 Hz, 1H), (dd, J=2.0, 2.5 Hz, 1H); MS (DCI/NH$_3$) m/z 191, 193 (M+H)$^+$ 208, 210 (M+NH$_4$)$^+$.

126c. 5-Amino-2-fluoro-3-vinylpyridine

To a stirred solution of 5-amino-2-fluoro-3-bromopyridine from step 126b above (3.25 g, 17.0 mmol) in toluene (20 mL) was added tributyl(vinyl)tin (Aldrich, 7.64 g, 20.4 mmol) followed by tetrakis(triphenylphosphine)palladium (Aldrich, 0.63 g, 1.7 mmol). The reaction mixture was heated at 100° C. for 24 h. The solvent was removed in vacuo and the residue was purified by column chromatography (silica gel; EtOAc/hexane, 4:6) to afford the desired material as beige solids (2.30 g, 98%): $^1$H NMR (CDCl$_3$, 300 MHz) δ3.61 (br s, 2H), 5.44 (d, J=11.5 Hz, 1H), 5.83 (d, J=17.5 Hz, 1H), 6.66 (m, 1H), 7.18 (dd, J=3.0 Hz, 5.0 Hz, 1H), 7.52 (m, 1H); MS (CI/NH$_3$) m/z 139 (M+H)$^+$, 156 (M+NH$_4$)$^+$.

126d. 5-Amino-3-ethyl-2-fluoropyridine

A solution of the 5-amino-2-fluoro-3-vinylpyridine from Step 126c above (2.30 g, 16.6 mmol) in MeOH (50 mL) was added to a suspension of 10% palladium on activated carbon (Aldrich, 0.10 g) in MeOH (75 mL). The mixture was placed under an atmosphere of H$_2$ (balloon) for 48 h. The catalyst was removed by filtration and the solvent was evaporated to yield the title compound as a beige solid (2.31 g, 99%): $^1$H NMR (CDCl$_3$, 300 MHz) δ1.22 (t, J=7.5 Hz, 3H), 2.58 (q, J=7.5 Hz, 2H), 6.96 (dd, J=3.0, 5.1 Hz, 1H), 7.45 (m, 1H); MS (CI/NH$_3$) m/z 141 (M+H)$^+$, 158 (M+NH$_4$)$^+$.

126e. 5-Acetoxy-3-ethyl-2-fluoropyridine

To a stirred solution of the 5-amino-3-ethyl-2-fluoropyridine from Step 126d above (2.30 g, 16.4 mmol) in 3:1 dimethoxyethane:CH$_2$Cl$_2$ (50 mL) at −10° C. was slowly added borontrifluoride etherate (Aldrich, 4.23 mL, 34.5 mmol). t-Butylnitrite (Aldrich, 2.34 mL, 19.7 mmol) was added over the course of 15 min., keeping the reaction temperature below −5° C. The reaction mixture was warmed to 0° C. and stirred for 30 minutes. Pentane (500 mL) was added and the solid tetrafluoroborate diazonium salt was collected by filtration. The diazonium salt was dissolved in acetic anhydride (40 mL) and heated at 95° C. for 2 h (N$_2$ evolution was noted at 85° C.). The solvent was evaporated, the residue was dissolved in Et$_2$O (250 mL), and washed with saturated aqueous NaHCO$_3$ (2×150 mL). The combined aqueous phases were extracted with Et$_2$O (2×150 mL). The combined organic phases were washed with brine (50 mL), dried (MgSO$_4$), and concentrated. The crude product was purified by column chromatography (silica gel; EtOAc/hexane, 4:6) to afford the title compound as a yellow oil (2.22 g, 74%): $^1$H NMR (CDCl$_3$, 300 MHz) δ1.26 (t, J=7.5 Hz, 3H), 2.32 (s, 3H), 2.67 (q, J=7.0 Hz, 2H), 7.35 (dd, J=2.5, 8.0 Hz, 1H), 7.84 (m, 1H); MS (CI/NH$_3$) m/z 184 (M+H)$^+$, 201 (M+NH$_4$)$^+$.

126f. 3-Ethyl-2-fluoro-5-hydroxyypyridine

To a stirred solution of the 5-acetoxy-3-ethyl-2-fluoropyridine from Step 126e above (2.22 g, 12.1 mmol) in MeOH (50 mL) was added K$_2$CO$_3$ (0.84 g, 6.10 mmol). The reaction mixture was allowed to stir at room temperature 24 h. The solvent was evaporated and the residue was diluted with Et$_2$O (100 mL) and water (100 mL). The phases were separated and the aqueous phase was neutralized (pH 7) by the addition of 1 N aqueous HCl, and extracted with diethyl ether (2×100 mL). The combined ethereal extracts were washed with brine (50 mL), dried (MgSO$_4$), and the solvent evaporated. The crude product was purified by column chromatography (silica gel; EtOAc/hexane, 4:6) to afford the desired material as an off-white solid (1.18 g, 69%): $^1$H NMR (CDCl$_3$, 300 MHz) δ1.24 (t, J=7.5 Hz, 3H), 2.63 (q, J=7.5 Hz, 2H), 7.24 (dd, J=2.0, 5.0 Hz, 1H), 7.62 (m, 1H); MS (CI/NH$_3$) m/z 142 (M+H)$^+$, 159 (M+NH$_4$)$^+$.

126g. 5-(1-tert-Butaloxy-(2S)-azetidinylmethoxy)-3-ethyl-2-fluoropyridine

To a solution of 3-ethyl-2-fluoro-5-hydroxypyridine from example 126f (0.53 g, 3.8 mmol) in DMF (10 mL) was added powdered potassium hydroxide (J T Baker, 0.34 g, 6.1 mmol) and the reaction mixture was stirred at room temperature for 1.5 hour until the KOH was dissolved. (S)-1-(tert-Butyloxycarbonyl)-2-para-toluenesulfonyloxymethyl) azetidine from Example 10c (1.28 g, 3.8 mmol) was then added and the reaction mixture was heated at 80° C. for 18 h. After cooling to ambient temperature the solution was diluted with water (50 mL) and extracted with EtOAc (3×30 mL). The combined organic extracts were washed with brine (25 ml), dried ($MgSO_4$), and the solvent was removed in vacuo. The crude reaction product was purified by column chromatography (silica gel; EtOAc/hexane, 3:7) to afford the title compound as a yellow oil (0.93 g, 79%): $^1$H NMR ($CDCl_3$, 300 MHz) δ1.23 (t, J=7.7 Hz, 3H), 1.42 (s, 9H), 2.33 (m, 2H), 2.62 (q, J=7.7 Hz, 2H), 3.90 (m, 2H), 4.11 (dd, J=3.0, 7.0 Hz, 2H), 4.29 (m, 1H), 4.51 (m, 1H), 7.25 (m, 1H), 7.68 (m, 1H); MS (CI/$NH_3$) m/z 311 (M+H)$^+$, 328 (M+$NH_4$)$^+$.

126h. 5-((2S)-Azetidinylmethoxy)-3-ethyl-2-fluoropyridine tosylate

A solution of the coupled product from Step 126g above (0.93 g, 3.0 mmol) was dissolved in dry $CH_2Cl_2$ (10 mL), and cooled to 0° C. Trifluoroacetic acid (Aldrich, 10 mL) was added, and the solution was allowed to stir at 0° C. for 1 hour. The reaction mixture was carefully poured into saturated aqueous $NaHCO_3$ (50 mL), and extracted with EtOAc (3×30 mL). The combined organic extracts were washed with brine (25 mL), dried ($MgSO_4$), and the solvent was evaporated. The crude product was purified by column chromatography (silica gel; MeOH/$CH_2Cl_2$, 1:9, then $CHCl_3$/MeOH/$NH_4OH$, 80:20:1) to afford the free base of the title compound as a yellow oil (0.22 g, 35%). The oil was dissolved in EtOH, cooled to 0° C., and p-toluenesulfonic acid monohydrate (Aldrich, 0.20 g, 1.0 mmol) was added. After stirring at 0° C. for 30 minutes, the solvent was evaporated and the residue was triturated from $Et_2O$ to afford an off-white solid (0.27 g, 24% from isolated free amine): mp 106–108° C.; $[\alpha]_D^{21}$ −20.4 (c 0.6, $CH_2Cl_2$) free base; $^1$H NMR (DMSO-$d_6$) δ1.18 (t, 3H, J=7.5 Hz), 2.28 (s, 3H), 2.39 (m, 1H), 2.50 (m, 1H), 2.61 (q, 2H, J=7 Hz), 3.85 (m, 1H), 3.95 (m, 1H), 4.37 (m, 2H), 4.70 (m, 1H), 7.10 (d, 2H, J=7.5 Hz), 7.47 (d, 2H, J=7.5 Hz), 7.54 (dd, 1H, J=3,5 Hz), 7.78 (m, 1H), 8.83 (br s, 2H); MS (CI/$NH_3$) m/z 211 (M+H)$^+$, 228 (M+$NH_4$)$^+$. Anal. Calcd for $C_{11}H_{15}FN_2O.1.5$ TsOH: C, 55.11; H, 5.81; N, 6.24. Found: C, 54.94; H, 5.86; N, 6.23.

Example 127

2-Chloro-3-methyl-5-(2-(R)--azetidinylmethoxy) pyridine citrate

Following the procedure of Example 25 Steps a and b, except substituting (R)-1-t-butyloxycarbonyl-2-azetidinemethanol for the (S)-1-t-butyloxycarbonyl-2-azetidinemethanol thereof, the title compound was prepared: mp 104–106° C.; $[\alpha]_D^{25}$+10.3 (c 0.3, MeOH); MS (DCI/$NH_3$) m/z: 213 (M+H)$^+$; $^1$H NMR ($D_2O$, 300 MHz) δ: 2.27 (d, J=10.5 Hz, 1H), 2.37 (s, 3H), 2.41–2.91 (m, 8H), 4.08–4.13 (m, 2H), 4.40 (d, J=4 Hz, 1H), 4.93 (m, 1H), 7.49 (d, J=3.1 Hz, 1H), 7.97 (d, J=3.0 Hz, 1H); Anal. Calcd for $C_{10}H_{13}N_2OCl.C_6H_8O_7$: C, 47.45; H, 5.19; N, 6.92. Found: C, 47.16; H, 5.48; N, 7.08.

Example 128

5-(2-(R)-azetidinylmethoxy)-2-bromo-pyridine tosylate

128a. 5-amino-2-bromopyridine

A mixture of 2-bromo-5-nitropyridine (Aldrich, 30.75 g, 151.5 mmol), water (250 mL), and acetic acid (110 mL) was heated to 45° C. Iron powder (24.5 g, 439 mmol) was added at a rate which kept the temperature below 53° C., then the mixture was stirred at 48° C.±5° C. The mixture was cooled to room temperature and filtered through diatomaceous earth. The filter cake was washed with ethyl acetate, and the aqueous mixture was extracted with ethyl acetate. The combined organic fractions were washed with saturated $Na_2CO_3$ and brine, dried over $MgSO_4$, and the solvent was removed in vacuo. The residue was chromatographed on silica gel, eluting with 100:0 to 50:50 hexane:ethyl acetate to give 20.4 g of the title compound: $^1$H NMR ($CDCl_3$ 300 MHz) δ6.88 (dd, 1H, J=8.5, 2.4 Hz) 7.22 (d, 1H, J=8.2 Hz) 7.85 (d, 1H, J=3 Hz); MS (CI/$NH_3$) m/z: 173 (M+H)$^+$, 190 (M+$NH_4$)$^+$.

128b. 5-acetoxy-2-bromopyridine

To 25.6 mL of boron trifluoride etherate (208 mmol, Aldrich) cooled to −15° C. under $N_2$ was added 18 g (104 mmol) of 5-amino-2-bromopyridine from step 128a above dissolved in 35 mL of DME. Then tert-butyl nitrite (14.7 mL, 125 mmol, Aldrich) was added at a rate which kept the temperature below 0° C. DME (65 mL) and methylene chloride (60 mL) were then added. After 10 minutes at −10° C. the mixture was warmed to 5° C. and stirred for 30 min. Pentane (400 mL) was then added to the reaction mixture, the solid was collected by suction filtration, washed with cold ether, air dried, and dissolved in 125 mL acetic anhydride. The resulting solution was heated to 100° C.±5° C. for 1 hour. The solvent was removed in vacuo, and the residue was suspended in saturated aqueous $Na_2CO_3$, and extracted with ethyl ether. The ether solution was dried over $MgSO_4$, the solvent was removed in vacuo, and the residue was chromatographed on silica gel, eluting with 100:0 to 60:40 hexane:ethyl acetate to give 13.6 g of the title compound: $^1$H NMR ($CDCl_3$, 300 MHz) δ2.35 (s, 3H) 7.37 (dd, 1H), 7.51 (d, 1H), 8.19–8.21 (d, 1H) MS m/z: 216 (M+H)$^+$, 233 (M+$NH_4$)$^+$.

128c. 2-bromo-5-hydroxypyridine

5-Acetoxy-2-bromopyridine (12.8 g, 60 mmol) from step 128b above was dissolved in 15% aqueous NaOH (50 mL) at 0° C., and the solution was warmed to room temperature and stirred for 60 minutes. After complete consumption of the starting material the solution was neutralized by addition of 1 N HCl. The aqueous mixture was extracted with ethyl acetate (3×200 mL). The organic extracts were washed with brine (4×50 mL), water (2×50 mL), dried ($MgSO_4$), and the solvent was evaporated to yield 9.8 g of the title compound: $^1$H NMR ($CDCl_3$, 300 MHz) δ7.14 (dd, 1H, J=3.2 Hz),7.37 (d, 1H, J=8.5 Hz), 8.04 (d, 1H, J=2.4 Hz) MS (CI/$NH_3$) m/z: 174 (M+H)$^+$.

128d. 5-(2-(1-Boc-(R)-azetidinylmethoxy)-2-bromopyridine

2-Bromo-5-hydroxypyridine from step 128c above (0.130 g, 0.75 mmol) and Boc-(R)-(toluensulfonyloxymethyl) azetidine (0.255 g, 0.75 mmol) from Example 1 were allowed to react under the conditions of Example 1 to afford a colorless oil (0.208 g, 81.3% yield). $^1$H NMR (CDCl$_3$, 300 MHz) δ1.41 (s, 9H), 2.20–2.42 (m, 2H, obscured by solvent), 3.88 (t, 2H, J=7.5 Hz), 4.11 (dd, 1H, J=2.9, 10.0 Hz), 4.32 (m, 1H), 4.50 (m, 1H), 7.16 (dd, 1H, J=3.2, 8.7 Hz), 7.37 (d, 1H, J=8.8 Hz), 8.11 (d, 1H, J=3.8 Hz); MS (CI/NH$_3$); m/z 343 (M+H)$^+$, 360 (M+NH$_4$)$^+$.

128e. 5-(2-(R)-azetidinylmethoxy)-2-bromopyridine tosylate

The product of step 128d (0.17 g, 0.52 mmol) was dissolved in dichloromethane (5.6 mL) and cooled to 0° C. Trifluoroacetic acid (1.4 mL) was then added and the mixture was stirred for two hours at 0° C. The solvents were removed under reduced pressure and the residue was taken up in brine (25 mL) and extracted with a 3:1 mixture of chloroform/isopropanol (3×20 mL). The combined organic extracts were washed with brine, dried over sodium sulfate and concentrated to leave the free base as a colorless oil (0.127 g, 100% yield). The free base (0.123 g, 0.506 mmol was dissolved in ethanol (10 mL), cooled to 0° C., and treated with p-toluenesulfonic acid (0.096 g, 0.505 mmol). After stirring for 30 minutes at 0° C., the ethanol was removed to give the title compound as a white solid (0.209 g, 100% yield). mp 174–176° C.; [α]$_D^{25}$+5.2 (c 0.9, MeOH); $^1$H NMR (DMSO, 300 MHz) δ2.29 (s, 3H), 2.34–2.59 (m, 2H), 3.82–4.04 (m, 2H), 4.29–4.46 (m, 2H), 4.74 (m, 1H), 7.11 (d, 2H, J=8.1 Hz), 7.42–7.51 (m, 3H), 7.61 (d, 1H, J=8.9 Hz), 8.19 (d, 1H, J=3.4 Hz), 8.79–8.96 (bs, 1H); MS (CI/NH$_3$); m/z 243 (M+H)$^+$, 260 (M+NH$_4$)$^+$. Anal. Calcd for C$_9$H$_{11}$BrN$_2$O.TsOH: C, 46.27; H, 4.61; N, 6.75. Found: C, 46.65; H, 4.63; N, 6.37.

Example 129

5-((2R)-Azetidinylmethoxy)-2-fluoro-3-vinylpyridine tosylate

129a. 5-(1-Boc-2-(R)-azetidinylmethoxy)-3-ethenyl-2-fluoropyridine

Following the procedures of Example 131 below, replacing (S)-1-(tert-butyloxycarbonyl)-2-para-toluenesulfonyloxymethyl)azetidine thereof with its enantiomer (R-1-(tert-butyloxycarbonyl)-2-para-toluenesulfonyloxymethyl)azetidine from Example 1 above, the title compound was prepared as a clear oil in 76% yield: $^1$H NMR (CDCl$_3$, 300 MHz) δ1.42 (s, 9H), 2.24–2.42 (m, 2H), 3.92 (m, 1H), 4.13 (dd, J=3.0, 7.0 Hz, 2H), 4.35 (m, 1H), 4.54 (m, 1H), 5.49 (d, J=11.0 Hz, 1H), 5.89 (d, J=18.0 Hz, 1H), 6.75 (m, 1H), 7.47 (dd, J=2.7, 5.1 Hz, 1H), 7.76 (m, 1H); MS (CI/NH$_3$) m/z 309 (M+H)$^+$, 326 (M+NH$_4$)$^+$.

129b. 5-(2-(R)-Azetidinylmethoxy)-3-ethenyl-2-fluoropyridine tosylate

To a solution of the product from step 129a above (0.21 g, 0.7 mmol) in methylene chloride (10 mL) at 0° C. was added trifluoroacetic acid (10 mL). After stirring for 1 hour at 0° C., the volatile components were removed in vacuo. The residue was diluted with saturated aqueous NaHCO$_3$ and extracted with EtOAc (3x). The combined organic extracts were washed with brine, dried (MgSO$_4$), and concentrated. The residue was purified by column chromatography (silica gel; MeOH/CH$_2$Cl$_2$, 1:9, then CHCl$_3$/MeOH/NH$_4$OH, 80:20:1) to afford the desired material as a yellow oil (0.10 g, 68%). The oil was dissolved in EtOH, cooled to 0° C., and p-toluenesulfonic acid monohydrate (0.09 g, 0.5 mmol) was added. After stirring at 0° C. for 30 minutes, the solvent was evaporated and the solid was triturated with Et$_2$O to afford the title compound as a light yellow solid (0.05 g, 20% from isolated free amine): mp 84–85° C.; [α]$_D^{23}$+12.6 (c 0.5, MeOH); $^1$H NMR (DMSO-d$_6$, 300 MHz) δ2.28 (s, 3H), 2.40 (m, 1H), 2.51 (m, 1H), 3.86–4.02 (br m, 2H), 4.38 (m, 2H), 4.74 (m, 1H), 5.60 (d, J=11.0 Hz, 1H), 6.09 (d, J=17.5 Hz, 1H), 6.75 (m, 1H), 7.11 (d, J=8.0 Hz, 2H), 7.48 (d, J=8.0 Hz, 2H), 7.86 (m, 2H), 8.85 (br s, 2H); MS (CI/NH$_3$) m/z 209 (M+H)$^+$, 226 (M+NH$_4$)$^+$. Anal. Calcd for C$_{11}$H$_{13}$FN$_2$O.TsOH.0.3 H$_2$O: C, 56.03; H, 5.64; N, 7.26. Found: C, 55.87; H, 5.43; N, 7.20.

Example 130

3-(2-(S)-azetidinylmethoxy)-5-(3-propenyl)pyridine hydrochloride

130a. 3-(1-Boc-2-(S)-azetidinylmethoxy)-5-(3-propenyl)pyridine 3-(1-Boc-2-(S)-azetidinylmethoxy)-5-bromopyridine (0.95 g, 2.77 mmol, from Example 12 Step a) in toluene (10 mL) was added tetrakis(triphenylphosphine)palladium (100 mg) and allyltributyltin (1.72 mL, 5.54 mmol). The mixture was stirred and refluxed for two days. Solvent was evaporated and the residue was chromatographed (silica gel; hexane/EtOAc, 5:1 to 1:1) to afford an oil (250 mg, 30%): $^1$H NMR (CDCl$_3$, 300 MHz) δ1.42 (s, 9H), 2.22–2.42 (m, 2H), 3.37 (d, 2H, J=7.0 Hz), 3.87–3.92 (m, 2H), 4.16 (m, 1H), 4.30 (m, 1H), 4.50 (m, 1H), 5.07–5.17 (m, 2H), 5.9 (m, 1H), 7.07 (m, 1H), 8.08 (m, 1H), 8.19 (d, 1H, J=3.0 Hz); MS (CI/NH$_3$) m/z 305 (M+H)$^+$.

130b. 3-(2-(S)-azetidinylmethoxy)-5-(3-propenyl) pyridine

The product from step 130a above (250 mg, 0.82 mmol) in CH$_2$Cl$_2$ (2 mL) was cooled to 0° C., TFA (1.1 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with CH$_2$Cl$_2$ (3x). The combined organic layers were dried (MgSO$_4$), concentrated and chromatographed (silica gel; CH$_2$Cl$_2$/MeOH/NH$_4$OH, 10:0.3:0 to 10:1:0.03) to afford a light yellow oil (365 mg, 69%): $^1$H NMR (CDCl$_3$, 300 MHz) δ2.28 (m, 1H), 2.42 (m, 1H), 3.37 (d, 2H, J=6.5 Hz), 3.52 (m, 1H), 3.76 (m, 1H), 4.04 (m, 2H), 4.30 (m, 1H), 5.06–5.16 (m, 2H), 5.94 (m, 1H), 7.04 (m, 1H), 8.08 (d, 1H, J=2.0 Hz), 8.18 (d, 1H, J=3.0 Hz); MS (CI/NH$_3$) m/z 239 (M+H)$^+$.

130 c. 3-(2-(S)-azetidinylmethoxy)-5-(3-propenyl) pyridine hydrochloride

To the product of step 130b above in Et$_2$O was added hydrogen chloride (1.0 M in Et$_2$O) carefully to afford the title compound: $^1$H NMR (D$_2$O) δ2.70 (q, 2H, J=8.5 Hz), 3.49 (d, 2H, J=6.5 Hz), 4.02–4.20 (m, 2H), 4.44 (d, 2H, J=4.5 Hz), 4.95 (m, 1H), 5.12–5.20 (m, 2H), 6.05 (m, 1H), 7.53 (s, 1H), 8.15 (s, 1H), 8.24 (d, 1H, J=2.0 Hz); MS (CI/NH$_3$) m/z 205 (M+H)$^+$. Anal. Calcd for C$_{12}$H$_{16}$N$_2$O.2 HCl.0.2 H$_2$O: C, 54.14; H, 6.82; N, 10.52. Found: C, 54.30; H, 6.82; N, 10.49. [α]$_D^{25}$–3.5 (c 0.63, MeOH).

Example 131

5-(2-(S)-Azetidinylmethoxy)-3-ethenyl-2-fluoropyridine tosylate

131 a. 3-Bromo-2-fluoro-5-nitropyridine

3-Bromo-2-chloro-5-nitropyridine (119 g, 0.500 mol, prepared according to V. Koch and S. Schnatterer, *Synthesis,*

1990, 497–498), potassium fluoride (79.5 g, 1.37 mol), and tetraphenylphosphonium bromide (109 g, 0.260 mol) were combined in acetonitrile (1.5 L) and heated at reflux for 4 days until GLC indicated complete consumption of the 3-bromo-2-chloro-5-nitropyridine. The volume of the mixture was reduced to 750 mL in vacuo then and diluted with 2 L of ether. The mixture was filtered and the filtrate concentrated. The residue was triturated with hot hexane (2×1 L then 2×0.5 L) and the combined hexane extracts were concentrated to give 62.8 g (54%) of the title compound: $^1$H NMR (DMSO-$d_6$ 300 MHz) δ9.14 (m, 2H).

131b. 5-Amino-3-bromo-2-fluoropyridine

To a solution of 3-bromo-2-fluoro-5-nitropyridine from step 131a above (5.0 g, 23 mmol) in MeOH (100 mL) was added tin(II) chloride dihydrate. The mixture was heated at reflux for 3 hours, then cooled to ambient temperature and concentrated in vacuo. The residue was diluted with saturated aqueous $NaHCO_3$ and EtOAc resulting in formation of an emulsion which was filtered. The filtrate was poured into a separatory funnel and the layers were separated. The aqueous phase was extracted with EtOAc (2×). The combined organic extracts were washed with brine, dried ($MgSO_4$), and concentrated. Purification by chromatography (silica gel; hexane/EtOAc, 70:30) afforded 3.61 g (83%) of the title compound as a yellow solid: mp 91–92° C.; $^1$H NMR ($CDCl_3$, 300 MHz) δ7.15 (dd, J=2.5, 7.5 Hz, 1H), (dd, J=2.0, 2.5 Hz, 1H); MS (CI/$NH_3$) m/z 191, 193 (M+H)$^+$ 208, 210 (M+$NH_4$)$^+$.

131 c 5-Amino-3-ethenyl-2-fluoropyridine

To a stirred solution of 5-amino-3-bromo-2-fluoropyridine (3.25 g, 17.0 mmol) from step 131b above in toluene (20 mL) was added tributyl(vinyl)tin (7.64 g, 20.4 mmol) followed by tetrakis(triphenylphosphine)palladium (Aldrich, 0.63 g, 1.7 mmol). The reaction mixture was heated at 100° C. for 24 h. The solvent was removed in vacuo and the residue was purified by column chromatography (silica gel; EtOAc/hexane, 4:6) to afford the title compound as a beige solid (2.30 g, 98%): $^1$H NMR ($CDCl_3$, 300 MHz) δ3.61 (br s, 2H), 5.44 (d, J=11.5 Hz, 1H), 5.83 (d, J=17.5 Hz, 1H), 6.66 (m, 1H), 7.18 (dd, J=3.0, 5.0 Hz, 1H), 7.52 (m, 1H); MS (CI/$NH_3$) m/z 139 (M+H)$^+$, 156 (M+$NH_4$)$^+$.

131 d. 5-Acetoxy-3-ethenyl-2-fluoropyridine

To a solution of the product from step 131c above (3.00 g, 21.7 mmol) in 3:1 dimethoxyethane:$CH_2Cl_2$ (50 mL) at −10° C. was slowly added borontrifluoride etherate (Aldrich, 5.60 mL, 45.6 mmol). t-Butylnitrite (Aldrich, 3.10 mL, 26.0 mmol) was added over the course of 15 minutes, maintaining the reaction temperature below −5° C. The reaction mixture was warmed to 0° C. and stirred for 30 minutes. Pentane (500 mL) was added and the solid tetrafluoroborate diazonium salt was collected by filtration. The diazonium salt was dissolved in acetic anhydride (40 mL) and heated at 95° C. for 2 hours ($N_2$ evolution was noted ~85° C.). After cooling to ambient temperature, the dark mixture was concentrated in vacuo. The residue was diluted with saturated aqueous $NaHCO_3$ and extracted with $Et_2O$ (3×150 mL). The combined organic extracts were washed with brine (50 mL), dried ($MgSO_4$), and concentrated. The crude product was purified by column chromatography (silica gel; EtOAc/hexane, 40:60) to afford the title compound as a yellow oil (1.51 g, 40%): $^1$H NMR ($CDCl_3$, 300 MHz) δ2.35 (s, 3H), 5.54 (d, J=11.0 Hz, 1H), 5.90 (d, J=18.0 Hz, 2H), 6.75 (m, 1H), 7.66 (dd, J=2.0, 5.0 Hz, 1H); MS (CI/$NH_3$) m/z 182 (M+H)$^+$, 199 (M+$NH_4$)$^+$.

131 e. 3-Ethenyl-2-fluoro-5-hydroxypyridine

To a stirred solution of the the product from step 131d above (1.40 g, 7.70 mmol) in MeOH (50 mL) was added $K_2CO_3$ (0.53 g, 3.9 mmol). After stirring at room temperature 24 hours, the solvent was evaporated and the residue was diluted with $Et_2O$ (100 mL) and water (100 mL). The phases were separated and the aqueous phase was neutralized (pH 7) by the addition of 1 N aqueous HCl, and extracted with diethyl ether (2×100 mL). The combined ethereal extracts were washed with brine (50 mL), dried ($MgSO_4$), and concentrated. The crude product was purified by column chromatography (silica gel; EtOAc/hexane, 40:60) to afford the title compound as an off-white solid (0.81 g, 76%): $^1$H NMR ($CDCl_3$, 300 MHz) δ5.50 (d, J=11.0 Hz, 1H), 5.87 (d, J=17.5 Hz, 1H), 6.75 (m, 1H), 7.72 (dd, J=3.0, 5.0 Hz, 1H), 7.69 (m, 1H); MS (CI/$NH_3$) m/z 140 (M+H)$^+$, 157 (M+$NH_4$)$^+$.

131f. 5-(1-Boc-2-(S)-azetidinylmethoxy)-3-ethenyl-2-fluoropyridine

To the product from step 131e above (0.60 g, 4.3 mmol) in DMF (10 mL) was added powdered potassium hydroxide (0.36 g, 6.5 mmol) and the reaction mixture was stirred at room temperature for 1.5 h until the KOH was dissolved. 1-Boc-2-(S)-azetidinemethyl-p-toluenesulfonate (1.96 g, 4.3 mmol, from Example 10) was then added and the reaction mixture was heated at 80° C. for 18 h. The reaction mixture was diluted with water (50 mL) and extracted with EtOAc (3×30 mL). The combined organic extracts were washed with brine (25 ml), dried ($MgSO_4$), and the solvent was removed in vacuo. The crude reaction product was purified by column chromatography (silica gel; $CH_2Cl_2$/MeOH, 98:2) to afford the desired material as a yellow oil (1.44 g, >100%): $^1$H NMR ($CDCl_3$, 300 MHz) δ1.42 (s, 9H), 2.45 (m, 2H), 3.90 (m, 1H), 4.13 (dd, J=3.0, 7.5 Hz, 2H), 4.35 (m, 1H), 4.54 (m, 1H), 5.49 (d, J=11.0 Hz, 1H), 5.89 (d, J=17.5 Hz, 1H), 6.74 (m, 1H), 7.47 (m, 1H), 7.76 (m, 1H); MS (CI/$NH_3$) m/z 309 (M+H)$^+$, 326 (M+$NH_4$)$^+$.

131g 5-(2-(S)-Azetidinylmethoxy)-3-ethenyl-2-fluoropyridine tosylate

To a solution of the coupled product from Step 131f above (1.44 g, 4.70 mmol) in methylene chloride (10 mL) at 0° C. was added trifluoroacetic acid (10 mL). After stirring for 1 hour at 0° C., the volatile components were removed in vacuo. The residue was diluted with saturated aqueous $NaHCO_3$ and extracted with EtOAc (3×). The combined organic extracts were washed with brine, dried ($MgSO_4$), and concentrated. The residue was purified by column chromatography (silica gel; MeOH/$CH_2Cl_2$, 1:9, then $CHCl_3$/MeOH/$NH_4OH$, 80:20:1) to afford the desired material as a yellow oil (0.37 g, 41%): $[α]_D^{25}$ −2.8 (c 0.4, MeOH). The oil was dissolved in EtOH, cooled to 0° C., and p-toluenesulfonic acid monohydrate (0.34 g, 1.8 mmol) was added. After stirring at 0° C. for 30 minutes, the solvent was evaporated and the solid was triturated with $Et_2O$ to afford the title compound as a white solid (0.30 g, 48% from isolated free amine): mp 251–253° C.; $^1$H NMR (DMSO-$d_6$, 300 MHz) δ2.29 (s, 3H), 2.38 (m, 1H), 2.43 (m, 1H), 3.86–4.02 (m, 2H), 4.40 (m, 2H), 4.74 (m, 1H), 5.60 (d, J=11.0 Hz, 1H), 6.09 (d, J=16.5 Hz, 1H), 6.74 (m, 1H), 7.11 (d, J=8.5 Hz, 2H), 7.48 (d, J=8.0 Hz, 2H), 7.87 (m, 2H), 8.86 (br s, 2H); MS (CI/$NH_3$) m/z 209 (M+H)$^+$, 226 (M+$NH_4$)$^+$.

Anal. Calcd for $C_{11}H_{13}FN_2O\cdot1.3$ TsOH: C, 55.87; H, 5.46; N, 6.48. Found: C, 56.23; H, 5.68; N, 6.28.

Example 132

5-nitro-3-(2-(S)-azetidinylmethoxy)pyridine hydrochloride

132a. 3-benzyloxy-5-bromopyridine

NaH (60% in mineral oil) (40.9 g 1.0225 mol) in 800 mL of DMF was cooled to 0° C., and benzyl alcohol (105 mL 1.014 mol) was added slowly. The reaction mixture was stirred for 1 hour at 20° C., then 3,5-dibromopyridine (200.4 g, 846 mmol) was added and the mixture was stirred for 16 hours. The mixture was quenched with saturated $NH_4Cl$ (500 mL), diluted with 400 mL water and extracted with $Et_2O$ (5×300 mL). The combined $Et_2O$ extracts were washed with 50% brine (6×300 mL) and dried ($MgSO_4$). The solvent was evaporated in vacuo and the crude product was recrystallized from $Et_2O$ to afford 161 g (72%) of the title product, mp 63–68° C. $^1H$ NMR ($CDCl_3$, 300 MHz) δ8.37–8.27 (m, 2H), 7.5–7.35 (m, 6H), 5.1 (s, 1H). MS ($DCI/NH_3$) m/z 264, 266 $(M+H)^+$.

132b. 3-amino-5-benzyloxypyridine

The product of Example 132a (41.3 g 156 mmol), copper (I) bromide (22.43 g 156 mmol), MeOH (275 mL ), and liquid $NH_3$ (50 mL ) were combined in a stainless steel reactor and heated to 130° C. for 24 hours. The mixture was allowed to cool to ambient temperature, then concentrated. The residue was suspended in 300 mL of saturated aqueous $Na_2CO_3$ and extracted with $CH_2Cl_2$ (4×500 mL). The combined $CH_2Cl_2$ extracts were washed with brine, dried ($MgSO_4$), and concentrated. The crude product was chromatographed (silica gel; hexane/EtOAc, 9:1 to 7:3) to afford 15.6 g (50%) of the title compound. $^1H$ NMR ($CDCl_3$, 300 MHz) δ8.21–8.29 (m, 2H), 7.44–1.26 (m, 6H), 5.10 (s, 2H). MS ($DCI/NH_3$) m/z 201 $(M+H)^+$.

132c. 3-amino-5-hydroxypyridine

The product of Example 132b (15.47 g, 77.25 mmol) in MeOH (25 mL) was stirred under an atmosphere of $H_2$ in the presence of 5% Pd/C (100 mg) for 48 hours. The mixture was filtered and concentrated, then the crude product was chromatographed (silica gel; $CHCl_3$/MeOH, 9:1) to afford 4.5 g (53%) of the title compound MS ($DCI/NH_3$) m/z 111 $(M+H)^+$, 128 $(M+NH_4)^+$. $^1H$ NMR ($CDCl_3$, 300 MHz) δ7.4 (d, J=3 Hz, 1H), 7.3 (d, J=2.5 Hz, 1H), 6.33 (dd, J 2.6 Hz, 1H).

132d. 3-hydroxy-5-nitropyridine

Potassium persulfate (56.8 g 210 mmol) was ground into 31.5 mL of concd sulfuric acid, and the solution was added to a solution of the product of Example 132c (2.75 g 25 mmol) in concd sulfuric acid (27 mL). The mixture was allowed to stand for 72 hours, then was poured over ice and adjusted to pH 6 with concd $NH_4OH$. The solution was extracted with EtOAc (4×100 mL), then the EtOAc extracts were dried ($MgSO_4$) and concentrated. The crude product was chromatographed (silica gel; $CHCl_3$/MeOH, 99:1 to 9:1) to afford 1.65 g (47%) of the title compound. 1H NMR ($CDCl_3$, 300 MHz) δ8.81(d, J=3 Hz, 1H), 8.51 (d, H=3 Hz, 1H), 7.82 (dd, J=2.5 Hz, 1H). MS ($DCI/NH_3$) m/z 141 $(M+H)^+$, 158 $(M+NH_4)^+$.

132e. 5-nitro-3-(1-BOC-2-(S)-azetidinylmethoxy)pyridine

1-BOC-2-(S)-azetidinylmethanol (868 mg, 4.64 mmol) and 3-hydroxy-5-nitropyridine from Example 132d (500 mg, 3.57 mmol) were coupled according the procedure of Example 17a. Solvent was removed, and the residue was chromatographed (silica gel, hexane/ethyl acetate, 5:1) to afford the title compound (800 mg, 73%). $^1H$ NMR ($CHCl_3$, 300 MHz) δ1.45 (s, 9H), 2.56 (m, 2H), 4.52 (m, 4H), 4.82 (m, 1H), 8.25 (t, J=3 Hz, 1 H), 8.65 (d, J=3 Hz, 1H), 9.05 (d, J=3 Hz, 1H). MS ($DCI/NH_3$) m/z 310 $(M+H)^+$.

132f. 5-nitro-3-(2-(S)-azetidinylmethoxy)pyridine hydrochloride

To the product of Example 132e (800 mg, 2.58 mmol) in methylene chloride at 0° C. was added $HCl/Et_2O$ and the solution was stirred for 1 hour. Solvent was removed and the residue was recrystallized from $EtOH/Et_2O$ to afford the title compound (750 mg): mp 162–164° C. (dec). $^1H$ NMR ($D_2O$, 300 MHz) δ2.45 (m, 2H), 4.62 (m, 4H), 4.96 (m, 1H), 8.26 (t, J=3 Hz, 1H), 8.75 (d, J=3 Hz, 1H), 9.25 (d, J=3 Hz, 1H). MS (APCI) m/z 210 $(M+H)^+$. Anal. Calcd. for $C_9H_{12}ClN_3O_3\cdot0.30$ HCl: C, 42.13; H, 4.83; N, 16.38. Found: C, 42.28; H, 4.87; N, 16.24.

The examples listed above and those within the scope of formula I with the variables as recited herein are useful in the prevention or treatment of pain with certain exceptions as identified herein. The compounds are also useful in the treatment of neuronal cell death and in the treatment of inflammation. Applicants are also claiming those (S) compounds and those (R) compounds which have not been previously claimed or disclosed.

We claim:

1. The compound 5-((2R)-azetidinylmethoxy)-2-chloropyridine, or a pharmaceutically acceptable salt thereof.

2. An analgesic composition comprising a therapeutically effective amount of 5-((2R)-azetidinylmethoxy)-2-chloropyridine and a pharmaceutically acceptable carrier or diluent.

3. The compound 5-((2R)-azetidinylmethoxy)-2-chloropyridine or a prodrug thereof formed by the addition of a substituent to the nitrogen of the azetidinyl group selected from the group consisting of alkyl, acyl, alkoxycarbonyl, aryloxycarbonyl, amidomethyl, vinyl and carbamyl.

4. A composition for the treatment of neuropathic pain comprising a therapeutically effective amount of the compound or prodrug of claim 3 and a pharmaceutically acceptable carrier or diluent.

* * * * *